US012570758B2

(12) United States Patent (10) Patent No.: US 12,570,758 B2
Turtle et al. (45) Date of Patent: Mar. 10, 2026

(54) CHIMERIC ANTIGEN RECEPTORS TARGETING CD33

(71) Applicant: Fred Hutchinson Cancer Center, Seattle, WA (US)

(72) Inventors: Cameron J. Turtle, Seattle, WA (US); Roland B. Walter, Seattle, WA (US); George S. Laszlo, Seattle, WA (US); Salvatore Fiorenza, Seattle, WA (US)

(73) Assignee: Fred Hutchinson Cancer Center, Seattle, WA (US)

( * ) Notice: Subject to any disclaimer, the term of this patent is extended or adjusted under 35 U.S.C. 154(b) by 736 days.

(21) Appl. No.: 17/907,648

(22) PCT Filed: Mar. 31, 2021

(86) PCT No.: PCT/US2021/025255
§ 371 (c)(1),
(2) Date: Sep. 28, 2022

(87) PCT Pub. No.: WO2021/202799
PCT Pub. Date: Oct. 7, 2021

(65) Prior Publication Data
US 2023/0220103 A1 Jul. 13, 2023

Related U.S. Application Data

(60) Provisional application No. 63/003,196, filed on Mar. 31, 2020.

(51) Int. Cl.
| | |
|---|---|
| *C07K 16/28* | (2006.01) |
| *A61K 40/11* | (2025.01) |
| *A61K 40/31* | (2025.01) |
| *A61K 40/42* | (2025.01) |
| *C07K 14/705* | (2006.01) |
| *C07K 14/725* | (2006.01) |
| *C12N 15/63* | (2006.01) |

(52) U.S. Cl.
CPC .......... *C07K 16/2896* (2013.01); *A61K 40/11* (2025.01); *A61K 40/31* (2025.01); *A61K 40/421* (2025.01); *C07K 14/7051* (2013.01); *C07K 14/70521* (2013.01); *C12N 15/63* (2013.01); *A61K 2239/25* (2023.05); *A61K 2239/48* (2023.05); *C07K 2317/526* (2013.01); *C07K 2317/565* (2013.01); *C07K 2317/622* (2013.01); *C07K 2319/03* (2013.01)

(58) Field of Classification Search
CPC .................................................... A61K 40/31
See application file for complete search history.

(56) References Cited

U.S. PATENT DOCUMENTS

| | | | |
|---|---|---|---|
| 2010/0104577 A1 | 4/2010 | Golde et al. | |
| 2015/0038684 A1 | 2/2015 | Jensen | |
| 2016/0317657 A1 | 11/2016 | Walter | |
| 2017/0145094 A1 | 5/2017 | Galetto | |
| 2017/0224733 A1 | 8/2017 | Badie et al. | |
| 2017/0313759 A1 | 11/2017 | Batuwangala | |
| 2018/0002397 A1* | 1/2018 | Shah ................ C07K 14/70517 |
| 2019/0016820 A1 | 1/2019 | Pule et al. | |
| 2019/0233534 A1 | 8/2019 | Mehlin et al. | |
| 2023/0144405 A1* | 5/2023 | Walter ............... C07K 16/2803 |
| | | | 424/136.1 |
| 2023/0151094 A1 | 5/2023 | Turtle | |

FOREIGN PATENT DOCUMENTS

| | | | |
|---|---|---|---|
| JP | 2020509050 A | 3/2020 |
| WO | 2018160768 A1 | 9/2018 |
| WO | 2018175988 A1 | 9/2018 |
| WO | WO2018211245 A1 | 11/2018 |
| WO | WO2018218207 A1 | 11/2018 |
| WO | WO2019084234 A1 | 5/2019 |
| WO | 2019178382 A1 | 9/2019 |
| WO | 2019224711 A2 | 11/2019 |
| WO | WO2019246593 A2 | 12/2019 |

OTHER PUBLICATIONS

Jena et al. (Blood Aug. 19, 2010 116(7): 1035-1044) (Year: 2010).*
Bluemel, et al., "Epitope distance to the target cell membrane and antigen size determine the potency of T cell-mediated lysis by BiTE antibodies specific for a large melanoma surface antigen," Cancer Immunol Immunother, vol. 58, No. 8, 2010, pp. 1197-11209.
Clearly, et al., "Antibody Distance from the Cell Membrane Regulates Antibody Effector Mechanisms," J. Immunol., vol. 198, No. 10, 2017, pp. 3999-4011.
Cowan, et al., "Antibody-based therapy of acute myeloid leukemia with gemtuzumab ozogamicin," Front Biosci., vol. 18, No. 4, 2013, pp. 1311-1334.
Duan and Paulson, "Siglecs as Immune Cell Checkpoints in Disease," Annu. Rev. Immunol., vol. 38, 2020, pp. 365-395.
Godwin, et al., "Gemtuzumab ozogamicin in acute myeloid leukemia," Leukemia, vol. 31, No. 9, 2017, pp. 1855-1868.
Grossbard, et al., "Monoclonal antibody-based therapies of leukemia and lymphoma," Blood., vol. 80, No. 4, 1992, pp. 863-878.
Haso, et al., "Anti-CD22-chimeric antigen receptors targeting B-cell precursor acute lymphoblastic leukemia," Blood, vol. 121, No. 7, 2013, pp. 1165-1174.
Humbert, et al., "Engineering resistance to CD33-targeted immunotherapy in normal hematopoiesis by CRISPR/Cas9-deletion of CD33 exon 2," Leukimia, vol. 33, No. 3, 2019, pp. 762-808.

(Continued)

*Primary Examiner* — Peter J Reddig
(74) *Attorney, Agent, or Firm* — C. Rachal Winger; Chrystal Quisenberry; Lee & Hayes PC

(57) ABSTRACT

Chimeric antigen receptors (CARs) with binding domains derived from a novel suite of human CD33-binding antibodies are described. The CARs include optimized short and intermediate spacer regions. The current disclosure also provides methods of cell expansion/activation processes utilizing IL-2, IL-7, IL-15, and/or IL-21 that improve cellular proliferation and cell lysis of the CARs as described.

4 Claims, 71 Drawing Sheets

Specification includes a Sequence Listing.

(56)  References Cited

OTHER PUBLICATIONS

Kenderian, et al., "CD33-specific chimeric antigen receptor Tcells exhibi potent preclinical activity against human acute myeloid muekemia," Leukemia, vol. 29, 2015, pp. 1637-1647.

Laszlo, et al., "The past and future of CD33 as therapeutic target in acute myeloid leukemia," Blood Rev., vol. 28, No. 4, 2014, pp. 143-153.

Lin, Thomas S., "Ofatumumab: a novel monoclonal anti-CD20 antibody," Pharmgenomics Pers. Med., vol. 3, 2010, pp. 51-59.

NCT03971799, "Phase 1/2 Study of Anti-CD33 Chimeric Antigen Receptor-Expressing T Cells (CD33CART) in Children and Young Adults With Relapsed/Refractory Acute Myeloid Leukemia," May 16, 2022, Accessed online Nov. 29, 2022 at https://clinicaltrials.gov/ct2/show/NCT03971799?term=NCT03971799&draw=2&rank=1.

Invitation to to Pay Additional Fees Dated Jul. 6, 2021 in International Application No. PCT/US2021/025248, 2 pages.

Turtle, et al., "Immunotherapy of non-Hodgkin lymphoma with a defined ratio of CD8+ CD19-specific chimeric antigen receptor modified T cells," Sci. Transl. Med., vol. 8, No. 355, 2016, 24 pages.

Walter, et al., "Acute myeloid leukemia stem cells and CD33-targeted immunotherapy," Blood, vol. 119, No. 26, 2012, pp. 6198-6208.

Walter, Roland B., "Expanding use of CD33-directed immunotherapy," Expert Opin. Biol. Ther., vol. 20, No. 9, 2020, pp. 955-958.

Walter, Roland B., "Investigational CD33-targeted therapeutics for acute myeloid leukemia," Expert Opin. Investig Drugs., vol. 27, No. 4, 2018, pp. 339-348.

Extended European Search Report Dated Apr. 8, 2024 for European Application No. 21780751.0, a foreign counterpart to U.S. Appl. No. 17/907,648, 8 pages.

Gbadamosi, et al., "Novel CD33 Antibodies Unravel Localization, Biology and Therapeutic Implications of CD33 Isoforms", Blood, American Society of Hematology, vol. 134, Nov. 13, 2019, pp. 908.

Godwin, et al., "Targeting the membrane-proximal C2-set domain of CD33 for improved CD33-directed immunotherapy", Blood Cancer Journal, vol. 35, No. 9, Feb. 15, 2021, pp. 2496-2507.

Partial European Search Report Dated Apr. 2, 2024 for European Application No. 21780312.1, a foreign counterpart to U.S. Appl. No. 17/995,085, 15 pages.

Batra, et al., "Glypican-3-Specific CAR T Cells Coexpressing IL 15 and IL21 Have Superior Expansion and Antitumor Activity against Hepatocellular Carcinoma," Cancer Immunology Research, vol. 8, No. 3, 2020, pp. 309-320.

Gargett & Brown, "Different cytokine and stimulation conditions influence the expansion and immune phenotype of third-generation chimeric antigen receptor T cells specific for tumor antigen GD2," Cytotherapy, vol. 17, No. 4, 2015, pp. 487-495.

Invitation to Pay Additional Fees Dated Jul. 19, 2021 for International Application No. PCT/US2021/025255, 3 pages.

Nair-Gupta et al., "A novel C2 domain binding CD33×CD3 bispecific antibody with potent T-cell redirection activity against acute myeloid leukemia," Blood Adv., vol. 4, No. 5, 2020, pp. 906-919.

Search Report and Written Opinion Dated Sep. 21, 2021 for International Application No. PCT/US2021/025248, 13 Pages.

Search Report and Written Opinion Dated Sep. 23, 2021 for International Application No. PCT/US2021/025255, 12 pages.

Singh, et al., "Reprogramming CD19-Specific T Cells with IL-21 Signaling Can Improve Adoptive Immunotherapy of B-Lineage Malignancies," Cancer Res., vol. 71, No. 10, 2011, pp. 3516-3527.

Search Report and Written Opinion for European Application No. 21780312.1, Dated Jun. 24, 2024, 13 pages.

* cited by examiner

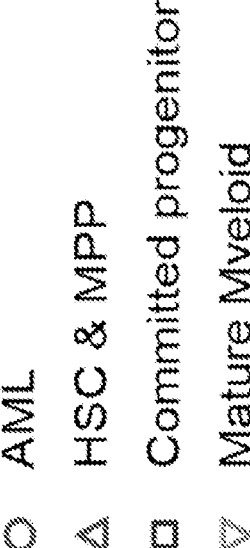
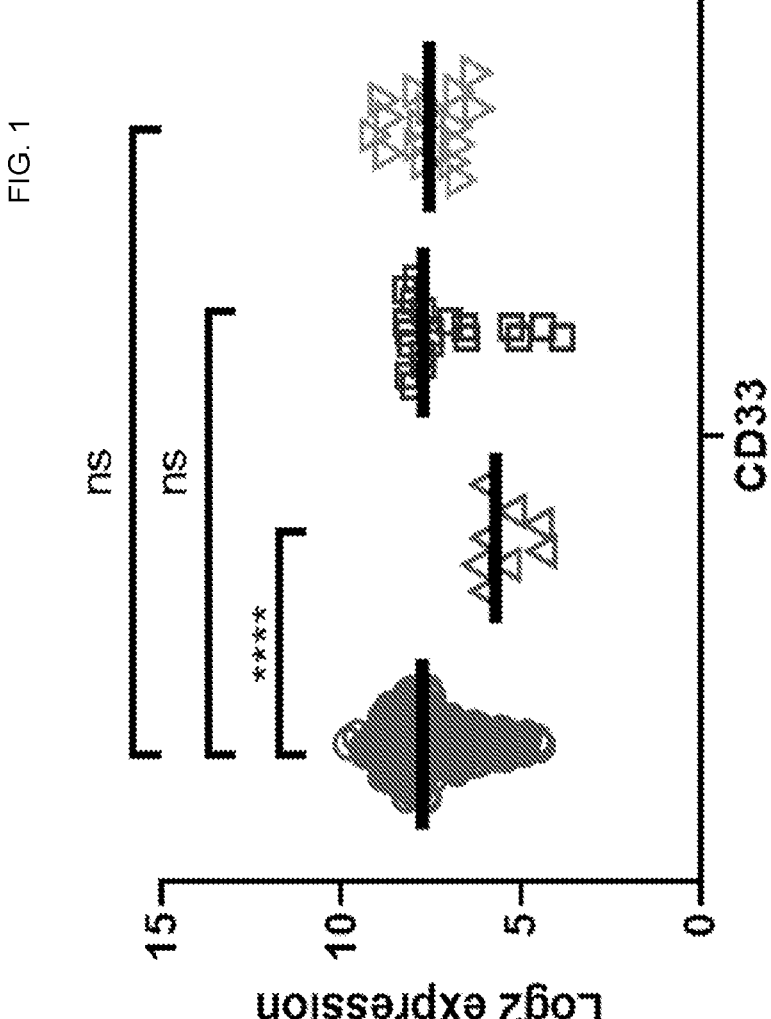
FIG. 1

Gibson Assembly cloning of scFvs into CAR backbone

Figure 6:
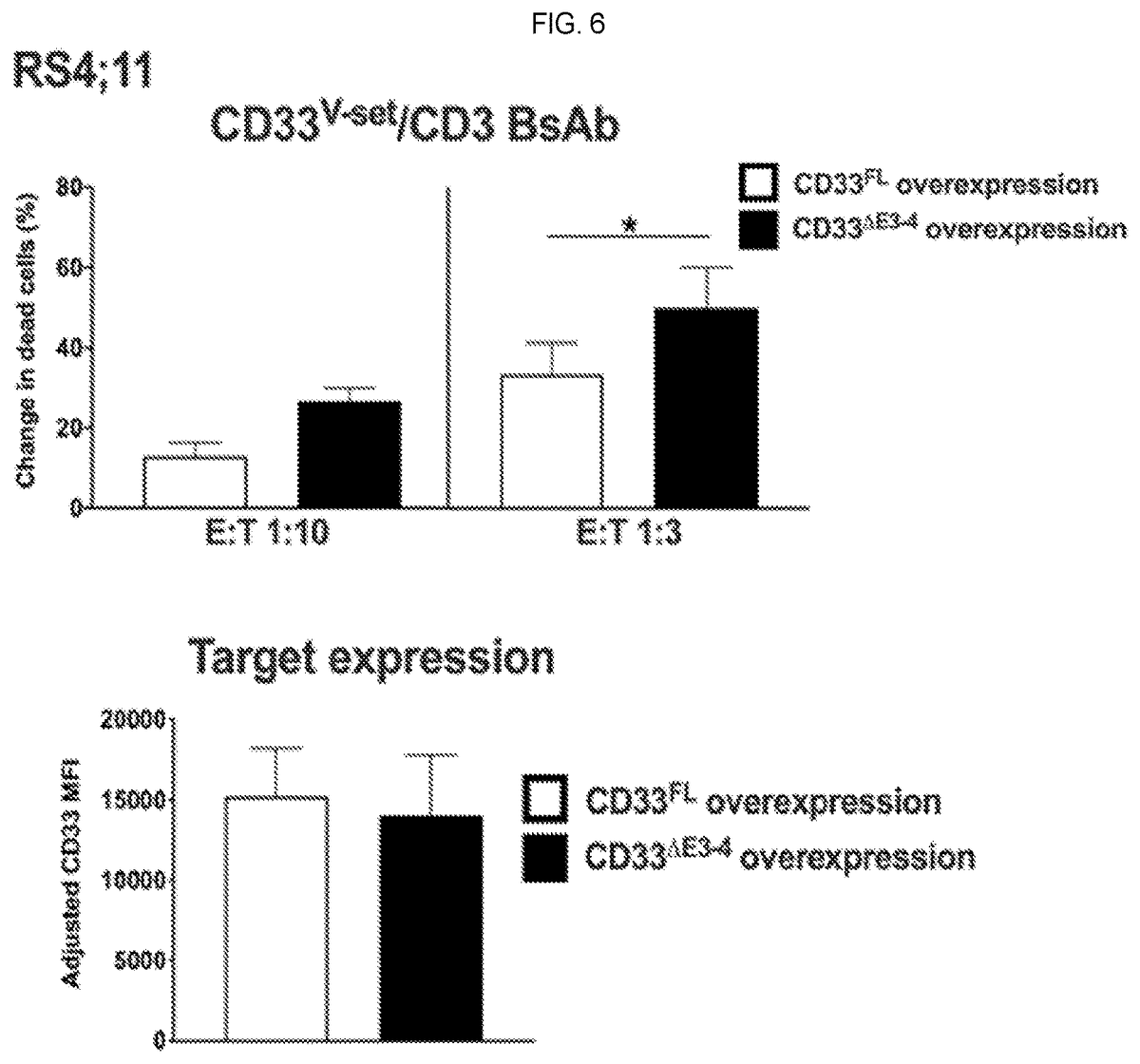

CD33$^{V\text{-set}}$/CD3 BsAb

□ CD33$^{FL}$ overexpression
■ CD33$^{\Delta E3\text{-}4}$ overexpression

*

Y-axis: Change in dead cells (%)

X-axis: E:T 1:10    E:T 1:3

Target expression

□ CD33$^{FL}$ overexpression
■ CD33$^{\Delta E3\text{-}4}$ overexpression

Y-axis: Adjusted CD33 MFI

FIG. 8
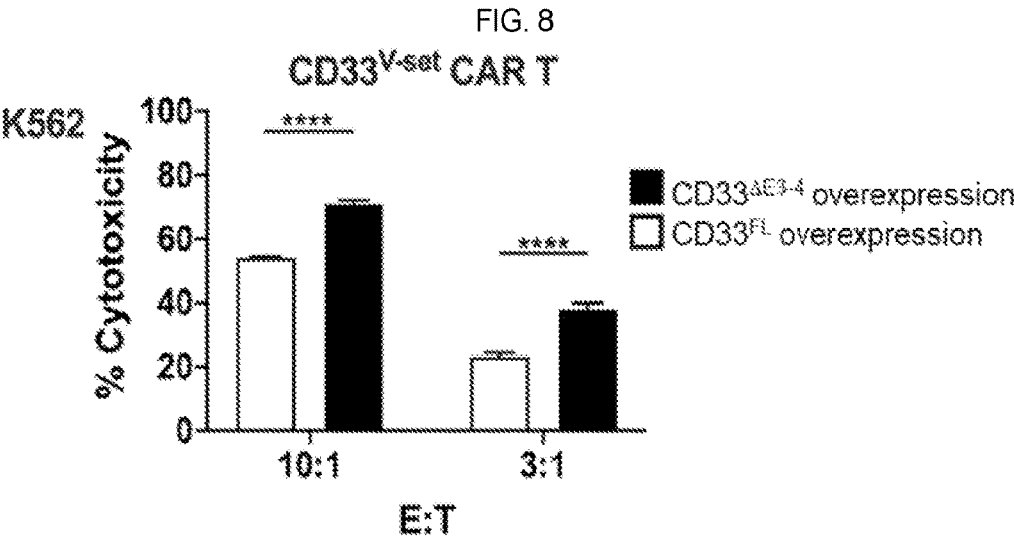
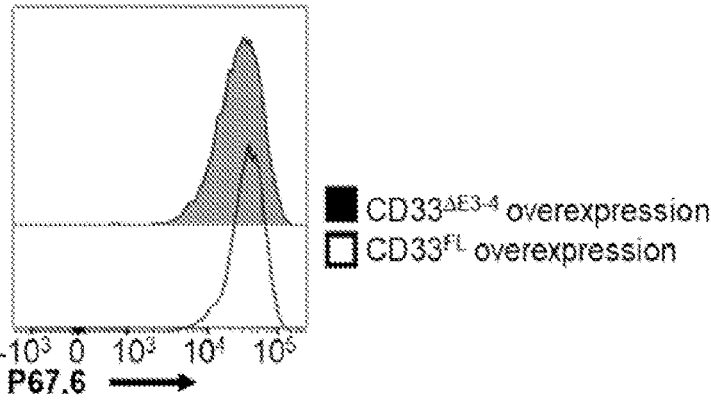
FIG. 9
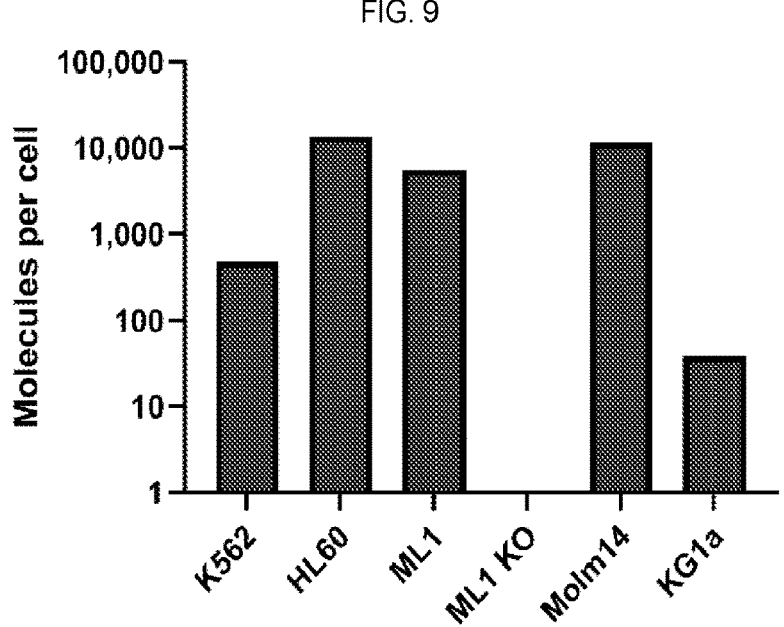

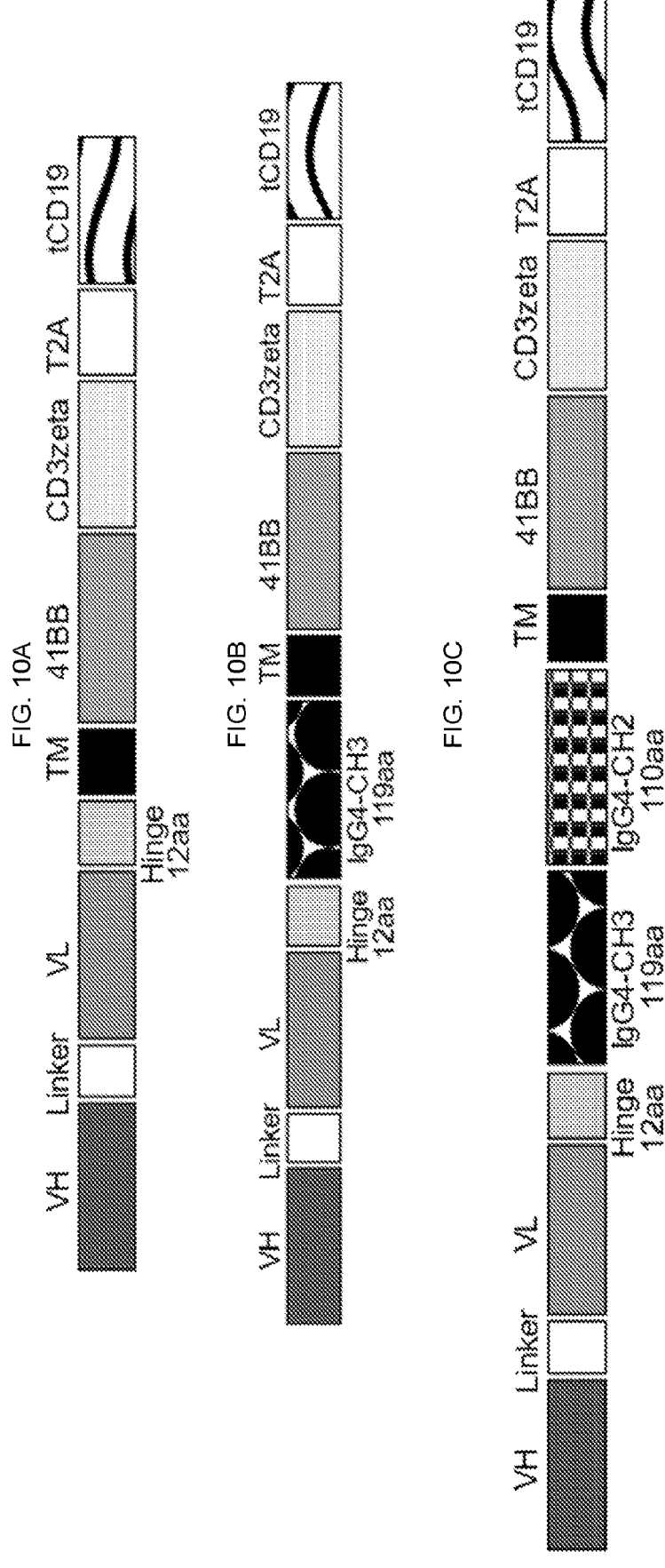

FIG. 12A

Cartera binding data for purified monoclonal anti-CD33 antibodies (Trianni mice)

| Clone | CD33$^{FL}$ kD (nM), 4 µg/mL | CD33$^{FL}$ kD (nM), 1 µg/mL | Hybridoma supernatant (CD33$^{FL}$) | CD33$^{\Delta E2}$ kD (nM), 4 µg/mL | CD33$^{\Delta E2}$ kD (nM), 1 µg/mL | Hybridoma supernatant (CD33$^{\Delta E2}$) | mAb type |
|---|---|---|---|---|---|---|---|
| 1H10 | 42 | 13 | 112 | 13 | 0.154 | 31 | Pan |
| 2D3 | 27 | 18 | N.D. | --- | --- | N.D. | V-set |
| 1H8 | 40 | 24 | --- | --- | --- | --- | V-set |
| 1A9 | 130 | 36 | 67 | 23 | 1.3 | 19 | Pan |
| 1B9 | --- | --- | 77 | --- | --- | 44 | Pan |
| 1E6 | 78 | 67 | 69 | 49 | 25 | 37 | Pan |
| 1D2 | --- | --- | 116 | --- | --- | 115 | Pan |
| 2E3 | 2300 | --- | 3000 | --- | --- | --- | V-set |

FIG. 12B
CD33$^{FL}$
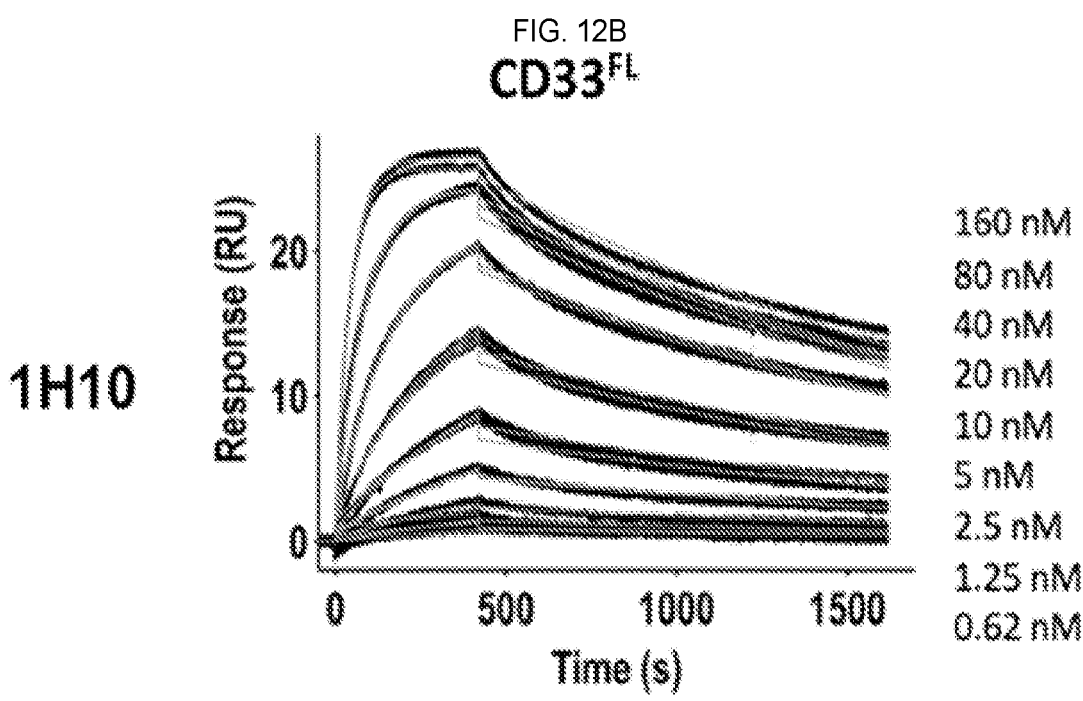
1H10
160 nM
80 nM
40 nM
20 nM
10 nM
5 nM
2.5 nM
1.25 nM
0.62 nM
$k_a = 1.40 \times 10^5 \ M^{-1}s^{-1}$
$k_d = 5.20 \times 10^{-4} \ s^{-1}$
$K_D = 3.71 \ nM$
57.2 ± 0.8 RUs captured 1H10
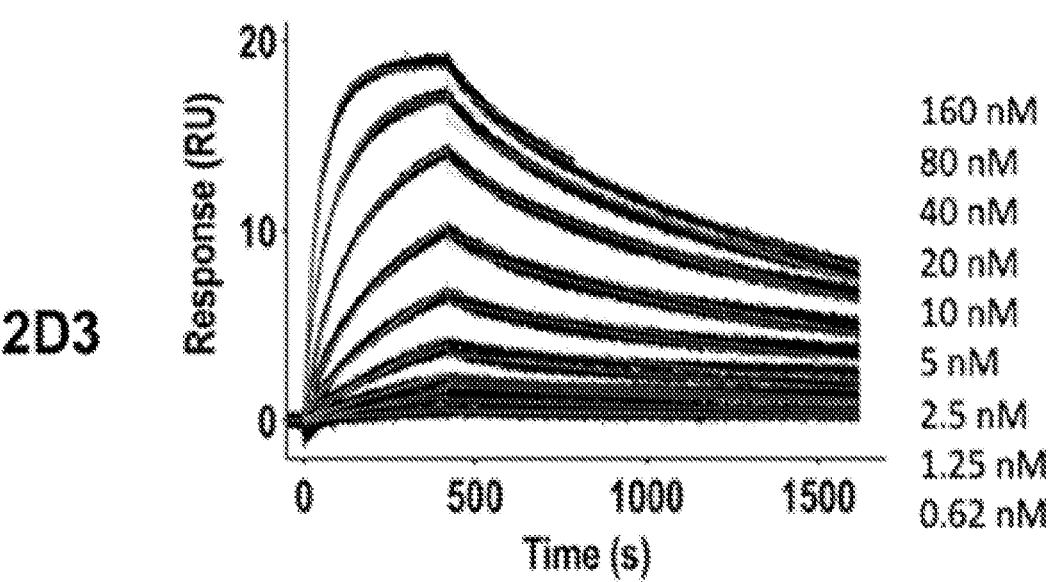
2D3
160 nM
80 nM
40 nM
20 nM
10 nM
5 nM
2.5 nM
1.25 nM
0.62 nM
$k_a = 1.28 \times 10^5 \ M^{-1}s^{-1}$     39.7 ± 0.5 RUs captured 2D3
$k_d = 6.27 \times 10^{-4} \ s^{-1}$
$K_D = 4.89 \ nM$

CD33ΔE2

1H10

$k_a = 3.87 \times 10^5\ M^{-1}s^{-1}$
$k_d = 5.27 \times 10^{-5}\ s^{-1}$
$K_D = 136\ pM$ 95 ± 1 RUs
captured 1H10

2D3

Did not bind

IL2 - Cells per mL

IL7 & 15 - Cells per mL

IL7, 15 & 21 - Cells per mL

IL2 - Total Cells

IL7 & 15 - Total Cells

IL7, 15 & 21 - Total Cells

IL2 - Fold Change

IL7 & 15 - Fold Change

IL7, 15 & 21 - Fold Change

IL2 Viability

IL7 & 15 Viability

IL7, 15 & 21 Viability

IL2 Diameter

IL7 & 15 Diameter

Trianni - IL2

IL2

1E6 – Media

1E6 – ML1

1E6 – CD33 KO

1E6 – CFSE neg

1A9 – Media

1A9 – ML1

1A9 – CD33 KO

1A9 – CFSE neg

1H10 – Media

1H10 – ML1

1H10 – CD33 KO

1H10 – CFSE neg

*CFSE*

IL7 & 15

1E6 – Media

1E6 – ML1

1E6 – CD33 KO

1E6 – CFSE neg

1A9 – Media

1A9 – ML1

1A9 – CD33 KO

1A9 – CFSE neg

1H10 – Media

1H10 – ML1

1H10 – CD33 KO

1H10 – CFSE neg

*CFSE*

IL7, 15, & 21

1E6 – Media

1E6 – ML1

1E6 – CD33 KO

1E6 – CFSE neg

1A9 – Media

1A9 – ML1

1A9 – CD33 KO

1A9 – CFSE neg

1H10 – Media

1H10 – ML1

1H10 – CD33 KO

1H10 – CFSE neg

*CFSE*

<u>scFv coding sequence in VH-VL orientation, codon optimized for use in CAR:</u>
The sequences encoding the starter methionine is in bold, the signal peptide is underlined and italicized, the G4Sx3 linker is underlined, and the variable light chain is in italics.

1H10 VH-VL scFv coding sequence:
ATG<u>*CTGCTGCTCGTGACCAGCCTGCTGCTGTGCGAACTGCCCCACCCTGCCTTTCTGCTG*</u>
<u>*ATCCCCC*</u>AAGTACAGCTTGTTCAAAGTGGTGCTGAAGTTAAAAAGCCAGGGGCCAGCGTTA
AGGTATCCTGCAAGGGAAGTGGTTACATCTTCACATCTTACGACATGCACTGGGTACGACA
GGCTCCTGGACAGGGTCTGGAATGGATGGGTATCATAGACCCCTCAGGAGGATCTACGAG
CTATGCCCAAAAATTTCAGGGAAGAGTAACAATGACCAGGGACACGTCCATGAGCACAGTC
TACATGGAACTCAGCAGTCTCAGATCAGAGGATACGGCGGTTTACTACTGTACTAGGGATT
ATTCATGGAGCTATTTCGACTATTGGGGACAAGGAACCTTGGTAACAGTGTCTTCA<u>GGAGG</u>
<u>CGGAGGATCTGGCGGAGGGGGCTCTGGAGGAGGAGGATCT</u>*GCGATACAAATGACGCAAA*
*GTCCAGCAGTTTGTCCGCCTCAGTAGGCGACCGCGTTACGATTACGTGTAGGGCGTCTC*
*AAGGGATCAGGATCTATCTGGGCTGGTATCAACAAAAGCCTGGGAAAGCCCCAAAGCTCC*
*TTATATATGCAACATCATCCCTGCAAAGCGGCGTTCCATCCCGATTCAGTGGTTCTGGTAG*
*CGGTACGGACTTCACTCTCACAATCTCATCTCTTCAACCAGAAGACTTTGCGACGTATTACT*
*GTTTGCAAGACTACAATTATCCATGGACGTTCGGCCAAGGCACGAAAGTCGAGATAAAG*
(SEQ ID NO: 2)

1A9 VH-VL scFv coding sequence:
ATG<u>*CTGCTGCTCGTGACCAGCCTGCTGCTGTGCGAACTGCCCCACCCTGCCTTTCTGCTG*</u>
<u>*ATCCCC*</u>GAAGTGCAGTTGGTTGAGTCTGGAGGAGGCCTGGTACAGCCGGGTGGTAGTCTT
CGGCTTTCCTGTGCTGCTAGCGGGTTTACTTTCTCCATATACGATATGCACTGGGTGAGGC
AAGCGACCGGAAAAGGTCTGGAGTGGGTCTCAGCGATCGGTACAGCTGGCGATACTTACT
ATGCGGGCAGTGTCAAGGGACGATTCACCATAAGCCGCGAAAACGCTAAAAATTCCCTCTA
CTTGCAAATGAATAGCCTGCGAGCGGGGGACACCGCCGTATATTATTGTGCTAGAGAGTAT
AGCGGATATTACTTTGACTATTGGGGTCAAGGCACTCTGGTAACGGTGTCTAGC<u>GGAGGC</u>
<u>GGAGGATCTGGCGGAGGGGGCTCTGGAGGAGGAGGATCT</u>*GCGATTCAGATGACTCAATC*
*CCCCTCCTCTCTCTCCGCGTCCGTAGGGGATAGGGTGACAATAACTTGTAGGGCGAGCCA*
*GGACATCCGCAATGACCTCGGCTGGTATCAACAAAACCAGGCAAGGCACCTAAGATACT*
*GATTTATGGCGCGTCCTCCTTGCAATCCGGGGTGCCGTCTCGGTTCAGTGGTTCAGGTAG*
*TGGTACGGACTTTACCTTCACAATCTCTAGTCTGCAACCGGAGGATTTCGCTACTTACTATT*
*GTCTCCAGGAGTATAATTACCCCTGTACATTTGGGCAAGGCACCAAGTTGGAGATAAAA*
(SEQ ID NO: 3)

1E6 VH-VL scFv coding sequence:
ATG<u>*CTGCTGCTCGTGACCAGCCTGCTGCTGTGCGAACTGCCCCACCCTGCCTTTCTGCTG*</u>
<u>*ATCCCCC*</u>AAGTGCAGTTGGTTGAATCCGGTGGCGGTGTGGTTCAACCAGGCAGGAGCTTG
AGACTTTCATGTGCAGCGTCCGGCTTTACATTCTCCAGCTACGACATACATTGGGTCCGGC
AGGCGCCAGGAAAGGGCCTCGAATGGGTCGCGGTAATATGGTACGACGGCAGTCATAACT
ACTACAGTGATTCTGTAAAAGGCCGCTTTACGATTTCACGCGACAACAGCAAGAATACACT
CTATTTGCAAATGAACTCTCTGCGCGCGGAAGATACCGCCGTGTATTATTGTGCGCGGGAC
TACAGCGGGTCTTACTACGACTACTGGGGCCAAGGAACCCTTGTAACGGTCTCTAGC<u>GGA</u>
<u>GGCGGAGGATCTGGCGGAGGGGGCTCTGGAGGAGGAGGATCT</u>*GCAATACAAATGACGCA*
*GTCTCCTAGCTCACTTTCTGCAAGCGTCGGAGACCGAGTTACAATTACGTGTCGGGCGAG*
*CCAGGGAATTCGGAACGATCTCGGCTGGTATCAACAGAAACCCGGCAAAGCGCCAAAATT*
*GCTTATATACGCGGCATCAAACCTTCAGAGTGGTGTGCCGTCAAGATTCAGTGGGTCAGG*
*CAGCGGAACTGACTTTACCCTGACTATCTCTAGTCTCCAACCCGAGGACTTCGCAACGTAC*

FIG. 19 cont'd

*TATTGCCTGCAAGATTACTCCTACCCGCGAACGTTCGGCCAAGGGACAAAGGTTGAGATTA*
*AA* (SEQ ID NO: 4)

1D2 VH-VL scFv coding sequence:
ATG*CTGCTGCTCGTGACCAGCCTGCTGCTGTGCGAACTGCCCCACCCTGCCTTTCTGCTG*
*ATCCCCC*AGGTGCAGCTGGTGGAAAGCGGCGGCGGCGTGGTGCAGCCGGGCCGCAGCC
TGCGCCTGAGCTGCGCGGCGAGCGGCTTTACCTTTAGCAGCTATGATATTCATTGGGTGC
GCCAGGCGCCGGGCAAAGGCCTGGAATGGGTGGCGGTGATTTGGTATGATGGCAGCCAG
AAATATTATGCGGATAGCGTGAAAGGCCGCTTTACCATTAGCCGCGATAACAGCAAAAACA
CCCTGTATCTGCAGATGAACAGCCTGCGCGCGGAAGATACCGCGGTGTATTATTGCGCGC
GCGATTATAGCGGCAGCTATTATGATTATTGGGGCCAGGGCACCCTGGTGACCGTGAGCA
GC*GGAGGCGGAGGATCTGGCGGAGGGGGCTCTGGAGGAGGAGGATCT*GCGATTCAGAT
GACCCAGAGCCCGAGCAGCCTGAGCGCGAGCGTGGGCGATCGCGTGACCATTACCTGCC
GCGCGAGCCAGGGCATTCGCAACGATCTGGGCTGGTATCAGCAGAAACCGGGCAAAGCG
CCGGAACTGCTGATTTATGCGACCAGCAGCCTGCAGAGCGGCGTGCCGAGCCGCTTTAG
CGGCAGCGGCAGCGGCACCGATTTTACCCTGATTATTAGCAGCCTGCAGCCGGAAGATTT
TGCGACCTATTATTGCCTGCAGGATTATAGCTATCCGCGCACCTTTGGCCAGGGCACCAAA
GTGGAAATTAAA (SEQ ID NO: 5)

1B9 VH-VL scFv coding sequence:
ATG*CTGCTGCTCGTGACCAGCCTGCTGCTGTGCGAACTGCCCCACCCTGCCTTTCTGCTG*
*ATCCCCC*AGGTGCAGCTGGTGGAAAGCGGCGGCGGCGTGGTGCAGCCGGGCCGCAGCC
TGCGCCTGAGCTGCGCGGCGAGCGGCTTTATTTTTAGCAGCTATGATATTCATTGGGTGC
GCCAGGCGCCGGGCAAAGGCCTGGAATGGGTGGCGGTGATTTGGTATGATGGCAGCCAT
AACTATTATAGCGATAGCGTGAAAGGCCGCTTTACCATTAGCCGCGATAACAGCAAAAACA
CCCTGTATCTGCAGATGAACAGCCTGCGCGCGGAAGATACCGCGGTGTATTATTGCGCGC
GCGATTATAGCGGCAGCTATTTTGATTATTGGGGCCAGGGCACCCTGGTGACCGTGAGCA
GC*GGAGGCGGAGGATCTGGCGGAGGGGGCTCTGGAGGAGGAGGATCT*GCGATTCAGAT
GACCCAGAGCCCGAGCAGCCTGAGCGCGAGCGTGGGCGATCGCGTGACCATTACCTGCC
GCGCGAGCCAGGATATTCGCAACGATCTGGGCTGGTATCTGCAGCGCCCGGGCAAAGCG
CCGAAACTGCTGATTTATGCGGCGAGCAGCCTGCAGAGCGGCGTGCCGAGCCGCTTTAG
CGGCAGCGGCAGCGGCACCGATTTTACCCTGACCATTAGCAGCCTGCAGCCGGAAGATTT
TGCGACCTATTATTGCCTGCAGGATTATAGCTATCCGCGCACCTTTGGCCAGGGCACCACC
GTGGAAATTAAA (SEQ ID NO: 6)

1H8 VH-VL scFv coding sequence:
ATG*CTGCTGCTCGTGACCAGCCTGCTGCTGTGCGAACTGCCCCACCCTGCCTTTCTGCTG*
*ATCCCCC*AGGTTCAGTTGGTTGAATCAGGAGGTGGTGTTGTTCAGCCTGGTGGGAGTCTC
CGCCTTTCCTGTGCGGCATCTGGCTTCACCTTCGGTAGTTATGGGATGCATTGGGTACGC
CAAGCGCCTGGCAAAGGTCTGGAATGGGTGGCCGTAATATGGTACGATGGATCTAATGAG
TACTACGCAGACTCCGTGAAAGGGAGATTCACTGTATCAAGAGATAATTCTAAGCACACGT
TGTATCTTCAGATGAACAGACTCCGGGCAGAGGACACAGCAGTTTACTACTGTGCGCGGG
ACCTCGATTATGACTCTAGCGGGGGTGATTACTGGGGCCAAGGGATTTTGGTTCTCGTAAG
CTCT*GGAGGCGGAGGATCTGGCGGAGGGGGCTCTGGAGGAGGAGGATCT*GAAATAGTTT
*TGACCCAAAGCCCCGACTTTCAGTCCGTAACCCCTAAAGAAAAGGTCACTATTACCTGTAG*
*GGCTTCCCAAAACATAGGAGGCAACCTTCACTGGTATCAGCAGAAGCCGGACCAGTCCCC*
*TAAATTGTTGATTAGGTATGCGACACAGCCTTTTTCAGGCGTCCCCTCAAGATTCGGAGGC*

FIG. 19 cont'd

*TCTGGTTCTGGGACTGACTTCACCCTGACTATCAATAGTCTCGAGGCAGAAGACGCGGCC*
*ACTTATTACTGCCACCAAAGTAGCTCCCTCCCACTCACTTTCGGTGGTGGCACCAAAGTAG*
*AGATAAAG* (SEQ ID NO: 7)

2D3 VH-VL scFv coding sequence:
ATG<u>*CTGCTGCTCGTGACCAGCCTGCTGCTGTGCGAACTGCCCCACCCTGCCTTTCTGCTG*</u>
<u>*ATCCCC*</u>GAGGTGCAATTGCTGGAAAGTGGAGGAGGACTCGTGCAGCCCGGAGGTTCCCTT
AGCCTTTCTTGCGCTGCAAGTGGGTTTACGTTCTCTATATATGCCATGTCTTGGGTGCGGC
AAGCCCCCGGAAAAGGATTGGAATGGGTATCTGCCATTAGTGATTCTGGGGGTACGACCT
ATTATGCAGATAGTGTAAAAGGGAGATTCACTATCTCACGCGACAATTCAAAGAATATGCTT
TACCTTGAGATGAACAGTCTTCGAGCAGAGGATACAGCCATATACTATTGCGCTAAACGCA
CCCGCTACTTCAACGGAATGGATGTATGGGGACAGGGTACAACAGTTACTGTTTCTAGC<u>G</u>
<u>GAGGCGGAGGATCTGGCGGAGGGGGCTCTGGAGGAGGAGGATCT</u>*GAGATTGTAATGACG*
*CAGTCTCCAGCGACGCTTTCTCTTAGTCCGGGAGAAAGAGCCACACTGTCCTGCCGGGCG*
*TCCCAATCCGGTTCTAGCTCCTTTCTGTCATGGTATCAACAGAAGCCAGGTCAGGCACCTC*
*GCCTTCTTATTTACGGTGCATCCACTCGCGCGACCGGGATTCCTGCAAGATTTTCCGGGTC*
*TGGGTCTGGCACAGATTTCACGTTGACTATCAGTAGTCTGCAGCCAGAGGATTTCGCAGTC*
*TATTACTGTCAACAAGACTACAATCTTCCTTTCACGTTTGGTCCCGGAACTAAGGTTGATAT*
*AAAA* (SEQ ID NO: 8)

2E3 VH-VL scFv coding sequence:
ATG<u>*CTGCTGCTCGTGACCAGCCTGCTGCTGTGCGAACTGCCCCACCCTGCCTTTCTGCTG*</u>
<u>*ATCCCCC*</u>AAGTGTGTCTGGTCGAGAGTGGTGGAGGCGTGGTTCAACCAGGGAAGAGCCT
CCGGCTCTCCTGTGCAGCCAGTGGATTTACCTTTTCATCCTACGGTATGCACTGGGTCCGC
CAGGCACCCGGAAAAGGACTTGAATGGGTGGCTGTAATTTGGTATGGTGGCTCCAACAAA
TACTATGCAGATAGTGTAAAAGGTCGCTTTACTATCAGTCGGGACAATAGCAAAAATACCCT
CTACTTGCAGATGAATAGCTTGCGGGCCGAGGATACCGCTGTCTACTACTGTGCAAGAGAT
GGTACCGGCGAAAACTATTACTACTACGTAATGGATGTCTGGGGACAGGGCACGACCGTT
ACAGTCTCATCC<u>GGAGGCGGAGGATCTGGCGGAGGGGGCTCTGGAGGAGGAGGATCT</u>*GA*
*GATTGTATTGACTCAAAGTCCAGGTACCCTCTCCCTTAGCCCCGGAGAAAGAGCTACGCTC*
*AGCTGCCGCGCTTCACAGTCTGTATCATCCTCCTATCTCGCTTGGTATCAGCAGAAGCCTG*
*GTCAAGCTCCTCGCCTTTTGATCTATGGTACATCCAGCCGGGCCACAGGCATCCCGGATC*
*GGTTTTCCGGTAGCGGATCTGGTACGGATTTTACTCTTACAATTTCCCGACTCGAACCAGA*
*AGACTTTGCGGTATATTATTGTCAGCAATACGGTTCTTCACCGACCTTTGGGGGAGGCACA*
*AAAGTCGAGATCAAA* (SEQ ID NO: 9)

Signal peptide coding sequence:
CTGCTGCTCGTGACCAGCCTGCTGCTGTGCGAACTGCCCCACCCTGCCTTTCTGCTGATC
CCC (SEQ ID NO: 188)

G4Sx3 linker coding sequence:
GGAGGCGGAGGATCTGGCGGAGGGGGCTCTGGAGGAGGAGGATCT (SEQ ID NO: 189)

IgK signal peptide: METDTLLLWVLLLWVPGSTG (SEQ ID NO: 158)

**1H10 scFv VH-VL orientation (*IgK signal peptide is bold and italicized*; <u>VH is underlined</u>;**
*G₄Sx3 linker is italicized*; VL is normal font):

FIG. 19 cont'd

*METDTLLLWVLLLWVPGSTG*QVQLVQSGAEVKKPGASVKVSCKGSGYIFTSYDMHWVRQAP
GQGLEWMGIIDPSGGSTSYAQKFQGRVTMTRDTSMSTVYMELSSLRSEDTAVYYCTRDYSWS
YFDYWGQGTLVTVSS*GGGGSGGGGSGGGGS*AIQMTQSPSSLSASVGDRVTITCRASQGIRIY
LGWYQQKPGKAPKLLIYATSSLQSGVPSRFSGSGSGTDFTLTISSLQPEDFATYYCLQDYNYP
WTFGQGTKVEIK (SEQ ID NO: 190)

1H10 scFv VL-VH orientation (*IgK signal peptide is bold and italicized*; VL is normal font;
*G₄Sx3 linker is italicized*; <u>VH is underlined</u>):
*METDTLLLWVLLLWVPGSTG*AIQMTQSPSSLSASVGDRVTITCRASQGIRIYLGWYQQKPGKA
PKLLIYATSSLQSGVPSRFSGSGSGTDFTLTISSLQPEDFATYYCLQDYNYPWTFGQGTKVEIK
*GGGGSGGGGSGGGGS*<u>QVQLVQSGAEVKKPGASVKVSCKGSGYIFTSYDMHWVRQAPGQGL
EWMGIIDPSGGSTSYAQKFQGRVTMTRDTSMSTVYMELSSLRSEDTAVYYCTRDYSWSYFDY
WGQGTLVTVSS</u> (SEQ ID NO: 191)

1A9 scFv VH-VL orientation (*IgK signal peptide is bold and italicized*; <u>VH is underlined</u>;
*G₄Sx3 linker is italicized*; VL is normal font):
*METDTLLLWVLLLWVPGSTG*<u>EVQLVESGGGLVQPGGSLRLSCAASGFTFSIYDMHWVRQAT
GKGLEWVSAIGTAGDTYYAGSVKGRFTISRENAKNSLYLQMNSLRAGDTAVYYCAREYSGYYF
DYWGQGTLVTVSS</u>*GGGGSGGGGSGGGGS*AIQMTQSPSSLSASVGDRVTITCRASQDIRNDL
GWYQQKPGKAPKILIYGASSLQSGVPSRFSGSGSGTDFTFTISSLQPEDFATYYCLQEYNYPCT
FGQGTKLEIK (SEQ ID NO: 192)

1A9 scFv VL-VH orientation (*IgK signal peptide is bold and italicized*; VL is normal font;
*G₄Sx3 linker is italicized*; <u>VH is underlined</u>):
*METDTLLLWVLLLWVPGSTG*AIQMTQSPSSLSASVGDRVTITCRASQDIRNDLGWYQQKPGK
APKILIYGASSLQSGVPSRFSGSGSGTDFTFTISSLQPEDFATYYCLQEYNYPCTFGQGTKLEIK
*GGGGSGGGGSGGGGS*<u>EVQLVESGGGLVQPGGSLRLSCAASGFTFSIYDMHWVRQATGKGL
EWVSAIGTAGDTYYAGSVKGRFTISRENAKNSLYLQMNSLRAGDTAVYYCAREYSGYYFDYW
GQGTLVTVSS</u> (SEQ ID NO: 193)

1E6 scFv VH-VL orientation (*IgK signal peptide is bold and italicized*; <u>VH is underlined</u>;
*G₄Sx3 linker is italicized*; VL is normal font):
*METDTLLLWVLLLWVPGSTG*<u>QVQLVESGGGVVQPGRSLRLSCAASGFTFSSYDIHWVRQAP
GKGLEWVAVIWYDGSHNYYSDSVKGRFTISRDNSKNTLYLQMNSLRAEDTAVYYCARDYSGS
YYDYWGQGTLVTVSS</u>*GGGGSGGGGSGGGGS*AIQMTQSPSSLSASVGDRVTITCRASQGIRN
DLGWYQQKPGKAPKLLIYAASNLQSGVPSRFSGSGSGTDFTLTISSLQPEDFATYYCLQDYSY
PRTFGQGTKVEIK (SEQ ID NO: 194)

1E6 scFv VL-VH orientation (*IgK signal peptide is bold and italicized*; VL is normal font;
*G₄Sx3 linker is italicized*; <u>VH is underlined</u>):
*METDTLLLWVLLLWVPGSTG*AIQMTQSPSSLSASVGDRVTITCRASQGIRNDLGWYQQKPGK
APKLLIYAASNLQSGVPSRFSGSGSGTDFTLTISSLQPEDFATYYCLQDYSYPRTFGQGTKVEIK
*GGGGSGGGGSGGGGS*<u>QVQLVESGGGVVQPGRSLRLSCAASGFTFSSYDIHWVRQAPGKGL
EWVAVIWYDGSHNYYSDSVKGRFTISRDNSKNTLYLQMNSLRAEDTAVYYCARDYSGSYYDY
WGQGTLVTVSS</u> (SEQ ID NO: 195)

2D3 scFv VH-VL orientation (*IgK signal peptide is bold and italicized*; <u>VH is underlined</u>;
*G₄Sx3 linker is italicized*; VL is normal font):

FIG. 19 cont'd

*METDTLLLWVLLLWVPGST*EVQLLESGGGLVQPGGSLSLSCAASGFTFSIYAMSWVRQAPG
KGLEWVSAISDSGGTTYYADSVKGRFTISRDNSKNMLYLEMNSLRAEDTAIYYCAKRTRYFNG
MDVWGQGTTVTVSS*GGGGSGGGGSGGGGS*EIVMTQSPATLSLSPGERATLSCRASQSGSS
SFLSWYQQKPGQAPRLLIYGASTRATGIPARFSGSGSGTDFTLTISSLQPEDFAVYYCQQDYNL
PFTFGPGTKVDIK (SEQ ID NO: 196)

2D3 scFv VL-VH orientation (*IgK signal peptide is bold and italicized*; VL is normal font;
*G₄Sx3 linker is italicized*; <u>VH is underlined</u>):
*METDTLLLWVLLLWVPGST*GEIVMTQSPATLSLSPGERATLSCRASQSGSSSFLSWYQQKPG
QAPRLLIYGASTRATGIPARFSGSGSGTDFTLTISSLQPEDFAVYYCQQDYNLPFTFGPGTKVDI
K*GGGGSGGGGSGGGGS*<u>EVQLLESGGGLVQPGGSLSLSCAASGFTFSIYAMSWVRQAPGKG
LEWVSAISDSGGTTYYADSVKGRFTISRDNSKNMLYLEMNSLRAEDTAIYYCAKRTRYFNGMD
VWGQGTTVTVSS</u> (SEQ ID NO: 197)

**human CD33 full length DNA coding (used for cell based immunogen; CD33 signal
peptide coding sequence in bold):**
ATGCCGCTGCTGCTACTGCTGCCCCTGCTGTGGGCAGGGGCCCTGGCTATGGATCCAAA
TTTCTGGCTGCAAGTGCAGGAGTCAGTGACGGTACAGGAGGGTTTGTGCGTCCTCGTGCC
CTGCACTTTCTTCCATCCCATACCCTACTACGACAAGAACTCCCCAGTTCATGGTTACTGGT
TCCGGGAAGGAGCCATTATATCCAGGGACTCTCCAGTGGCCACAAACAAGCTAGATCAAG
AAGTACAGGAGGAGACTCAGGGCAGATTCCGCCTCCTTGGGGATCCCAGTAGGAACAACT
GCTCCCTGAGCATCGTAGACGCCAGGAGGAGGGATAATGGTTCATACTTCTTTCGGATGG
AGAGAGGAAGTACCAAATACAGTTACAAATCTCCCCAGCTCTCTGTGCATGTGACAGACTT
GACCCACAGGCCCAAAATCCTCATCCCTGGCACTCTAGAACCCGGCCACTCCAAAAACCT
GACCTGCTCTGTGTCCTGGGCCTGTGAGCAGGGAACACCCCCGATCTTCTCCTGGTTGTC
AGCTGCCCCCACCTCCCTGGGCCCCAGGACTACTCACTCCTCGGTGCTCATAATCACCCC
ACGGCCCCAGGACCACGGCACCAACCTGACCTGTCAGGTGAAGTTCGCTGGAGCTGGTG
TGACTACGGAGAGAACCATCCAGCTCAACGTCACCTATGTTCCACAGAACCCAACAACTGG
TATCTTTCCAGGAGATGGCTCAGGGAAACAAGAGACCAGAGCAGGAGTGGTTCATGGGGC
CATTGGAGGAGCTGGTGTTACAGCCCTGCTCGCTCTTTGTCTCTGCCTCATCTTCTTCATA
GTGAAGACCCACAGGAGGAAAGCAGCCAGGACAGCAGTGGGCAGGAATGACACCCACCC
TACCACAGGGTCAGCCTCCCCGAAACACCAGAAGAAGTCCAAGTTACATGGCCCCACTGA
AACCTCAAGCTGTTCAGGTGCCGCCCCTACTGTGGAGATGGATGAGGAGCTGCATTATGC
TTCCCTCAACTTTCATGGGATGAATCCTTCCAAGGACACCTCCACCGAATACTCAGAGGTC
AGGACCCAG (SEQ ID NO: 198)

human CD33 full length protein (used for cell based immunogen):
MPLLLLLPLLWAGALAMDPNFWLQVQESVTVQEGLCVLVPCTFFHPIPYYDKNSPVHGYWFRE
GAIISRDSPVATNKLDQEVQEETQGRFRLLGDPSRNNCSLSIVDARRRDNGSYFFRMERGSTK
YSYKSPQLSVHVTDLTHRPKILIPGTLEPGHSKNLTCSVSWACEQGTPPIFSWLSAAPTSLGPR
TTHSSVLIITPRPQDHGTNLTCQVKFAGAGVTTERTIQLNVTYVPQNPTTGIFPGDGSGKQETR
AGVVHGAIGGAGVTALLALCLCLIFFIVKTHRRKAARTAVGRNDTHPTTGSASPKHQKKSKLHG
PTETSSCSGAAPTVEMDEELHYASLNFHGMNPSKDTSTEYSEVRTQ* (SEQ ID NO: 199)

IgG4 hinge coding sequence-A
GAGTCTAAGTACGGACCGCCCTGCCCCCCCTTGCCCT (SEQ ID NO: 10)

IgG4 hinge coding sequence-B

FIG. 19 cont'd

GAGTCTAAGTACGGACCGCCTTGCCCACCGTGCCCA (SEQ ID NO: 11)

IgG4-int(DS) coding sequence
GGCCAGCCTAGAGAACCCCAGGTGTACACCCTGCCTCCCAGCCAGGAAGAGATGACCAA
GAACCAGGTGTCCCTGACCTGCCTGGTCAAAGGCTTCTACCCCAGCGATATCGCCGTGGA
ATGGGAGAGCAACGGCCAGCCCGAGAACAACTACAAGACCACCCCCCCTGTGCTGGACA
GCGACGGCAGCTTCTTCCTGTACTCCCGGCTGACCGTGGACAAGAGCCGGTGGCAGGAA
GGCAACGTCTTCAGCTGCAGCGTGATGCACGAGGCCCTGCACAACCACTACACCCAGAAG
TCCCTGAGCCTGAGCCTGGGCAAG (SEQ ID NO: 12)

IgG4-long coding sequence
GCACCACCTGTGGCAGGACCGTCAGTCTTCCTCTTCCCACCAAAACCCAAGGACACCCTG
ATGATCAGCCGGACCCCCGAGGTGACCTGCGTGGTGGTGGACGTGAGCCAGGAAGATCC
CGAGGTCCAGTTCAATTGGTACGTGGACGGCGTGGAAGTGCACAACGCCAAGACCAAGCC
CAGAGAGGAACAGTTCCAAAGCACCTACCGGGTGGTGTCTGTGCTGACCGTGCTGCACCA
GGACTGGCTGAACGGCAAAGAATACAAGTGCAAGGTGTCCAACAAGGGCCTGCCCAGCA
GCATCGAAAAGACCATCAGCAAGGCCAAGGGCCAGCCTCGCGAGCCCCAGGTGTACACC
CTGCCTCCCTCCCAGGAAGAGATGACCAAGAACCAGGTGTCCCTGACCTGCCTGGTGAAG
GGCTTCTACCCCAGCGACATCGCCGTGGAGTGGGAGAGCAACGGCCAGCCTGAGAACAA
CTACAAGACCACCCCTCCCGTGCTGGACAGCGACGGCAGCTTCTTCCTGTACAGCCGGCT
GACCGTGGACAAGAGCCGGTGGCAGGAAGGCAACGTCTTTAGCTGCAGCGTGATGCACG
AGGCCCTGCACAACCACTACACCCAGAAGAGCCTGAGCCTGTCCCTGGGCAAG (SEQ ID
NO: 13)

CD3ζ coding sequence
CGGGTGAAGTTCAGCAGAAGCGCCGACGCCCCTGCCTACCAGCAGGGCCAGAATCAGCT
GTACAACGAGCTGAACCTGGGCAGAAGGGAAGAGTACGACGTCCTGGATAAGCGGAGAG
GCCGGGACCCTGAGATGGGCGGCAAGCCTCGGCGGAAGAACCCCCAGGAAGGCCTGTAT
AACGAACTGCAGAAAGACAAGATGGCCGAGGCCTACAGCGAGATCGGCATGAAGGGCGA
GCGGAGGCGGGGCAAGGGCCACGACGGCCTGTATCAGGGCCTGTCCACCGCCACCAAG
GATACCTACGACGCCCTGCACATGCAGGCCCTGCCCCCAAGG (SEQ ID NO: 14)

CD3ζ protein-A
RVKFSRSADAPAYQQGQNQLYNELNLGRREEYDVLDKRRGRDPEMGGKPRRKNPQEGLYNE
LQKDKMAEAYSEIGMKGERRRGKGHDGLYQGLSTATKDTYDALHMQALPPR (SEQ ID NO:
15)

CD3ζ protein-B
ELRVKFSRSADAPAYQQGQNQLYNELNLGRREEYDVLDKRRGRDPEMGGKPRRKNPQEGLY
NELQKDKMAEAYSEIGMKGERRRGKGHDGLYQGLSTATKDTYDALHMQALPPR (SEQ ID NO:
16)

4-1BB signaling coding sequence-A
AAACGGGGCAGAAAGAAACTCCTGTATATATTCAAACAACCATTTATGAGACCAGTACAAAC
TACTCAAGAGGAAGATGGCTGTAGCTGCCGATTTCCAGAAGAAGAAGAAGGAGGATGTGA
ACTG (SEQ ID NO: 17)

4-1BB signaling coding sequence-B

FIG. 19 cont'd

GTGAAACGGGGCAGAAAGAAACTCCTGTATATATTCAAACAACCATTTATGAGACCAGTAC
AAACTACTCAAGAGGAAGATGGCTGTAGCTGCCGATTTCCAGAAGAAGAAGAAGGAGGAT
GTGAACTG (SEQ ID NO: 18)

4-1BB protein-A
VKRGRKKLLYIFKQPFMRPVQTTQEEDGCSCRFPEEEEGGCEL (SEQ ID NO: 19)

4-1BB protein-B
VKRGRKKLLYIFKQPFMRPVQTTQEEDGCSCRFPEEEEGGC (SEQ ID NO: 20)

CD28TM coding sequence-A
ATGTTCTGGGTGCTGGTGGTGGTCGGAGGCGTGCTGGCCTGCTACAGCCTGCTGGTCAC
CGTGGCCTTCATCATCTTTTGGGTG (SEQ ID NO: 21)

CD28TM coding sequence-B
ATGTTCTGGGTGCTGGTGGTGGTCGGAGGCGTGCTGGCCTGCTACAGCCTGCTGGTCAC
CGTGGCCTTCATCATCTTTTGG (SEQ ID NO: 22)

CD28TM coding sequence-C
ATGTTCTGGGTGCTGGTGGTGGTGGGCGGGGTGCTGGCCTGCTACAGCCTGCTGGTGAC
AGTGGCCTTCATCATCTTTTGG (SEQ ID NO: 23)

CD28TM protein-A
MFWVLVVVGGVLACYSLLVTVAFIIFW (SEQ ID NO: 24)

CD28TM protein-B
FWVLVVVGGVLACYSLLVTVAFIIFW (SEQ ID NO: 25)

tCD19 coding sequence
ATGCCACCTCCAAGACTCCTCTTCTTCCTCCTCTTCCTGACACCAATGGAAGTCAGGCCTG
AGGAACCTCTAGTGGTGAAGGTGGAAGAGGGAGATAACGCTGTGTTACAGTGCCTCAAGG
GAACCTCAGATGGACCCACTCAGCAGCTGACCTGGTCTCGGGAGTCTCCGCTTAAACCCT
TCCTGAAACTCAGCCTTGGACTGCCAGGTCTGGGAATCCACATGAGGCCACTGGCTATCT
GGCTGTTCATCTTCAACGTCTCTCAACAGATGGGAGGCTTCTACCTGTGTCAGCCTGGACC
ACCTTCTGAGAAGGCATGGCAGCCTGGTTGGACAGTCAATGTGGAGGGTTCTGGTGAGCT
GTTCCGGTGGAATGTTTCGGACCTAGGTGGACTGGGATGTGGTCTGAAGAACAGGTCCTC
AGAGGGACCTAGCTCTCCTTCCGGGAAGCTCATGAGCCCCAAGCTGTATGTGTGGGCCAA
AGACCGCCCTGAGATCTGGGAGGGAGAGCCTCCGTGTGTCCCACCGAGGGACAGCCTGA
ACCAGAGCCTCAGCCAGGACCTCACCATGGCCCCTGGCTCCACACTCTGGCTGTCCTGTG
GGGTACCCCCTGACTCTGTGTCCAGGGGCCCCCTCTCCTGGACCCATGTGCACCCCAAG
GGGCCTAAGTCATTGCTGAGCCTAGAGCTGAAGGACGATCGCCCTGCCAGAGATATGTGG
GTAATGGAGACGGGTCTGTTGTTGCCCCGGGCCACAGCTCAAGACGCTGGAAAGTATTAT
TGTCACCGTGGCAACCTGACCATGTCATTCCACCTGGAGATCACTGCTCGGCCAGTACTAT
GGCACTGGCTGCTGAGGACTGGTGGCTGGAAGGTCTCAGCTGTGACTTTGGCTTATCTGA
TCTTCTGCCTGTGTTCCCTTGTGGGCATTCTTCATCTTCAAAGAGCCCTGGTCCTGAGGAG
GAAAAGATGA (SEQ ID NO: 26)

T2A coding sequence

FIG. 19 cont'd

CTCGAGGGCGGCGGAGAGGGCAGAGGAAGTCTTCTAACATGCGGTGACGTGGAGGAGAA
TCCAGGCCCTAGG (SEQ ID NO: 27)

Thoseaasigna Virus 2A (T2A) Peptide
GSGEGRGSLLTCGDVEENPGP (SEQ ID NO: 28)

Porcine Teschovirus-1 2a (P2A) Peptide
GSGATNFSLLKQAGDVEENPGP (SEQ ID NO: 29)

Equine Rhinitis A Virus (ERAV) 2A (E2A) Peptide
GSGQCTNYALLKLAGDVESNPGP (SEQ ID NO: 30)

Foot-And-Mouth Disease Virus 2A (F2A) Peptide
GSGVKQTLNFDLLKLAGDVESNPGP (SEQ ID NO: 31)

EF1 promoter-A
GGATCTGCGATCGCTCCGGTGCCCGTCAGTGGGCAGAGCGCACATCGCCCACAGTCCCC
GAGAAGTTGGGGGGGAGGGGTCGGCAATTGAACCGGTGCCTAGAGAAGGTGGCGCGGGG
TAAACTGGGAAAGTGATGTCGTGTACTGGCTCCGCCTTTTTCCCGAGGGTGGGGGAGAAC
CGTATATAAGTGCAGTAGTCGCCGTGAACGTTCTTTTTCGCAACGGGTTTGCCGCCAGAAC
ACAGCTGAAGCTTCGAGGGGCTCGCATCTCTCCTTCACGCGCCCGCCGCCCTACCTGAGG
CCGCCATCCACGCCGGTTGAGTCGCGTTCTGCCGCCTCCCGCCTGTGGTGCCTCCTGAAC
TGCGTCCGCCGTCTAGGTAAGTTTAAAGCTCAGGTCGAGACCGGGCCTTTGTCCGGCGCT
CCCTTGGAGCCTACCTAGACTCAGCCGGCTCTCCACGCTTTGCCTGACCCTGCTTGCTCA
ACTCTACGTCTTTGTTTCGTTTTCTGTTCTGCGCCGTTACAGATCCAAGCTGTGACCGGCG
CCTAC (SEQ ID NO: 32)

EF1 promoter-B
GGATCTGCGATCGCTCCGGTGCCCGTCAGTGGGCAGAGCGCACATCGCCCACAGTCCCC
GAGAAGTTGGGGGGGAGGGGTCGGCAATTGAACCGGTGCCTAGAGAAGGTGGCGCGGGG
TAAACTGGGAAAGTGATGTCGTGTACTGGCTCCGCCTTTTTCCCGAGGGTGGGGGAGAAC
CGTATATAAGTGCAGTAGTCGCCGTGAACGTTCTTTTTCGCAACGGGTTTGCCGCCAGAAC
ACAGCTGAAGCTTCGAGGGGCTCGCATCTCTCCTTCACGCGCCCGCCGCCCTACCTGAGG
CCGCCATCCACGCCGGTTGAGTCGCGTTCTGCCGCCTCCCGCCTGTGGTGCCTCCTGAAC
TGCGTCCGCCGTCTAGGTAAGTTTAAAGCTCAGGTCGAGACCGGGCCTTTGTCCGGCGCT
CCCTTGGAGCCTACCTAGACTCAGCCGGCTCTCCACGCTTTGCCTGACCCTGCTTGCTCA
ACTCTACGTCTTTGTTTCGTTTTCTGTTCTGCGCCGTTACAGATCCAAGCTGTGACCGGCG
CCTACG (SEQ ID NO: 33)

Psi
CTCGGCTTGCTGAAGCGCGCACGGCAAGAGGCGAGGGGCGGCGACTGGTGAGTACGCC
AAAAATTTTGACTAGCGGAGGCTAGAAGGAGAGAGATGGGTGCGAGAGCGTCAGT (SEQ
ID NO: 34)

RRE
GCAAAGAGAAGAGTGGTGCAGAGAGAAAAAAGAGCAGTGGGAATAGGAGCTTTGTTCCTT
GGGTTCTTGGGAGCAGCAGGAAGCACTATGGGCGCAGCGTCAATGACGCTGACGGTACA
GGCCAGACAATTATTGTCTGGTATAGTGCAGCAGCAGAACAATTTGCTGAGGGCTATTGAG

FIG. 19 cont'd

GCGCAACAGCATCTGTTGCAACTCACAGTCTGGGGCATCAAGCAGCTCCAGGCAAGAATC
CTGGCTGTGGAAAGATACCTAAAGGATCAACAGCTCCTGGGGATTTGGGGGTTGCTCTGGA
AAACTCATTTGCACCACTGCTGTGCCTTGGATC (SEQ ID NO: 35)
Flap
TACAAATGGCAGTATTCATCCACAATTTTAAAAGAAAAGGGGGGGATTGGGGGGGTACAGTGC
AGGGGAAAGAATAGTAGACATAATAGCAACAGACATACAAACTAAAGAATTACAAAAACAAA
TTACAAAAATTCAAAATTTTCGGGTTTATTACAGGGACAGCAGAGATCCAGTTTGG (SEQ ID
NO: 36)

GM-CSFR encoding sequence
ATGCTGCTGCTCGTGACCAGCCTGCTGCTGTGCGAACTGCCCCACCCTGCCTTTCTGCTG
ATCCCC (SEQ ID NO: 37)

WPRE
ATCGATAATCAACCTCTGGATTACAAAATTTGTGAAAGATTGACTGGTATTCTTAACTATGTT
GCTCCTTTTACGCTATGTGGATACGCTGCTTTAATGCCTTTGTATCATGCTATTGCTTCCCG
TATGGCTTTCATTTTCTCCTCCTTGTATAAATCCTGGTTGCTGTCTCTTTATGAGGAGTTGTG
GCCCGTTGTCAGGCAACGTGGCGTGGTGTGCACTGTGTTTGCTGACGCAACCCCCACTGG
TTGGGGCATTGCCACCACCTGTCAGCTCCTTTCCGGGACTTTCGCTTTCCCCCTCCCTATT
GCCACGGCGGAACTCATCGCCGCCTGCCTTGCCCGCTGCTGGACAGGGGCTCGGCTGTT
GGGCACTGACAATTCCGTGGTGTTGTCGGGGAAATCATCGTCCTTTCCTTGGCTGCTCGC
CTGTGTTGCCACCTGGATTCTGCGCGGGACGTCCTTCTGCTACGTCCCTTCGGCCCTCAA
TCCAGCGGACCTTCCTTCCCGCGGCCTGCTGCCGGCTCTGCGGCCTCTTCCGCGTCTTCG
CCTTCGCCCTCAGACGAGTCGGATCTCCCTTTGGGCCGCCTCCCCGCATCGAT (SEQ ID
NO: 38)

delU3
GTACCTTTAAGACCAATGACTTACAAGGCAGCTGTAGATCTTAGCCACTTTTTAAAAGAAAA
GGGGGGACTGGAAGGGCTAATTCACTCCCAAAGAAGACAAGAT (SEQ ID NO: 39)

R
CTGCTTTTTGCCTGTACTGGGTCTCTCTGGTTAGACCAGATCTGAGCCTGGGAGCTCTCTG
GCTAACTAGGGAACCCACTG (SEQ ID NO: 40)

U5
CTTAAGCCTCAATAAAGCTTGCCTTGAGTGCTTCAAGTAGTGTGTGCCCGTCTGTTGTGTG
ACTCTGGTAACTAGAGATCCCTCAGACCCTTTTAGTCAGTGTGGAAAATCTCT (SEQ ID NO:
41)

AmpR
ATGAGTATTCAACATTTCCGTGTCGCCCTTATTCCCTTTTTTGCGGCATTTTGCCTTCCTGTT
TTTGCTCACCCAGAAACGCTGGTGAAAGTAAAAGATGCTGAAGATCAGTTGGGTGCACGA
GTGGGTTACATCGAACTGGATCTCAACAGCGGTAAGATCCTTGAGAGTTTTCGCCCCGAAG
AACGTTTTCCAATGATGAGCACTTTTAAAGTTCTGCTATGTGGCGCGGTATTATCCCGTATT
GACGCCGGGCAAGAGCAACTCGGTCGCCGCATACACTATTCTCAGAATGACTTGGTTGAG
TACTCACCAGTCACAGAAAAGCATCTTACGGATGGCATGACAGTAAGAGAATTATGCAGTG
CTGCCATAACCATGAGTGATAACACTGCGGCCAACTTACTTCTGACAACGATCGGAGGACC
GAAGGAGCTAACCGCTTTTTTGCACAACATGGGGGATCATGTAACTCGCCTTGATCGTTGG

FIG. 19 cont'd

GAACCGGAGCTGAATGAAGCCATACCAAACGACGAGCGTGACACCACGATGCCTGTAGCA
ATGGCAACAACGTTGCGCAAACTATTAACTGGCGAACTACTTACTCTAGCTTCCCGGCAAC
AATTAATAGACTGGATGGAGGCGGATAAAGTTGCAGGACCACTTCTGCGCTCGGCCCTTC
CGGCTGGCTGGTTTATTGCTGATAAATCTGGAGCCGGTGAGCGTGGGTCTCGCGGTATCA
TTGCAGCACTGGGGCCAGATGGTAAGCCCTCCCGTATCGTAGTTATCTACACGACGGGGA
GTCAGGCAACTATGGATGAACGAAATAGACAGATCGCTGAGATAGGTGCCTCACTGATTAA
GCATTGGT (SEQ ID NO: 42)

CoE1 origin
AAAAGGATCTAGGTGAAGATCCTTTTTGATAATCTCATGACCAAAATCCCTTAACGTGAGTT
TTCGTTCCACTGAGCGTCAGACCCCGTAGAAAAGATCAAAGGATCTTCTTGAGATCCTTTTT
TTCTGCGCGTAATCTGCTGCTTGCAAACAAAAAAACCACCGCTACCAGCGGTGGTTTGTTT
GCCGGATCAAGAGCTACCAACTCTTTTTCCGAAGGTAACTGGCTTCAGCAGAGCGCAGATA
CCAAATACTGTTCTTCTAGTGTAGCCGTAGTTAGGCCACCACTTCAAGAACTCTGTAGCAC
CGCCTACATACCTCGCTCTGCTAATCCTGTTACCAGTGGCTGCTGCCAGTGGCGATAAGTC
GTGTCTTACCGGGTTGGACTCAAGACGATAGTTACCGGATAAGGCGCAGCGGTCGGGCTG
AACGGGGGGTTCGTGCACACAGCCCAGCTTGGAGCGAACGACCTACACCGAACTGAGATA
CCTACAGCGTGAGCTATGAGAAAGCGCCACGCTTCCCGAAGGGAGAAAGGCGGACAGGT
ATCCGGTAAGCGGCAGGGTCGGAACAGGAGAGCGCACGAGGGAGCTTCCAGGGGGAAA
CGCCTGGTATCTTTATAGTCCTGTCGGGTTTCGCCACCTCTGACTTGAGCGTCGATTTTTG
TGATGCTCGTCAGGGGGGCGGAGCCTATGGAAAAACGCCAGCAACGCGGCCTTTTTACG
GTTCCTGGCCTTTTGCTGGCCTTTTGCTCACATGTTCTTTCCTGCGTTATCCCCTGATTCTG
TGGATAACCGTATTACCGCCTTTGAGTGAGCTGATACCGCTCGCCGCAGCCGAACGACCG
AGCGCAGCGAGTCAGTGAGCGAGGAAGCGGAAGAG (SEQ ID NO: 43)

SV40
GGTCGAGATCCGGTCGACCAGCAACCATAGTCCCGCCCCTAACTCCGCCCATCCCGCCCC
TAACTCCGCCCAGTTCCGCCCATTCTCCGCCCCATGGCTGACTAATTTTTTTTATTTATGCA
GAGGCCGAGGCCGCCTCGGCCTCTGAGCTATTCCAGAAGTAGTGAGGAGGCTTTTTTGGA
GGCCTAGGCTTTTGCAAA (SEQ ID NO: 44)

CMV
ATCGATTGGCTCATGTCCAACATTACCGCCATGTTGACATTGATTATTGACTAGTTATTAATA
GTAATCAATTACGGGGTCATTAGTTCATAGCCCATATATGGAGTTCCGCGTTACATAACTTA
CGGTAAATGGCCCGCCTGGCTGACCGCCCAACGACCCCCGCCCATTGACGTCAATAATGA
CGTATGTTCCCATAGTAACGCCAATAGGGACTTTCCATTGACGTCAATGGGTGGAGTATTT
ACGGTAAACTGCCCACTTGGCAGTACATCAAGTGTATCATATGCCAAGTACGCCCCCTATT
GACGTCAATGACGGTAAATGGCCCGCCTGGCATTATGCCCAGTACATGACCTTATGGGAC
TTTCCTACTTGGCAGTACATCTACGTATTAGTCATCGCTATTACCATGGTGATGCGGTTTTG
GCAGTACATCAATGGGCGTGGATAGCGGTTTGACTCACGGGGATTTCCAAGTCTCCACCC
CATTGACGTCAATGGGAGTTTGTTTTGGCACCAAAATCAACGGGACTTTCCAAAATGTCGT
AACAACTCCGCCCCATTGACGCAAATGGGCGGTAGGCGTGTACGGAATTC (SEQ ID NO:
45)

Glycosylation site
CAA

1H10-intDS-41bb-3z-T-CD19t Top Strand

FIG. 19 cont'd

GGATCTGCGATCGCTCCGGTGCCCGTCAGTGGGCAGAGCGCACATCGCCCACAGTCCC
CGAGAAGTTGGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTCTGTTCTGCGCCGTTACAGATCCAAGCTGT
GACCGGCGCCTAC<u>GGCTAGCCACCATGCTGCTGCTCGTGACCAGCCTGCTGCTGTGCGA
ACTGCCCCACCCTGCCTTTCTGCTGATCCCCC</u>*AAGTACAGCTTGTTCAAAGTGGTGCTGAA*
*GTTAAAAAGCCAGGGGCCAGCGTTAAGGTATCCTGCAAGGGAAGTGGTTACATCTTCACAT*
*CTTACGACATGCACTGGGTACGACAGGCTCCTGGACAGGGTCTGGAATGGATGGGTATCA*
*TAGACCCCTCAGGAGGATCTACGAGCTATGCCCAAAAATTTCAGGGAAGAGTAACAATGAC*
*CAGGGACACGTCCATGAGCACAGTCTACATGGAACTCAGCAGTCTCAGATCAGAGGATAC*
*GGCGGTTTACTACTGTACTAGGGATTATTCATGGAGCTATTTCGACTATTGGGGACAAGGA*
*ACCTTGGTAACAGTGTCTTCAGGAGGCGGAGGATCTGGCGGAGGGGGCTCTGGAGGAGG*
*AGGATCTGCGATACAAATGACGCAAAGTCCCAGCAGTTTGTCCGCCTCAGTAGGCGACCG*
*CGTTACGATTACGTGTAGGGCGTCTCAAGGGATCAGGATCTATCTGGGCTGGTATCAACAA*
*AAGCCTGGGAAAGCCCCAAAGCTCCTTATATATGCAACATCATCCCTGCAAAGCGGCGTTC*
*CATCCCGATTCAGTGGTTCTGGTAGCGGTACGGACTTCACTCTCACAATCTCATCTCTTCA*
*ACCAGAAGACTTTGCGACGTATTACTGTTTGCAAGACTACAATTATCCATGGACGTTCGGC*
*CAAGGCACGAAAGTCGAGATAAAG*GAGTCTAAGTACGGACCGCCCTGCCCCCCTTGCCC
<u>TGGCCAGCCTAGAGAACCCCAGGTGTACACCCTGCCTCCCAGCCAGGAAGAGATGACCAA
GAACCAGGTGTCCCTGACCTGCCTGGTCAAAGGCTTCTACCCCAGCGATATCGCCGTGGA
ATGGGAGAGCAACGGCCAGCCCGAGAACAACTACAAGACCACCCCCCCTGTGCTGGACA
GCGACGGCAGCTTCTTCCTGTACTCCCGGCTGACCGTGGACAAGAGCCGGTGGCAGGAA
GGCAACGTCTTCAGCTGCAGCGTGATGCACGAGGCCCTGCACAACCACTACACCCAGAAG
TCCCTGAGCCTGAGCCTGGGCAAGA</u>*TGTTCTGGGTGCTGGTGGTGGTCGGAGGCGTGCT*
*GGCCTGCTACAGCCTGCTGGTCACCGTGGCCTTCATCATCTTTTGGGT*GAAACGGGGCAG
AAAGAAACTCCTGTATATATTCAAACAACCATTTATGAGACCAGTACAAACTACTCAAGA
GGAAGATGGCTGTAGCTGCCGATTTCCAGAAGAAGAAGAAGGAGGATGTGAACTG<u>CGG
GTGAAGTTCAGCAGAAGCGCCGACGCCCCTGCCTACCAGCAGGGCCAGAATCAGCTGTA
CAACGAGCTGAACCTGGGCAGAAGGGAAGAGTACGACGTCCTGGATAAGCGGAGAGGCC
GGGACCCTGAGATGGGCGGCAAGCCTCGGCGGAAGAACCCCCAGGAAGGCCTGTATAAC
GAACTGCAGAAAGACAAGATGGCCGAGGCCTACAGCGAGATCGGCATGAAGGGCGAGCG
GAGGCGGGGCAAGGGCCACGACGGCCTGTATCAGGGCCTGTCCACCGCCACCAAGGATA
CCTACGACGCCCTGCACATGCAGGCCCTGCCCCCAAGGC</u>*TCGAGGGCGGCGGAGAGGG*
*CAGAGGAAGTCTTCTAACATGCGGTGACGTGGAGGAGAATCCAGGCCCTAGG*ATGCCACC
TCCAAGACTCCTCTTCTTCCTCCTCTTCCTGACACCAATGGAAGTCAGGCCTGAGGAACC
TCTAGTGGTGAAGGTGGAAGAGGGAGATAACGCTGTGTTACAGTGCCTCAAGGGAACCT
CAGATGGACCCACTCAGCAGCTGACCTGGTCTCGGGAGTCTCCGCTTAAACCCTTCCTG
AAACTCAGCCTTGGACTGCCAGGTCTGGGAATCCACATGAGGCCACTGGCTATCTGGCT
GTTCATCTTCAACGTCTCTCAACAGATGGGAGGCTTCTACCTGTGTCAGCCTGGACCACC
TTCTGAGAAGGCATGGCAGCCTGGTTGGACAGTCAATGTGGAGGGTTCTGGTGAGCTGT
TCCGGTGGAATGTTTCGGACCTAGGTGGACTGGGATGTGGTCTGAAGAACAGGTCCTCA
GAGGGACCTAGCTCTCCTTCCGGGAAGCTCATGAGCCCCAAGCTGTATGTGTGGGCCAA
AGACCGCCCTGAGATCTGGGAGGGAGAGCCTCCGTGTGTCCCACCGAGGGACAGCCTG

FIG. 19 cont'd

AACCAGAGCCTCAGCCAGGACCTCACCATGGCCCCTGGCTCCACACTCTGGCTGTCCTG
TGGGGTACCCCCTGACTCTGTGTCCAGGGGCCCCCTCTCCTGGACCCATGTGCACCCCA
AGGGGCCTAAGTCATTGCTGAGCCTAGAGCTGAAGGACGATCGCCCTGCCAGAGATATG
TGGGTAATGGAGACGGGTCTGTTGTTGCCCCGGGCCACAGCTCAAGACGCTGGAAAGTA
TTATTGTCACCGTGGCAACCTGACCATGTCATTCCACCTGGAGATCACTGCTCGGCCAGT
ACTATGGCACTGGCTGCTGAGGACTGGTGGCTGGAAGGTCTCAGCTGTGACTTTGGCTT
ATCTGATCTTCTGCCTGTGTTCCCTTGTGGGCATTCTTCATCTTCAAAGAGCCCTGGTCCT
GAGGAGGAAAAGATGA (SEQ ID NO: 46)

Within the above sequence, EF1 promoter is the first bolded sequence; the sequence encoding
GM-CSFR signal peptide is the first underlined sequence; the sequence encoding 1H10_HvLv
is the first italicized sequence; the sequence encoding IgG4hinge S10P is the second bold
sequence; the sequence encoding IgG4-int(DS) is the second underlined sequence; the
sequence encoding CD28tm is the second italicized sequence; the sequence encoding 4-1BB
signaling is the third bold sequence; the sequence encoding CD3z is the third underlined
sequence; the sequence encoding T2A is the third italicized sequence; and tCD19-Fully
sequenced is the fourth bold sequence section in the above sequence.

1H10-sh-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCAC<u>ATGCTGCTGCTCGTGACCAGCCTGCTGCTGTGCGA</u>
<u>ACTGCCCCACCCTGCCTTTCTGCTGATCCCC</u>CAAGTACAGCTTGTTCAAAGTGGTGCTGAA
*GTTAAAAAGCCAGGGGCCAGCGTTAAGGTATCCTGCAAGGGAAGTGGTTACATCTTCACAT*
*CTTACGACATGCACTGGGTACGACAGGCTCCTGGACAGGGTCTGGAATGGATGGGTATCA*
*TAGACCCCTCAGGAGGATCTACGAGCTATGCCCAAAAATTTCAGGGAAGAGTAACAATGAC*
*CAGGGACACGTCCATGAGCACAGTCTACATGGAACTCAGCAGTCTCAGATCAGAGGATAC*
*GGCGGTTTACTACTGTACTAGGGATTATTCATGGAGCTATTTCGACTATTGGGGACAAGGA*
*ACCTTGGTAACAGTGTCTTCAGGAGGCGGAGGATCTGGCGGAGGGGGCTCTGGAGGAGG*
*AGGATCTGCGATACAAATGACGCAAAGTCCCAGCAGTTTGTCCGCCTCAGTAGGCGACCG*
*CGTTACGATTACGTGTAGGGCGTCTCAAGGGATCAGGATCTATCTGGGCTGGTATCAACAA*
*AAGCCTGGGAAAGCCCCAAAGCTCCTTATATATGCAACATCATCCCTGCAAAGCGGCGTTC*
*CATCCCGATTCAGTGGTTCTGGTAGCGGTACGGACTTCACTCTCACAATCTCATCTCTTCA*
*ACCAGAAGACTTTGCGACGTATTACTGTTTGCAAGACTACAATTATCCATGGACGTTCGGC*
*CAAGGCACGAAAGTCGAGATAAAG*GAGTCTAAGTACGGACCGCCCTGCCCCCCTTGCCC
<u>TATGTTCTGGGTGCTGGTGGTGGTCGGAGGCGTGCTGGCCTGCTACAGCCTGCTGGTCAC</u>
<u>CGTGGCCTTCATCATCTTTTGGGTG</u>AAACGGGGCAGAAAGAAACTCCTGTATATATTCAAA
CAACCATTTATGAGACCAGTACAAACTACTCAAGAGGAAGATGGCTGTAGCTGCCGATTTC
CAGAAGAAGAAGAAGGAGGATGTGAACTGCGGGTGAAGTTCAGCAGAAGCGCCGACGCC
CCTGCCTACCAGCAGGGCCAGAATCAGCTGTACAACGAGCTGAACCTGGGCAGAAGGG
AAGAGTACGACGTCCTGGATAAGCGGAGAGGCCGGGACCCTGAGATGGGCGGCAAGCC
TCGGCGGAAGAACCCCCAGGAAGGCCTGTATAACGAACTGCAGAAAGACAAGATGGCC

FIG. 19 cont'd

GAGGCCTACAGCGAGATCGGCATGAAGGGCGAGCGGAGGCGGGGCAAGGGCCACGAC
GGCCTGTATCAGGGCCTGTCCACCGCCACCAAGGATACCTACGACGCCCTGCACATGCA
GGCCCTGCCCCCAAGG<u>CTCGAGGGCGGCGGAGAGGGCAGAGGAAGTCTTCTAACATGC</u>
<u>GGTGACGTGGAGGAGAATCCAGGCCCTAGG</u>*ATGCCACCTCCAAGACTCCTCTTCTTCCTC*
*CTCTTCCTGACACCAATGGAAGTCAGGCCTGAGGAACCTCTAGTGGTGAAGGTGGAAGAG*
*GGAGATAACGCTGTGTTACAGTGCCTCAAGGGAACCTCAGATGGACCCACTCAGCAGCTG*
*ACCTGGTCTCGGGAGTCTCCGCTTAAACCCTTCCTGAAACTCAGCCTTGGACTGCCAGGT*
*CTGGGAATCCACATGAGGCCACTGGCTATCTGGCTGTTCATCTTCAACGTCTCTCAACAGA*
*TGGGAGGCTTCTACCTGTGTCAGCCTGGACCACCTTCTGAGAAGGCATGGCAGCCTGGTT*
*GGACAGTCAATGTGGAGGGTTCTGGTGAGCTGTTCCGGTGGAATGTTTCGGACCTAGGTG*
*GACTGGGATGTGGTCTGAAGAACAGGTCCTCAGAGGGACCTAGCTCTCCTTCCGGGAAGC*
*TCATGAGCCCCAAGCTGTATGTGTGGGCCAAAGACCGCCCTGAGATCTGGGAGGGAGAG*
*CCTCCGTGTGTCCCACCGAGGGACAGCCTGAACCAGAGCCTCAGCCAGGACCTCACCAT*
*GGCCCCTGGCTCCACACTCTGGCTGTCCTGTGGGGTACCCCCTGACTCTGTGTCCAGGG*
*GCCCCCTCTCCTGGACCCATGTGCACCCCAAGGGGCCTAAGTCATTGCTGAGCCTAGAGC*
*TGAAGGACGATCGCCCTGCCAGAGATATGTGGGTAATGGAGACGGGTCTGTTGTTGCCCC*
*GGGCCACAGCTCAAGACGCTGGAAAGTATTATTGTCACCGTGGCAACCTGACCATGTCATT*
*CCACCTGGAGATCACTGCTCGGCCAGTACTATGGCACTGGCTGCTGAGGACTGGTGGCTG*
*GAAGGTCTCAGCTGTGACTTTGGCTTATCTGATCTTCTGCCTGTGTTCCCTTGTGGGCATT*
*CTTCATCTTCAAAGAGCCCTGGTCCTGAGGAGGAAAAGATGA* (SEQ ID NO: 47)
Within the above sequence,
EF1 promoter is the first bold sequence; the sequence encoding GM-CSFR signal peptide is the
first underlined sequence; the sequence encoding 1H10_HvLv is first italicized sequence; the
sequence encoding IgG4hinge S10P is the second bold sequence; the sequence encoding
CD28-TM is the second underlined sequence; the sequence encoding 4-1BB is the second
italicized sequence; the sequences encoding CD3z is the third bold sequence; the sequence
encoding T2A is the third underlined sequence; and tCD19-Fully sequenced is the third
italicized sequence section in the above sequence.

1A9-intDS-41bb-3z-T-CD19t Top Strand
GGATCTGCGATCGCTCCGGTGCCCGTCAGTGGGCAGAGCGCACATCGCCCACAGTCCC
CGAGAAGTTGGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACC<u>ATGCTGCTGCTCGTGACCAGCCTGCTGCTGTGCGA</u>
<u>ACTGCCCCACCCTGCCTTTCTGCTGATCCCC</u>*GAAGTGCAGTTGGTTGAGTCTGGAGGAGG*
*CCTGGTACAGCCGGGTGGTAGTCTTCGGCTTTCCTGTGCTGCTAGCGGGTTTACTTTCTCC*
*ATATACGATATGCACTGGGTGAGGCAAGCGACCGGAAAAGGTCTGGAGTGGGTCTCAGCG*
*ATCGGTACAGCTGGCGATACTTACTATGCGGGCAGTGTCAAGGGACGATTCACCATAAGC*
*CGCGAAAACGCTAAAAATTCCCTCTACTTGCAAATGAATAGCCTGCGAGCGGGGGACACC*
*GCCGTATATTATTGTGCTAGAGAGTATAGCGGATATTACTTTGACTATTGGGGTCAAGGCA*
*CTCTGGTAACGGTGTCTAGCGGAGGCGGAGGATCTGGCGGAGGGGGCTCTGGAGGAGG*

FIG. 19 cont'd

*AGGATCTGCGATTCAGATGACTCAATCCCCCTCCTCTCTCTCCGCGTCCGTAGGGGATAG*
*GGTGACAATAACTTGTAGGGCGAGCCAGGACATCCGCAATGACCTCGGCTGGTATCAACA*
*AAAACCAGGCAAGGCACCTAAGATACTGATTTATGGCGCGTCCTCCTTGCAATCCGGGGT*
*GCCGTCTCGGTTCAGTGGTTCAGGTAGTGGTACGGACTTTACCTTCACAATCTCTAGTCTG*
*CAACCGGAGGATTTCGCTACTTACTATTGTCTCCAGGAGTATAATTACCCCTGTACATTTGG*
*GCAAGGCACCAAGTTGGAGATAAAA*GAGTCTAAGTACGGACCGCCCTGCCCCCCTTGCC
CT<u>GGCCAGCCTAGAGAACCCCAGGTGTACACCCTGCCTCCCAGCCAGGAAGAGATGACCA</u>
<u>AGAACCAGGTGTCCCTGACCTGCCTGGTCAAAGGCTTCTACCCCAGCGATATCGCCGTGG</u>
<u>AATGGGAGAGCAACGGCCAGCCCGAGAACAACTACAAGACCACCCCCCCTGTGCTGGAC</u>
<u>AGCGACGGCAGCTTCTTCCTGTACTCCCGGCTGACCGTGGACAAGAGCCGGTGGCAGGA</u>
<u>AGGCAACGTCTTCAGCTGCAGCGTGATGCACGAGGCCCTGCACAACCACTACACCCAGAA</u>
<u>GTCCCTGAGCCTGAGCCTGGGCAAGA</u>*TGTTCTGGGTGCTGGTGGTGGTCGGAGGCGTGC*
*TGGCCTGCTACAGCCTGCTGGTCACCGTGGCCTTCATCATCTTTTGGGTG*AAACGGGGCA
GAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTG<u>CG</u>
<u>GGTGAAGTTCAGCAGAAGCGCCGACGCCCCTGCCTACCAGCAGGGCCAGAATCAGCTGT</u>
<u>ACAACGAGCTGAACCTGGGCAGAAGGGAAGAGTACGACGTCCTGGATAAGCGGAGAGGC</u>
<u>CGGGACCCTGAGATGGGCGGCAAGCCTCGGCGGAAGAACCCCCAGGAAGGCCTGTATAA</u>
<u>CGAACTGCAGAAAGACAAGATGGCCGAGGCCTACAGCGAGATCGGCATGAAGGGCGAGC</u>
<u>GGAGGCGGGGCAAGGGCCACGACGGCCTGTATCAGGGCCTGTCCACCGCCACCAAGGAT</u>
<u>ACCTACGACGCCCTGCACATGCAGGCCCTGCCCCCAAGGC</u>*TCGAGGGCGGCGGAGAGG*
*GCAGAGGAAGTCTTCTAACATGCGGTGACGTGGAGGAGAATCCAGGCCCTAGG*ATGCCA
CCTCCAAGACTCCTCTTCTTCCTCCTCTTCCTGACACCAATGGAAGTCAGGCCTGAGGAA
CCTCTAGTGGTGAAGGTGGAAGAGGGAGATAACGCTGTGTTACAGTGCCTCAAGGGAAC
CTCAGATGGACCCACTCAGCAGCTGACCTGGTCTCGGGAGTCTCCGCTTAAACCCTTCCT
GAAACTCAGCCTTGGACTGCCAGGTCTGGGAATCCACATGAGGCCACTGGCTATCTGGC
TGTTCATCTTCAACGTCTCTCAACAGATGGGAGGCTTCTACCTGTGTCAGCCTGGACCAC
CTTCTGAGAAGGCATGGCAGCCTGGTTGGACAGTCAATGTGGAGGGTTCTGGTGAGCTG
TTCCGGTGGAATGTTTCGGACCTAGGTGGACTGGGATGTGGTCTGAAGAACAGGTCCTC
AGAGGGACCTAGCTCTCCTTCCGGGAAGCTCATGAGCCCCAAGCTGTATGTGTGGGCCA
AAGACCGCCCTGAGATCTGGGAGGGAGAGCCTCCGTGTGTCCCACCGAGGGACAGCCT
GAACCAGAGCCTCAGCCAGGACCTCACCATGGCCCCTGGCTCCACACTCTGGCTGTCCT
GTGGGGTACCCCCTGACTCTGTGTCCAGGGGCCCCCTCTCCTGGACCCATGTGCACCCC
AAGGGGCCTAAGTCATTGCTGAGCCTAGAGCTGAAGGACGATCGCCCTGCCAGAGATAT
GTGGGTAATGGAGACGGGTCTGTTGTTGCCCCGGGCCACAGCTCAAGACGCTGGAAAGT
ATTATTGTCACCGTGGCAACCTGACCATGTCATTCCACCTGGAGATCACTGCTCGGCCAG
TACTATGGCACTGGCTGCTGAGGACTGGTGGCTGGAAGGTCTCAGCTGTGACTTTGGCTT
ATCTGATCTTCTGCCTGTGTTCCCTTGTGGGCATTCTTCATCTTCAAAGAGCCCTGGTCCT
GAGGAGGAAAAGATGA (SEQ ID NO: 48)

Within the above sequence, EF1 promoter is the first bold sequence; the sequence encoding GM-CSFR signal peptide encoding sequence is the first underlined sequence; the sequence encoding 1A9-Hvlv is the first italicized sequence; the sequence encoding IgG4hinge S10P is the second bold sequence; the sequence encoding IgG4-int(DS) is the second underlined sequence; the sequence encoding CD28tm is the second italicized sequence; the sequence encoding 4-1BB signaling is the third bold sequence; the sequence encoding CD3z is the third underlined sequence; the sequence encoding T2A is the third italicized sequence; and tCD19-Fully sequenced is the fourth bold sequence section in the above sequence.

FIG. 19 cont'd

1A9-sh-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTCTGTTCTGCGCCGTTACAGATCCAAGCTGT
GACCGGCGCCTACGGCTAGCCACC<u>ATGCTGCTGCTCGTGACCAGCCTGCTGCTGTGCGA</u>
<u>ACTGCCCCACCCTGCCTTTCTGCTGATCCCC</u>*GAAGTGCAGTTGGTTGAGTCTGGAGGAGG*
*CCTGGTACAGCCGGGTGGTAGTCTTCGGCTTTCCTGTGCTGCTAGCGGGTTTACTTTCTCC*
*ATATACGATATGCACTGGGTGAGGCAAGCGACCGGAAAAGGTCTGGAGTGGGTCTCAGCG*
*ATCGGTACAGCTGGCGATACTTACTATGCGGGCAGTGTCAAGGGACGATTCACCATAAGC*
*CGCGAAAACGCTAAAAATTCCCTCTACTTGCAAATGAATAGCCTGCGAGCGGGGGACACC*
*GCCGTATATTATTGTGCTAGAGAGTATAGCGGATATTACTTTGACTATTGGGGTCAAGGCA*
*CTCTGGTAACGGTGTCTAGCGGAGGCGGAGGATCTGGCGGAGGGGGCTCTGGAGGAGG*
*AGGATCTGCGATTCAGATGACTCAATCCCCCTCCTCTCTCCGCGTCCGTAGGGGATAG*
*GGTGACAATAACTTGTAGGGCGAGCCAGGACATCCGCAATGACCTCGGCTGGTATCAACA*
*AAAACCAGGCAAGGCACCTAAGATACTGATTTATGGCGCGTCCTCCTTGCAATCCGGGGT*
*GCCGTCTCGGTTCAGTGGTTCAGGTAGTGGTACGGACTTTACCTTCACAATCTCTAGTCTG*
*CAACCGGAGGATTTCGCTACTTACTATTGTCTCCAGGAGTATAATTACCCCTGTACATTTGG*
*GCAAGGCACCAAGTTGGAGATAAAA*GAGTCTAAGTACGGACCGCCCTGCCCCCCTTGCC
CT<u>ATGTTCTGGGTGCTGGTGGTGGTCGGAGGCGTGCTGGCCTGCTACAGCCTGCTGGTCA</u>
<u>CCGTGGCCTTCATCATCTTTTGGGTGAAACGGGGCAGAAAGAAACTCCTGTATATATTCAA</u>
*ACAACCATTTATGAGACCAGTACAAACTACTCAAGAGGAAGATGGCTGTAGCTGCCGATTT*
*CCAGAAGAAGAAGAAGGAGGATGTGAACTGCGGGTGAAGTTCAGCAGAAGCGCCGACGC*
CCCTGCCTACCAGCAGGGCCAGAATCAGCTGTACAACGAGCTGAACCTGGGCAGAAGG
GAAGAGTACGACGTCCTGGATAAGCGGAGAGGCCGGGACCCTGAGATGGGCGGCAAG
CCTCGGCGGAAGAACCCCCAGGAAGGCCTGTATAACGAACTGCAGAAAGACAAGATGG
CCGAGGCCTACAGCGAGATCGGCATGAAGGGCGAGCGGAGGCGGGGCAAGGGCCACG
ACGGCCTGTATCAGGGCCTGTCCACCGCCACCAAGGATACCTACGACGCCCTGCACATG
CAGGCCCTGCCCCAAGG<u>CTCGAGGGCGGCGGAGAGGGCAGAGGAAGTCTTCTAACATG</u>
<u>CGGTGACGTGGAGGAGAATCCAGGCCCTAGG</u>*ATGCCACCTCCAAGACTCCTCTTCTTCCT*
*CCTCTTCCTGACACCAATGGAAGTCAGGCCTGAGGAACCTCTAGTGGTGAAGGTGGAAGA*
*GGGAGATAACGCTGTGTTACAGTGCCTCAAGGGAACCTCAGATGGACCCACTCAGCAGCT*
*GACCTGGTCTCGGGAGTCTCCGCTTAAACCCTTCCTGAAACTCAGCCTTGGACTGCCAGG*
*TCTGGGAATCCACATGAGGCCACTGGCTATCTGGCTGTTCATCTTCAACGTCTCTCAACAG*
*ATGGGAGGCTTCTACCTGTGTCAGCCTGGACCACCTTCTGAGAAGGCATGGCAGCCTGGT*
*TGGACAGTCAATGTGGAGGGTTCTGGTGAGCTGTTCCGGTGGAATGTTTCGGACCTAGGT*
*GGACTGGGATGTGGTCTGAAGAACAGGTCCTCAGAGGGACCTAGCTCTCCTTCCGGGAAG*
*CTCATGAGCCCCAAGCTGTATGTGTGGGCCAAAGACCGCCCTGAGATCTGGGAGGGAGA*
*GCCTCCGTGTGTCCCACCGAGGGACAGCCTGAACCAGAGCCTCAGCCAGGACCTCACCA*
*TGGCCCCTGGCTCCACACTCTGGCTGTCCTGTGGGGTACCCCCTGACTCTGTGTCCAGGG*
*GCCCCCTCTCCTGGACCCATGTGCACCCCAAGGGGCCTAAGTCATTGCTGAGCCTAGAGC*
*TGAAGGACGATCGCCCTGCCAGAGATATGTGGGTAATGGAGACGGGTCTGTTGTTGCCCC*
*GGGCCACAGCTCAAGACGCTGGAAAGTATTATTGTCACCGTGGCAACCTGACCATGTCATT*

FIG. 19 cont'd

*CCACCTGGAGATCACTGCTCGGCCAGTACTATGGCACTGGCTGCTGAGGACTGGTGGCTG*
*GAAGGTCTCAGCTGTGACTTTGGCTTATCTGATCTTCTGCCTGTGTTCCCTTGTGGGCATT*
*CTTCATCTTCAAAGAGCCCTGGTCCTGAGGAGGAAAAGATGA* (SEQ ID NO: 49)
Within the above sequence, EF1a promoter the first bold sequence; the sequence encoding
GM-CSFR signal peptide is the first underlined sequence; the sequence encoding 1A9-Hvlv is
the first italicized sequence; the sequence encoding IgG4hinge S10P is the second bold
sequence; the sequence encoding CD28-TM is the second underlined sequence; the sequence
encoding 4-1BB is the second italicized sequence; the sequence encoding CD3Z the third bold
sequence; the sequence encoding T2A is the third underlined sequence; and tCD19-Fully
sequenced is the third italicized sequence section in the above sequence.

1E6-intDS-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACC<u>ATGCTGCTGCTCGTGACCAGCCTGCTGCTGTGCGA</u>
<u>ACTGCCCCACCCTGCCTTTCTGCTGATCCCCCAAGTGCAGTTGGTTGAATCCGGTGGCGG</u>
*TGTGGTTCAACCAGGCAGGAGCTTGAGACTTTCATGTGCAGCGTCCGGCTTTACATTCTCC*
*AGCTACGACATACATTGGGTCCGGCAGGCGCCAGGAAAGGGCCTCGAATGGGTCGCGGT*
*AATATGGTACGACGGCAGTCATAACTACTACAGTGATTCTGTAAAAGGCCGCTTTACGATTT*
*CACGCGACAACAGCAAGAATACACTCTATTTGCAAATGAACTCTCTGCGCGCGGAAGATAC*
*CGCCGTGTATTATTGTGCGCGGGACTACAGCGGGTCTTACTACGACTACTGGGGCCAAGG*
*AACCCTTGTAACGGTCTCTAGCGGAGGCGGAGGATCTGGCGGAGGGGGCTCTGGAGGAG*
*GAGGATCTGCAATACAAATGACGCAGTCTCCTAGCTCACTTTCTGCAAGCGTCGGAGACC*
*GAGTTACAATTACGTGTCGGGCGAGCCAGGGAATTCGGAACGATCTCGGCTGGTATCAAC*
*AGAAACCCGGCAAAGCGCCAAAATTGCTTATATACGCGGCATCAAACCTTCAGAGTGGTGT*
*GCCGTCAAGATTCAGTGGGTCAGGCAGCGGAACTGACTTTACCCTGACTATCTCTAGTCTC*
*CAACCCGAGGACTTCGCAACGTACTATTGCCTGCAAGATTACTCCTACCCGCGAACGTTCG*
*GCCAAGGGACAAAGGTTGAGATTAAA*GAGTCTAAGTACGGACCGCCCTGCCCCCCTTGCC
CTG<u>GCCAGCCTAGAGAACCCCAGGTGTACACCCTGCCTCCCAGCCAGGAAGAGATGACCA</u>
<u>AGAACCAGGTGTCCCTGACCTGCCTGGTCAAAGGCTTCTACCCCAGCGATATCGCCGTGG</u>
<u>AATGGGAGAGCAACGGCCAGCCCGAGAACAACTACAAGACCACCCCCCCTGTGCTGGAC</u>
<u>AGCGACGGCAGCTTCTTCCTGTACTCCCGGCTGACCGTGGACAAGAGCCGGTGGCAGGA</u>
<u>AGGCAACGTCTTCAGCTGCAGCGTGATGCACGAGGCCCTGCACAACCACTACACCCAGAA</u>
<u>GTCCCTGAGCCTGAGCCTGGGCAAG</u>*ATGTTCTGGGTGCTGGTGGTGGTCGGAGGCGTGC*
*TGGCCTGCTACAGCCTGCTGGTCACCGTGGCCTTCATCATCTTTTGGGTG*AAACGGGGCA
GAAAGAAACTCCTGTATATATTCAAACAACCATTTATGAGACCAGTACAAACTACTCAAG
AGGAAGATGGCTGTAGCTGCCGATTTCCAGAAGAAGAAGAAGGAGGATGTGAACTGC<u>CG</u>
<u>GGTGAAGTTCAGCAGAAGCGCCGACGCCCCTGCCTACCAGCAGGGCCAGAATCAGCTGT</u>
<u>ACAACGAGCTGAACCTGGGCAGAAGGGAAGAGTACGACGTCCTGGATAAGCGGAGAGGC</u>
<u>CGGGACCCTGAGATGGGCGGCAAGCCTCGGCGGAAGAACCCCCAGGAAGGCCTGTATAA</u>
<u>CGAACTGCAGAAAGACAAGATGGCCGAGGCCTACAGCGAGATCGGCATGAAGGGCGAGC</u>

FIG. 19 cont'd

GGAGGCGGGGCAAGGGCCACGACGGCCTGTATCAGGGCCTGTCCACCGCCACCAAGGAT
ACCTACGACGCCCTGCACATGCAGGCCCTGCCCCCAAGGCTCGAGGGCGGCGGAGAGG
GCAGAGGAAGTCTTCTAACATGCGGTGACGTGGAGGAGAATCCAGGCCCTAGGATGCCA
CCTCCAAGACTCCTCTTCTTCCTCCTCTTCCTGACACCAATGGAAGTCAGGCCTGAGGAA
CCTCTAGTGGTGAAGGTGGAAGAGGGAGATAACGCTGTGTTACAGTGCCTCAAGGGAAC
CTCAGATGGACCCACTCAGCAGCTGACCTGGTCTCGGGAGTCTCCGCTTAAACCCTTCCT
GAAACTCAGCCTTGGACTGCCAGGTCTGGGAATCCACATGAGGCCACTGGCTATCTGGC
TGTTCATCTTCAACGTCTCTCAACAGATGGGAGGCTTCTACCTGTGTCAGCCTGGACCAC
CTTCTGAGAAGGCATGGCAGCCTGGTTGGACAGTCAATGTGGAGGGTTCTGGTGAGCTG
TTCCGGTGGAATGTTTCGGACCTAGGTGGACTGGGATGTGGTCTGAAGAACAGGTCCTC
AGAGGGACCTAGCTCTCCTTCCGGGAAGCTCATGAGCCCCAAGCTGTATGTGTGGGCCA
AAGACCGCCCTGAGATCTGGGAGGGAGAGCCTCCGTGTGTCCCACCGAGGGACAGCCT
GAACCAGAGCCTCAGCCAGGACCTCACCATGGCCCCTGGCTCCACACTCTGGCTGTCCT
GTGGGGTACCCCCTGACTCTGTGTCCAGGGGCCCCCTCTCCTGGACCCATGTGCACCCC
AAGGGGCCTAAGTCATTGCTGAGCCTAGAGCTGAAGGACGATCGCCCTGCCAGAGATAT
GTGGGTAATGGAGACGGGTCTGTTGTTGCCCCGGGCCACAGCTCAAGACGCTGGAAAGT
ATTATTGTCACCGTGGCAACCTGACCATGTCATTCCACCTGGAGATCACTGCTCGGCCAG
TACTATGGCACTGGCTGCTGAGGACTGGTGGCTGGAAGGTCTCAGCTGTGACTTTGGCTT
ATCTGATCTTCTGCCTGTGTTCCCTTGTGGGCATTCTTCATCTTCAAAGAGCCCTGGTCCT
GAGGAGGAAAAGATGA (SEQ ID NO: 50)

Within the above sequence, EF1 is the first bold sequence; the sequence encoding GM-CSFR signal peptide is the first underlined sequence; the sequence encoding 1E6_HvLv is the first italicized sequence; the sequence encoding IgG4hinge S10P is the second bold sequence; the sequence encoding IgG4-int(DS) is the second underlined sequence; the sequence encoding CD28tm is the second italicized sequence; the sequence encoding 4-1BB signaling is the third bold sequence; the sequence encoding CD3z is the third underlined sequence; the sequence encoding T2A is the third italicized sequence; and tCD19-Fully sequenced is the fourth bold sequence section in the above sequence.

1E6-sh-41bb-3z-T-CD19t Top Strand
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACC<u>ATGCTGCTGCTCGTGACCAGCCTGCTGCTGTGCGA
ACTGCCCCACCCTGCCTTTCTGCTGATCCCC</u>*CAAGTGCAGTTGGTTGAATCCGGTGGCGG
TGTGGTTCAACCAGGCAGGAGCTTGAGACTTTCATGTGCAGCGTCCGGCTTTACATTCTCC
AGCTACGACATACATTGGGTCCGGCAGGCGCCAGGAAAGGGCCTCGAATGGGTCGCGGT
AATATGGTACGACGGCAGTCATAACTACTACAGTGATTCTGTAAAAGGCCGCTTTACGATTT
CACGCGACAACAGCAAGAATACACTCTATTTGCAAATGAACTCTCTGCGCGCGGAAGATAC
CGCCGTGTATTATTGTGCGCGGGACTACAGCGGGTCTTACTACGACTACTGGGGCCAAGG
AACCCTTGTAACGGTCTCTAGCGGAGGCGGAGGATCTGGCGGAGGGGGCTCTGGAGGAG
GAGGATCTGCAATACAAATGACGCAGTCTCCTAGCTCACTTTCTGCAAGCGTCGGAGACC*

FIG. 19 cont'd

*GAGTTACAATTACGTGTCGGGCGAGCCAGGGAATTCGGAACGATCTCGGCTGGTATCAAC*
*AGAAACCCGGCAAAGCGCCAAAATTGCTTATATACGCGGCATCAAACCTTCAGAGTGGTGT*
*GCCGTCAAGATTCAGTGGGTCAGGCAGCGGAACTGACTTTACCCTGACTATCTCTAGTCTC*
*CAACCCGAGGACTTCGCAACGTACTATTGCCTGCAAGATTACTCCTACCCGCGAACGTTCG*
*GCCAAGGGACAAAGGTTGAGATTAAA*__**GAGTCTAAGTACGGACCGCCCTGCCCCCCTTGCC
CT**ATGTTCTGGGTGCTGGTGGTGGTCGGAGGCGTGCTGGCCTGCTACAGCCTGCTGGTCA
CCGTGGCCTTCATCATCTTTTGGGTG__*AAACGGGGCAGAAAGAAACTCCTGTATATATTCAA*
*ACAACCATTTATGAGACCAGTACAAACTACTCAAGAGGAAGATGGCTGTAGCTGCCGATTT*
*CCAGAAGAAGAAGAAGGAGGATGTGAACTGCGGGTGAAGTTCAGCAGAAGCGCCGACGC*
CCCTGCCTACCAGCAGGGCCAGAATCAGCTGTACAACGAGCTGAACCTGGGCAGAAGG
GAAGAGTACGACGTCCTGGATAAGCGGAGAGGCCGGGACCCTGAGATGGGCGGCAAG
CCTCGGCGGAAGAACCCCCAGGAAGGCCTGTATAACGAACTGCAGAAAGACAAGATGG
CCGAGGCCTACAGCGAGATCGGCATGAAGGGCGAGCGGAGGCGGGGCAAGGGCCACG
ACGGCCTGTATCAGGGCCTGTCCACCGCCACCAAGGATACCTACGACGCCCTGCACATG
CAGGCCCTGCCCCCAAGG__CTCGAGGGCGGCGGAGAGGGCAGAGGAAGTCTTCTAACATG
CGGTGACGTGGAGGAGAATCCAGGCCCTAGG__*ATGCCACCTCCAAGACTCCTCTTCTTCCT*
*CCTCTTCCTGACACCAATGGAAGTCAGGCCTGAGGAACCTCTAGTGGTGAAGGTGGAAGA*
*GGGAGATAACGCTGTGTTACAGTGCCTCAAGGGAACCTCAGATGGACCCACTCAGCAGCT*
*GACCTGGTCTCGGGAGTCTCCGCTTAAACCCTTCCTGAAACTCAGCCTTGGACTGCCAGG*
*TCTGGGAATCCACATGAGGCCACTGGCTATCTGGCTGTTCATCTTCAACGTCTCTCAACAG*
*ATGGGAGGCTTCTACCTGTGTCAGCCTGGACCACCTTCTGAGAAGGCATGGCAGCCTGGT*
*TGGACAGTCAATGTGGAGGGTTCTGGTGAGCTGTTCCGGTGGAATGTTTCGGACCTAGGT*
*GGACTGGGATGTGGTCTGAAGAACAGGTCCTCAGAGGGACCTAGCTCTCCTTCCGGGAAG*
*CTCATGAGCCCCAAGCTGTATGTGTGGGCCAAAGACCGCCCTGAGATCTGGGAGGGAGA*
*GCCTCCGTGTGTCCCACCGAGGGACAGCCTGAACCAGAGCCTCAGCCAGGACCTCACCA*
*TGGCCCCTGGCTCCACACTCTGGCTGTCCTGTGGGGTACCCCCTGACTCTGTGTCCAGGG*
*GCCCCCTCTCCTGGACCCATGTGCACCCCAAGGGGCCTAAGTCATTGCTGAGCCTAGAGC*
*TGAAGGACGATCGCCCTGCCAGAGATATGTGGGTAATGGAGACGGGTCTGTTGTTGCCCC*
*GGGCCACAGCTCAAGACGCTGGAAAGTATTATTGTCACCGTGGCAACCTGACCATGTCATT*
*CCACCTGGAGATCACTGCTCGGCCAGTACTATGGCACTGGCTGCTGAGGACTGGTGGCTG*
*GAAGGTCTCAGCTGTGACTTTGGCTTATCTGATCTTCTGCCTGTGTTCCCTTGTGGGCATT*
*CTTCATCTTCAAAGAGCCCTGGTCCTGAGGAGGAAAAGATGA* (SEQ ID NO: 51)

Within the above sequence, EF1a promoter is the first bold sequence; the sequence encoding GM-CSFR signal peptide is the first underlined sequence; the sequence encoding 1E6_HvLv is the first italicized sequence; the sequence encoding IgG4hinge S10P is the second bold sequence; the sequence encoding CD28-TM is the second underlined sequence; the sequence encoding 4-1BB is the second italicized sequence; the sequence encoding CD3Z is the third bold sequence; the sequence encoding T2A is the third underlined sequence; and tCD19-Fully sequenced is the third italicized sequence section in the above sequence.

1H10-LvHv-intDS-41bb-3z-T-CD19t Top Strand:
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC

FIG. 19 cont'd

CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTAC*GGCTAGCCACC*ATGCTGCTGCTCGTGACCAGCCTGCTGCTGTGCGA
*ACTGCCCCACCCTGCCTTTCTGCTGATCCCC*GCGATACAAATGACGCAAAGTCCCAGCAG
*TTTGTCCGCCTCAGTAGGCGACCGCGTTACGATTACGTGTAGGGCGTCTCAAGGGATCAG*
*GATCTATCTGGGCTGGTATCAACAAAAGCCTGGGAAAGCCCCAAAGCTCCTTATATATGCA*
*ACATCATCCCTGCAAAGCGGCGTTCCATCCCGATTCAGTGGTTCTGGTAGCGGTACGGAC*
*TTCACTCTCACAATCTCATCTCTTCAACCAGAAGACTTTGCGACGTATTACTGTTTGCAAGA*
*CTACAATTATCCATGGACGTTCGGCCAAGGCACGAAAGTCGAGATAAAGGGAGGCGGAGG*
*ATCTGGCGGAGGGGGCTCTGGAGGAGGAGGATCTCAAGTACAGCTTGTTCAAAGTGGTGC*
*TGAAGTTAAAAAGCCAGGGGCCAGCGTTAAGGTATCCTGCAAGGGAAGTGGTTACATCTTC*
*ACATCTTACGACATGCACTGGGTACGACAGGCTCCTGGACAGGGTCTGGAATGGATGGGT*
*ATCATAGACCCCTCAGGAGGATCTACGAGCTATGCCCAAAAATTTCAGGGAAGAGTAACAA*
*TGACCAGGGACACGTCCATGAGCACAGTCTACATGGAACTCAGCAGTCTCAGATCAGAGG*
*ATACGGCGGTTTACTACTGTACTAGGGATTATTCATGGAGCTATTTCGACTATTGGGGACA*
*AGGAACCTTGGTAACAGTGTCTTCA*GAGTCTAAGTACGGACCGCCCTGCCCCCCTTGCCC
TGGCCAGCCTAGAGAACCCCAGGTGTACACCCTGCCTCCCAGCCAGGAAGAGATGACCAA
GAACCAGGTGTCCCTGACCTGCCTGGTCAAAGGCTTCTACCCCAGCGATATCGCCGTGGA
ATGGGAGAGCAACGGCCAGCCCGAGAACAACTACAAGACCACCCCCCCTGTGCTGGACA
GCGACGGCAGCTTCTTCCTGTACTCCCGGCTGACCGTGGACAAGAGCCGGTGGCAGGAA
GGCAACGTCTTCAGCTGCAGCGTGATGCACGAGGCCCTGCACAACCACTACACCCAGAAG
TCCCTGAGCCTGAGCCTGGGCAAGA*TGTTCTGGGTGCTGGTGGTGGTCGGAGGCGTGCT*
*GGCCTGCTACAGCCTGCTGGTCACCGTGGCCTTCATCATCTTTTGGGTGAAACGGGGCAG*
AAAGAAACTCCTGTATATATTCAAACAACCATTTATGAGACCAGTACAAACTACTCAAGA
GGAAGATGGCTGTAGCTGCCGATTTCCAGAAGAAGAAGAAGGAGGATGTGAACTGCGG
GTGAAGTTCAGCAGAAGCGCCGACGCCCCTGCCTACCAGCAGGGCCAGAATCAGCTGTA
CAACGAGCTGAACCTGGGCAGAAGGGAAGAGTACGACGTCCTGGATAAGCGGAGAGGCC
GGGACCCTGAGATGGGCGGCAAGCCTCGGCGGAAGAACCCCCAGGAAGGCCTGTATAAC
GAACTGCAGAAAGACAAGATGGCCGAGGCCTACAGCGAGATCGGCATGAAGGGCGAGCG
GAGGCGGGGCAAGGGCCACGACGGCCTGTATCAGGGCCTGTCCACCGCCACCAAGGATA
CCTACGACGCCCTGCACATGCAGGCCCTGCCCCCAAGGCTCGAGGGCGGCGGAGAGGG
*CAGAGGAAGTCTTCTAACATGCGGTGACGTGGAGGAGAATCCAGGCCCTAGGA*TGCCACC
TCCAAGACTCCTCTTCTTCCTCCTCTTCCTGACACCAATGGAAGTCAGGCCTGAGGAACC
TCTAGTGGTGAAGGTGGAAGAGGGAGATAACGCTGTGTTACAGTGCCTCAAGGGAACCT
CAGATGGACCCACTCAGCAGCTGACCTGGTCTCGGGAGTCTCCGCTTAAACCCTTCCTG
AAACTCAGCCTTGGACTGCCAGGTCTGGGAATCCACATGAGGCCACTGGCTATCTGGCT
GTTCATCTTCAACGTCTCTCAACAGATGGGAGGCTTCTACCTGTGTCAGCCTGGACCACC
TTCTGAGAAGGCATGGCAGCCTGGTTGGACAGTCAATGTGGAGGGTTCTGGTGAGCTGT
TCCGGTGGAATGTTTCGGACCTAGGTGGACTGGGATGTGGTCTGAAGAACAGGTCCTCA
GAGGGACCTAGCTCTCCTTCCGGGAAGCTCATGAGCCCCAAGCTGTATGTGTGGGCCAA
AGACCGCCCTGAGATCTGGGAGGGAGAGCCTCCGTGTGTCCCACCGAGGGACAGCCTG
AACCAGAGCCTCAGCCAGGACCTCACCATGGCCCCTGGCTCCACACTCTGGCTGTCCTG
TGGGGTACCCCCTGACTCTGTGTCCAGGGCCCCCTCTCCTGGACCCATGTGCACCCCA
AGGGGCCTAAGTCATTGCTGAGCCTAGAGCTGAAGGACGATCGCCCTGCCAGAGATATG
TGGGTAATGGAGACGGGTCTGTTGTTGCCCCGGGCCACAGCTCAAGACGCTGGAAAGTA
TTATTGTCACCGTGGCAACCTGACCATGTCATTCCACCTGGAGATCACTGCTCGGCCAGT
ACTATGGCACTGGCTGCTGAGGACTGGTGGCTGGAAGGTCTCAGCTGTGACTTTGGCTT

FIG. 19 cont'd

ATCTGATCTTCTGCCTGTGTTCCCTTGTGGGCATTCTTCATCTTCAAAGAGCCCTGGTCCT
GAGGAGGAAAAGATGA (SEQ ID NO: 200)
Within the above sequence, EF1 promoter is the first bold sequence; the sequence encoding
GM-CSFR signal peptide is the first underlined sequence; the sequence encoding 5D12_LvHv
is the first italicized sequence; the sequence encoding IgG4hinge S10P is the second bold
sequence; the sequence encoding IgG4-int(DS) is the second underlined sequence; the
sequence encoding CD28tm is the second italicized sequence; the sequence encoding 4-1BB
signaling is the third bold sequence; the sequence encoding CD3z is the third underlined
sequence; the sequence encoding T2A is the third italicized sequence; and tCD19-Fully
sequenced is the fourth bold sequence section of the sequence.

1A9-LvHv-intDS-41bb-3z-T-CD19t Top Strand:
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTAC<u>GGCTAGCCACC</u><u>ATGCTGCTGCTCGTGACCAGCCTGCTGCTGTGCGA</u>
<u>ACTGCCCCACCCTGCCTTTCTGCTGATCCCCGCGATTCAGATGACTCAATCCCCCTCCTCT</u>
<u>CTCTCCGCGTCCGTAGGGGATAGGGTGACAATAACTTGTAGGGCGAGCCAGGACATCCGC</u>
<u>AATGACCTCGGCTGGTATCAACAAAACCAGGCAAGGCACCTAAGATACTGATTTATGGCG</u>
<u>CGTCCTCCTTGCAATCCGGGGTGCCGTCTCGGTTCAGTGGTTCAGGTAGTGGTACGGACT</u>
<u>TTACCTTCACAATCTCTAGTCTGCAACCGGAGGATTTCGCTACTTACTATTGTCTCCAGGAG</u>
<u>TATAATTACCCCTGTACATTTGGGCAAGGCACCAAGTTGGAGATAAAAGGAGGCGGAGGAT</u>
<u>CTGGCGGAGGGGGCTCTGGAGGAGGAGGATCTGAAGTGCAGTTGGTTGAGTCTGGAGGA</u>
<u>GGCCTGGTACAGCCGGGTGGTAGTCTTCGGCTTTCCTGTGCTGCTAGCGGGTTTACTTTC</u>
<u>TCCATATACGATATGCACTGGGTGAGGCAAGCGACCGGAAAAGGTCTGGAGTGGGTCTCA</u>
<u>GCGATCGGTACAGCTGGCGATACTTACTATGCGGGCAGTGTCAAGGGACGATTCACCATA</u>
<u>AGCCGCGAAAACGCTAAAAATTCCCTCTACTTGCAAATGAATAGCCTGCGAGCGGGGGAC</u>
<u>ACCGCCGTATATTATTGTGCTAGAGAGTATAGCGGATATTACTTTGACTATTGGGGTCAAG</u>
<u>GCACTCTGGTAACGGTGTCTAGC</u>GAGTCTAAGTACGGACCGCCCTGCCCCCCTTGCCCT
<u>GGCCAGCCTAGAGAACCCCAGGTGTACACCCTGCCTCCCAGCCAGGAAGAGATGACCAA</u>
<u>GAACCAGGTGTCCCTGACCTGCCTGGTCAAAGGCTTCTACCCCAGCGATATCGCCGTGGA</u>
<u>ATGGGAGAGCAACGGCCAGCCCGAGAACAACTACAAGACCACCCCCCCTGTGCTGGACA</u>
<u>GCGACGGCAGCTTCTTCCTGTACTCCCGGCTGACCGTGGACAAGAGCCGGTGGCAGGAA</u>
<u>GGCAACGTCTTCAGCTGCAGCGTGATGCACGAGGCCCTGCACAACCACTACACCCAGAAG</u>
<u>TCCCTGAGCCTGAGCCTGGGCAAG</u>*ATGTTCTGGGTGCTGGTGGTGGTCGGAGGCGTGCT*
*GGCCTGCTACAGCCTGCTGGTCACCGTGGCCTTCATCATCTTTTGGGT*<u>GAAACGGGGCAG</u>
AAAGAAACTCCTGTATATATTCAAACAACCATTTATGAGACCAGTACAAACTACTCAAGA
GGAAGATGGCTGTAGCTGCCGATTTCCAGAAGAAGAAGAAGGAGGATGTGAACTG<u>CGG</u>
<u>GTGAAGTTCAGCAGAAGCGCCGACGCCCCTGCCTACCAGCAGGGCCAGAATCAGCTGTA</u>
<u>CAACGAGCTGAACCTGGGCAGAAGGGAAGAGTACGACGTCCTGGATAAGCGGAGAGGCC</u>
<u>GGGACCCTGAGATGGGCGGCAAGCCTCGGCGGAAGAACCCCCAGGAAGGCCTGTATAAC</u>
<u>GAACTGCAGAAAGACAAGATGGCCGAGGCCTACAGCGAGATCGGCATGAAGGGCGAGCG</u>

FIG. 19 cont'd

GAGGCGGGGCAAGGGCCACGACGGCCTGTATCAGGGCCTGTCCACCGCCACCAAGGATA
CCTACGACGCCCTGCACATGCAGGCCCTGCCCCCAAGGCTCGAGGGCGGCGGAGAGGG
CAGAGGAAGTCTTCTAACATGCGGTGACGTGGAGGAGAATCCAGGCCCTAGGATGCCACC
TCCAAGACTCCTCTTCTTCCTCCTCTTCCTGACACCAATGGAAGTCAGGCCTGAGGAACC
TCTAGTGGTGAAGGTGGAAGAGGGAGATAACGCTGTGTTACAGTGCCTCAAGGGAACCT
CAGATGGACCCACTCAGCAGCTGACCTGGTCTCGGGAGTCTCCGCTTAAACCCTTCCTG
AAACTCAGCCTTGGACTGCCAGGTCTGGGAATCCACATGAGGCCACTGGCTATCTGGCT
GTTCATCTTCAACGTCTCTCAACAGATGGGAGGCTTCTACCTGTGTCAGCCTGGACCACC
TTCTGAGAAGGCATGGCAGCCTGGTTGGACAGTCAATGTGGAGGGTTCTGGTGAGCTGT
TCCGGTGGAATGTTTCGGACCTAGGTGGACTGGGATGTGGTCTGAAGAACAGGTCCTCA
GAGGGACCTAGCTCTCCTTCCGGGAAGCTCATGAGCCCCAAGCTGTATGTGTGGGCCAA
AGACCGCCCTGAGATCTGGGAGGGAGAGCCTCCGTGTGTCCCACCGAGGGACAGCCTG
AACCAGAGCCTCAGCCAGGACCTCACCATGGCCCCTGGCTCCACACTCTGGCTGTCCTG
TGGGGTACCCCCTGACTCTGTGTCCAGGGGCCCCCTCTCCTGGACCCATGTGCACCCCA
AGGGGCCTAAGTCATTGCTGAGCCTAGAGCTGAAGGACGATCGCCCTGCCAGAGATATG
TGGGTAATGGAGACGGGTCTGTTGTTGCCCCGGGCCACAGCTCAAGACGCTGGAAAGTA
TTATTGTCACCGTGGCAACCTGACCATGTCATTCCACCTGGAGATCACTGCTCGGCCAGT
ACTATGGCACTGGCTGCTGAGGACTGGTGGCTGGAAGGTCTCAGCTGTGACTTTGGCTT
ATCTGATCTTCTGCCTGTGTTCCCTTGTGGGCATTCTTCATCTTCAAAGAGCCCTGGTCCT
GAGGAGGAAAAGATGA (SEQ ID NO: 201)

Within the above sequence, EF1 promoter is the first bold sequence; the sequence encoding GM-CSFR signal peptide is the first underlined sequence; the sequence encoding 5D12_LvHv is the first italicized sequence; the sequence encoding IgG4hinge S10P is the second bold sequence; the sequence encoding IgG4-int(DS) is the second underlined sequence; the sequence encoding CD28tm is the second italicized sequence; the sequence encoding 4-1BB signaling is the third bold sequence; the sequence encoding CD3z is the third underlined sequence; the sequence encoding T2A is the third italicized sequence; and tCD19-Fully sequenced is the fourth bold sequence section of the sequence.

1E6-LvHv-intDS-41bb-3z-T-CD19t Top Strand:
GGATCTGCGATCGCTCCGGTGCCCGTCAGTGGGCAGAGCGCACATCGCCCACAGTCCC
CGAGAAGTTGGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGT
GACCGGCGCCTACGGCTAGCCACC<u>ATGCTGCTGCTCGTGACCAGCCTGCTGCTGTGCGA</u>
<u>ACTGCCCCACCCTGCCTTTCTGCTGATCCCC</u>*GCAATACAAATGACGCAGTCTCCTAGCTCA*
*CTTTCTGCAAGCGTCGGAGACCGAGTTACAATTACGTGTCGGGCGAGCCAGGGAATTCGG*
*AACGATCTCGGCTGGTATCAACAGAAACCCGGCAAAGCGCCAAAATTGCTTATATACGCGG*
*CATCAAACCTTCAGAGTGGTGTGCCGTCAAGATTCAGTGGGTCAGGCAGCGGAACTGACT*
*TTACCCTGACTATCTCTAGTCTCCAACCCGAGGACTTCGCAACGTACTATTGCCTGCAAGA*
*TTACTCCTACCCGCGAACGTTCGGCCAAGGGACAAAGGTTGAGATTAAAGGAGGCGGAGG*
*ATCTGGCGGAGGGGGCTCTGGAGGAGGAGGATCTATGCTGCTGCTCGTGACCAGCCTGC*
*TGCTGTGCGAACTGCCCCACCCTGCCTTTCTGCTGATCCCCCAAGTGCAGTTGGTTGAATC*

FIG. 19 cont'd

*CGGTGGCGGTGTGGTTCAACCAGGCAGGAGCTTGAGACTTTCATGTGCAGCGTCCGGCTT*
*TACATTCTCCAGCTACGACATACATTGGGTCCGGCAGGCGCCAGGAAAGGGCCTCGAATG*
*GGTCGCGGTAATATGGTACGACGGCAGTCATAACTACTACAGTGATTCTGTAAAAGGCCGC*
*TTTACGATTTCACGCGACAACAGCAAGAATACACTCTATTTGCAAATGAACTCTCTGCGCGC*
*GGAAGATACCGCCGTGTATTATTGTGCGCGGGACTACAGCGGGTCTTACTACGACTACTG*
*GGGCCAAGGAACCCTTGTAACGGTCTCTAGC*GAGTCTAAGTACGGACCGCCCTGCCCCC
CTTGCCCTGGCCAGCCTAGAGAACCCCAGGTGTACACCCTGCCTCCAGCCAGGAAGAGA
TGACCAAGAACCAGGTGTCCCTGACCTGCCTGGTCAAAGGCTTCTACCCCAGCGATATCG
CCGTGGAATGGGAGAGCAACGGCCAGCCCGAGAACAACTACAAGACCACCCCCCCTGTG
CTGGACAGCGACGGCAGCTTCTTCCTGTACTCCCGGCTGACCGTGGACAAGAGCCGGTG
GCAGGAAGGCAACGTCTTCAGCTGCAGCGTGATGCACGAGGCCCTGCACAACCACTACAC
CCAGAAGTCCCTGAGCCTGAGCCTGGGCAAG*ATGTTCTGGGTGCTGGTGGTGGTCGGAG*
*GCGTGCTGGCCTGCTACAGCCTGCTGGTCACCGTGGCCTTCATCATCTTTTGGGTG*AAAC
GGGGCAGAAAGAAACTCCTGTATATATTCAAACAACCATTTATGAGACCAGTACAAACTA
CTCAAGAGGAAGATGGCTGTAGCTGCCGATTTCCAGAAGAAGAAGAAGGAGGATGTGA
ACTGCGGGTGAAGTTCAGCAGAAGCGCCGACGCCCCTGCCTACCAGCAGGGCCAGAATC
AGCTGTACAACGAGCTGAACCTGGGCAGAAGGGAAGAGTACGACGTCCTGGATAAGCGG
AGAGGCCGGGACCCTGAGATGGGCGGCAAGCCTCGGCGGAAGAACCCCCAGGAAGGCC
TGTATAACGAACTGCAGAAAGACAAGATGGCCGAGGCCTACAGCGAGATCGGCATGAAGG
GCGAGCGGAGGCGGGGCAAGGGCCACGACGGCCTGTATCAGGGCCTGTCCACCGCCAC
CAAGGATACCTACGACGCCCTGCACATGCAGGCCCTGCCCCCAAGGCTCGAGGGCGGCG
*GAGAGGGCAGAGGAAGTCTTCTAACATGCGGTGACGTGGAGGAGAATCCAGGCCCTAGG*
ATGCCACCTCCAAGACTCCTCTTCTTCCTCCTCTTCCTGACACCAATGGAAGTCAGGCCT
GAGGAACCTCTAGTGGTGAAGGTGGAAGAGGGAGATAACGCTGTGTTACAGTGCCTCAA
GGGAACCTCAGATGGACCCACTCAGCAGCTGACCTGGTCTCGGGAGTCTCCGCTTAAAC
CCTTCCTGAAACTCAGCCTTGGACTGCCAGGTCTGGGAATCCACATGAGGCCACTGGCT
ATCTGGCTGTTCATCTTCAACGTCTCTCAACAGATGGGAGGCTTCTACCTGTGTCAGCCT
GGACCACCTTCTGAGAAGGCATGGCAGCCTGGTTGGACAGTCAATGTGGAGGGTTCTGG
TGAGCTGTTCCGGTGGAATGTTTCGGACCTAGGTGGACTGGGATGTGGTCTGAAGAACA
GGTCCTCAGAGGGACCTAGCTCTCCTTCCGGGAAGCTCATGAGCCCCAAGCTGTATGTG
TGGGCCAAAGACCGCCCTGAGATCTGGGAGGGAGAGCCTCCGTGTGTCCCACCGAGGG
ACAGCCTGAACCAGAGCCTCAGCCAGGACCTCACCATGGCCCCTGGCTCCACACTCTGG
CTGTCCTGTGGGGTACCCCTGACTCTGTGTCCAGGGGCCCCCTCTCCTGGACCCATGT
GCACCCCAAGGGGCCTAAGTCATTGCTGAGCCTAGAGCTGAAGGACGATCGCCCTGCC
AGAGATATGTGGGTAATGGAGACGGGTCTGTTGTTGCCCCGGGCCACAGCTCAAGACGC
TGGAAAGTATTATTGTCACCGTGGCAACCTGACCATGTCATTCCACCTGGAGATCACTGC
TCGGCCAGTACTATGGCACTGGCTGCTGAGGACTGGTGGCTGGAAGGTCTCAGCTGTGA
CTTTGGCTTATCTGATCTTCTGCCTGTGTTCCCTTGTGGGCATTCTTCATCTTCAAAGAGC
CCTGGTCCTGAGGAGGAAAAGATGA (SEQ ID NO: 202)

Within the above sequence, EF1 promoter is the first bold sequence; the sequence encoding GM-CSFR signal peptide is the first underlined sequence; the sequence encoding 5D12_LvHv is the first italicized sequence; the sequence encoding IgG4hinge S10P is the second bold sequence; the sequence encoding IgG4-int(DS) is the second underlined sequence; the sequence encoding CD28tm is the second italicized sequence; the sequence encoding 4-1BB signaling is the third bold sequence; the sequence encoding CD3z is the third underlined sequence; the sequence encoding T2A is the third italicized sequence; and tCD19-Fully sequenced is the fourth bold sequence section of the sequence.

FIG. 19 cont'd

2D3-LvHv-intDS-41bb-3z-T-CD19t Top Strand:
GGATCTGCGATCGCTCCGGTGCCCGTCAGTGGGCAGAGCGCACATCGCCCACAGTCCC
CGAGAAGTTGGGGGGAGGGGTCGGCAATTGAACCGGTGCCTAGAGAAGGTGGCGCGG
GGTAAACTGGGAAAGTGATGTCGTGTACTGGCTCCGCCTTTTTCCCGAGGGTGGGGGAG
AACCGTATATAAGTGCAGTAGTCGCCGTGAACGTTCTTTTTCGCAACGGGTTTGCCGCCA
GAACACAGCTGAAGCTTCGAGGGGCTCGCATCTCTCCTTCACGCGCCCGCCGCCCTACC
TGAGGCCGCCATCCACGCCGGTTGAGTCGCGTTCTGCCGCCTCCCGCCTGTGGTGCCTC
CTGAACTGCGTCCGCCGTCTAGGTAAGTTTAAAGCTCAGGTCGAGACCGGGCCTTTGTC
CGGCGCTCCCTTGGAGCCTACCTAGACTCAGCCGGCTCTCCACGCTTTGCCTGACCCTG
CTTGCTCAACTCTACGTCTTTGTTTCGTTTCTGTTCTGCGCCGTTACAGATCCAAGCTGT
GACCGGCGCCTACGGCTAGCCACCATGCTGCTGCTCGTGACCAGCCTGCTGCTGTGCGA
ACTGCCCCACCCTGCCTTTCTGCTGATCCCCGAGATTGTAATGACGCAGTCTCCAGCGAC
GCTTTCTCTTAGTCCGGGAGAAAGAGCCACACTGTCCTGCCGGGCGTCCCAATCCGGTTC
TAGCTCCTTTCTGTCATGGTATCAACAGAAGCCAGGTCAGGCACCTCGCCTTCTTATTTAC
GGTGCATCCACTCGCGCGACCGGGATTCCTGCAAGATTTTCCGGGTCTGGGTCTGGCACA
GATTTCACGTTGACTATCAGTAGTCTGCAGCCAGAGGATTTCGCAGTCTATTACTGTCAACA
AGACTACAATCTTCCTTTCACGTTTGGTCCCGGAACTAAGGTTGATATAAAAGGAGGCGGA
GGATCTGGCGGAGGGGGCTCTGGAGGAGGAGGATCTGAGGTGCAATTGCTGGAAAGTGG
AGGAGGACTCGTGCAGCCCGGAGGTTCCCTTAGCCTTTCTTGCGCTGCAAGTGGGTTTAC
GTTCTCTATATATGCCATGTCTTGGGTGCGGCAAGCCCCCGGAAAAGGATTGGAATGGGT
ATCTGCCATTAGTGATTCTGGGGGTACGACCTATTATGCAGATAGTGTAAAAGGGAGATTC
ACTATCTCACGCGACAATTCAAAGAATATGCTTTACCTTGAGATGAACAGTCTTCGAGCAGA
GGATACAGCCATATACTATTGCGCTAAACGCACCCGCTACTTCAACGGAATGGATGTATGG
GGACAGGGTACAACAGTTACTGTTTCTAGCGAGTCTAAGTACGGACCGCCCTGCCCCCCT
TGCCCTGGCCAGCCTAGAGAACCCCAGGTGTACACCCTGCCTCCCAGCCAGGAAGAGAT
GACCAAGAACCAGGTGTCCCTGACCTGCCTGGTCAAAGGCTTCTACCCCAGCGATATCGC
CGTGGAATGGGAGAGCAACGGCCAGCCCGAGAACAACTACAAGACCACCCCCCCTGTGC
TGGACAGCGACGGCAGCTTCTTCCTGTACTCCCGGCTGACCGTGGACAAGAGCCGGTGG
CAGGAAGGCAACGTCTTCAGCTGCAGCGTGATGCACGAGGCCCTGCACAACCACTACACC
CAGAAGTCCCTGAGCCTGAGCCTGGGCAAGATGTTCTGGGTGCTGGTGGTGGTCGGAGG
CGTGCTGGCCTGCTACAGCCTGCTGGTCACCGTGGCCTTCATCATCTTTTGGGTGAAACG
GGGCAGAAAGAAACTCCTGTATATATTCAAACAACCATTTATGAGACCAGTACAAACTAC
TCAAGAGGAAGATGGCTGTAGCTGCCGATTCCAGAAGAAGAAGAAGGAGGATGTGAA
CTGCGGGTGAAGTTCAGCAGAAGCGCCGACGCCCCTGCCTACCAGCAGGGCCAGAATCA
GCTGTACAACGAGCTGAACCTGGGCAGAAGGGAAGAGTACGACGTCCTGGATAAGCGGA
GAGGCCGGGACCCTGAGATGGGCGGCAAGCCTCGGCGGAAGAACCCCCAGGAAGGCCT
GTATAACGAACTGCAGAAAGACAAGATGGCCGAGGCCTACAGCGAGATCGGCATGAAGGG
CGAGCGGAGGCGGGGCAAGGGCCACGACGGCCTGTATCAGGGCCTGTCCACCGCCACC
AAGGATACCTACGACGCCCTGCACATGCAGGCCCTGCCCCCAAGGCTCGAGGGCGGCGG
AGAGGGCAGAGGAAGTCTTCTAACATGCGGTGACGTGGAGGAGAATCCAGGCCCTAGGA
TGCCACCTCCAAGACTCCTCTTCTTCCTCCTCTTCCTGACACCAATGGAAGTCAGGCCTG
AGGAACCTCTAGTGGTGAAGGTGGAAGAGGGAGATAACGCTGTGTTACAGTGCCTCAAG
GGAACCTCAGATGGACCCACTCAGCAGCTGACCTGGTCTCGGGAGTCTCCGCTTAAACC
CTTCCTGAAACTCAGCCTTGGACTGCCAGGTCTGGGAATCCACATGAGGCCACTGGCTA
TCTGGCTGTTCATCTTCAACGTCTCTCAACAGATGGGAGGCTTCTACCTGTGTCAGCCTG
GACCACCTTCTGAGAAGGCATGGCAGCCTGGTTGGACAGTCAATGTGGAGGGTTCTGGT
GAGCTGTTCCGGTGGAATGTTTCGGACCTAGGTGGACTGGGATGTGGTCTGAAGAACAG
GTCCTCAGAGGGACCTAGCTCTCCTTCCGGGAAGCTCATGAGCCCCAAGCTGTATGTGT

FIG. 19 cont'd

GGGCCAAAGACCGCCCTGAGATCTGGGAGGGAGAGCCTCCGTGTGTCCCACCGAGGGA
CAGCCTGAACCAGAGCCTCAGCCAGGACCTCACCATGGCCCCTGGCTCCACACTCTGGC
TGTCCTGTGGGGTACCCCCTGACTCTGTGTCCAGGGGCCCCCTCTCCTGGACCCATGTG
CACCCCAAGGGGCCTAAGTCATTGCTGAGCCTAGAGCTGAAGGACGATCGCCCTGCCA
GAGATATGTGGGTAATGGAGACGGGTCTGTTGTTGCCCCGGGCCACAGCTCAAGACGCT
GGAAAGTATTATTGTCACCGTGGCAACCTGACCATGTCATTCCACCTGGAGATCACTGCT
CGGCCAGTACTATGGCACTGGCTGCTGAGGACTGGTGGCTGGAAGGTCTCAGCTGTGAC
TTTGGCTTATCTGATCTTCTGCCTGTGTTCCCTTGTGGGCATTCTTCATCTTCAAAGAGCC
CTGGTCCTGAGGAGGAAAAGATGA (SEQ ID NO: 203)
Within the above sequence, EF1 promoter is the first bold sequence; the sequence encoding
GM-CSFR signal peptide is the first underlined sequence; the sequence encoding 5D12_LvHv
is the first italicized sequence; the sequence encoding IgG4hinge S10P is the second bold
sequence; the sequence encoding IgG4-int(DS) is the second underlined sequence; the
sequence encoding CD28tm is the second italicized sequence; the sequence encoding 4-1BB
signaling is the third bold sequence; the sequence encoding CD3z is the third underlined
sequence; the sequence encoding T2A is the third italicized sequence; and tCD19-Fully
sequenced is the fourth bold sequence section of the sequence.

**CD33:CD22 4D protein (*CD33 signal peptide is in bold and italicized*; 6-histidine tag is
underlined; *3 x glycine linker is italicized, bold, and underlined*; CD33 extracellular domain
is in normal font; the portion of CD22 extracellular domain that contains CD22 domains
defined as Ig-like C2-type 3, Ig-like C2-type 4, Ig-like C2-type 5, Ig-like C2-type 6 is in
bold; CD33 transmembrane domain is double underlined; and *CD33 intracellular domain is
italicized*):**
*MPLLLLLPLLWAGALAM*HHHHHH*GGG*DPNFWLQVQESVTVQEGLCVLVPCTFFHPIPYYDK
NSPVHGYWFREGAIISRDSPVATNKLDQEVQEETQGRFRLLGDPSRNNCSLSIVDARRRDNGS
YFFRMERGSTKYSYKSPQLSVHVTDLTHRPKILIPGTLEPGHSKNLTCSVSWACEQGTPPIFSW
LSAAPTSLGPRTTHSSVLIITPRPQDHGTNLTCQVKFAGAGVTTERTIQLNVTYVPQNPTTGIFP
GDGSGKQETRAGVVH**PEPSTVQILHSPAVEGSQVEFLCMSLANPLPTNYTWYHNGKEMQGR
TEEKVHIPKILPWHAGTYSCVAENILGTGQRGPGAELDVQYPPKKVTTVIQNPMPIREGDTVTL
SCNYNSSNPSVTRYEWKPHGAWEEPSLGVLKIQNVGWDNTTIACAACNSWCSWASPVALN
VQYAPRDVRVRKIKPLSEIHSGNSVSLQCDFSSSHPKEVQFFWEKNGRLLGKESQLNFDSISP
EDAGSYSCWVNNSIGQTASKAWTLEVLYAPRRLRVSMSPGDQVMEGKSATLTCESDANPPV
SHYTWFDWNNQSLPYHSQKLRLEPVKVQHSGAYWCQGTNSVGKGRSPLSTLTVYYSPET**G
AIGGAGVTALLALCLCLIFFIV*KTHRRKAARTAVGRNDTHPTTGSASPKHQKKSKLHGPTETSSC
SGAAPTVEMDEELHYASLNFHGMNPSKDTSTEYSEVRTQ* (SEQ ID NO: 204)

**CD33:CD22 4D nucleotides (*CD33 signal peptide is in bold and italicized*; 6-histidine tag is
underlined; *3 x glycine linker is italicized, bold, and underlined*; CD33 extracellular domain
is in normal font; the portion of CD22 extracellular domain that contains CD22 domains
defined as Ig-like C2-type 3, Ig-like C2-type 4, Ig-like C2-type 5, Ig-like C2-type 6 is in
bold; CD33 transmembrane domain is double underlined; and *CD33 intracellular domain is
italicized*):**
*ATGCCTCTGCTGCTACTGCTACCTCTGCTGTGGGCTGGAGCCCTGGCTATG*CATCATCAC
CACCATCAC*GGCGGCGGC*GATCCAAATTTCTGGCTGCAAGTGCAGGAGTCAGTGACGGTA
CAGGAGGGTTTGTGCGTCCTCGTGCCCTGCACTTTCTTCCATCCCATACCCTACTACGACA
AGAACTCCCCAGTTCATGGTTACTGGTTCCGGGAAGGAGCCATTATATCCAGGGACTCTCC
AGTGGCCACAAACAAGCTAGATCAAGAAGTACAGGAGGAGACTCAGGGCAGATTCCGCCT

FIG. 19 cont'd

CCTTGGGGATCCCAGTAGGAACAACTGCTCCCTGAGCATCGTAGACGCCAGGAGGAGGG
ATAATGGTTCATACTTCTTTCGGATGGAGAGAGGAAGTACCAAATACAGTTACAAATCTCCC
CAGCTCTCTGTGCATGTGACAGACTTGACCCACAGGCCCAAAATCCTCATCCCTGGCACTC
TAGAACCCGGCCACTCCAAAAACCTGACCTGCTCTGTGTCCTGGGCCTGTGAGCAGGGAA
CACCCCCGATCTTCTCCTGGTTGTCAGCTGCCCCCACCTCCCTGGGCCCCAGGACTACTC
ACTCCTCGGTGCTCATAATCACCCCACGGCCCCAGGACCACGGCACCAACCTGACCTGTC
AGGTGAAGTTCGCTGGAGCTGGTGTGACTACGGAGAGAACCATCCAGCTGAACGTCACCT
ATGTTCCACAGAACCCAACAACTGGTATCTTTCCAGGAGATGGCTCAGGGAAACAAGAGAC
CAGAGCAGGAGTGGTTCATCCGGAACCTTCCACGGTTCAGATCCTCCACTCACCGGCTGT
GGAGGGAAGTCAAGTCGAGTTTCTTTGCATGTCACTGGCCAATCCTCTTCCAACAAATTA
CACGTGGTACCACAATGGGAAAGAAATGCAGGGAAGGACAGAGGAGAAAGTCCACATC
CCAAAGATCCTCCCTTGGCACGCTGGGACTTATTCCTGTGTGGCAGAAAACATTCTTGGT
ACTGGACAGAGGGGCCCTGGAGCTGAGCTGGATGTCCAGTATCCTCCCAAGAAGGTGA
CCACAGTGATTCAAAACCCCATGCCGATTCGAGAAGGAGACACAGTGACCCTTTCCTGT
AACTACAATTCCAGTAACCCCAGTGTTACCCGGTATGAATGGAAACCCCATGGCGCCTG
GGAGGAGCCATCGCTTGGGGTGCTGAAGATCCAAAACGTTGGCTGGGACAACACAACC
ATCGCCTGCGCAGCTTGTAATAGTTGGTGCTCGTGGGCCTCCCCTGTCGCCCTGAATGTC
CAGTATGCCCCCCGAGACGTGAGGGTCCGGAAAATCAAGCCCCTTTCCGAGATTCACTC
TGGAAACTCGGTCAGCCTCCAATGTGACTTCTCAAGCAGCCACCCCAAAGAAGTCCAGT
TCTTCTGGGAGAAAAATGGCAGGCTTCTGGGGAAAGAAAGCCAGCTGAATTTTGACTCC
ATCTCCCCAGAAGATGCTGGGAGTTACAGCTGCTGGGTGAACAACTCCATAGGACAGAC
AGCGTCCAAGGCCTGGACACTTGAAGTGCTGTATGCACCCAGGAGGCTGCGTGTGTCCA
TGAGCCCAGGGGACCAAGTGATGGAGGGGAAGAGTGCAACCCTGACCTGTGAGAGCGA
CGCCAACCCTCCCGTCTCCCACTACACCTGGTTTGACTGGAATAACCAAAGCCTCCCCTA
CCACAGCCAGAAGCTGAGATTGGAGCCGGTGAAGGTCCAGCACTCGGGTGCCTACTGG
TGCCAGGGGACCAACAGTGTGGGCAAGGGCCGTTCGCCTCTCAGCACCCTCACCGTCTA
CTATAGCCCGGAGACC<u>GGGGCCATTGGAGGAGCTGGTGTTACAGCCCTGCTCGCTCTTT</u>
<u>GTCTCTGCCTCATCTTCTTCATAGTG</u>*AAGACCCACAGGAGGAAAGCAGCCAGGACAGCAG*
*TGGGCAGGAATGACACCCACCCTACCACAGGGTCAGCCTCCCCGAAACACCAGAAGAAGT*
*CCAAGTTACATGGCCCCACTGAAACCTCAAGCTGTTCAGGTGCCGCCCCTACTGTGGAGA*
*TGGATGAGGAGCTGCATTATGCTTCCCTCAACTTTCATGGGATGAATCCTTCCAAGGACAC*
*CTCCACCGAATACTCAGAGGTCAGGACCCAG* (SEQ ID NO: 205)

CD33:CD22 2D protein *(CD33 signal peptide is in bold and italicized*; <u>6-histidine tag is</u> <u>underlined</u>; *<u>3 x glycine linker is italicized, bold, and underlined</u>*; CD33 extracellular domain is in normal font; the portion of CD22 extracellular domain that contains CD22 domains defined as Ig-like C2-type 5, Ig-like C2-type 6is in bold; <u>CD33 transmembrane domain is</u> <u>double underlined</u>; and *CD33 intracellular domain is italicized*):
*MPLLLLLPLLWAGALAM*<u>HHHHHH</u>*GGG*DPNFWLQVQESVTVQEGLCVLVPCTFFHPIPYYDK
NSPVHGYWFREGAIISRDSPVATNKLDQEVQEETQGRFRLLGDPSRNNCSLSIVDARRRDNGS
YFFRMERGSTKYSYKSPQLSVHVTDLTHRPKILIPGTLEPGHSKNLTCSVSWACEQGTPPIFSW
LSAAPTSLGPRTTHSSVLIITPRPQDHGTNLTCQVKFAGAGVTTERTIQLNVTYVPQNPTTGIFP
GDGSGKQETRAGVVHPRDVRVRKIKPLSEIHSGNSVSLQCDFSSSHPKEVQFFWEKNGRLLG
KESQLNFDSISPEDAGSYSCWVNNSIGQTASKAWTLEVLYAPRRLRVSMSPGDQVMEGKSA
TLTCESDANPPVSHYTWFDWNNQSLPYHSQKLRLEPVKVQHSGAYWCQGTNSVGKGRSPL
STLTVYYSPET<u>GAIGGAGVTALLALCLCLIFFIV</u>*KTHRRKAARTAVGRNDTHPTTGSASPKHQKK*
*SKLHGPTETSSCSGAAPTVEMDEELHYASLNFHGMNPSKDTSTEYSEVRTQ* (SEQ ID NO:
206)

FIG. 19 cont'd

CD33:CD22 2D nucleotides *(CD33 signal peptide is in bold and italicized*; <u>6-histidine tag is underlined</u>; *<u>3 x glycine linker is italicized, bold, and underlined</u>*; CD33 extracellular domain is in normal font; the portion of CD22 extracellular domain that contains CD22 domains defined as Ig-like C2-type 5, Ig-like C2-type 6is in bold; <u>CD33 transmembrane domain is double underlined</u>; and *CD33 intracellular domain is italicized)*:

*ATGCCTCTGCTGCTACTGCTACCTCTGCTGTGGGCTGGAGCCCTGGCTATG*<u>CATCATCAC CACCATCAC</u>*<u>GGCGGCGGC</u>*GATCCAAATTTCTGGCTGCAAGTGCAGGAGTCAGTGACGGTA CAGGAGGGTTTGTGCGTCCTCGTGCCCTGCACTTTCTTCCATCCCATACCCTACTACGACA AGAACTCCCCAGTTCATGGTTACTGGTTCCGGGAAGGAGCCATTATATCCAGGGACTCTCC AGTGGCCACAAACAAGCTAGATCAAGAAGTACAGGAGGAGACTCAGGGCAGATTCCGCCT CCTTGGGGATCCCAGTAGGAACAACTGCTCCCTGAGCATCGTAGACGCCAGGAGGAGGG ATAATGGTTCATACTTCTTTCGGATGGAGAGAGGAAGTACCAAATACAGTTACAAATCTCCC CAGCTCTCTGTGCATGTGACAGACTTGACCCACAGGCCCAAAATCCTCATCCCTGGCACTC TAGAACCCGGCCACTCCAAAAACCTGACCTGCTCTGTGTCCTGGGCCTGTGAGCAGGGAA CACCCCCGATCTTCTCCTGGTTGTCAGCTGCCCCCACCTCCCTGGGCCCCAGGACTACTC ACTCCTCGGTGCTCATAATCACCCCACGGCCCCAGGACCACGGCACCAACCTGACCTGTC AGGTGAAGTTCGCTGGAGCTGGTGTGACTACGGAGAGAACCATCCAGCTGAACGTCACCT ATGTTCCACAGAACCCAACAACTGGTATCTTTCCAGGAGATGGCTCAGGGAAACAAGAGAC CAGAGCAGGAGTGGTTCATCCCCGAGACGTGAGGGTCCGGAAAATCAAGCCCCTTTCCG AGATTCACTCTGGAAACTCGGTCAGCCTCCAATGTGACTTCTCAAGCAGCCACCCCAAA GAAGTCCAGTTCTTCTGGGAGAAAAATGGCAGGCTTCTGGGGAAAGAAAGCCAGCTGAA TTTTGACTCCATCTCCCCAGAAGATGCTGGGAGTTACAGCTGCTGGGTGAACAACTCCAT AGGACAGACAGCGTCCAAGGCCTGGACACTTGAAGTGCTGTATGCACCCAGGAGGCTG CGTGTGTCCATGAGCCCAGGGGACCAAGTGATGGAGGGGAAGAGTGCAACCCTGACCT GTGAGAGCGACGCCAACCCTCCCGTCTCCCACTACACCTGGTTTGACTGGAATAACCAA AGCCTCCCCTACCACAGCCAGAAGCTGAGATTGGAGCCGGTGAAGGTCCAGCACTCGG GTGCCTACTGGTGCCAGGGGACCAACAGTGTGGGCAAGGGCCGTTCGCCTCTCAGCAC CCTCACCGTCTACTATAGCCCGGAGACC<u>GGGGCCATTGGAGGAGCTGGTGTTACAGCCC TGCTCGCTCTTTGTCTCTGCCTCATCTTCTTCATAGTG</u>AAGACCCACAGGAGGAAAGCAGC *CAGGACAGCAGTGGGCAGGAATGACACCCACCCTACCACAGGGTCAGCCTCCCCGAAAC ACCAGAAGAAGTCCAAGTTACATGGCCCCACTGAAACCTCAAGCTGTTCAGGTGCCGCCC CTACTGTGGAGATGGATGAGGAGCTGCATTATGCTTCCCTCAACTTTCATGGGATGAATCC TTCCAAGGACACCTCCACCGAATACTCAGAGGTCAGGACCCAG* (SEQ ID NO: 207)

CD33 V-set construct (exon 3 and 4 deleted) protein *(CD33 signal peptide is in bold and italicized*; <u>6-histidine tag is underlined</u>; *<u>3 x glycine linker is italicized, bold, and underlined</u>*; CD33 extracellular domain lacking CD33 amino acids 140-232 is in normal font; <u>CD33 transmembrane domain is double underlined</u>; and *CD33 intracellular domain is italicized)*:

*MPLLLLLPLLWAGALAM*<u>HHHHHH</u>*GGG*DPNFWLQVQESVTVQEGLCVLVPCTFFHPIPYYDK NSPVHGYWFREGAIISRDSPVATNKLDQEVQEETQGRFRLLGDPSRNNCSLSIVDARRRDNGS YFFRMERGSTKYSYKSPQLSVHVTYVPQNPTTGIFPGDGSGKQETRAGVVH<u>GAIGGAGVTALL ALCLCLIFFIVK</u>*THRRKAARTAVGRNDTHPTTGSASPKHQKKSKLHGPTETSSCSGAAPTVEMD EELHYASLNFHGMNPSKDTSTEYSEVRTQ* (SEQ ID NO: 208)

CD33 V-set construct (exon 3 and 4 deleted) nucleotides *(CD33 signal peptide is in bold and italicized*; <u>6-histidine tag is underlined</u>; *<u>3 x glycine linker is italicized, bold, and</u>*

FIG. 19 cont'd

_underlined_; CD33 extracellular domain lacking CD33 amino acids 140-232 is in normal font; CD33 transmembrane domain is double underlined; and _CD33 intracellular domain is italicized_):
_ATGCCTCTGCTGCTACTGCTACCTCTGCTGTGGGCTGGAGCCCTGGCTATG_CATCATCAC CACCATCACGGCGGCGGCGATCCAAATTTCTGGCTGCAAGTGCAGGAGTCAGTGACGGTA CAGGAGGGTTTGTGCGTCCTCGTGCCCTGCACTTTCTTCCATCCCATACCCTACTACGACA AGAACTCCCCAGTTCATGGTTACTGGTTCCGGGAAGGAGCCATTATATCCAGGGACTCTCC AGTGGCCACAAACAAGCTAGATCAAGAAGTACAGGAGGAGACTCAGGGCAGATTCCGCCT CCTTGGGGATCCCAGTAGGAACAACTGCTCCCTGAGCATCGTAGACGCCAGGAGGAGGG ATAATGGTTCATACTTCTTTCGGATGGAGAGAGGAAGTACCAAATACAGTTACAAATCTCCC CAGCTCTCTGTGCATGTGACATATGTTCCACAGAACCCAACAACTGGTATCTTTCCAGGAG ATGGCTCAGGGAAACAAGAGACCAGAGCAGGAGTGGTTCAT<u>GGGGCCATTGGAGGAGCT GGTGTTACAGCCCTGCTCGCTCTTTGTCTCTGCCTCATCTTCTTCATAGTG</u>_AAGACCCACA GGAGGAAAGCAGCCAGGACAGCAGTGGGCAGGAATGACACCCACCCTACCACAGGGTCA GCCTCCCCGAAACACCAGAAGAAGTCCAAGTTACATGGCCCCACTGAAACCTCAAGCTGTT CAGGTGCCGCCCCTACTGTGGAGATGGATGAGGAGCTGCATTATGCTTCCCTCAACTTTCA TGGGATGAATCCTTCCAAGGACACCTCCACCGAATACTCAGAGGTCAGGACCCAG_(SEQ ID NO: 209)

CD33 signal peptide: MPLLLLLPLLWAGALAM (SEQ ID NO: 210)

CD33 signal peptide coding sequence:
ATGCCTCTGCTGCTACTGCTACCTCTGCTGTGGGCTGGAGCCCTGGCTATG (SEQ ID NO: 211)

6-histidine tag coding sequence: CATCATCACCACCATCAC (SEQ ID NO: 212)

3 x glycine linker: GGG

3 x glycine linker coding sequence: GGCGGCGGC

CD33 extracellular domain:
DPNFWLQVQESVTVQEGLCVLVPCTFFHPIPYYDKNSPVHGYWFREGAIISRDSPVATNKLDQ EVQEETQGRFRLLGDPSRNNCSLSIVDARRRDNGSYFFRMERGSTKYSYKSPQLSVHVTDLT HRPKILIPGTLEPGHSKNLTCSVSWACEQGTPPIFSWLSAAPTSLGPRTTHSSVLIITPRPQDHG TNLTCQVKFAGAGVTTERTIQLNVTYVPQNPTTGIFPGDGSGKQETRAGVVH (SEQ ID NO: 213)

CD33 extracellular domain coding sequence:
GATCCAAATTTCTGGCTGCAAGTGCAGGAGTCAGTGACGGTACAGGAGGGTTTGTGCGTC CTCGTGCCCTGCACTTTCTTCCATCCCATACCCTACTACGACAAGAACTCCCCAGTTCATG GTTACTGGTTCCGGGAAGGAGCCATTATATCCAGGGACTCTCCAGTGGCCACAAACAAGC TAGATCAAGAAGTACAGGAGGAGACTCAGGGCAGATTCCGCCTCCTTGGGGATCCCAGTA GGAACAACTGCTCCCTGAGCATCGTAGACGCCAGGAGGAGGGATAATGGTTCATACTTCT TTCGGATGGAGAGAGGAAGTACCAAATACAGTTACAAATCTCCCCAGCTCTCTGTGCATGT GACAGACTTGACCCACAGGCCCAAAATCCTCATCCCTGGCACTCTAGAACCCGGCCACTC CAAAAACCTGACCTGCTCTGTGTCCTGGGCCTGTGAGCAGGGAACACCCCGATCTTCTC CTGGTTGTCAGCTGCCCCCACCTCCCTGGGCCCCAGGACTACTCACTCCTCGGTGCTCAT AATCACCCCACGGCCCCAGGACCACGGCACCAACCTGACCTGTCAGGTGAAGTTCGCTGG

FIG. 19 cont'd

AGCTGGTGTGACTACGGAGAGAACCATCCAGCTGAACGTCACCTATGTTCCACAGAACCC
AACAACTGGTATCTTTCCAGGAGATGGCTCAGGGAAACAAGAGACCAGAGCAGGAGTGGT
TCAT (SEQ ID NO: 214)

CD33 extracellular domain lacking CD33 amino acids 140-232:
DPNFWLQVQESVTVQEGLCVLVPCTFFHPIPYYDKNSPVHGYWFREGAIISRDSPVATNKLDQ
EVQEETQGRFRLLGDPSRNNCSLSIVDARRRDNGSYFFRMERGSTKYSYKSPQLSVHVTYVP
QNPTTGIFPGDGSGKQETRAGVVH (SEQ ID NO: 215)

CD33 extracellular domain lacking CD33 amino acids 140-232 coding sequence:
GATCCAAATTTCTGGCTGCAAGTGCAGGAGTCAGTGACGGTACAGGAGGGTTTGTGCGTC
CTCGTGCCCTGCACTTTCTTCCATCCCATACCCTACTACGACAAGAACTCCCCAGTTCATG
GTTACTGGTTCCGGGAAGGAGCCATTATATCCAGGGACTCTCCAGTGGCCACAAACAAGC
TAGATCAAGAAGTACAGGAGGAGACTCAGGGCAGATTCCGCCTCCTTGGGGATCCCAGTA
GGAACAACTGCTCCCTGAGCATCGTAGACGCCAGGAGGAGGGATAATGGTTCATACTTCT
TTCGGATGGAGAGAGGAAGTACCAAATACAGTTACAAATCTCCCCAGCTCTCTGTGCATGT
GACATATGTTCCACAGAACCCAACAACTGGTATCTTTCCAGGAGATGGCTCAGGGAAACAA
GAGACCAGAGCAGGAGTGGTTCAT (SEQ ID NO: 216)

CD33 transmembrane domain: GAIGGAGVTALLALCLCLIFFIV (SEQ ID NO: 217)

CD33 transmembrane domain coding sequence:
GGGGCCATTGGAGGAGCTGGTGTTACAGCCCTGCTCGCTCTTTGTCTCTGCCTCATCTTCT
TCATAGTG (SEQ ID NO: 218)

CD33 intracellular domain:
KTHRRKAARTAVGRNDTHPTTGSASPKHQKKSKLHGPTETSSCSGAAPTVEMDEELHYASLN
FHGMNPSKDTSTEYSEVRTQ (SEQ ID NO: 219)

CD33 intracellular domain coding sequence:
AAGACCCACAGGAGGAAAGCAGCCAGGACAGCAGTGGGCAGGAATGACACCCACCCTAC
CACAGGGTCAGCCTCCCCGAAACACCAGAAGAAGTCCAAGTTACATGGCCCCACTGAAAC
CTCAAGCTGTTCAGGTGCCGCCCCTACTGTGGAGATGGATGAGGAGCTGCATTATGCTTC
CCTCAACTTTCATGGGATGAATCCTTCCAAGGACACCTCCACCGAATACTCAGAGGTCAGG
ACCCAG (SEQ ID NO: 220)

Portion of CD22 extracellular domain that contains CD22 domains defined as Ig-like C2-type 3, Ig-like C2-type 4, Ig-like C2-type 5, Ig-like C2-type 6:
PEPSTVQILHSPAVEGSQVEFLCMSLANPLPTNYTWYHNGKEMQGRTEEKVHIPKILPWHAGT
YSCVAENILGTGQRGPGAELDVQYPPKKVTTVIQNPMPIREGDTVTLSCNYNSSNPSVTRYEW
KPHGAWEEPSLGVLKIQNVGWDNTTIACAACNSWCSWASPVALNVQYAPRDVRVRKIKPLSEI
HSGNSVSLQCDFSSSHPKEVQFFWEKNGRLLGKESQLNFDSISPEDAGSYSCWVNNSIGQTA
SKAWTLEVLYAPRRLRVSMSPGDQVMEGKSATLTCESDANPPVSHYTWFDWNNQSLPYHSQ
KLRLEPVKVQHSGAYWCQGTNSVGKGRSPLSTLTVYYSPET (SEQ ID NO: 221)

Portion of CD22 extracellular domain that contains CD22 domains defined as Ig-like C2-type 3, Ig-like C2-type 4, Ig-like C2-type 5, Ig-like C2-type 6 coding sequence:
CCGGAACCTTCCACGGTTCAGATCCTCCACTCACCGGCTGTGGAGGGAAGTCAAGTCGAG

FIG. 19 cont'd

TTTCTTTGCATGTCACTGGCCAATCCTCTTCCAACAAATTACACGTGGTACCACAATGGGAA
AGAAATGCAGGGAAGGACAGAGGAGAAAGTCCACATCCCAAAGATCCTCCCTTGGCACGC
TGGGACTTATTCCTGTGTGGCAGAAAACATTCTTGGTACTGGACAGAGGGGCCCTGGAGC
TGAGCTGGATGTCCAGTATCCTCCCAAGAAGGTGACCACAGTGATTCAAAACCCCATGCC
GATTCGAGAAGGAGACACAGTGACCCTTTCCTGTAACTACAATTCCAGTAACCCCAGTGTT
ACCCGGTATGAATGGAAACCCCATGGCGCCTGGGAGGAGCCATCGCTTGGGGTGCTGAA
GATCCAAAACGTTGGCTGGGACAACACAACCATCGCCTGCGCAGCTTGTAATAGTTGGTG
CTCGTGGGCCTCCCCTGTCGCCCTGAATGTCCAGTATGCCCCCCGAGACGTGAGGGTCC
GGAAAATCAAGCCCCTTTCCGAGATTCACTCTGGAAACTCGGTCAGCCTCCAATGTGACTT
CTCAAGCAGCCACCCCAAAGAAGTCCAGTTCTTCTGGGAGAAAAATGGCAGGCTTCTGGG
GAAAGAAAGCCAGCTGAATTTTGACTCCATCTCCCCAGAAGATGCTGGGAGTTACAGCTGC
TGGGTGAACAACTCCATAGGACAGACAGCGTCCAAGGCCTGGACACTTGAAGTGCTGTAT
GCACCCAGGAGGCTGCGTGTGTCCATGAGCCCAGGGGACCAAGTGATGGAGGGGAAGAG
TGCAACCCTGACCTGTGAGAGCGACGCCAACCCTCCCGTCTCCCACTACACCTGGTTTGA
CTGGAATAACCAAAGCCTCCCCTACCACAGCCAGAAGCTGAGATTGGAGCCGGTGAAGGT
CCAGCACTCGGGTGCCTACTGGTGCCAGGGGACCAACAGTGTGGGCAAGGGCCGTTCGC
CTCTCAGCACCCTCACCGTCTACTATAGCCCGGAGACC (SEQ ID NO: 222)

Portion of CD22 extracellular domain that contains CD22 domains defined as Ig-like C2-type 5, Ig-like C2-type 6:
PRDVRVRKIKPLSEIHSGNSVSLQCDFSSSHPKEVQFFWEKNGRLLGKESQLNFDSISPEDAG
SYSCWVNNSIGQTASKAWTLEVLYAPRRLRVSMSPGDQVMEGKSATLTCESDANPPVSHYT
WFDWNNQSLPYHSQKLRLEPVKVQHSGAYWCQGTNSVGKGRSPLSTLTVYYSPET (SEQ ID
NO: 223)

Portion of CD22 extracellular domain that contains CD22 domains defined as Ig-like C2-type 5, Ig-like C2-type 6 coding sequence:
CCCCGAGACGTGAGGGTCCGGAAAATCAAGCCCCTTTCCGAGATTCACTCTGGAAACTCG
GTCAGCCTCCAATGTGACTTCTCAAGCAGCCACCCCAAAGAAGTCCAGTTCTTCTGGGAGA
AAAATGGCAGGCTTCTGGGGAAAGAAAGCCAGCTGAATTTTGACTCCATCTCCCCAGAAGA
TGCTGGGAGTTACAGCTGCTGGGTGAACAACTCCATAGGACAGACAGCGTCCAAGGCCTG
GACACTTGAAGTGCTGTATGCACCCAGGAGGCTGCGTGTGTCCATGAGCCCAGGGGACCA
AGTGATGGAGGGGAAGAGTGCAACCCTGACCTGTGAGAGCGACGCCAACCCTCCCGTCT
CCCACTACACCTGGTTTGACTGGAATAACCAAAGCCTCCCCTACCACAGCCAGAAGCTGA
GATTGGAGCCGGTGAAGGTCCAGCACTCGGGTGCCTACTGGTGCCAGGGGACCAACAGT
GTGGGCAAGGGCCGTTCGCCTCTCAGCACCCTCACCGTCTACTATAGCCCGGAGACC
(SEQ ID NO: 224)

1H10, 1A9, 1E6, and/or 1B9 light chain signal peptide: MDMRVPAQLLGLLLLWLPGARC
(SEQ ID NO: 225)

1D2 light chain signal peptide: MRVPAQLLGLLLLWLPGARC (SEQ ID NO: 226)

1H8 light chain signal peptide: MDMRLPAQLLGLLMLWVPASRG (SEQ ID NO: 227)

2D3 light chain signal peptide: MEPWKPQHSFFFLLLWLPDSTG (SEQ ID NO: 228)

1H10 heavy chain signal peptide: MDWTWRVFCLLAVAPGVHS (SEQ ID NO: 229)

FIG. 19 cont'd

1A9 heavy chain signal peptide: MELGLSWVFLVAILEGVQC (SEQ ID NO: 230)

1E6 and/or 2E3 heavy chain signal peptide: MEFGLSWVFLVALLRGVQC (SEQ ID NO: 231)

1D2 heavy chain signal peptide: MESGLSWVFLVALLRGVQC (SEQ ID NO: 232)

1B9 heavy chain signal peptide: MEFGLSWVFLIALLRGVQC (SEQ ID NO: 233)

1H8 heavy chain signal peptide: MLLLVTSLLLCELPHPAFLLIP (SEQ ID NO: 234)

2D3 heavy chain signal peptide: MEFGLSWLFLVAILKGVQC (SEQ ID NO: 235)

My96 Coding Sequence:
GAGATCGTGCTGACACAGAGCCCTGGAAGCCTGGCCGTGTCTCCTGGCGAGCGCGTGAC
AATGAGCTGCAAGAGCAGCCAGAGCGTGTTCTTCAGCAGCTCCCAGAAGAACTACCTGGC
CTGGTATCAGCAGATCCCCGGCCAGAGCCCCAGACTGCTGATCTACTGGGCCAGCACCAG
AGAAAGCGGCGTGCCCGATAGATTCACCGGCAGCGGCTCTGGCACCGACTTCACCCTGA
CAATCAGCAGCGTGCAGCCCGAGGACCTGGCCATCTACTACTGCCACCAGTACCTGAGCA
GCCGGACCTTTGGCCAGGGCACCAAGCTGGAAATCAAGAGAGGCGGCGGAGGCTCTGGC
GGAGGCGGATCTAGTGGCGGAGGATCTCAGGTGCAGCTGCAGCAGCCTGGCGCCGAGGT
CGTGAAACCTGGCGCCTCTGTGAAGATGTCCTGCAAGGCCAGCGGCTACACCTTCACCAG
CTACTACATCCACTGGATCAAGCAGACCCCTGGACAGGGCCTGGAATGGGTGGGAGTGAT
CTACCCCGGCAACGACGACATCAGCTACAACCAGAAGTTCCAGGGCAAGGCCACCCTGAC
CGCCGACAAGTCTAGCACCACCGCCTACATGCAGCTGTCCAGCCTGACCAGCGAGGACA
GCGCCGTGTACTACTGCGCCAGAGAAGTGCGGCTGCGGTACTTCGATGTGTGGGGCCAG
GGAACCACCGTGACCGTGTCATCT (SEQ ID NO: 236)

My96_int_41BB_3z_TCD19 Coding Sequence:
GTTAGACCAGATCTGAGCCTGGGAGCTCTCTGGCTAACTAGGGAACCCACTGCTTAAGCC
TCAATAAAGCTTGCCTTGAGTGCTTCAAGTAGTGTGTGCCCGTCTGTTGTGTGACTCTGGT
AACTAGAGATCCCTCAGACCCTTTTAGTCAGTGTGGAAAATCTCTAGCAGTGGCGCCCGAA
CAGGGACTTGAAAGCGAAAGGGAAACCAGAGGAGCTCTCTCGACGCAGGACTCGGCTTG
CTGAAGCGCGCACGGCAAGAGGCGAGGGGCGGCGACTGGTGAGTACGCCAAAAATTTTG
ACTAGCGGAGGCTAGAAGGAGAGAGATGGGTGCGAGAGCGTCAGTATTAAGCGGGGGAG
AATTAGATCGATGGGAAAAAATTCGGTTAAGGCCAGGGGGAAAGAAAAAATATAAATTAAA
ACATATAGTATGGGCAAGCAGGGAGCTAGAACGATTCGCAGTTAATCCTGGCCTGTTAGAA
ACATCAGAAGGCTGTAGACAAATACTGGGACAGCTACAACCATCCCTTCAGACAGGATCAG
AAGAACTTAGATCATTATATAATACAGTAGCAACCCTCTATTGTGTGCATCAAAGGATAGAG
ATAAAAGACACCAAGGAAGCTTTAGACAAGATAGAGGAAGAGCAAAACAAAAGTAAGAAAA
AAGCACAGCAAGCAGCAGCTGACACAGGACACAGCAATCAGGTCAGCCAAAATTACCCTA
TAGTGCAGAACATCCAGGGGCAAATGGTACATCAGGCCATATCACCTAGAACTTTAAATGC
ATGGGTAAAAGTAGTAGAAGAGAAGGCTTTCAGCCCAGAAGTGATACCCATGTTTTCAGCA
TTATCAGAAGGAGCCACCCCACAAGATTTAAACACCATGCTAAACACAGTGGGGGGACATC
AAGCAGCCATGCAAATGTTAAAAGAGACCATCAATGAGGAAGCTGCAGGCAAAGAGAAGA
GTGGTGCAGAGAGAAAAAAGAGCAGTGGGAATAGGAGCTTTGTTCCTTGGGTTCTTGGGA
GCAGCAGGAAGCACTATGGGCGCAGCGTCAATGACGCTGACGGTACAGGCCAGACAATTA
TTGTCTGGTATAGTGCAGCAGCAGAACAATTTGCTGAGGGCTATTGAGGCGCAACAGCATC

FIG. 19 cont'd

```
TGTTGCAACTCACAGTCTGGGGGCATCAAGCAGCTCCAGGCAAGAATCCTGGCTGTGGAAA
GATACCTAAAGGATCAACAGCTCCTGGGGATTTGGGGTTGCTCTGGAAAACTCATTTGCAC
CACTGCTGTGCCTTGGATCTACAAATGGCAGTATTCATCCACAATTTTAAAAGAAAAGGGG
GGATTGGGGGGTACAGTGCAGGGGAAAGAATAGTAGACATAATAGCAACAGACATACAAA
CTAAAGAATTACAAAAACAAATTACAAAAATTCAAAATTTTCGGGTTTATTACAGGGACAGCA
GAGATCCAGTTTGGGGATCAATTGCATGAAGAATCTGCTTAGGGTTAGGCGTTTTGCGCTG
CTTCGCGAGGATCTGCGATCGCTCCGGTGCCCGTCAGTGGGCAGAGCGCACATCGCCCA
CAGTCCCCGAGAAGTTGGGGGGGAGGGGTCGGCAATTGAACCGGTGCCTAGAGAAGGTGG
CGCGGGGTAAACTGGGAAAGTGATGTCGTGTACTGGCTCCGCCTTTTTCCCGAGGGTGGG
GGAGAACCGTATATAAGTGCAGTAGTCGCCGTGAACGTTCTTTTTCGCAACGGGTTTGCCG
CCAGAACACAGCTGAAGCTTCGAGGGGCTCGCATCTCTCCTTCACGCGCCCGCCGCCCTA
CCTGAGGCCGCCATCCACGCCGGTTGAGTCGCGTTCTGCCGCCTCCCGCCTGTGGTGCC
TCCTGAACTGCGTCCGCCGTCTAGGTAAGTTTAAAGCTCAGGTCGAGACCGGGCCTTTGT
CCGGCGCTCCCTTGGAGCCTACCTAGACTCAGCCGGCTCTCCACGCTTTGCCTGACCCTG
CTTGCTCAACTCTACGTCTTTGTTTCGTTTTCTGTTCTGCGCCGTTACAGATCCAAGCTGTG
ACCGGCGCCTACGGCTAGCCACCATGCTGCTGCTCGTGACCAGCCTGCTGCTGTGCGAA
CTGCCCCACCCTGCCTTTCTGCTGATCCCCGAGATCGTGCTGACACAGAGCCCTGGAAGC
CTGGCCGTGTCTCCTGGCGAGCGCGTGACAATGAGCTGCAAGAGCAGCCAGAGCGTGTT
CTTCAGCAGCTCCCAGAAGAACTACCTGGCCTGGTATCAGCAGATCCCCGGCCAGAGCCC
CAGACTGCTGATCTACTGGGCCAGCACCAGAGAAAGCGGCGTGCCCGATAGATTCACCGG
CAGCGGCTCTGGCACCGACTTCACCCTGACAATCAGCAGCGTGCAGCCCGAGGACCTGG
CCATCTACTACTGCCACCAGTACCTGAGCAGCCGGACCTTTGGCCAGGGCACCAAGCTGG
AAATCAAGAGAGGCGGCGGAGGCTCTGGCGGAGGCGGATCTAGTGGCGGAGGATCTCAG
GTGCAGCTGCAGCAGCCTGGCGCCGAGGTCGTGAAACCTGGCGCCTCTGTGAAGATGTC
CTGCAAGGCCAGCGGCTACACCTTCACCAGCTACTACATCCACTGGATCAAGCAGACCCC
TGGACAGGGCCTGGAATGGGTGGGAGTGATCTACCCCGGCAACGACGACATCAGCTACA
ACCAGAAGTTCCAGGGCAAGGCCACCCTGACCGCCGACAAGTCTAGCACCACCGCCTACA
TGCAGCTGTCCAGCCTGACCAGCGAGGACAGCGCCGTGTACTACTGCGCCAGAGAAGTG
CGGCTGCGGTACTTCGATGTGTGGGGCCAGGGAACCACCGTGACCGTGTCATCTGAGTCT
AAGTACGGACCGCCCTGCCCCCCTTGCCCTATGTTCTGGGTGCTGGTGGTGGTCGGAGG
CGTGCTGGCCTGCTACAGCCTGCTGGTCACCGTGGCCTTCATCATCTTTTGGGTGAAACG
GGGCAGAAAGAAACTCCTGTATATATTCAAACAACCATTTATGAGACCAGTACAAACTACTC
AAGAGGAAGATGGCTGTAGCTGCCGATTTCCAGAAGAAGAAGAAGGAGGATGTGAACTGC
GGGTGAAGTTCAGCAGAAGCGCCGACGCCCCTGCCTACCAGCAGGGCCAGAATCAGCTG
TACAACGAGCTGAACCTGGGCAGAAGGGAAGAGTACGACGTCCTGGATAAGCGGAGAGG
CCGGGACCCTGAGATGGGCGGCAAGCCTCGGCGGAAGAACCCCCAGGAAGGCCTGTATA
ACGAACTGCAGAAAGACAAGATGGCCGAGGCCTACAGCGAGATCGGCATGAAGGGCGAG
CGGAGGCGGGGCAAGGGCCACGACGGCCTGTATCAGGGCCTGTCCACCGCCACCAAGG
ATACCTACGACGCCCTGCACATGCAGGCCCTGCCCCCAAGGCTCGAGGGCGGCGGAGAG
GGCAGAGGAAGTCTTCTAACATGCGGTGACGTGGAGGAGAATCCAGGCCCTAGGATGCCA
CCTCCAAGACTCCTCTTCTTCCTCCTCTTCCTGACACCAATGGAAGTCAGGCCTGAGGAAC
CTCTAGTGGTGAAGGTGGAAGAGGGAGATAACGCTGTGTTACAGTGCCTCAAGGGAACCT
CAGATGGACCCACTCAGCAGCTGACCTGGTCTCGGGAGTCTCCGCTTAAACCCTTCCTGA
AACTCAGCCTTGGACTGCCAGGTCTGGGAATCCACATGAGGCCACTGGCTATCTGGCTGT
TCATCTTCAACGTCTCTCAACAGATGGGAGGCTTCTACCTGTGTCAGCCTGGACCACCTTC
TGAGAAGGCATGGCAGCCTGGTTGGACAGTCAATGTGGAGGGTTCTGGTGAGCTGTTCCG
GTGGAATGTTTCGGACCTAGGTGGACTGGGATGTGGTCTGAAGAACAGGTCCTCAGAGGG
ACCTAGCTCTCCTTCCGGGAAGCTCATGAGCCCCAAGCTGTATGTGTGGGCCAAAGACCG
```

FIG. 19 cont'd

```
CCCTGAGATCTGGGAGGGAGAGCCTCCGTGTGTCCCACCGAGGGACAGCCTGAACCAGA
GCCTCAGCCAGGACCTCACCATGGCCCCTGGCTCCACACTCTGGCTGTCCTGTGGGGTAC
CCCCTGACTCTGTGTCCAGGGGCCCCCTCTCCTGGACCCATGTGCACCCCAAGGGGCCTA
AGTCATTGCTGAGCCTAGAGCTGAAGGACGATCGCCCTGCCAGAGATATGTGGGTAATGG
AGACGGGTCTGTTGTTGCCCCGGGCCACAGCTCAAGACGCTGGAAAGTATTATTGTCACC
GTGGCAACCTGACCATGTCATTCCACCTGGAGATCACTGCTCGGCCAGTACTATGGCACT
GGCTGCTGAGGACTGGTGGCTGGAAGGTCTCAGCTGTGACTTTGGCTTATCTGATCTTCT
GCCTGTGTTCCCTTGTGGGCATTCTTCATCTTCAAAGAGCCCTGGTCCTGAGGAGGAAAAG
ATGAGCGGCCGCTCTAGACCCGGGCTGCAGGAATTCGATATCAAGCTTATCGATAATCAAC
CTCTGGATTACAAAATTTGTGAAAGATTGACTGGTATTCTTAACTATGTTGCTCCTTTTACGC
TATGTGGATACGCTGCTTTAATGCCTTTGTATCATGCTATTGCTTCCCGTATGGCTTTCATTT
TCTCCTCCTTGTATAAATCCTGGTTGCTGTCTCTTTATGAGGAGTTGTGGCCCGTTGTCAG
GCAACGTGGCGTGGTGTGCACTGTGTTTGCTGACGCAACCCCCACTGGTTGGGGCATTGC
CACCACCTGTCAGCTCCTTTCCGGGACTTTCGCTTTCCCCCTCCCTATTGCCACGGCGGAA
CTCATCGCCGCCTGCCTTGCCCGCTGCTGGACAGGGGCTCGGCTGTTGGGCACTGACAA
TTCCGTGGTGTTGTCGGGGAAATCATCGTCCTTTCCTTGGCTGCTCGCCTGTGTTGCCACC
TGGATTCTGCGCGGGACGTCCTTCTGCTACGTCCCTTCGGCCCTCAATCCAGCGGACCTT
CCTTCCCGCGGCCTGCTGCCGGCTCTGCGGCCTCTTCCGCGTCTTCGCCTTCGCCCTCAG
ACGAGTCGGATCTCCCTTTGGGCCGCCTCCCCGCATCGATACCGTCGACTAGCCGTACCT
TTAAGACCAATGACTTACAAGGCAGCTGTAGATCTTAGCCACTTTTTAAAAGAAAAGGGGG
GACTGGAAGGGCTAATTCACTCCCAAAGAAGACAAGATCTGCTTTTTGCCTGTACTGGGTC
TCTCTGGTTAGACCAGATCTGAGCCTGGGAGCTCTCTGGCTAACTAGGGAACCCACTGCTT
AAGCCTCAATAAAGCTTGCCTTGAGTGCTTCAAGTAGTGTGTGCCCGTCTGTTGTGTGACT
CTGGTAACTAGAGATCCCTCAGACCCTTTTAGTCAGTGTGGAAAATCTCTAGCAGAATTCG
ATATCAAGCTTATCGATACCGTCGACCTCGAGGGGGGGCCCGGTACCCAATTCGCCCTAT
AGTGAGTCGTATTACAATTCACTGGCCGTCGTTTTACAACGTCGTGACTGGGAAAACCCTG
GCGTTACCCAACTTAATCGCCTTGCAGCACATCCCCCTTTCGCCAGCTGGCGTAATAGCGA
AGAGGCCCGCACCGATCGCCCTTCCCAACAGTTGCGCAGCCTGAATGGCGAATGGAAATT
GTAAGCGTTAATATTTTGTTAAAATTCGCGTTAAATTTTTGTTAAATCAGCTCATTTTTTAACC
AATAGGCCGAAATCGGCAAAATCCCTTATAAATCAAAAGAATAGACCGAGATAGGGTTGAG
TGTTGTTCCAGTTTGGAACAAGAGTCCACTATTAAAGAACGTGGACTCCAACGTCAAAGGG
CGAAAAACCGTCTATCAGGGCGATGGCCCACTACGTGAACCATCACCCTAATCAAGTTTTT
TGGGGTCGAGGTGCCGTAAAGCACTAAATCGGAACCCTAAAGGGAGCCCCCGATTTAGAG
CTTGACGGGGAAAGCCGGCGAACGTGGCGAGAAAGGAAGGGAAGAAAGCGAAAGGAGC
GGGCGCTAGGGCGCTGGCAAGTGTAGCGGTCACGCTGCGCGTAACCACCACACCCGCCG
CGCTTAATGCGCCGCTACAGGGCGCGTCAGGTGGCACTTTTCGGGGAAATGTGCGCGGA
ACCCCTATTTGTTTATTTTTCTAAATACATTCAAATATGTATCCGCTCATGAGACAATAACCC
TGATAAATGCTTCAATAATATTGAAAAAGGAAGAGTATGAGTATTCAACATTTCCGTGTCGC
CCTTATTCCCTTTTTTGCGGCATTTTGCCTTCCTGTTTTTGCTCACCCAGAAACGCTGGTGA
AAGTAAAAGATGCTGAAGATCAGTTGGGTGCACGAGTGGGTTACATCGAACTGGATCTCAA
CAGCGGTAAGATCCTTGAGAGTTTTCGCCCCGAAGAACGTTTTCCAATGATGAGCACTTTT
AAAGTTCTGCTATGTGGCGCGGTATTATCCCGTATTGACGCCGGGCAAGAGCAACTCGGT
CGCCGCATACACTATTCTCAGAATGACTTGGTTGAGTACTCACCAGTCACAGAAAAGCATC
TTACGGATGGCATGACAGTAAGAGAATTATGCAGTGCTGCCATAACCATGAGTGATAACAC
TGCGGCCAACTTACTTCTGACAACGATCGGAGGACCGAAGGAGCTAACCGCTTTTTTGCAC
AACATGGGGGATCATGTAACTCGCCTTGATCGTTGGGAACCGGAGCTGAATGAAGCCATA
CCAAACGACGAGCGTGACACCACGATGCCTGTAGCAATGGCAACAACGTTGCGCAAACTA
TTAACTGGCGAACTACTTACTCTAGCTTCCCGGCAACAATTAATAGACTGGATGGAGGCGG
```

FIG. 19 cont'd

```
ATAAAGTTGCAGGACCACTTCTGCGCTCGGCCCTTCCGGCTGGCTGGTTTATTGCTGATAA
ATCTGGAGCCGGTGAGCGTGGGTCTCGCGGTATCATTGCAGCACTGGGGCCAGATGGTA
AGCCCTCCCGTATCGTAGTTATCTACACGACGGGGAGTCAGGCAACTATGGATGAACGAA
ATAGACAGATCGCTGAGATAGGTGCCTCACTGATTAAGCATTGGTAACTGTCAGACCAAGT
TTACTCATATATACTTTAGATTGATTTAAAACTTCATTTTTAATTTAAAAGGATCTAGGTGAAG
ATCCTTTTTGATAATCTCATGACCAAAATCCCTTAACGTGAGTTTTCGTTCCACTGAGCGTC
AGACCCCGTAGAAAAGATCAAAGGATCTTCTTGAGATCCTTTTTTTCTGCGCGTAATCTGCT
GCTTGCAAACAAAAAAACCACCGCTACCAGCGGTGGTTTGTTTGCCGGATCAAGAGCTACC
AACTCTTTTTCCGAAGGTAACTGGCTTCAGCAGAGCGCAGATACCAAATACTGTTCTTCTAG
TGTAGCCGTAGTTAGGCCACCACTTCAAGAACTCTGTAGCACCGCCTACATACCTCGCTCT
GCTAATCCTGTTACCAGTGGCTGCTGCCAGTGGCGATAAGTCGTGTCTTACCGGGTTGGA
CTCAAGACGATAGTTACCGGATAAGGCGCAGCGGTCGGGCTGAACGGGGGGTTCGTGCA
CACAGCCCAGCTTGGAGCGAACGACCTACACCGAACTGAGATACCTACAGCGTGAGCTAT
GAGAAAGCGCCACGCTTCCCGAAGGGAGAAAGGCGGACAGGTATCCGGTAAGCGGCAGG
GTCGGAACAGGAGAGCGCACGAGGGAGCTTCCAGGGGGAAACGCCTGGTATCTTTATAGT
CCTGTCGGGTTTCGCCACCTCTGACTTGAGCGTCGATTTTGTGATGCTCGTCAGGGGGG
CGGAGCCTATGGAAAAACGCCAGCAACGCGGCCTTTTTACGGTTCCTGGCCTTTTGCTGG
CCTTTTGCTCACATGTTCTTTCCTGCGTTATCCCCTGATTCTGTGGATAACCGTATTACCGC
CTTTGAGTGAGCTGATACCGCTCGCCGCAGCCGAACGACCGAGCGCAGCGAGTCAGTGA
GCGAGGAAGCGGAAGAGCGCCCAATACGCAAACCGCCTCTCCCCGCGCGTTGGCCGATT
CATTAATGCAGCTGGCACGACAGGTTTCCCGACTGGAAAGCGGGCAGTGAGCGCAACGCA
ATTAATGTGAGTTAGCTCACTCATTAGGCACCCCAGGCTTTACACTTTATGCTTCCGGCTCG
TATGTTGTGTGGAATTGTGAGCGGATAACAATTTCACACAGGAAACAGCTATGACCATGATT
ACGCCAAGCTCGAAATTAACCCTCACTAAAGGGAACAAAAGCTGGAGCTCCACCGCGGTG
GCGGCCTCGAGGTCGAGATCCGGTCGACCAGCAACCATAGTCCCGCCCCTAACTCCGCC
CATCCCGCCCCTAACTCCGCCCAGTTCCGCCCATTCTCCGCCCCATGGCTGACTAATTTTT
TTTATTTATGCAGAGGCCGAGGCCGCCTCGGCCTCTGAGCTATTCCAGAAGTAGTGAGGA
GGCTTTTTTGGAGGCCTAGGCTTTTGCAAAAAGCTTCGACGGTATCGATTGGCTCATGTCC
AACATTACCGCCATGTTGACATTGATTATTGACTAGTTATTAATAGTAATCAATTACGGGGT
CATTAGTTCATAGCCCATATATGGAGTTCCGCGTTACATAACTTACGGTAAATGGCCCGCC
TGGCTGACCGCCCAACGACCCCCGCCCATTGACGTCAATAATGACGTATGTTCCCATAGTA
ACGCCAATAGGGACTTTCCATTGACGTCAATGGGTGGAGTATTTACGGTAAACTGCCCACT
TGGCAGTACATCAAGTGTATCATATGCCAAGTACGCCCCCTATTGACGTCAATGACGGTAA
ATGGCCCGCCTGGCATTATGCCCAGTACATGACCTTATGGGACTTTCCTACTTGGCAGTAC
ATCTACGTATTAGTCATCGCTATTACCATGGTGATGCGGTTTTGGCAGTACATCAATGGGC
GTGGATAGCGGTTTGACTCACGGGGATTTCCAAGTCTCCACCCCATTGACGTCAATGGGA
GTTTGTTTTGGCACCAAAATCAACGGGACTTTCCAAAATGTCGTAACAACTCCGCCCCATT
GACGCAAATGGGCGGTAGGCGTGTACGGAATTCGGAGTGGCGAGCCCTCAGATCCTGCA
TATAAGCAGCTGCTTTTTGCCTGTACTGGGTCTCTCTG (SEQ ID NO: 237)
```

V-set directed CD33/CD3 BsAb (RC1) (*Igk leader sequence italicized*; CD33 scFv in bold; *linker is italicized and underlined*; CD3 scFv is in normal text; and His tag is underlined):
*METDTLLLWVLLLWVPGSTG*GQVQLVQSGAEVKKPGESVKVSCKASGYTFTNYGMNWVKQA
PGQGLEWMGWINTYTGEPTYADKFQGRVTMTTDTSTSTAYMEIRNLGGDDTAVYYCARWS
WSDGYYVYFDYWGQGTSVTVSSGGGGSGGGGSGGGGSDIVMTQSPDSLTVSLGERTTINC
KSSQSVLDSSTNKNSLAWYQQKPGQPPKLLLSWASTRESGIPDRFSGSGSGTDFTLTIDSPQ
PEDSATYYCQQSAHFPITFGQGTRLEIK_SGGGGS_EVQLVESGGGLVQPGGSLKLSCAASGFT
FNKYAMNWVRQAPGKGLEWVARIRSKYNNYATYYADSVKDRFTISRDDSKNTAYLQMNNLKT

FIG. 19 cont'd

EDTAVYYCVRHGNFGNSYISYWAYWGQGTLVTVSSGGGGSGGGGSGGGGSQTVVTQEPSL
TVSPGGTVTLTCGSSTGAVTSGNYPNWVQQKPGQAPRGLIGGTKFLAPGTPARFSGSLLGGK
AALTLSGVQPEDEAEYYCVLWYSNRWVFGGGTKLTVL<u>HHHHHH</u> (SEQ ID NO: 254)

V-set directed CD33/CD3 BsAb (RC1) without leader sequence or His tag (CD33 scFv in bold; *linker is italicized and underlined*; CD3 scFv is in normal text):
QVQLVQSGAEVKKPGESVKVSCKASGYTFTNYGMNWVKQAPGQGLEWMGWINTYTGEPTY
ADKFQGRVTMTTDTSTSTAYMEIRNLGGDDTAVYYCARWSWSDGYYVYFDYWGQGTSVTV
SSGGGGSGGGGSGGGGSDIVMTQSPDSLTVSLGERTTINCKSSQSVLDSSTNKNSLAWYQQ
KPGQPPKLLLSWASTRESGIPDRFSGSGSGTDFTLTIDSPQPEDSATYYCQQSAHFPITFGQG
TRLEIK*SGGGGS*EVQLVESGGGLVQPGGSLKLSCAASGFTFNKYAMNWVRQAPGKGLEWVA
RIRSKYNNYATYYADSVKDRFTISRDDSKNTAYLQMNNLKTEDTAVYYCVRHGNFGNSYISYW
AYWGQGTLVTVSSGGGGSGGGGSGGGGSQTVVTQEPSLTVSPGGTVTLTCGSSTGAVTSG
NYPNWVQQKPGQAPRGLIGGTKFLAPGTPARFSGSLLGGKAALTLSGVQPEDEAEYYCVLWY
SNRWVFGGGTKLTVL (SEQ ID NO: 255)

V-set directed CD33 scFv:
QVQLVQSGAEVKKPGESVKVSCKASGYTFTNYGMNWVKQAPGQGLEWMGWINTYTGEPTY
ADKFQGRVTMTTDTSTSTAYMEIRNLGGDDTAVYYCARWSWSDGYYVYFDYWGQGTSVTVS
SGGGGSGGGGSGGGGSDIVMTQSPDSLTVSLGERTTINCKSSQSVLDSSTNKNSLAWYQQK
PGQPPKLLLSWASTRESGIPDRFSGSGSGTDFTLTIDSPQPEDSATYYCQQSAHFPITFGQGT
RLEIK (SEQ ID NO: 256)

V-set directed CD33 scFv coding sequence:
CAAGTTCAGCTCGTGCAGAGTGGTGCAGAGGTCAAGAAGCCTGGAGAGAGCGTCAAGGT
CAGCTGTAAAGCATCTGGCTATACATTCACTAATTACGGAATGAACTGGGTCAAGCAGGCG
CCAGGTCAGGGACTTGAATGGATGGGCTGGATAAACACATATACAGGAGAGCCAACTTAT
GCTGACAAATTCCAGGGTAGAGTCACGATGACGACGGACACATCAACCTCCACCGCGTAT
ATGGAAATCAGGAATTTGGGCGGAGACGATACAGCGGTTTACTACTGCGCCCGATGGAGT
TGGTCTGATGGCTATTATGTGTATTTCGACTACTGGGGTCAGGGTACAAGCGTCACAGTAA
GTTCAGGAGGCGGAGGATCTGGCGGAGGGGGCTCTGGAGGAGGAGGATCTGATATTGTA
ATGACCCAATCCCCTGACTCATTGACAGTATCCCTCGGAGAGCGGACCACTATAAACTGCA
AATCCAGCCAGTCTGTATTGGACTCCAGCACCAACAAAAATAGCCTTGCGTGGTATCAGCA
AAAGCCGGGTCAACCACCCAAGCTGCTCTTGAGTTGGGCGAGTACCAGAGAGAGTGGGAT
ACCCGACAGGTTTAGTGGATCTGGCTCTGGCACCGATTTTACGCTTACAATCGACAGTCCG
CAACCCGAAGACTCCGCGACGTACTACTGTCAGCAATCTGCACACTTTCCAATAACCTTCG
GGCAAGGGACACGGCTGGAGATCAAA (SEQ ID NO: 257)

SEQUENCE LISTING

```
<160> NUMBER OF SEQ ID NOS: 258

<210> SEQ ID NO 1

<400> SEQUENCE: 1

000

<210> SEQ ID NO 2
<211> LENGTH: 786
<212> TYPE: DNA
<213> ORGANISM: Artificial Sequence
<220> FEATURE:
<223> OTHER INFORMATION: 1H10 VH-VL scFv coding sequence

<400> SEQUENCE: 2
atgctgctgc tcgtgaccag cctgctgctg tgcgaactgc cccaccctgc ctttctgctg      60
atcccccaag tacagcttgt tcaaagtggt gctgaagtta aaaagccagg ggccagcgtt     120
aaggtatcct gcaagggaag tggttacatc ttcacatctt acgacatgca ctgggtacga     180
caggctcctg gacagggtct ggaatggatg ggtatcatag acccctcagg aggatctacg     240
agctatgccc aaaaatttca gggaagagta acaatgacca gggacacgtc catgagcaca     300
gtctacatgg aactcagcag tctcagatca gaggatacgg cggtttacta ctgtactagg     360
gattattcat ggagctattt cgactattgg ggacaaggaa ccttggtaac agtgtcttca     420
ggaggcggag gatctggcgg aggggctct ggaggaggag gatctgcgat acaaatgacg     480
caaagtccca gcagtttgtc cgcctcagta ggcgaccgcg ttacgattac gtgtagggcg     540
tctcaaggga tcaggatcta tctgggctgg tatcaacaaa agcctgggaa agccccaaag     600
ctccttatat atgcaacatc atccctgcaa agcggcgttc catcccgatt cagtggttct     660
ggtagcggta cggacttcac tctcacaatc tcatctcttc aaccagaaga ctttgcgacg     720
tattactgtt tgcaagacta caattatcca tggacgttcg gccaaggcac gaaagtcgag     780
ataaag                                                                  786

<210> SEQ ID NO 3
<211> LENGTH: 783
<212> TYPE: DNA
<213> ORGANISM: Artificial Sequence
<220> FEATURE:
<223> OTHER INFORMATION: 1A9 VH-VL scFv coding sequence

<400> SEQUENCE: 3
atgctgctgc tcgtgaccag cctgctgctg tgcgaactgc cccaccctgc ctttctgctg      60
atccccgaag tgcagttggt tgagtctgga ggaggcctgg tacagccggg tggtagtctt     120
```
cggctttcct gtgctgctag cgggtttact ttctccatat acgatatgca ctgggtgagg      180
caagcgaccg aaaaggtct  ggagtgggtc tcagcgatcg gtacagctgg cgatacttac      240
tatgcgggca gtgtcaaggg acgattcacc ataagccgcg aaaacgctaa aaattccctc      300
tacttgcaaa tgaatagcct gcgagcgggg gacaccgccg tatattattg tgctagagag      360
tatagcggat attactttga ctattggggt caaggcactc tggtaacggt gtctagcgga      420
ggcggaggat ctggcggagg gggctctgga ggaggaggat ctgcgattca gatgactcaa      480
tccccctcct ctctctccgc gtccgtaggg gataggggtga caataacttg tagggcgagc      540
caggacatcc gcaatgacct cggctggtat caacaaaaac caggcaaggc acctaagata      600
ctgatttatg gcgcgtcctc cttgcaatcc ggggtgccgt ctcggttcag tggttcaggt      660
agtggtacgg actttacctt cacaatctct agtctgcaac cggaggattt cgctacttac      720
tattgtctcc aggagtataa ttacccctgt acatttgggc aaggcaccaa gttggagata      780
aaa                                                                     783

<210> SEQ ID NO 4
<211> LENGTH: 786
<212> TYPE: DNA
<213> ORGANISM: Artificial Sequence
<220> FEATURE:
<223> OTHER INFORMATION: 1E6 VH-VL scFv coding sequence

<400> SEQUENCE: 4
atgctgctgc tcgtgaccag cctgctgctg tgcgaactgc cccaccctgc ctttctgctg       60
atcccccaag tgcagttggt tgaatccggt ggcggtgtgg ttcaaccagg caggagcttg      120
agactttcat gtgcagcgtc cggctttaca ttctccagct acgacataca ttgggtccgg      180
caggcgccag aaaagggcct cgaatgggtc gcggtaatat ggtacgacgg cagtcataac      240
tactacagtg attctgtaaa aggccgcttt acgatttcac gcgacaacag caagaataca      300
ctctatttgc aaatgaactc tctgcgcgcg aagataccg  ccgtgtatta ttgtgcgcgg      360
gactacagcg ggtcttacta cgactactgg ggccaaggaa cccttgtaac ggtctctagc      420
ggaggcggag gatctggcgg aggggggctct ggaggaggag gatctgcaat acaaatgacg      480
cagtctccta gctcacttt  tgcaagcgtc ggagaccgag ttacaattac gtgtcgggcg      540
agccagggaa ttcggaacga tctcggctgg tatcaacaga aacccggcaa agcgccaaaa      600
ttgcttatat acgcggcatc aaaccttcag agtggtgtgc cgtcaagatt cagtgggtca      660
ggcagcggaa ctgactttac cctgactatc tctagtctcc aacccgagga cttcgcaacg      720
tactattgcc tgcaagatta tcctacccg cgaacgttcg gccaagggac aaaggttgag      780
attaaa                                                                  786

<210> SEQ ID NO 5
<211> LENGTH: 786
<212> TYPE: DNA
<213> ORGANISM: Artificial Sequence
<220> FEATURE:
<223> OTHER INFORMATION: 1D2 VH-VL scFv coding sequence

<400> SEQUENCE: 5
atgctgctgc tcgtgaccag cctgctgctg tgcgaactgc cccaccctgc ctttctgctg       60
atcccccagg tgcagctggt ggaaagcggc ggcggcgtgg tgcagccggg ccgcagcctg      120
cgcctgagct gcgcggcgag cggctttacc tttagcagct atgatattca ttgggtcgcg      180
caggcgccgg gcaaaggcct ggaatgggtg gcggtgattt ggtatgatgg cagccagaaa      240

-continued

```
tattatgcgg atagcgtgaa aggccgcttt accattagcc gcgataacag caaaaacacc    300
ctgtatctgc agatgaacag cctgcgcgcg gaagataccg cggtgtatta ttgcgcgcgc    360
gattatagcg gcagctatta tgattattgg ggccagggca ccctggtgac cgtgagcagc    420
ggaggcggag gatctggcgg aggggctct ggaggaggag gatctgcgat tcagatgacc     480
cagagcccga gcagcctgag cgcgagcgtg ggcgatcgcg tgaccattac ctgccgcgcg    540
agccagggca ttcgcaacga tctgggctgg tatcagcaga aaccgggcaa agcgccggaa    600
ctgctgattt atgcgaccag cagcctgcag agcggcgtgc cgagccgctt tagcggcagc    660
ggcagcggca ccgattttac cctgattatt agcagcctgc agccggaaga ttttgcgacc    720
tattattgcc tgcaggatta tagctatccg cgcacctttg gccagggcac caaagtggaa    780
attaaa                                                               786
```

```
<210> SEQ ID NO 6
<211> LENGTH: 786
<212> TYPE: DNA
<213> ORGANISM: Artificial Sequence
<220> FEATURE:
<223> OTHER INFORMATION: 1B9 VH-VL scFv coding sequence

<400> SEQUENCE: 6
```

```
atgctgctgc tcgtgaccag cctgctgctg tgcgaactgc cccaccctgc ctttctgctg     60
atcccccagg tgcagctggt ggaaagcggc ggcggcgtgg tgcagccggg ccgcagcctg    120
cgcctgagct gcgcggcgag cggctttatt tttagcagct atgatattca ttgggtgcgc    180
caggcgccgg gcaaaggcct ggaatgggtg gcggtgattt ggtatgatgg cagccataac    240
tattatagcg atagcgtgaa aggccgcttt accattagcc gcgataacag caaaaacacc    300
ctgtatctgc agatgaacag cctgcgcgcg gaagataccg cggtgtatta ttgcgcgcgc    360
gattatagcg gcagctattt tgattattgg ggccagggca ccctggtgac cgtgagcagc    420
ggaggcggag gatctggcgg aggggctct ggaggaggag gatctgcgat tcagatgacc     480
cagagcccga gcagcctgag cgcgagcgtg ggcgatcgcg tgaccattac ctgccgcgcg    540
agccaggata ttcgcaacga tctgggctgg tatctgcagc gcccgggcaa agcgccgaaa    600
ctgctgattt atgcggcgag cagcctgcag agcggcgtgc cgagccgctt tagcggcagc    660
ggcagcggca ccgattttac cctgaccatt agcagcctgc agccggaaga ttttgcgacc    720
tattattgcc tgcaggatta tagctatccg cgcacctttg gccagggcac caccgtggaa    780
attaaa                                                               786
```

```
<210> SEQ ID NO 7
<211> LENGTH: 792
<212> TYPE: DNA
<213> ORGANISM: Artificial Sequence
<220> FEATURE:
<223> OTHER INFORMATION: 1H8 VH-VL scFv coding sequence

<400> SEQUENCE: 7
```

```
atgctgctgc tcgtgaccag cctgctgctg tgcgaactgc cccaccctgc ctttctgctg     60
atcccccagg ttcagttggt tgaatcagga ggtggtgttg ttcagcctgg tgggagtctc    120
cgcctttcct gtgcggcatc tggcttcacc ttcggtagtt atgggatgca ttgggtacgc    180
caagcgcctg gcaaaggtct ggaatgggtg gccgtaatat ggtacgatgg atctaatgag    240
tactacgcag actccgtgaa agggagattc actgtatcaa gagataattc taagcacacg    300
```

-continued

```
ttgtatcttc agatgaacag actccgggca gaggacacag cagtttacta ctgtgcgcgg    360
gacctcgatt atgactctag cggggggtgat tactgggggcc aagggatttt ggttctcgta    420
agctctggag gcggaggatc tggcggaggg ggctctggag gaggaggatc tgaaatagtt    480
ttgacccaaa gccccgactt tcagtccgta accectaaag aaaaggtcac tattacctgt    540
agggcttccc aaaacatagg aggcaacctt cactggtatc agcagaagcc ggaccagtcc    600
cctaaattgt tgattaggta tgcgacacag ccttttttcag gcgtcccctc aagattcgga    660
ggctctggtt ctgggactga cttcacccctg actatcaata gtctcgaggc agaagacgcg    720
gccacttatt actgccacca aagtagctcc ctcccactca ctttcggtgg tggcaccaaa    780
gtagagataa ag                                                         792
```

<210> SEQ ID NO 8
<211> LENGTH: 792
<212> TYPE: DNA
<213> ORGANISM: Artificial Sequence
<220> FEATURE:
<223> OTHER INFORMATION: 2D3 VH-VL scFv coding sequence

<400> SEQUENCE: 8

```
atgctgctgc tcgtgaccag cctgctgctg tgcgaactgc cccaccctgc ctttctgctg     60
atccccgagg tgcaattgct ggaaagtgga ggaggactcg tgcagcccgg aggttccctt    120
agcctttctt cgctgcaag tgggtttacg ttctctatat atgccatgtc ttgggtgcgg    180
caagcccccg aaaaggatt ggaatgggta tctgccatta gtgattctgg gggtacgacc    240
tattatgcag atagtgtaaa agggagattc actatctcac gcgacaattc aaagaatatg    300
ctttaccttg agatgaacag tcttcgagca gaggatacag ccatatacta ttgcgctaaa    360
cgcacccgct acttcaacgg aatggatgta tggggacagg gtacaacagt tactgtttct    420
agcggaggcg gaggatctgg cggagggggc tctggaggag gaggatctga gattgtaatg    480
acgcagtctc cagcgacgct ttctcttagt ccgggagaaa gagccacact gtcctgccgg    540
gcgtcccaat ccggttctag ctcctttctg tcatggtatc aacagaagcc aggtcaggca    600
cctcgccttc ttatttacgg tgcatccact cgcgcgaccg ggattcctgc aagattttcc    660
gggtctgggt ctggcacaga tttcacgttg actatcagta gtctgcagcc agaggatttc    720
gcagtctatt actgtcaaca agactacaat cttcctttca cgtttggtcc cggaactaag    780
gttgatataa aa                                                         792
```

<210> SEQ ID NO 9
<211> LENGTH: 801
<212> TYPE: DNA
<213> ORGANISM: Artificial Sequence
<220> FEATURE:
<223> OTHER INFORMATION: 2E3 VH-VL scFv coding sequence

<400> SEQUENCE: 9

```
atgctgctgc tcgtgaccag cctgctgctg tgcgaactgc cccaccctgc ctttctgctg     60
atcccccaag tgtgtctggt cgagagtggt ggaggcgtgg ttcaaccagg aagagcctc    120 cggctctcct gtgcagccag tggatttacc ttttcatcct acggtatgca ctgggtccgc    180
caggcacccg aaaaggact tgaatgggtg gctgtaattt ggtatggtgg ctccaacaaa    240
tactatgcag atagtgtaaa aggtcgcttt actatcagtc gggacaatag caaaaatacc    300
ctctacttgc agatgaatag cttgcggggcc gaggataccg ctgtctacta ctgtgcaaga    360
gatggtaccg gcgaaaacta ttactactac gtaatggatg tctggggaca gggcacgacc    420
```

-continued

```
gttacagtct catccggagg cggaggatct ggcggagggg gctctggagg aggaggatct      480
gagattgtat tgactcaaag tccaggtacc ctctccctta gccccggaga aagagctacg      540
ctcagctgcc gcgcttcaca gtctgtatca tcctcctatc tcgcttggta tcagcagaag      600
cctggtcaag ctcctcgcct tttgatctat ggtacatcca gccgggccac aggcatcccg      660
gatcggtttt ccggtagcgg atctggtacg gattttactc ttacaatttc ccgactcgaa      720
ccagaagact ttgcggtata ttattgtcag caatacggtt cttcaccgac ctttggggga      780
ggcacaaaag tcgagatcaa a                                               801

<210> SEQ ID NO 10
<211> LENGTH: 36
<212> TYPE: DNA
<213> ORGANISM: Artificial Sequence
<220> FEATURE:
<223> OTHER INFORMATION: IgG4 hinge coding sequence-A

<400> SEQUENCE: 10
gagtctaagt acggaccgcc ctgcccccct tgccct                                36

<210> SEQ ID NO 11
<211> LENGTH: 36
<212> TYPE: DNA
<213> ORGANISM: Artificial Sequence
<220> FEATURE:
<223> OTHER INFORMATION: IgG4 hinge coding sequence-B

<400> SEQUENCE: 11
gagtctaagt acggaccgcc ttgcccaccg tgccca                                36

<210> SEQ ID NO 12
<211> LENGTH: 321
<212> TYPE: DNA
<213> ORGANISM: Artificial Sequence
<220> FEATURE:
<223> OTHER INFORMATION: IgG4-int(DS) coding sequence

<400> SEQUENCE: 12
ggccagccta gagaacccca ggtgtacacc ctgcctccca gccaggaaga gatgaccaag       60
aaccaggtgt ccctgacctg cctggtcaaa ggcttctacc ccagcgatat cgccgtggaa      120
tgggagagca cggccagcc cgagaacaac tacaagacca cccccctgt gctggacagc       180 gacggcagct tcttcctgta ctcccggctg accgtggaca gagccggtg gcaggaaggc       240 aacgtcttca gctgcagcgt gatgcacgag gccctgcaca accactacac ccagaagtcc      300
ctgagcctga gcctgggcaa g                                               321

<210> SEQ ID NO 13
<211> LENGTH: 648
<212> TYPE: DNA
<213> ORGANISM: Artificial Sequence
<220> FEATURE:
<223> OTHER INFORMATION: IgG4-long coding sequence

<400> SEQUENCE: 13
gcaccacctg tggcaggacc gtcagtcttc ctcttcccac caaaacccaa ggacaccctg       60
atgatcagcc ggacccccga ggtgacctgc gtggtggtgg acgtgagcca ggaagatccc      120
gaggtccagt tcaattggta cgtggacggc gtggaagtgc acaacgccaa gaccaagccc      180
agagaggaac agttccaaag cacctaccgg gtggtgtctg tgctgaccgt gctgcaccag      240
```

-continued

```
gactggctga acggcaaaga atacaagtgc aaggtgtcca acaagggcct gcccagcagc      300
atcgaaaaga ccatcagcaa ggccaagggc cagcctcgcg agccccaggt gtacaccctg      360
cctccctccc aggaagagat gaccaagaac caggtgtccc tgacctgcct ggtgaagggc      420
ttctacccca gcgacatcgc cgtggagtgg gagagcaacg gccagcctga gaacaactac      480
aagaccaccc ctcccgtgct ggacagcgac ggcagcttct tcctgtacag ccggctgacc      540
gtggacaaga gccggtggca ggaaggcaac gtctttagct gcagcgtgat gcacgaggcc      600
ctgcacaacc actacaccca gaagagcctg agcctgtccc tgggcaag               648
```

```
<210> SEQ ID NO 14
<211> LENGTH: 336
<212> TYPE: DNA
<213> ORGANISM: Artificial Sequence
<220> FEATURE:
<223> OTHER INFORMATION: CD3z coding sequence

<400> SEQUENCE: 14
cgggtgaagt tcagcagaag cgccgacgcc cctgcctacc agcagggcca gaatcagctg       60
tacaacgagc tgaacctggg cagaagggaa gagtacgacg tcctggataa gcggagaggc      120
cgggaccctg agatgggcgg caagcctcgg cggaagaacc cccaggaagg cctgtataac      180
gaactgcaga agacaagat ggccgaggcc tacagcgaga tcggcatgaa gggcgagcgg      240
aggcggggca agggccacga cggcctgtat caggcctgt ccaccgccac caaggatacc      300
tacgacgccc tgcacatgca ggccctgccc ccaagg                              336
```

```
<210> SEQ ID NO 15
<211> LENGTH: 112
<212> TYPE: PRT
<213> ORGANISM: Artificial Sequence
<220> FEATURE:
<223> OTHER INFORMATION: CD3z protein-A

<400> SEQUENCE: 15

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110
```

```
<210> SEQ ID NO 16
<211> LENGTH: 114
<212> TYPE: PRT
<213> ORGANISM: Artificial Sequence
<220> FEATURE:
<223> OTHER INFORMATION: CD3z protein-B

<400> SEQUENCE: 16

Glu Leu Arg Val Lys Phe Ser Arg Ser Ala Asp Ala Pro Ala Tyr Gln
1               5                   10                  15
```

```
Gln Gly Gln Asn Gln Leu Tyr Asn Glu Leu Asn Leu Gly Arg Arg Glu
            20                  25                  30

Glu Tyr Asp Val Leu Asp Lys Arg Arg Gly Arg Asp Pro Glu Met Gly
            35                  40                  45

Gly Lys Pro Arg Arg Lys Asn Pro Gln Glu Gly Leu Tyr Asn Glu Leu
        50                  55                  60

Gln Lys Asp Lys Met Ala Glu Ala Tyr Ser Glu Ile Gly Met Lys Gly
65                  70                  75                  80

Glu Arg Arg Arg Gly Lys Gly His Asp Gly Leu Tyr Gln Gly Leu Ser
                85                  90                  95

Thr Ala Thr Lys Asp Thr Tyr Asp Ala Leu His Met Gln Ala Leu Pro
            100                 105                 110

Pro Arg
```

```
<210> SEQ ID NO 17
<211> LENGTH: 126
<212> TYPE: DNA
<213> ORGANISM: Artificial Sequence
<220> FEATURE:
<223> OTHER INFORMATION: 4-1BB signaling coding sequence-A

<400> SEQUENCE: 17
aaacggggca gaaagaaact cctgtatata ttcaaacaac catttatgag accagtacaa      60
actactcaag aggaagatgg ctgtagctgc cgatttccag aagaagaaga aggaggatgt     120
gaactg                                                                 126
```

```
<210> SEQ ID NO 18
<211> LENGTH: 129
<212> TYPE: DNA
<213> ORGANISM: Artificial Sequence
<220> FEATURE:
<223> OTHER INFORMATION: 4-1BB signaling coding sequence-B

<400> SEQUENCE: 18
gtgaaacggg gcagaaagaa actcctgtat atattcaaac aaccatttat gagaccagta      60
caaactactc aagaggaaga tggctgtagc tgccgatttc agaagaagaa agaaggagga     120
tgtgaactg                                                              129
```

```
<210> SEQ ID NO 19
<211> LENGTH: 43
<212> TYPE: PRT
<213> ORGANISM: Artificial Sequence
<220> FEATURE:
<223> OTHER INFORMATION: 4-1BB protein-a

<400> SEQUENCE: 19

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys Glu Leu
        35                  40
```

```
<210> SEQ ID NO 20
<211> LENGTH: 41
<212> TYPE: PRT
<213> ORGANISM: Artificial Sequence
<220> FEATURE:
<223> OTHER INFORMATION: 4-1BB protein-B
```

<400> SEQUENCE: 20

Val Lys Arg Gly Arg Lys Lys Leu Leu Tyr Ile Phe Lys Gln Pro Phe
1               5                   10                  15

Met Arg Pro Val Gln Thr Thr Gln Glu Glu Asp Gly Cys Ser Cys Arg
            20                  25                  30

Phe Pro Glu Glu Glu Glu Gly Gly Cys
        35                  40

<210> SEQ ID NO 21
<211> LENGTH: 84
<212> TYPE: DNA
<213> ORGANISM: Artificial Sequence
<220> FEATURE:
<223> OTHER INFORMATION: CD28TM coding sequence-A

<400> SEQUENCE: 21
atgttctggg tgctggtggt ggtcggaggc gtgctggcct gctacagcct gctggtcacc      60
gtggccttca tcatcttttg ggtg                                            84

<210> SEQ ID NO 22
<211> LENGTH: 81
<212> TYPE: DNA
<213> ORGANISM: Artificial Sequence
<220> FEATURE:
<223> OTHER INFORMATION: CD28TM coding sequence-B

<400> SEQUENCE: 22
atgttctggg tgctggtggt ggtcggaggc gtgctggcct gctacagcct gctggtcacc      60
gtggccttca tcatcttttg g                                               81

<210> SEQ ID NO 23
<211> LENGTH: 81
<212> TYPE: DNA
<213> ORGANISM: Artificial Sequence
<220> FEATURE:
<223> OTHER INFORMATION: CD28TM coding sequence-C

<400> SEQUENCE: 23
atgttctggg tgctggtggt ggtgggcggg gtgctggcct gctacagcct gctggtgaca      60
gtggccttca tcatcttttg g                                               81

<210> SEQ ID NO 24
<211> LENGTH: 27
<212> TYPE: PRT
<213> ORGANISM: Artificial Sequence
<220> FEATURE:
<223> OTHER INFORMATION: CD28TM protein-A

<400> SEQUENCE: 24

Met Phe Trp Val Leu Val Val Val Gly Gly Val Leu Ala Cys Tyr Ser
1               5                   10                  15

Leu Leu Val Thr Val Ala Phe Ile Ile Phe Trp
            20                  25

<210> SEQ ID NO 25
<211> LENGTH: 26
<212> TYPE: PRT
<213> ORGANISM: Artificial Sequence
<220> FEATURE:
<223> OTHER INFORMATION: CD28TM protein-B

<400> SEQUENCE: 25

```
Phe Trp Val Leu Val Val Val Gly Gly Val Leu Ala Cys Tyr Ser Leu
1               5                   10                  15

Leu Val Thr Val Ala Phe Ile Ile Phe Trp
            20                  25
```

```
<210> SEQ ID NO 26
<211> LENGTH: 972
<212> TYPE: DNA
<213> ORGANISM: Artificial Sequence
<220> FEATURE:
<223> OTHER INFORMATION: tCD19 coding sequence

<400> SEQUENCE: 26
atgccacctc caagactcct cttcttcctc ctcttcctga caccaatgga agtcaggcct        60
gaggaacctc tagtggtgaa ggtggaagag ggagataacg ctgtgttaca gtgcctcaag       120
ggaacctcag atggacccac tcagcagctg acctggtctc gggagtctcc gcttaaaccc       180
ttcctgaaac tcagccttgg actgccaggt ctgggaatcc acatgaggcc actggctatc       240
tggctgttca tcttcaacgt ctctcaacag atgggaggct ctacctgtg tcagcctgga        300 ccaccttctg agaaggcatg gcagcctggt tggacagtca atgtggaggg ttctggtgag       360
ctgttccggt ggaatgtttc ggacctaggt ggactgggat gtggtctgaa gaacaggtcc       420
tcagagggac ctagctctcc ttccgggaag ctcatgagcc ccaagctgta tgtgtgggcc       480
aaagaccgcc ctgagatctg ggagggagag cctccgtgtg tcccaccgag ggacagcctg       540
aaccagagcc tcagccagga cctcaccatg gccctggct ccacactctg gctgtcctgt        600
ggggtacccc ctgactctgt gtccagggc ccctctcct ggacccatgt gcaccccaag         660
gggcctaagt cattgctgag cctagagctg aaggacgatc gccctgccag agatatgtgg       720
gtaatggaga cgggtctgtt gttgccccgg gccacagctc aagacgctgg aaagtattat       780
tgtcaccgtg gcaacctgac catgtcattc cacctggaga tcactgctcg gccagtacta       840
tggcactggc tgctgaggac tggtggctgg aaggtctcag ctgtgacttt ggcttatctg       900
atcttctgcc tgtgttccct tgtgggcatt cttcatcttc aaagagccct ggtcctgagg       960
aggaaaagat ga                                                           972
```

```
<210> SEQ ID NO 27
<211> LENGTH: 72
<212> TYPE: DNA
<213> ORGANISM: Artificial Sequence
<220> FEATURE:
<223> OTHER INFORMATION: T2A coding sequence

<400> SEQUENCE: 27
ctcgagggcg gcggagaggg cagaggaagt cttctaacat gcggtgacgt ggaggagaat        60
ccaggcccta gg                                                            72
```

```
<210> SEQ ID NO 28
<211> LENGTH: 21
<212> TYPE: PRT
<213> ORGANISM: Artificial Sequence
<220> FEATURE:
<223> OTHER INFORMATION: Thoseaasigna Virus 2A (T2A) Peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 28
```

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 29
<211> LENGTH: 22
<212> TYPE: PRT
<213> ORGANISM: Artificial Sequence
<220> FEATURE:
<223> OTHER INFORMATION: Porcine Teschovirus-1 2a (P2A) Peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 29

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 30
<211> LENGTH: 23
<212> TYPE: PRT
<213> ORGANISM: Artificial Sequence
<220> FEATURE:
<223> OTHER INFORMATION: Equine Rhinitis A Virus (E2A) Peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 30

Gly Ser Gly Gln Cys Thr Asn Tyr Ala Leu Leu Lys Leu Ala Gly Asp
1               5                   10                  15

Val Glu Ser Asn Pro Gly Pro
            20

<210> SEQ ID NO 31
<211> LENGTH: 25
<212> TYPE: PRT
<213> ORGANISM: Artificial Sequence
<220> FEATURE:
<223> OTHER INFORMATION: Foot-And-Mouth Disease Virus 2A (F2A) Peptide
<220> FEATURE:
<221> NAME/KEY: MISC_FEATURE
<222> LOCATION: (1)..(3)
<223> OTHER INFORMATION: (GlySerGly) residues can be added to the 5' end
      of the peptide to improve cleavage efficiency

<400> SEQUENCE: 31

Gly Ser Gly Val Lys Gln Thr Leu Asn Phe Asp Leu Leu Lys Leu Ala
1               5                   10                  15

Gly Asp Val Glu Ser Asn Pro Gly Pro
            20                  25

<210> SEQ ID NO 32
<211> LENGTH: 544
<212> TYPE: DNA
<213> ORGANISM: Artificial Sequence
<220> FEATURE:
<223> OTHER INFORMATION: EF1 promoter-A

<400> SEQUENCE: 32

```
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gccttttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctac                                                                544

<210> SEQ ID NO 33
<211> LENGTH: 545
<212> TYPE: DNA
<213> ORGANISM: Artificial Sequence
<220> FEATURE:
<223> OTHER INFORMATION: EF1 promoter-B

<400> SEQUENCE: 33
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gccttttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacg                                                               545

<210> SEQ ID NO 34
<211> LENGTH: 113
<212> TYPE: DNA
<213> ORGANISM: Artificial Sequence
<220> FEATURE:
<223> OTHER INFORMATION: Psi

<400> SEQUENCE: 34
ctcggcttgc tgaagcgcgc acggcaagag gcgaggggcg cgactggtg agtacgccaa       60 aaattttgac tagcggaggc tagaaggaga gagatgggtg cgagagcgtc agt           113

<210> SEQ ID NO 35
<211> LENGTH: 333
<212> TYPE: DNA
<213> ORGANISM: Artificial Sequence
<220> FEATURE:
<223> OTHER INFORMATION: RRE

<400> SEQUENCE: 35
gcaaagagaa gagtggtgca gagagaaaaa agagcagtgg gaataggagc tttgttcctt      60
gggttcttgg gagcagcagg aagcactatg ggcgcagcgt caatgacgct gacggtacag     120
```

-continued

```
gccagacaat tattgtctgg tatagtgcag cagcagaaca atttgctgag ggctattgag      180
gcgcaacagc atctgttgca actcacagtc tggggcatca agcagctcca ggcaagaatc      240
ctggctgtgg aaagatacct aaaggatcaa cagctcctgg ggatttgggg ttgctctgga      300
aaactcattt gcaccactgc tgtgccttgg atc                                   333

<210> SEQ ID NO 36
<211> LENGTH: 179
<212> TYPE: DNA
<213> ORGANISM: Artificial Sequence
<220> FEATURE:
<223> OTHER INFORMATION: Flap

<400> SEQUENCE: 36
tacaaatggc agtattcatc cacaatttta aaagaaaagg ggggattggg gggtacagtg       60 cagggggaaag aatagtagac ataatagcaa cagacataca aactaaagaa ttacaaaaac     120
aaattacaaa aattcaaaat tttcgggttt attacaggga cagcagagat ccagtttgg       179

<210> SEQ ID NO 37
<211> LENGTH: 66
<212> TYPE: DNA
<213> ORGANISM: Artificial Sequence
<220> FEATURE:
<223> OTHER INFORMATION: GM-CSFR encoding sequence

<400> SEQUENCE: 37
atgctgctgc tcgtgaccag cctgctgctg tgcgaactgc cccaccctgc ctttctgctg       60
atcccc                                                                  66

<210> SEQ ID NO 38
<211> LENGTH: 601
<212> TYPE: DNA
<213> ORGANISM: Artificial Sequence
<220> FEATURE:
<223> OTHER INFORMATION: WPRE

<400> SEQUENCE: 38
atcgataatc aacctctgga ttacaaaatt tgtgaaagat tgactggtat tcttaactat       60
gttgctcctt ttacgctatg tggatacgct gctttaatgc ctttgtatca tgctattgct      120
tcccgtatgg ctttcatttt ctcctccttg tataaatcct ggttgctgtc tctttatgag      180
gagttgtggc ccgttgtcag gcaacgtggc gtggtgtgca ctgtgtttgc tgacgcaacc      240
cccactggtt ggggcattgc caccacctgt cagctccttt ccgggacttt cgctttcccc      300
ctccctattg ccacggcgga actcatcgcc gcctgccttg cccgctgctg gacaggggct      360
cggctgttgg cactgacaa ttccgtggtg ttgtcgggga aatcatcgtc ctttccttgg      420
ctgctcgcct gtgttgccac ctggattctg cgcgggacgt ccttctgcta cgtcccttcg      480
gccctcaatc cagcggacct tccttcccgc ggcctgctgc cggctctgcg gcctcttccg      540
cgtcttcgcc ttcgccctca gacgagtcgg atctcccttt gggccgcctc cccgcatcga      600
t                                                                       601

<210> SEQ ID NO 39
<211> LENGTH: 105
<212> TYPE: DNA
<213> ORGANISM: Artificial Sequence
<220> FEATURE:
<223> OTHER INFORMATION: delU3

<400> SEQUENCE: 39
```
gtacctttaa gaccaatgac ttacaaggca gctgtagatc ttagccactt tttaaaagaa      60
aaggggggac tggaagggct aattcactcc caaagaagac aagat                     105

<210> SEQ ID NO 40
<211> LENGTH: 81
<212> TYPE: DNA
<213> ORGANISM: Artificial Sequence
<220> FEATURE:
<223> OTHER INFORMATION: R

<400> SEQUENCE: 40
ctgctttttg cctgtactgg gtctctctgg ttagaccaga tctgagcctg ggagctctct      60
ggctaactag ggaacccact g                                               81

<210> SEQ ID NO 41
<211> LENGTH: 114
<212> TYPE: DNA
<213> ORGANISM: Artificial Sequence
<220> FEATURE:
<223> OTHER INFORMATION: U5

<400> SEQUENCE: 41
cttaagcctc aataaagctt gccttgagtg cttcaagtag tgtgtgcccg tctgttgtgt      60
gactctggta actagagatc cctcagaccc ttttagtcag tgtggaaaat ctct          114

<210> SEQ ID NO 42
<211> LENGTH: 859
<212> TYPE: DNA
<213> ORGANISM: Artificial Sequence
<220> FEATURE:
<223> OTHER INFORMATION: AmpR

<400> SEQUENCE: 42
atgagtattc aacatttccg tgtcgccctt attccctttt ttgcggcatt ttgccttcct      60
gtttttgctc acccagaaac gctggtgaaa gtaaaagatg ctgaagatca gttgggtgca     120
cgagtgggtt acatcgaact ggatctcaac agcggtaaga tccttgagag ttttcgcccc     180
gaagaacgtt ttccaatgat gagcactttt aaagttctgc tatgtggcgc ggtattatcc     240
cgtattgacg ccgggcaaga gcaactcggt cgccgcatac actattctca gaatgacttg     300
gttgagtact caccagtcac agaaaagcat cttacggatg gcatgacagt aagagaatta     360
tgcagtgctg ccataaccat gagtgataac actgcggcca acttacttct gacaacgatc     420
ggaggaccga aggagctaac cgcttttttg cacaacatgg gggatcatgt aactcgcctt     480
gatcgttggg aaccggagct gaatgaagcc ataccaaacg acgagcgtga ccacgatg      540 cctgtagcaa tggcaacaac gttgcgcaaa ctattaactg gcgaactact tactctagct     600
tcccggcaac aattaataga ctggatggag gcggataaag ttgcaggacc acttctgcgc     660
tcggcccttc cggctggctg gtttattgct gataaatctg gagccggtga gcgtgggtct     720
cgcggtatca ttgcagcact ggggccagat ggtaagccct cccgtatcgt agttatctac     780
acgacgggga gtcaggcaac tatggatgaa cgaaatagac agatcgctga gataggtgcc     840
tcactgatta agcattggt                                                  859

<210> SEQ ID NO 43
<211> LENGTH: 882
<212> TYPE: DNA
<213> ORGANISM: Artificial Sequence
<220> FEATURE:

<223> OTHER INFORMATION: CoE1 origin

<400> SEQUENCE: 43
aaaaggatct aggtgaagat cctttttgat aatctcatga ccaaaatccc ttaacgtgag        60
ttttcgttcc actgagcgtc agaccccgta gaaaagatca aaggatcttc ttgagatcct       120
ttttttctgc gcgtaatctg ctgcttgcaa acaaaaaaac caccgctacc agcggtggtt       180
tgtttgccgg atcaagagct accaactctt tttccgaagg taactggctt cagcagagcg       240
cagataccaa atactgttct tctagtgtag ccgtagttag gccaccactt caagaactct       300
gtagcaccgc ctacatacct cgctctgcta atcctgttac cagtggctgc tgccagtggc       360
gataagtcgt gtcttaccgg gttggactca agacgatagt taccggataa ggcgcagcgg       420
tcgggctgaa cggggggttc gtgcacacag cccagcttgg agcgaacgac ctacaccgaa       480
ctgagatacc tacagcgtga gctatgagaa agcgccacgc ttcccgaagg agaaaggcg       540 gacaggtatc cggtaagcgg cagggtcgga acaggagagc gcacgaggga gcttccaggg       600
ggaaacgcct ggtatcttta tagtcctgtc gggtttcgcc acctctgact tgagcgtcga       660
tttttgtgat gctcgtcagg gggcggagc ctatggaaaa acgccagcaa cgcggccttt       720
ttacggttcc tggccttttg ctggcctttt gctcacatgt tctttcctgc gttatcccct       780
gattctgtgg ataaccgtat taccgccttt gagtgagctg ataccgctcg ccgcagccga       840
acgaccgagc gcagcgagtc agtgagcgag gaagcggaag ag                          882

<210> SEQ ID NO 44
<211> LENGTH: 200
<212> TYPE: DNA
<213> ORGANISM: Artificial Sequence
<220> FEATURE:
<223> OTHER INFORMATION: SV40

<400> SEQUENCE: 44
ggtcgagatc cggtcgacca gcaaccatag tcccgcccct aactccgccc atcccgcccc        60
taactccgcc cagttccgcc cattctccgc cccatggctg actaattttt tttatttatg       120
cagaggccga ggccgcctcg gcctctgagc tattccagaa gtagtgagga ggcttttttg       180
gaggcctagg cttttgcaaa                                                    200

<210> SEQ ID NO 45
<211> LENGTH: 600
<212> TYPE: DNA
<213> ORGANISM: Artificial Sequence
<220> FEATURE:
<223> OTHER INFORMATION: CMV

<400> SEQUENCE: 45
atcgattggc tcatgtccaa cattaccgcc atgttgacat tgattattga ctagttatta        60
atagtaatca attacggggt cattagttca tagcccatat atggagttcc gcgttacata       120
acttacggta aatggcccgc ctggctgacc gcccaacgac ccccgcccat tgacgtcaat       180
aatgacgtat gttcccatag taacgccaat agggactttc cattgacgtc aatgggtgga       240
gtatttacgg taaactgccc acttggcagt acatcaagtg tatcatatgc caagtacgcc       300
ccctattgac gtcaatgacg gtaaatggcc cgcctggcat tatgcccagt acatgacctt       360
atgggacttt cctacttggc agtacatcta cgtattagtc atcgctatta ccatggtgat       420
gcggttttgg cagtacatca atgggcgtgg atagcggttt gactcacggg gatttccaag       480
tctccacccc attgacgtca atgggagttt gttttggcac caaaatcaac gggactttcc       540
aaaatgtcgt aacaactccg ccccattgac gcaaatgggc ggtaggcgtg tacggaattc          600

<210> SEQ ID NO 46
<211> LENGTH: 3288
<212> TYPE: DNA
<213> ORGANISM: Artificial Sequence
<220> FEATURE:
<223> OTHER INFORMATION: 1H10-intDS-41bb-3z-T-CD19t Top Strand

<400> SEQUENCE: 46
ggatctgcga tcgctccggt gcccgtcagt gggcagagcg cacatcgccc acagtccccg           60
agaagttggg gggaggggtc ggcaattgaa ccggtgccta gagaaggtgg cgcggggtaa          120
actgggaaag tgatgtcgtg tactggctcc gccttttttcc cgagggtggg ggagaaccgt          180
atataagtgc agtagtcgcc gtgaacgttc tttttcgcaa cgggtttgcc gccagaacac          240
agctgaagct tcgaggggct cgcatctctc cttcacgcgc ccgccgccct acctgaggcc          300
gccatccacg ccggttgagt cgcgttctgc cgcctcccgc ctgtggtgcc tcctgaactg          360
cgtccgccgt ctaggtaagt ttaaagctca ggtcgagacc gggcctttgt ccggcgctcc          420
cttggagcct acctagactc agccggctct ccacgctttg cctgaccctg cttgctcaac          480
tctacgtctt tgtttcgttt tctgttctgc gccgttacag atccaagctg tgaccggcgc          540
ctacggctag ccaccatgct gctgctcgtg accagcctgc tgctgtgcga actgccccac          600
cctgcctttc tgctgatccc ccaagtacag cttgttcaaa gtggtgctga agttaaaaag          660 ccagggggcca gcgttaaggt atcctgcaag ggaagtggtt acatcttcac atcttacgac          720
atgcactggg tacgacaggc tcctggacag ggtctggaat ggatgggtat catagacccc          780
tcaggaggat ctacgagcta tgcccaaaaa tttcagggaa gagtaacaat gaccagggac          840
acgtccatga gcacagtcta catggaactc agcagtctca gatcagagga tacggcggtt          900
tactactgta ctaggggatta ttcatggagc tatttcgact attggggaca aggaaccttg          960
gtaacagtgt cttcaggagg cggaggatct ggcggagggg gctctggagg aggaggatct         1020
gcgatacaaa tgacgcaaag tcccagcagt ttgtccgcct cagtaggcga ccgcgttacg         1080
attacgtgta gggcgtctca agggatcagg atctatctgg gctggtatca acaaaagcct         1140
gggaaagccc caaagctcct tatatatgca acatcatccc tgcaaagcgg cgttccatcc         1200
cgattcagtg gttctggtag cggtacggac ttcactctca caatctcatc tcttcaacca         1260
gaagactttg cgacgtatta ctgtttgcaa gactacaatt atccatggac gttcggccaa         1320
ggcacgaaag tcgagataaa gggtctaaag tacggaccgc cctgcccccc ttgccctggc         1380
cagcctagag aacccccaggt gtacaccctg cctcccagcc aggaagagat gaccaagaac         1440
caggtgtccc tgacctgcct ggtcaaaggc ttctacccca gcgatatcgc cgtggaatgg         1500
gagagcaacg gccagcccga gaacaactac aagaccaccc ccctgtgct ggacagcgac         1560 ggcagcttct cctgtactc ccggctgacc gtggacaaga gccggtggca ggaaggcaac         1620
gtcttcagct gcagcgtgat gcacgaggcc ctgcacaacc actacaccca gaagtccctg         1680
agcctgagcc tgggcaagat gttctgggtg ctggtggtgg tcggaggcgt gctggcctgc         1740
tacagcctgc tggtcaccgt ggccttcatc atcttttggg tgaaacgggg cagaaagaaa         1800
ctcctgtata tattcaaaca accatttatg agaccagtac aaactactca gaggaagat         1860 ggctgtagct gccgatttcc agaagaagaa gaaggaggat gtgaactgcg ggtgaagttc         1920
agcagaagcg ccgacgcccc tgcctaccag cagggccaga atcagctgta caacgagctg         1980

-continued

```
aacctgggca gaagggaaga gtacgacgtc ctggataagc ggagaggccg ggaccctgag    2040
atgggcggca agcctcggcg gaagaacccc caggaaggcc tgtataacga actgcagaaa    2100
gacaagatgg ccgaggccta cagcgagatc ggcatgaagg gcgagcggag gcggggcaag    2160
ggccacgacg gcctgtatca gggcctgtcc accgccacca aggataccta cgacgccctg    2220
cacatgcagg ccctgccccc aaggctcgag ggcggcggag agggcagagg aagtcttcta    2280
acatgcggtg acgtggagga gaatccaggc cctaggatgc cacctccaag actcctcttc    2340
ttcctcctct tcctgacacc aatggaagtc aggcctgagg aacctctagt ggtgaaggtg    2400
gaagagggag ataacgctgt gttacagtgc ctcaagggaa cctcagatgg acccactcag    2460
cagctgacct ggtctcggga gtctccgctt aaacccttcc tgaaactcag ccttggactg    2520
ccaggtctgg gaatccacat gaggccactg gctatctggc tgttcatctt caacgtctct    2580
caacagatgg gaggcttcta cctgtgtcag cctggaccac cttctgagaa ggcatggcag    2640
cctggttgga cagtcaatgt ggagggttct ggtgagctgt ccggtggaa tgtttcggac    2700 ctaggtggac tgggatgtgg tctgaagaac aggtcctcag agggacctag ctctccttcc    2760
gggaagctca tgagccccaa gctgtatgtg tgggccaaag accgccctga gatctgggag    2820
ggagagcctc cgtgtgtccc accgagggac agcctgaacc agagcctcag ccaggacctc    2880
accatggccc ctggctccac actctggctg tcctgtgggg tacccctga ctctgtgtcc    2940 aggggccccc tctcctggac ccatgtgcac cccaaggggc ctaagtcatt gctgagccta    3000
gagctgaagg acgatcgccc tgccagagat atgtgggtaa tggagacggg tctgttgttg    3060
ccccgggcca cagctcaaga cgctggaaag tattattgtc accgtggcaa cctgaccatg    3120
tcattccacc tggagatcac tgctcggcca gtactatggc actggctgct gaggactggt    3180
ggctggaagg tctcagctgt gactttggct tatctgatct tctgcctgtg ttcccttgtg    3240
ggcattcttc atcttcaaag agccctggtc ctgaggagga aaagatga                 3288
```

<210> SEQ ID NO 47
<211> LENGTH: 2967
<212> TYPE: DNA
<213> ORGANISM: Artificial Sequence
<220> FEATURE:
<223> OTHER INFORMATION: 1H10-sh-41bb-3z-T-CD19t Top Strand

<400> SEQUENCE: 47

```
ggatctgcga tcgctccggt gcccgtcagt gggcagagcg cacatcgccc acagtccccg     60
agaagttggg gggagggggtc ggcaattgaa ccggtgccta gagaaggtgg cgcggggtaa    120
actgggaaag tgatgtcgtg tactggctcc gcctttttcc cgagggtggg ggagaaccgt    180
atataagtgc agtagtcgcc gtgaacgttc tttttcgcaa cgggtttgcc gccagaacac    240
agctgaagct tcgagggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt ctgttctgc gccgttacag atccaagctg tgaccggcgc    540
ctacggctag ccaccatgct gctgctcgtg accagcctgc tgctgtgcga actgccccac    600
cctgcctttc tgctgatccc ccaagtacag cttgttcaaa gtggtgctga agttaaaaag    660 ccagggggcca gcgttaaggt atcctgcaag ggaagtggtt acatcttcac atcttacgac    720
atgcactggg tacgacaggc tcctggacag ggtctggaat ggatgggtat catagacccc    780
```

```
tcaggaggat ctacgagcta tgcccaaaaa tttcagggaa gagtaacaat gaccagggac      840
acgtccatga gcacagtcta catggaactc agcagtctca gatcagagga tacggcggtt      900
tactactgta ctagggatta ttcatggagc tatttcgact attggggaca aggaaccttg      960
gtaacagtgt cttcaggagg cggaggatct ggcggagggg gctctggagg aggaggatct     1020
gcgatacaaa tgacgcaaag tcccagcagt ttgtccgcct cagtaggcga ccgcgttacg     1080
attacgtgta gggcgtctca agggatcagg atctatctgg gctggtatca acaaaagcct     1140
gggaaagccc caaagctcct tatatatgca acatcatccc tgcaaagcgg cgttccatcc     1200
cgattcagtg gttctggtag cggtacggac ttcactctca caatctcatc tcttcaacca     1260
gaagactttg cgacgtatta ctgtttgcaa gactacaatt atccatggac gttcggccaa     1320
ggcacgaaag tcgagataaa ggagtctaag tacggaccgc cctgcccccc ttgccctatg     1380
ttctgggtgc tggtggtggt cggaggcgtg ctggcctgct acagcctgct ggtcaccgtg     1440
gccttcatca tctttggggt gaaacggggc agaaagaaac tcctgtatat attcaaacaa     1500
ccatttatga gaccagtaca aactactcaa gaggaagatg gctgtagctg ccgatttcca     1560
gaagaagaag aaggaggatg tgaactgcgg gtgaagttca gcagaagcgc cgacgcccct     1620
gcctaccagc agggccagaa tcagctgtac aacgagctga acctgggcag aagggaagag     1680
tacgacgtcc tggataagcg gagaggccgg gaccctgaga tgggcggcaa gcctcggcgg     1740
aagaacccac aggaaggcct gtataacgaa ctgcagaaag acaagatggc cgaggcctac     1800
agcgagatcg gcatgaaggg cgagcggagg cggggcaagg gccacgacgg cctgtatcag     1860
ggcctgtcca ccgccaccaa ggatacctac gacgccctgc acatgcaggc cctgcccca      1920 aggctcgagg gcggcggaga gggcagagga agtcttctaa catgcggtga cgtggaggag     1980
aatccaggcc ctaggatgcc acctccaaga ctcctcttct tcctcctctt cctgacacca     2040
atggaagtca ggcctgagga acctctagtg gtgaaggtgg aagagggaga taacgctgtg     2100
ttacagtgcc tcaagggaac ctcagatgga cccactcagc agctgacctg gtctcgggag     2160
tctccgctta aacccttcct gaaactcagc cttggactgc caggtctggg aatccacatg     2220
aggccactgg ctatctggct gttcatcttc aacgtctctc aacagatggg aggcttctac     2280
ctgtgtcagc ctggaccacc ttctgagaag gcatggcagc ctggttggac agtcaatgtg     2340
gagggttctg gtgagctgtt ccggtggaat gtttcggacc taggtggact gggatgtggt     2400
ctgaagaaca ggtcctcaga gggacctagc tctccttccg ggaagctcat gagccccaag     2460
ctgtatgtgt gggccaaaga ccgccctgag atctgggagg gagagcctcc gtgtgtccca     2520
ccgagggaca gcctgaacca gagcctcagc caggacctca ccatggcccc tggctccaca     2580
ctctggctgt cctgtggggt accccctgac tctgtgtcca ggggcccct ctcctggacc      2640 catgtgcacc ccaaggggcc taagtcattg ctgagcctag agctgaagga cgatcgccct     2700
gccagagata tgtgggtaat ggagacgggt ctgttgttgc cccgggccac agctcaagac     2760
gctggaaagt attattgtca ccgtggcaac ctgaccatgt cattccacct ggagatcact     2820
gctcggccag tactatggca ctggctgctg aggactggtg gctggaaggt ctcagctgtg     2880
actttggctt atctgatctt ctgcctgtgt tcccttgtgg gcattcttca tcttcaaaga     2940
gccctggtcc tgaggaggaa aagatga                                         2967
```

<210> SEQ ID NO 48
<211> LENGTH: 3285
<212> TYPE: DNA

```
<213> ORGANISM: Artificial Sequence
<220> FEATURE:
<223> OTHER INFORMATION: 1A9-intDS-41bb-3z-T-CD19t Top Strand

<400> SEQUENCE: 48
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gcctttttcc cgagggtggg ggagaaccgt     180
atataagtgc agtagtcgcc gtgaacgttc tttttcgcaa cgggtttgcc gccagaacac     240
agctgaagct tcgagggget cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacggctag ccaccatgct gctgctcgtg accagcctgc tgctgtgcga actgccccac     600
cctgcctttc tgctgatccc cgaagtgcag ttggttgagt ctggaggagg cctggtacag     660
ccgggtggta gtcttcggct ttcctgtgct gctagcgggt ttactttctc catatacgat     720
atgcactggg tgaggcaagc gaccggaaaa ggtctggagt gggtctcagc gatcggtaca     780
gctggcgata cttactatgc gggcagtgtc aaggacgat tcaccataag ccgcgaaaac     840
gctaaaaatt ccctctactt gcaaatgaat agcctgcgag cggggggacac cgccgtatat     900 tattgtgcta gagagtatag cggatattac tttgactatt ggggtcaagg cactctggta     960
acggtgtcta gcggaggcgg aggatctggc ggagggggct ctggaggagg aggatctgcg    1020
attcagatga ctcaatcccc ctcctctctc tccgcgtccg tagggggatag ggtgacaata    1080 acttgtaggg cgagccagga catccgcaat gacctcggct ggtatcaaca aaaaccaggc    1140
aaggcaccta agatactgat ttatggcgcg tcctccttgc aatccggggt gccgtctcgg    1200
ttcagtggtt caggtagtgg tacggacttt accttcacaa tctctagtct gcaaccggag    1260
gatttcgcta cttactattg tctccaggag tataattacc cctgtacatt tgggcaaggc    1320
accaagttgg agataaaaga gtctaagtac ggaccgccct gccccccttg ccctggccag    1380
cctagagaac cccaggtgta caccctgcct cccagccagg aagagatgac caagaaccag    1440
gtgtccctga cctgcctggt caaaggcttc taccccagcg atatcgccgt ggaatgggag    1500
agcaacggcc agcccgagaa caactacaag accacccccc ctgtgctgga cagcgacggc    1560
agcttcttcc tgtactcccg gctgaccgtg gacaagagcc ggtggcagga aggcaacgtc    1620
ttcagctgca gcgtgatgca cgaggccctg cacaaccact acacccagaa gtccctgagc    1680
ctgagcctgg gcaagatgtt ctgggtgctg gtggtggtcg gaggcgtgct ggcctgctac    1740
agcctgctgg tcaccgtggc cttcatcatc ttttgggtga acggggcag aaagaaactc    1800 ctgtatatat tcaaacaacc atttatgaga ccagtacaaa ctactcaaga ggaagatggc    1860
tgtagctgcc gatttccaga agaagaagaa ggaggatgtg aactgcgggt gaagttcagc    1920
agaagcgccg acgcccctgc ctaccagcag ggccagaatc agctgtacaa cgagctgaac    1980
ctgggcagaa gggaagagta cgacgtcctg gataagcgga gaggccggga ccctgagatg    2040
ggcggcaagc ctcggcggaa gaaccccag gaaggcctgt ataacgaact gcagaaagac    2100
aagatggccg aggcctacag cgagatcggc atgaagggcg agcggaggcg gggcaagggc    2160
cacgacggcc tgtatcaggg cctgtccacc gccaccaagg atacctacga cgccctgcac    2220
```

-continued

```
atgcaggccc tgcccccaag gctcgagggc ggcggagagg gcagaggaag tcttctaaca    2280
tgcggtgacg tggaggagaa tccaggccct aggatgccac ctccaagact cctcttcttc    2340
ctcctcttcc tgacaccaat ggaagtcagg cctgaggaac ctctagtggt gaaggtggaa    2400
gagggagata acgctgtgtt acagtgcctc aagggaacct cagatggacc cactcagcag    2460
ctgacctggt ctcgggagtc tccgcttaaa cccttcctga aactcagcct tggactgcca    2520
ggtctgggaa tccacatgag gccactggct atctggctgt tcatcttcaa cgtctctcaa    2580
cagatgggag gcttctacct gtgtcagcct ggaccacctt ctgagaaggc atggcagcct    2640
ggttggacag tcaatgtgga gggttctggt gagctgttcc ggtggaatgt ttcggaccta    2700
ggtggactgg gatgtggtct gaagaacagg tcctcagagg gacctagctc tccttccggg    2760
aagctcatga gccccaagct gtatgtgtgg gccaaagacc ccctgagat ctgggaggga    2820 gagcctccgt gtgtcccacc gagggacagc ctgaaccaga gcctcagcca ggacctcacc    2880
atggcccctg gctccacact ctggctgtcc tgtgggggtac cccctgactc tgtgtccagg    2940
ggccccctct cctggaccca tgtgcacccc aaggggccta agtcattgct gagcctagag    3000
ctgaaggacg atcgccctgc cagagatatg tgggtaatgg agacgggtct gttgttgccc    3060
cgggccacag ctcaagacgc tggaaagtat tattgtcacc gtggcaacct gaccatgtca    3120
ttccacctgg agatcactgc tcggccagta ctatggcact ggctgctgag gactggtggc    3180
tggaaggtct cagctgtgac tttggcttat ctgatcttct gcctgtgttc ccttgtgggc    3240
attcttcatc ttcaaagagc cctggtcctg aggaggaaaa gatga             3285
```

<210> SEQ ID NO 49
<211> LENGTH: 2964
<212> TYPE: DNA
<213> ORGANISM: Artificial Sequence
<220> FEATURE:
<223> OTHER INFORMATION: 1A9-sh-41bb-3z-T-CD19t Top Strand

<400> SEQUENCE: 49

```
ggatctgcga tcgctccggt gcccgtcagt gggcagagcg cacatcgccc acagtccccg     60
agaagttggg gggaggggtc ggcaattgaa ccggtgccta gagaaggtgg cgcggggtaa    120
actgggaaag tgatgtcgtg tactggctcc gccttttcc cgagggtggg ggagaaccgt    180
atataagtgc agtagtcgcc gtgaacgttc tttttcgcaa cgggtttgcc gccagaacac    240
agctgaagct tcgagggget cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacggctag ccaccatgct gctgctcgtg accagcctgc tgctgtgcga actgcccac     600 cctgcctttc tgctgatccc cgaagtgcag ttggttgagt ctggaggagg cctggtacag    660
ccgggtggta gtcttcggct ttcctgtgct gctagcgggt ttactttctc catatacgat    720
atgcactggg tgaggcaagc gaccggaaaa ggtctggagt gggtctcagc gatcggtaca    780
gctggcgata cttactatgc gggcagtgtc aaggacgat tcaccataag ccgcgaaaac    840
gctaaaaatt ccctctactt gcaaatgaat agcctgcgag cggggggacac cgccgtatat    900 tattgtgcta gagagtatag cggatattac tttgactatt ggggtcaagg cactctggta    960
```

-continued

```
acggtgtcta gcggaggcgg aggatctggc ggagggggct ctggaggagg aggatctgcg      1020
attcagatga ctcaatcccc ctcctctctc tccgcgtccg tagggggatag ggtgacaata      1080 acttgtaggg cgagccagga catccgcaat gacctcggct ggtatcaaca aaaaccaggc      1140
aaggcaccta agatactgat ttatggcgcg tcctccttgc aatccggggt gccgtctcgg      1200
ttcagtggtt caggtagtgg tacggacttt accttcacaa tctctagtct gcaaccggag      1260
gatttcgcta cttactattg tctccaggag tataattacc cctgtacatt tgggcaaggc      1320
accaagttgg agataaaaga gtctaagtac ggaccgccct gccccccttg ccctatgttc      1380
tgggtgctgg tggtggtcgg aggcgtgctg gcctgctaca gcctgctggt caccgtggcc      1440
ttcatcatct tttgggtgaa acggggcaga aagaaactcc tgtatatatt caaacaacca      1500
tttatgagac cagtacaaac tactcaagag gaagatggct gtagctgccg atttccagaa      1560
gaagaagaag gaggatgtga actgcgggtg aagttcagca gaagcgccga cgcccctgcc      1620
taccagcagg gccagaatca gctgtacaac gagctgaacc tgggcagaag ggaagagtac      1680
gacgtcctgg ataagcggag aggccgggac cctgagatgg gcggcaagcc tcggcggaag      1740 aaccccagg aaggcctgta taacgaactg cagaaagaca agatggccga ggcctacagc      1800
gagatcggca tgaagggcga gcggaggcgg ggcaagggcc acgacggcct gtatcagggc      1860
ctgtccaccg ccaccaagga tacctacgac gccctgcaca tgcaggccct gccccccaagg      1920 ctcgagggcg gcgagagggg cagaggaagt cttctaacat gcggtgacgt ggaggagaat      1980
ccaggcccta ggatgccacc tccaagactc ctcttcttcc tcctcttcct gacaccaatg      2040
gaagtcaggc ctgaggaacc tctagtggtg aaggtggaag agggagataa cgctgtgtta      2100
cagtgcctca agggaacctc agatggaccc actcagcagc tgacctggtc tcgggagtct      2160
ccgcttaaac ccttcctgaa actcagcctt ggactgccag gtctgggaat ccacatgagg      2220
ccactggcta tctggctgtt catcttcaac gtctctcaac agatgggagg cttctacctg      2280
tgtcagcctg gaccaccttc tgagaaggca tggcagcctg gttggacagt caatgtggag      2340
ggttctggtg agctgttccg gtggaatgtt tcggacctag gtggactggg atgtggtctg      2400
aagaacaggt cctcagaggg acctagctct ccttccggga agctcatgag ccccaagctg      2460
tatgtgtggg ccaaagaccg ccctgagatc tgggagggag agcctccgtg tgtcccaccg      2520
agggacagcc tgaaccagag cctcagccag gacctcacca tggcccctgg ctccacactc      2580
tggctgtcct gtggggtacc ccctgactct gtgtccaggg gcccctctc ctggacccat      2640 gtgcacccca aggggcctaa gtcattgctg agcctagagc tgaaggacga tcgccctgcc      2700
agagatatgt gggtaatgga cacgggtctg ttgttgcccc gggccacagc tcaagacgct      2760
ggaaagtatt attgtcaccg tggcaacctg accatgtcat tccacctgga gatcactgct      2820
cggccagtac tatggcactg gctgctgagg actggtggct ggaaggtctc agctgtgact      2880
ttggcttatc tgatcttctg cctgtgttcc cttgtgggca ttcttcatct tcaaagagcc      2940
ctggtcctga ggaggaaaag atga                                            2964
```

<210> SEQ ID NO 50
<211> LENGTH: 3288
<212> TYPE: DNA
<213> ORGANISM: Artificial Sequence
<220> FEATURE:
<223> OTHER INFORMATION: 1E6-intDS-41bb-3z-T-CD19t Top Strand

<400> SEQUENCE: 50

```
ggatctgcga tcgctccggt gcccgtcagt gggcagagcg cacatcgccc acagtccccg        60
```

-continued

```
agaagttggg gggaggggtc ggcaattgaa ccggtgccta gagaaggtgg cgcggggtaa      120
actgggaaag tgatgtcgtg tactggctcc gccttttttcc cgagggtggg ggagaaccgt      180
atataagtgc agtagtcgcc gtgaacgttc tttttcgcaa cgggtttgcc gccagaacac      240
agctgaagct tcgaggggct cgcatctctc cttcacgcgc ccgccgccct acctgaggcc      300
gccatccacg ccggttgagt cgcgttctgc cgcctcccgc ctgtggtgcc tcctgaactg      360
cgtccgccgt ctaggtaagt ttaaagctca ggtcgagacc gggcctttgt ccggcgctcc      420
cttggagcct acctagactc agccggctct ccacgctttg cctgaccctg cttgctcaac      480
tctacgtctt tgtttcgttt tctgttctgc gccgttacag atccaagctg tgaccggcgc      540
ctacggctag ccaccatgct gctgctcgtg accagcctgc tgctgtgcga actgccccac      600
cctgcctttc tgctgatccc ccaagtgcag ttggttgaat ccggtggcgg tgtgggttcaa      660 ccaggcagga gcttgagact ttcatgtgca gcgtccggct ttacattctc cagctacgac      720
atacattggg tccggcaggc gccaggaaag ggcctcgaat gggtcgcggt aatatggtac      780
gacggcagtc ataactacta cagtgattct gtaaaaggcc gctttacgat ttcacgcgac      840
aacagcaaga atacactcta tttgcaaatg aactctctgc gcgcggaaga taccgccgtg      900
tattattgtg cgcgggacta cagcgggtct tactacgact actggggcca aggaacccctt      960 gtaacggtct ctagcggagg cggaggatct ggcggagggg gctctggagg aggaggatct     1020
gcaatacaaa tgacgcagtc tcctagctca ctttctgcaa gcgtcggaga ccgagttaca     1080
attacgtgtc gggcgagcca gggaattcgg aacgatctcg gctggtatca acagaaaccc     1140
ggcaaagcgc caaaattgct tatatacgcg gcatcaaacc ttcagagtgg tgtgccgtca     1200
agattcagtg ggtcaggcag cggaactgac tttacccctga ctatctctag tctccaaccc     1260
gaggacttcg caacgtacta ttgcctgcaa gattactcct acccgcgaac gttcggccaa     1320
gggacaaagg ttgagattaa agagtctaag tacggaccgc cctgccccccc ttgccctggc     1380 cagcctagag aaccccaggt gtacaccctg cctcccagcc aggaagagat gaccaagaac     1440
caggtgtccc tgacctgcct ggtcaaaggc ttctaccccca gcgatatcgc cgtggaatgg     1500
gagagcaacg gccagcccga gaacaactac aagaccaccc ccctgtgct ggacagcgac     1560 ggcagcttct cctgtactc ccggctgacc gtggacaaga gccggtggca ggaaggcaac     1620
gtcttcagct gcagcgtgat gcacgaggcc ctgcacaacc actacaccca gaagtccctg     1680
agcctgagcc tgggcaagat gttctgggtg ctggtggtgg tcggaggcgt gctggcctgc     1740
tacagcctgc tggtcaccgt ggccttcatc atcttttggg tgaaacgggg cagaaagaaa     1800
ctcctgtata tattcaaaca accatttatg agaccagtac aaactactca agaggaagat     1860
ggctgtagct gccgatttcc agaagaagaa gaaggaggat gtgaactgcg ggtgaagttc     1920
agcagaagcg ccgacgcccc tgcctaccag cagggccaga atcagctgta caacgagctg     1980
aacctgggca gaagggaaga gtacgacgtc ctggataagc ggagaggccg ggaccctgag     2040
atgggcggca gcctcggcg gaagaacccc caggaaggcc tgtataacga actgcagaaa     2100
gacaagatgg ccgaggccta cagcgagatc ggcatgaagg gcgagcggag gcggggcaag     2160
ggccacgacg gcctgtatca gggcctgtcc accgccacca aggatacccta cgacgccctg     2220 cacatgcagg ccctgccccc aaggctcgag ggcggcggag agggcagagg aagtcttcta     2280
acatgcggtg acgtggagga gaatccaggc cctaggatgc cacctccaag actcctcttc     2340
ttcctcctct tcctgacacc aatggaagtc aggcctgagg aacctctagt ggtgaaggtg     2400
```

-continued

```
gaagagggag ataacgctgt gttacagtgc ctcaagggaa cctcagatgg acccactcag    2460
cagctgacct ggtctcggga gtctccgctt aaacccttcc tgaaactcag ccttggactg    2520
ccaggtctgg gaatccacat gaggccactg gctatctggc tgttcatctt caacgtctct    2580
caacagatgg gaggcttcta cctgtgtcag cctggaccac cttctgagaa ggcatggcag    2640
cctggttgga cagtcaatgt ggagggttct ggtgagctgt ccggtggaa tgtttcggac    2700 ctaggtggac tgggatgtgg tctgaagaac aggtcctcag agggacctag ctctccttcc    2760
gggaagctca tgagccccaa gctgtatgtg tgggccaaag accgccctga gatctgggag    2820
ggagagcctc cgtgtgtccc accgagggac agcctgaacc agagcctcag ccaggacctc    2880
accatggccc ctggctccac actctggctg tcctgtgggg taccccctga ctctgtgtcc    2940
aggggccccc tctcctggac ccatgtgcac cccaaggggc ctaagtcatt gctgagccta    3000
gagctgaagg acgatcgccc tgccagagat atgtgggtaa tggagacggg tctgttgttg    3060 cccccgggcca cagctcaaga cgctggaaag tattattgtc accgtggcaa cctgaccatg    3120
tcattccacc tggagatcac tgctcggcca gtactatggc actggctgct gaggactggt    3180
ggctggaagg tctcagctgt gactttggct tatctgatct tctgcctgtg ttcccttgtg    3240
ggcattcttc atcttcaaag agccctggtc ctgaggagga aaagatga              3288
```

```
<210> SEQ ID NO 51
<211> LENGTH: 2967
<212> TYPE: DNA
<213> ORGANISM: Artificial Sequence
<220> FEATURE:
<223> OTHER INFORMATION: 1E6-sh-41bb-3z-T-CD19t Top Strand

<400> SEQUENCE: 51
```

```
ggatctgcga tcgctccggt gcccgtcagt gggcagagcg cacatcgccc acagtccccg      60
agaagttggg gggaggggtc ggcaattgaa ccggtgccta gagaaggtgg cgcggggtaa     120
actgggaaag tgatgtcgtg tactggctcc gccttttcc cgagggtggg ggagaaccgt     180
atataagtgc agtagtcgcc gtgaacgttc tttttcgcaa cgggtttgcc gccagaacac     240
agctgaagct tcgaggggct cgcatctctc cttcacgcgc ccgccgccct acctgaggcc     300
gccatccacg ccggttgagt cgcgttctgc cgcctcccgc ctgtggtgcc tcctgaactg     360
cgtccgccgt ctaggtaagt ttaaagctca ggtcgagacc gggcctttgt ccggcgctcc     420
cttggagcct acctagactc agccggctct ccacgctttg cctgaccctg cttgctcaac     480
tctacgtctt tgtttcgttt tctgttctgc gccgttacag atccaagctg tgaccggcgc     540
ctacggctag ccaccatgct gctgctcgtg accagcctgc tgctgtgcga actgccccac     600
cctgcctttc tgctgatccc ccaagtgcag ttggttgaat ccggtggcgg tgtggttcaa     660
ccaggcagga gcttgagact ttcatgtgca gcgtccggct ttacattctc cagctacgac     720
atacattggg tccggcaggc gccaggaaag ggcctcgaat gggtcgcggt aatatggtac     780
gacggcagtc ataactacta cagtgattct gtaaaaggcc gctttacgat ttcacgcgac     840
aacagcaaga atacactcta tttgcaaatg aactctctgc gcgcggaaga taccgccgtg     900
tattattgtg cgcgggacta cagcgggtct tactacgact actggggcca aggaacccctt     960 gtaacggtct ctagcggagg cggaggatct ggcggagggg gctctggagg aggaggatct    1020
gcaatacaaa tgacgcagtc tcctagctca ctttctgcaa gcgtcggaga ccgagttaca    1080
attacgtgtc gggcgagcca gggaattcgg aacgatctcg gctggtatca acagaaaccc    1140
ggcaaagcgc caaaattgct tatatacgcg gcatcaaacc ttcagagtgg tgtgccgtca    1200
```

-continued

```
agattcagtg ggtcaggcag cggaactgac tttaccctga ctatctctag tctccaaccc      1260
gaggacttcg caacgtacta ttgcctgcaa gattactcct acccgcgaac gttcggccaa      1320
gggacaaagg ttgagattaa agagtctaag tacggaccgc cctgcccccc ttgccctatg      1380
ttctgggtgc tggtggtggt cggaggcgtg ctggcctgct acagcctgct ggtcaccgtg      1440
gccttcatca tcttttgggt gaaacggggc agaaagaaac tcctgtatat attcaaacaa      1500
ccatttatga gaccagtaca aactactcaa gaggaagatg gctgtagctg ccgatttcca      1560
gaagaagaag aaggaggatg tgaactgcgg gtgaagttca gcagaagcgc cgacgcccct      1620
gcctaccagc agggccagaa tcagctgtac aacgagctga acctgggcag aagggaagag      1680
tacgacgtcc tggataagcg gagaggccgg gaccctgaga tgggcggcaa gcctcggcgg      1740
aagaaccccc aggaaggcct gtataacgaa ctgcagaaag acaagatggc cgaggcctac      1800
agcgagatcg gcatgaaggg cgagcggagg cggggcaagg gccacgacgg cctgtatcag      1860
ggcctgtcca ccgccaccaa ggataccac gacgccctgc acatgcaggc cctgcccca      1920 aggctcgagg gcggcggaga gggcagagga agtcttctaa catgcggtga cgtggaggag      1980
aatccaggcc ctaggatgcc acctccaaga ctcctcttct tcctcctctt cctgacacca      2040
atggaagtca ggcctgagga acctctagtg gtgaaggtgg aagagggaga taacgctgtg      2100
ttacagtgcc tcaagggaac ctcagatgga cccactcagc agctgacctg gtctcgggag      2160
tctccgctta aacccttcct gaaactcagc cttggactgc caggtctggg aatccacatg      2220
aggccactgg ctatctggct gttcatcttc aacgtctctc aacagatggg aggcttctac      2280
ctgtgtcagc ctggaccacc ttctgagaag gcatggcagc ctggttggac agtcaatgtg      2340
gagggttctg gtgagctgtt ccggtggaat gtttcggacc taggtggact gggatgtggt      2400
ctgaagaaca ggtcctcaga gggacctagc tctccttccg ggaagctcat gagccccaag      2460
ctgtatgtgt gggccaaaga ccgccctgag atctgggagg gagagcctcc gtgtgtccca      2520
ccgagggaca gcctgaacca gagcctcagc caggacctca ccatggcccc tggctccaca      2580
ctctggctgt cctgtggggt accccctgac tctgtgtcca ggggccccct ctcctggacc      2640
catgtgcacc ccaaggggcc taagtcattg ctgagcctag agctgaagga cgatcgccct      2700
gccagagata tgtgggtaat ggagacgggt ctgttgttgc cccgggccac agctcaagac      2760 gctgaaagt attattgtca ccgtggcaac ctgaccatgt cattccacct ggagatcact      2820
gctcggccag tactatggca ctggctgctg aggactggtg ctggaaggt ctcagctgtg      2880 actttggctt atctgatctt ctgcctgtgt tcccttgtgg gcattcttca tcttcaaaga      2940
gccctggtcc tgaggaggaa aagatga                                        2967
```

<210> SEQ ID NO 52
<211> LENGTH: 6
<212> TYPE: PRT
<213> ORGANISM: Artificial Sequence
<220> FEATURE:
<223> OTHER INFORMATION: First six amino acids of the CH2 domain in IgG4

<400> SEQUENCE: 52

Ala Pro Glu Phe Leu Gly
1               5

<210> SEQ ID NO 53
<211> LENGTH: 5
<212> TYPE: PRT
<213> ORGANISM: Artificial Sequence

```
<220> FEATURE:
<223> OTHER INFORMATION: First five amino acids of IgG2

<400> SEQUENCE: 53

Ala Pro Pro Val Ala
1               5

<210> SEQ ID NO 54
<211> LENGTH: 11
<212> TYPE: PRT
<213> ORGANISM: Artificial Sequence
<220> FEATURE:
<223> OTHER INFORMATION: CDRL1 of 1H10

<400> SEQUENCE: 54

Arg Ala Ser Gln Gly Ile Arg Ile Tyr Leu Gly
1               5                   10

<210> SEQ ID NO 55
<211> LENGTH: 8
<212> TYPE: PRT
<213> ORGANISM: Artificial Sequence
<220> FEATURE:
<223> OTHER INFORMATION: CDRL2 of 1H10 and 1D2

<400> SEQUENCE: 55

Tyr Ala Thr Ser Ser Leu Gln Ser
1               5

<210> SEQ ID NO 56
<211> LENGTH: 9
<212> TYPE: PRT
<213> ORGANISM: Artificial Sequence
<220> FEATURE:
<223> OTHER INFORMATION: CDRL3 of 1H10

<400> SEQUENCE: 56

Leu Gln Asp Tyr Asn Tyr Pro Trp Thr
1               5

<210> SEQ ID NO 57
<211> LENGTH: 13
<212> TYPE: PRT
<213> ORGANISM: Artificial Sequence
<220> FEATURE:
<223> OTHER INFORMATION: CDRH1 of 1H10

<400> SEQUENCE: 57

Lys Gly Ser Gly Tyr Ile Phe Thr Ser Tyr Asp Met His
1               5                   10

<210> SEQ ID NO 58
<211> LENGTH: 10
<212> TYPE: PRT
<213> ORGANISM: Artificial Sequence
<220> FEATURE:
<223> OTHER INFORMATION: CDRH2 of 1H10

<400> SEQUENCE: 58

Ile Ile Asp Pro Ser Gly Gly Ser Thr Ser
1               5                   10

<210> SEQ ID NO 59
<211> LENGTH: 11
<212> TYPE: PRT
<213> ORGANISM: Artificial Sequence
<220> FEATURE:
```

<223> OTHER INFORMATION: CDRH3 of 1H10

<400> SEQUENCE: 59

```
Thr Arg Asp Tyr Ser Trp Ser Tyr Phe Asp Tyr
1               5                   10
```

<210> SEQ ID NO 60
<211> LENGTH: 11
<212> TYPE: PRT
<213> ORGANISM: Artificial Sequence
<220> FEATURE:
<223> OTHER INFORMATION: CDRL1 of 1A9 and 1B9

<400> SEQUENCE: 60

```
Arg Ala Ser Gln Asp Ile Arg Asn Asp Leu Gly
1               5                   10
```

<210> SEQ ID NO 61
<211> LENGTH: 8
<212> TYPE: PRT
<213> ORGANISM: Artificial Sequence
<220> FEATURE:
<223> OTHER INFORMATION: CDRL2 of 1A9

<400> SEQUENCE: 61

```
Tyr Gly Ala Ser Ser Leu Gln Ser
1               5
```

<210> SEQ ID NO 62
<211> LENGTH: 9
<212> TYPE: PRT
<213> ORGANISM: Artificial Sequence
<220> FEATURE:
<223> OTHER INFORMATION: CDRL3 of 1A9

<400> SEQUENCE: 62

```
Leu Gln Glu Tyr Asn Tyr Pro Cys Thr
1               5
```

<210> SEQ ID NO 63
<211> LENGTH: 13
<212> TYPE: PRT
<213> ORGANISM: Artificial Sequence
<220> FEATURE:
<223> OTHER INFORMATION: CDRH1 of 1A9

<400> SEQUENCE: 63

```
Ala Ala Ser Gly Phe Thr Phe Ser Ile Tyr Asp Met His
1               5                   10
```

<210> SEQ ID NO 64
<211> LENGTH: 9
<212> TYPE: PRT
<213> ORGANISM: Artificial Sequence
<220> FEATURE:
<223> OTHER INFORMATION: CDRH2 of 1A9

<400> SEQUENCE: 64

```
Ala Ile Gly Thr Ala Gly Asp Thr Tyr
1               5
```

<210> SEQ ID NO 65
<211> LENGTH: 11
<212> TYPE: PRT
<213> ORGANISM: Artificial Sequence
<220> FEATURE:
<223> OTHER INFORMATION: CDRH3 of 1A9

-continued

<400> SEQUENCE: 65

Ala Arg Glu Tyr Ser Gly Tyr Tyr Phe Asp Tyr
1               5                   10

<210> SEQ ID NO 66
<211> LENGTH: 11
<212> TYPE: PRT
<213> ORGANISM: Artificial Sequence
<220> FEATURE:
<223> OTHER INFORMATION: CDRL1 of 1E6 and 1D2

<400> SEQUENCE: 66

Arg Ala Ser Gln Gly Ile Arg Asn Asp Leu Gly
1               5                   10

<210> SEQ ID NO 67
<211> LENGTH: 8
<212> TYPE: PRT
<213> ORGANISM: Artificial Sequence
<220> FEATURE:
<223> OTHER INFORMATION: CDRL2 of 1E6

<400> SEQUENCE: 67

Tyr Ala Ala Ser Asn Leu Gln Ser
1               5

<210> SEQ ID NO 68
<211> LENGTH: 9
<212> TYPE: PRT
<213> ORGANISM: Artificial Sequence
<220> FEATURE:
<223> OTHER INFORMATION: CDRL3 of 1E6, 1D2, and 1B9

<400> SEQUENCE: 68

Leu Gln Asp Tyr Ser Tyr Pro Arg Thr
1               5

<210> SEQ ID NO 69
<211> LENGTH: 13
<212> TYPE: PRT
<213> ORGANISM: Artificial Sequence
<220> FEATURE:
<223> OTHER INFORMATION: CDRH1 of 1E6 and 1D2

<400> SEQUENCE: 69

Ala Ala Ser Gly Phe Thr Phe Ser Ser Tyr Asp Ile His
1               5                   10

<210> SEQ ID NO 70
<211> LENGTH: 10
<212> TYPE: PRT
<213> ORGANISM: Artificial Sequence
<220> FEATURE:
<223> OTHER INFORMATION: CDRH2 of 1E6 and 1B9

<400> SEQUENCE: 70

Val Ile Trp Tyr Asp Gly Ser His Asn Tyr
1               5                   10

<210> SEQ ID NO 71
<211> LENGTH: 11
<212> TYPE: PRT
<213> ORGANISM: Artificial Sequence
<220> FEATURE:
<223> OTHER INFORMATION: CDRH3 of 1E6 and 1D2

```
<400> SEQUENCE: 71

Ala Arg Asp Tyr Ser Gly Ser Tyr Tyr Asp Tyr
1               5                   10

<210> SEQ ID NO 72
<211> LENGTH: 10
<212> TYPE: PRT
<213> ORGANISM: Artificial Sequence
<220> FEATURE:
<223> OTHER INFORMATION: CDRH2 of 1D2

<400> SEQUENCE: 72

Val Ile Trp Tyr Asp Gly Ser Gln Lys Tyr
1               5                   10

<210> SEQ ID NO 73
<211> LENGTH: 8
<212> TYPE: PRT
<213> ORGANISM: Artificial Sequence
<220> FEATURE:
<223> OTHER INFORMATION: CDRL2 of 1B9

<400> SEQUENCE: 73

Tyr Ala Ala Ser Ser Leu Gln Ser
1               5

<210> SEQ ID NO 74
<211> LENGTH: 13
<212> TYPE: PRT
<213> ORGANISM: Artificial Sequence
<220> FEATURE:
<223> OTHER INFORMATION: CDRH1 of 1B9

<400> SEQUENCE: 74

Ala Ala Ser Gly Phe Ile Phe Ser Ser Tyr Asp Ile His
1               5                   10

<210> SEQ ID NO 75
<211> LENGTH: 11
<212> TYPE: PRT
<213> ORGANISM: Artificial Sequence
<220> FEATURE:
<223> OTHER INFORMATION: CDRH3 of 1B9

<400> SEQUENCE: 75

Ala Arg Asp Tyr Ser Gly Ser Tyr Phe Asp Tyr
1               5                   10

<210> SEQ ID NO 76
<211> LENGTH: 11
<212> TYPE: PRT
<213> ORGANISM: Artificial Sequence
<220> FEATURE:
<223> OTHER INFORMATION: CDRL1 of 1H8

<400> SEQUENCE: 76

Arg Ala Ser Gln Asn Ile Gly Gly Asn Leu His
1               5                   10

<210> SEQ ID NO 77
<211> LENGTH: 7
<212> TYPE: PRT
<213> ORGANISM: Artificial Sequence
<220> FEATURE:
<223> OTHER INFORMATION: CDRL2 of 1H8

<400> SEQUENCE: 77
```

Tyr Ala Thr Gln Pro Phe Ser
1               5

<210> SEQ ID NO 78
<211> LENGTH: 9
<212> TYPE: PRT
<213> ORGANISM: Artificial Sequence
<220> FEATURE:
<223> OTHER INFORMATION: CDRL3 of 1H8

<400> SEQUENCE: 78

His Gln Ser Ser Ser Leu Pro Leu Thr
1               5

<210> SEQ ID NO 79
<211> LENGTH: 5
<212> TYPE: PRT
<213> ORGANISM: Artificial Sequence
<220> FEATURE:
<223> OTHER INFORMATION: CDRH1 of 1H8 and 2E3

<400> SEQUENCE: 79

Ser Tyr Gly Met His
1               5

<210> SEQ ID NO 80
<211> LENGTH: 16
<212> TYPE: PRT
<213> ORGANISM: Artificial Sequence
<220> FEATURE:
<223> OTHER INFORMATION: CDRH2 of 1H8

<400> SEQUENCE: 80

Ile Trp Tyr Asp Gly Ser Asn Glu Tyr Tyr Ala Asp Ser Val Lys Gly
1               5                   10                  15

<210> SEQ ID NO 81
<211> LENGTH: 8
<212> TYPE: PRT
<213> ORGANISM: Artificial Sequence
<220> FEATURE:
<223> OTHER INFORMATION: CDRH3 of 1H8

<400> SEQUENCE: 81

Asp Leu Asp Tyr Asp Ser Ser Gly
1               5

<210> SEQ ID NO 82
<211> LENGTH: 9
<212> TYPE: PRT
<213> ORGANISM: Artificial Sequence
<220> FEATURE:
<223> OTHER INFORMATION: CDRL1 of 2D3

<400> SEQUENCE: 82

Gln Ser Gly Ser Ser Ser Phe Leu Ser
1               5

<210> SEQ ID NO 83
<211> LENGTH: 7
<212> TYPE: PRT
<213> ORGANISM: Artificial Sequence
<220> FEATURE:
<223> OTHER INFORMATION: CDRL2 of 2D3

<400> SEQUENCE: 83

```
Gly Ala Ser Thr Arg Ala Thr
1               5

<210> SEQ ID NO 84
<211> LENGTH: 9
<212> TYPE: PRT
<213> ORGANISM: Artificial Sequence
<220> FEATURE:
<223> OTHER INFORMATION: CDRL3 of 2D3

<400> SEQUENCE: 84

Gln Gln Asp Tyr Asn Leu Pro Phe Thr
1               5

<210> SEQ ID NO 85
<211> LENGTH: 5
<212> TYPE: PRT
<213> ORGANISM: Artificial Sequence
<220> FEATURE:
<223> OTHER INFORMATION: CDRH1 of 2D3

<400> SEQUENCE: 85

Ile Tyr Ala Met Ser
1               5

<210> SEQ ID NO 86
<211> LENGTH: 16
<212> TYPE: PRT
<213> ORGANISM: Artificial Sequence
<220> FEATURE:
<223> OTHER INFORMATION: CDRH2 of 2D3

<400> SEQUENCE: 86

Ile Ser Asp Ser Gly Gly Thr Thr Tyr Tyr Ala Asp Ser Val Lys Gly
1               5                   10                  15

<210> SEQ ID NO 87
<211> LENGTH: 7
<212> TYPE: PRT
<213> ORGANISM: Artificial Sequence
<220> FEATURE:
<223> OTHER INFORMATION: CDRH3 of 2D3

<400> SEQUENCE: 87

Arg Thr Arg Tyr Phe Asn Gly
1               5

<210> SEQ ID NO 88
<211> LENGTH: 9
<212> TYPE: PRT
<213> ORGANISM: Artificial Sequence
<220> FEATURE:
<223> OTHER INFORMATION: CDRL1 of 2E3

<400> SEQUENCE: 88

Gln Ser Val Ser Ser Ser Tyr Leu Ala
1               5

<210> SEQ ID NO 89
<211> LENGTH: 7
<212> TYPE: PRT
<213> ORGANISM: Artificial Sequence
<220> FEATURE:
<223> OTHER INFORMATION: CDRL2 of 2E3

<400> SEQUENCE: 89

Gly Thr Ser Ser Arg Ala Thr
```

-continued

```
1               5

<210> SEQ ID NO 90
<211> LENGTH: 8
<212> TYPE: PRT
<213> ORGANISM: Artificial Sequence
<220> FEATURE:
<223> OTHER INFORMATION: CDRL3 of 2E3

<400> SEQUENCE: 90

Gln Gln Tyr Gly Ser Ser Pro Thr
1               5

<210> SEQ ID NO 91
<211> LENGTH: 16
<212> TYPE: PRT
<213> ORGANISM: Artificial Sequence
<220> FEATURE:
<223> OTHER INFORMATION: CDRH2 of 2E3

<400> SEQUENCE: 91

Ile Trp Tyr Gly Gly Ser Asn Lys Tyr Tyr Ala Asp Ser Val Lys Gly
1               5                   10                  15

<210> SEQ ID NO 92
<211> LENGTH: 11
<212> TYPE: PRT
<213> ORGANISM: Artificial Sequence
<220> FEATURE:
<223> OTHER INFORMATION: CDRH3 of 2E3

<400> SEQUENCE: 92

Asp Gly Thr Gly Glu Asn Tyr Tyr Tyr Tyr Val
1               5                   10

<210> SEQ ID NO 93
<211> LENGTH: 8
<212> TYPE: PRT
<213> ORGANISM: Artificial Sequence
<220> FEATURE:
<223> OTHER INFORMATION: CDRL2 of 1H8

<400> SEQUENCE: 93

Arg Tyr Ala Thr Gln Pro Phe Ser
1               5

<210> SEQ ID NO 94
<211> LENGTH: 13
<212> TYPE: PRT
<213> ORGANISM: Artificial Sequence
<220> FEATURE:
<223> OTHER INFORMATION: CDRH1 of 1H8

<400> SEQUENCE: 94

Ala Ala Ser Gly Phe Thr Phe Gly Ser Tyr Gly Met His
1               5                   10

<210> SEQ ID NO 95
<211> LENGTH: 10
<212> TYPE: PRT
<213> ORGANISM: Artificial Sequence
<220> FEATURE:
<223> OTHER INFORMATION: CDRH2 of 1H8

<400> SEQUENCE: 95

Val Ile Trp Tyr Asp Gly Ser Asn Glu Tyr
1               5                   10
```

```
<210> SEQ ID NO 96
<211> LENGTH: 13
<212> TYPE: PRT
<213> ORGANISM: Artificial Sequence
<220> FEATURE:
<223> OTHER INFORMATION: CDRH3 of 1H8

<400> SEQUENCE: 96

Ala Arg Asp Leu Asp Tyr Asp Ser Ser Gly Gly Asp Tyr
1               5                   10

<210> SEQ ID NO 97
<211> LENGTH: 12
<212> TYPE: PRT
<213> ORGANISM: Artificial Sequence
<220> FEATURE:
<223> OTHER INFORMATION: CDRL1 of 2D3

<400> SEQUENCE: 97

Arg Ala Ser Gln Ser Gly Ser Ser Ser Phe Leu Ser
1               5                   10

<210> SEQ ID NO 98
<211> LENGTH: 8
<212> TYPE: PRT
<213> ORGANISM: Artificial Sequence
<220> FEATURE:
<223> OTHER INFORMATION: CDRL2 of 2D3

<400> SEQUENCE: 98

Tyr Gly Ala Ser Thr Arg Ala Thr
1               5

<210> SEQ ID NO 99
<211> LENGTH: 13
<212> TYPE: PRT
<213> ORGANISM: Artificial Sequence
<220> FEATURE:
<223> OTHER INFORMATION: CDRH1 of 2D3

<400> SEQUENCE: 99

Ala Ala Ser Gly Phe Thr Phe Ser Ile Tyr Ala Met Ser
1               5                   10

<210> SEQ ID NO 100
<211> LENGTH: 10
<212> TYPE: PRT
<213> ORGANISM: Artificial Sequence
<220> FEATURE:
<223> OTHER INFORMATION: CDRH2 of 2D3

<400> SEQUENCE: 100

Ala Ile Ser Asp Ser Gly Gly Thr Thr Tyr
1               5                   10

<210> SEQ ID NO 101
<211> LENGTH: 12
<212> TYPE: PRT
<213> ORGANISM: Artificial Sequence
<220> FEATURE:
<223> OTHER INFORMATION: CDRH3 of 2D3

<400> SEQUENCE: 101

Ala Lys Arg Thr Arg Tyr Phe Asn Gly Met Asp Val
1               5                   10
```

```
<210> SEQ ID NO 102
<211> LENGTH: 12
<212> TYPE: PRT
<213> ORGANISM: Artificial Sequence
<220> FEATURE:
<223> OTHER INFORMATION: CDRL1 of 2E3

<400> SEQUENCE: 102

Arg Ala Ser Gln Ser Val Ser Ser Ser Tyr Leu Ala
1               5               10

<210> SEQ ID NO 103
<211> LENGTH: 8
<212> TYPE: PRT
<213> ORGANISM: Artificial Sequence
<220> FEATURE:
<223> OTHER INFORMATION: CDRL2 of 2E3

<400> SEQUENCE: 103

Tyr Gly Thr Ser Ser Arg Ala Thr
1               5

<210> SEQ ID NO 104
<211> LENGTH: 13
<212> TYPE: PRT
<213> ORGANISM: Artificial Sequence
<220> FEATURE:
<223> OTHER INFORMATION: CDRH1 of 2E3

<400> SEQUENCE: 104

Ala Ala Ser Gly Phe Thr Phe Ser Ser Tyr Gly Met His
1               5               10

<210> SEQ ID NO 105
<211> LENGTH: 10
<212> TYPE: PRT
<213> ORGANISM: Artificial Sequence
<220> FEATURE:
<223> OTHER INFORMATION: CDRH2 of 2E3

<400> SEQUENCE: 105

Val Ile Trp Tyr Gly Gly Ser Asn Lys Tyr
1               5               10

<210> SEQ ID NO 106
<211> LENGTH: 16
<212> TYPE: PRT
<213> ORGANISM: Artificial Sequence
<220> FEATURE:
<223> OTHER INFORMATION: CDRH3 of 2E3

<400> SEQUENCE: 106

Ala Arg Asp Gly Thr Gly Glu Asn Tyr Tyr Tyr Tyr Val Met Asp Val
1               5               10              15

<210> SEQ ID NO 107
<211> LENGTH: 6
<212> TYPE: PRT
<213> ORGANISM: Artificial Sequence
<220> FEATURE:
<223> OTHER INFORMATION: CDRL1 of 1H10

<400> SEQUENCE: 107

Gln Gly Ile Arg Ile Tyr
1               5
```

```
<210> SEQ ID NO 108
<211> LENGTH: 8
<212> TYPE: PRT
<213> ORGANISM: Artificial Sequence
<220> FEATURE:
<223> OTHER INFORMATION: CDRH1 of 1H10

<400> SEQUENCE: 108

Gly Tyr Ile Phe Thr Ser Tyr Asp
1               5

<210> SEQ ID NO 109
<211> LENGTH: 8
<212> TYPE: PRT
<213> ORGANISM: Artificial Sequence
<220> FEATURE:
<223> OTHER INFORMATION: CDRH2 of 1H10

<400> SEQUENCE: 109

Ile Asp Pro Ser Gly Gly Ser Thr
1               5

<210> SEQ ID NO 110
<211> LENGTH: 6
<212> TYPE: PRT
<213> ORGANISM: Artificial Sequence
<220> FEATURE:
<223> OTHER INFORMATION: CDRL1 of 1A9 and 1B9

<400> SEQUENCE: 110

Gln Asp Ile Arg Asn Asp
1               5

<210> SEQ ID NO 111
<211> LENGTH: 8
<212> TYPE: PRT
<213> ORGANISM: Artificial Sequence
<220> FEATURE:
<223> OTHER INFORMATION: CDRH1 of 1A9

<400> SEQUENCE: 111

Gly Phe Thr Phe Ser Ile Tyr Asp
1               5

<210> SEQ ID NO 112
<211> LENGTH: 7
<212> TYPE: PRT
<213> ORGANISM: Artificial Sequence
<220> FEATURE:
<223> OTHER INFORMATION: CDRH2 of 1A9

<400> SEQUENCE: 112

Ile Gly Thr Ala Gly Asp Thr
1               5

<210> SEQ ID NO 113
<211> LENGTH: 6
<212> TYPE: PRT
<213> ORGANISM: Artificial Sequence
<220> FEATURE:
<223> OTHER INFORMATION: CDRL1 of 1E6 and 1D2

<400> SEQUENCE: 113

Gln Gly Ile Arg Asn Asp
1               5

<210> SEQ ID NO 114
```

<211> LENGTH: 8
<212> TYPE: PRT
<213> ORGANISM: Artificial Sequence
<220> FEATURE:
<223> OTHER INFORMATION: CDRH1 of 1E6 and 1D2

<400> SEQUENCE: 114

Gly Phe Thr Phe Ser Ser Tyr Asp
1               5

<210> SEQ ID NO 115
<211> LENGTH: 8
<212> TYPE: PRT
<213> ORGANISM: Artificial Sequence
<220> FEATURE:
<223> OTHER INFORMATION: CDRH2 of 1E6 and 1B9

<400> SEQUENCE: 115

Ile Trp Tyr Asp Gly Ser His Asn
1               5

<210> SEQ ID NO 116
<211> LENGTH: 8
<212> TYPE: PRT
<213> ORGANISM: Artificial Sequence
<220> FEATURE:
<223> OTHER INFORMATION: CDRH2 of 1D2

<400> SEQUENCE: 116

Ile Trp Tyr Asp Gly Ser Gln Lys
1               5

<210> SEQ ID NO 117
<211> LENGTH: 8
<212> TYPE: PRT
<213> ORGANISM: Artificial Sequence
<220> FEATURE:
<223> OTHER INFORMATION: CDRH1 of 1B9

<400> SEQUENCE: 117

Gly Phe Ile Phe Ser Ser Tyr Asp
1               5

<210> SEQ ID NO 118
<211> LENGTH: 6
<212> TYPE: PRT
<213> ORGANISM: Artificial Sequence
<220> FEATURE:
<223> OTHER INFORMATION: CDRL1 of 1H8

<400> SEQUENCE: 118

Gln Asn Ile Gly Gly Asn
1               5

<210> SEQ ID NO 119
<211> LENGTH: 8
<212> TYPE: PRT
<213> ORGANISM: Artificial Sequence
<220> FEATURE:
<223> OTHER INFORMATION: CDRH1 of 1H8

<400> SEQUENCE: 119

Gly Phe Thr Phe Gly Ser Tyr Gly
1               5

<210> SEQ ID NO 120
<211> LENGTH: 8

```
<212> TYPE: PRT
<213> ORGANISM: Artificial Sequence
<220> FEATURE:
<223> OTHER INFORMATION: CDRH2 of 1H8

<400> SEQUENCE: 120

Ile Trp Tyr Asp Gly Ser Asn Glu
1               5

<210> SEQ ID NO 121
<211> LENGTH: 7
<212> TYPE: PRT
<213> ORGANISM: Artificial Sequence
<220> FEATURE:
<223> OTHER INFORMATION: CDRL1 of 2D3

<400> SEQUENCE: 121

Gln Ser Gly Ser Ser Ser Phe
1               5

<210> SEQ ID NO 122
<211> LENGTH: 8
<212> TYPE: PRT
<213> ORGANISM: Artificial Sequence
<220> FEATURE:
<223> OTHER INFORMATION: CDRH1 of 2D3

<400> SEQUENCE: 122

Gly Phe Thr Phe Ser Ile Tyr Ala
1               5

<210> SEQ ID NO 123
<211> LENGTH: 8
<212> TYPE: PRT
<213> ORGANISM: Artificial Sequence
<220> FEATURE:
<223> OTHER INFORMATION: CDRH2 of 2D3

<400> SEQUENCE: 123

Ile Ser Asp Ser Gly Gly Thr Thr
1               5

<210> SEQ ID NO 124
<211> LENGTH: 7
<212> TYPE: PRT
<213> ORGANISM: Artificial Sequence
<220> FEATURE:
<223> OTHER INFORMATION: CDRL1 of 2E3

<400> SEQUENCE: 124

Gln Ser Val Ser Ser Ser Tyr
1               5

<210> SEQ ID NO 125
<211> LENGTH: 8
<212> TYPE: PRT
<213> ORGANISM: Artificial Sequence
<220> FEATURE:
<223> OTHER INFORMATION: CDRH1 of 2E3

<400> SEQUENCE: 125

Gly Phe Thr Phe Ser Ser Tyr Gly
1               5

<210> SEQ ID NO 126
<211> LENGTH: 8
<212> TYPE: PRT
```

-continued

```
<213> ORGANISM: Artificial Sequence
<220> FEATURE:
<223> OTHER INFORMATION: CDRH2 of 2E3

<400> SEQUENCE: 126

Ile Trp Tyr Gly Gly Ser Asn Lys
1               5

<210> SEQ ID NO 127
<211> LENGTH: 7
<212> TYPE: PRT
<213> ORGANISM: Artificial Sequence
<220> FEATURE:
<223> OTHER INFORMATION: CDRL2 of 1H10 and 1D2

<400> SEQUENCE: 127

Ala Thr Ser Ser Leu Gln Ser
1               5

<210> SEQ ID NO 128
<211> LENGTH: 5
<212> TYPE: PRT
<213> ORGANISM: Artificial Sequence
<220> FEATURE:
<223> OTHER INFORMATION: CDRH1 of 1H10

<400> SEQUENCE: 128

Ser Tyr Asp Met His
1               5

<210> SEQ ID NO 129
<211> LENGTH: 17
<212> TYPE: PRT
<213> ORGANISM: Artificial Sequence
<220> FEATURE:
<223> OTHER INFORMATION: CDRH2 of 1H10

<400> SEQUENCE: 129

Ile Ile Asp Pro Ser Gly Gly Ser Thr Ser Tyr Ala Gln Lys Phe Gln
1               5                   10                  15

Gly

<210> SEQ ID NO 130
<211> LENGTH: 9
<212> TYPE: PRT
<213> ORGANISM: Artificial Sequence
<220> FEATURE:
<223> OTHER INFORMATION: CDRH3 of 1H10

<400> SEQUENCE: 130

Asp Tyr Ser Trp Ser Tyr Phe Asp Tyr
1               5

<210> SEQ ID NO 131
<211> LENGTH: 7
<212> TYPE: PRT
<213> ORGANISM: Artificial Sequence
<220> FEATURE:
<223> OTHER INFORMATION: CDRL2 of 1A9

<400> SEQUENCE: 131

Gly Ala Ser Ser Leu Gln Ser
1               5

<210> SEQ ID NO 132
<211> LENGTH: 5
```

<212> TYPE: PRT
<213> ORGANISM: Artificial Sequence
<220> FEATURE:
<223> OTHER INFORMATION: CDRH1 of 1A9

<400> SEQUENCE: 132

Ile Tyr Asp Met His
1               5

<210> SEQ ID NO 133
<211> LENGTH: 16
<212> TYPE: PRT
<213> ORGANISM: Artificial Sequence
<220> FEATURE:
<223> OTHER INFORMATION: CDRH2 of 1A9

<400> SEQUENCE: 133

Ala Ile Gly Thr Ala Gly Asp Thr Tyr Tyr Ala Gly Ser Val Lys Gly
1               5                   10                  15

<210> SEQ ID NO 134
<211> LENGTH: 9
<212> TYPE: PRT
<213> ORGANISM: Artificial Sequence
<220> FEATURE:
<223> OTHER INFORMATION: CDRH3 of 1A9

<400> SEQUENCE: 134

Glu Tyr Ser Gly Tyr Tyr Phe Asp Tyr
1               5

<210> SEQ ID NO 135
<211> LENGTH: 7
<212> TYPE: PRT
<213> ORGANISM: Artificial Sequence
<220> FEATURE:
<223> OTHER INFORMATION: CDRL2 of 1E6

<400> SEQUENCE: 135

Ala Ala Ser Asn Leu Gln Ser
1               5

<210> SEQ ID NO 136
<211> LENGTH: 5
<212> TYPE: PRT
<213> ORGANISM: Artificial Sequence
<220> FEATURE:
<223> OTHER INFORMATION: CDRH1 of 1E6, 1D2, and 1B9

<400> SEQUENCE: 136

Ser Tyr Asp Ile His
1               5

<210> SEQ ID NO 137
<211> LENGTH: 17
<212> TYPE: PRT
<213> ORGANISM: Artificial Sequence
<220> FEATURE:
<223> OTHER INFORMATION: CDRH2 of 1E6 and 1B9

<400> SEQUENCE: 137

Val Ile Trp Tyr Asp Gly Ser His Asn Tyr Tyr Ser Asp Ser Val Lys
1               5                   10                  15

Gly

<210> SEQ ID NO 138

```
<211> LENGTH: 9
<212> TYPE: PRT
<213> ORGANISM: Artificial Sequence
<220> FEATURE:
<223> OTHER INFORMATION: CDRH3 of 1E6 and 1D2

<400> SEQUENCE: 138

Asp Tyr Ser Gly Ser Tyr Tyr Asp Tyr
1               5

<210> SEQ ID NO 139
<211> LENGTH: 17
<212> TYPE: PRT
<213> ORGANISM: Artificial Sequence
<220> FEATURE:
<223> OTHER INFORMATION: CDRH2 of 1D2

<400> SEQUENCE: 139

Val Ile Trp Tyr Asp Gly Ser Gln Lys Tyr Tyr Ala Asp Ser Val Lys
1               5                   10                  15

Gly

<210> SEQ ID NO 140
<211> LENGTH: 7
<212> TYPE: PRT
<213> ORGANISM: Artificial Sequence
<220> FEATURE:
<223> OTHER INFORMATION: CDRL2 of 1B9

<400> SEQUENCE: 140

Ala Ala Ser Ser Leu Gln Ser
1               5

<210> SEQ ID NO 141
<211> LENGTH: 9
<212> TYPE: PRT
<213> ORGANISM: Artificial Sequence
<220> FEATURE:
<223> OTHER INFORMATION: CDRH3 of 1B9

<400> SEQUENCE: 141

Asp Tyr Ser Gly Ser Tyr Phe Asp Tyr
1               5

<210> SEQ ID NO 142
<211> LENGTH: 17
<212> TYPE: PRT
<213> ORGANISM: Artificial Sequence
<220> FEATURE:
<223> OTHER INFORMATION: CDRH2 of 1H8

<400> SEQUENCE: 142

Val Ile Trp Tyr Asp Gly Ser Asn Glu Tyr Tyr Ala Asp Ser Val Lys
1               5                   10                  15

Gly

<210> SEQ ID NO 143
<211> LENGTH: 11
<212> TYPE: PRT
<213> ORGANISM: Artificial Sequence
<220> FEATURE:
<223> OTHER INFORMATION: CDRH3 of 1H8

<400> SEQUENCE: 143

Asp Leu Asp Tyr Asp Ser Ser Gly Gly Asp Tyr
1               5                   10
```

-continued

<210> SEQ ID NO 144
<211> LENGTH: 17
<212> TYPE: PRT
<213> ORGANISM: Artificial Sequence
<220> FEATURE:
<223> OTHER INFORMATION: CDRH2 of 2D3

<400> SEQUENCE: 144

Ala Ile Ser Asp Ser Gly Gly Thr Thr Tyr Tyr Ala Asp Ser Val Lys
1               5                   10                  15

Gly

<210> SEQ ID NO 145
<211> LENGTH: 10
<212> TYPE: PRT
<213> ORGANISM: Artificial Sequence
<220> FEATURE:
<223> OTHER INFORMATION: CDRH3 of 2D3

<400> SEQUENCE: 145

Arg Thr Arg Tyr Phe Asn Gly Met Asp Val
1               5                   10

<210> SEQ ID NO 146
<211> LENGTH: 17
<212> TYPE: PRT
<213> ORGANISM: Artificial Sequence
<220> FEATURE:
<223> OTHER INFORMATION: CDRH2 of 2E3

<400> SEQUENCE: 146

Val Ile Trp Tyr Gly Gly Ser Asn Lys Tyr Tyr Ala Asp Ser Val Lys
1               5                   10                  15

Gly

<210> SEQ ID NO 147
<211> LENGTH: 14
<212> TYPE: PRT
<213> ORGANISM: Artificial Sequence
<220> FEATURE:
<223> OTHER INFORMATION: CDRH3 of 2E3

<400> SEQUENCE: 147

Asp Gly Thr Gly Glu Asn Tyr Tyr Tyr Tyr Val Met Asp Val
1               5                   10

<210> SEQ ID NO 148
<211> LENGTH: 7
<212> TYPE: PRT
<213> ORGANISM: Artificial Sequence
<220> FEATURE:
<223> OTHER INFORMATION: CDRH1 of 1H10

<400> SEQUENCE: 148

Gly Tyr Ile Phe Thr Ser Tyr
1               5

<210> SEQ ID NO 149
<211> LENGTH: 6
<212> TYPE: PRT
<213> ORGANISM: Artificial Sequence
<220> FEATURE:
<223> OTHER INFORMATION: CDRH2 of 1H10

<400> SEQUENCE: 149

```
Asp Pro Ser Gly Gly Ser
1               5

<210> SEQ ID NO 150
<211> LENGTH: 7
<212> TYPE: PRT
<213> ORGANISM: Artificial Sequence
<220> FEATURE:
<223> OTHER INFORMATION: CDRH1 of 1A9 and 2D3

<400> SEQUENCE: 150

Gly Phe Thr Phe Ser Ile Tyr
1               5

<210> SEQ ID NO 151
<211> LENGTH: 5
<212> TYPE: PRT
<213> ORGANISM: Artificial Sequence
<220> FEATURE:
<223> OTHER INFORMATION: CDRH2 of 1A9

<400> SEQUENCE: 151

Gly Thr Ala Gly Asp
1               5

<210> SEQ ID NO 152
<211> LENGTH: 7
<212> TYPE: PRT
<213> ORGANISM: Artificial Sequence
<220> FEATURE:
<223> OTHER INFORMATION: CDRH1 of 1E6, 1D2, and 2E3

<400> SEQUENCE: 152

Gly Phe Thr Phe Ser Ser Tyr
1               5

<210> SEQ ID NO 153
<211> LENGTH: 6
<212> TYPE: PRT
<213> ORGANISM: Artificial Sequence
<220> FEATURE:
<223> OTHER INFORMATION: CDRH2 of 1E6 and 1B9

<400> SEQUENCE: 153

Trp Tyr Asp Gly Ser His
1               5

<210> SEQ ID NO 154
<211> LENGTH: 6
<212> TYPE: PRT
<213> ORGANISM: Artificial Sequence
<220> FEATURE:
<223> OTHER INFORMATION: CDRH2 of 1D2

<400> SEQUENCE: 154

Trp Tyr Asp Gly Ser Gln
1               5

<210> SEQ ID NO 155
<211> LENGTH: 7
<212> TYPE: PRT
<213> ORGANISM: Artificial Sequence
<220> FEATURE:
<223> OTHER INFORMATION: CDRH1 of 1B9

<400> SEQUENCE: 155
```

-continued

Gly Phe Ile Phe Ser Ser Tyr
1               5

<210> SEQ ID NO 156
<211> LENGTH: 7
<212> TYPE: PRT
<213> ORGANISM: Artificial Sequence
<220> FEATURE:
<223> OTHER INFORMATION: CDRH1 of 1H8

<400> SEQUENCE: 156

Gly Phe Thr Phe Gly Ser Tyr
1               5

<210> SEQ ID NO 157
<211> LENGTH: 6
<212> TYPE: PRT
<213> ORGANISM: Artificial Sequence
<220> FEATURE:
<223> OTHER INFORMATION: CDRH2 of 1H8

<400> SEQUENCE: 157

Trp Tyr Asp Gly Ser Asn
1               5

<210> SEQ ID NO 158
<211> LENGTH: 20
<212> TYPE: PRT
<213> ORGANISM: Artificial Sequence
<220> FEATURE:
<223> OTHER INFORMATION: IgK signal peptide

<400> SEQUENCE: 158

Met Glu Thr Asp Thr Leu Leu Leu Trp Val Leu Leu Leu Trp Val Pro
1               5                   10                  15

Gly Ser Thr Gly
            20

<210> SEQ ID NO 159
<211> LENGTH: 6
<212> TYPE: PRT
<213> ORGANISM: Artificial Sequence
<220> FEATURE:
<223> OTHER INFORMATION: CDRH2 of 2E3

<400> SEQUENCE: 159

Trp Tyr Gly Gly Ser Asn
1               5

<210> SEQ ID NO 160
<211> LENGTH: 5
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (1)..(5)
<223> OTHER INFORMATION: Entire sequence can be repeated n times wherein
      n is an integer including 1, 2, 3, 4, 5, 6, 7, 8, 9, or more

<400> SEQUENCE: 160

Gly Gly Gly Gly Ser
1               5

<210> SEQ ID NO 161
<211> LENGTH: 90

```
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)
<223> OTHER INFORMATION: Residues can be absent or present
<220> FEATURE:
<221> NAME/KEY: MISC_FEATURE
<222> LOCATION: (45)..(90)
<223> OTHER INFORMATION: Residues can be absent or present

<400> SEQUENCE: 161

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Gly Gly Ser Gly Gly Gly
        35                  40                  45

Gly Ser Gly Gly Gly Gly Ser Gly Gly Gly Gly Ser Gly Gly Gly Gly
    50                  55                  60

Ser Gly Gly Gly Gly Ser Gly Gly Gly Gly Ser Gly Gly Gly Gly Ser
65                  70                  75                  80

Gly Gly Gly Gly Ser Gly Gly Gly Gly Ser
            85                  90

<210> SEQ ID NO 162
<211> LENGTH: 70
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)
<223> OTHER INFORMATION: Residues can be absent or present
<220> FEATURE:
<221> NAME/KEY: MISC_FEATURE
<222> LOCATION: (44)..(70)
<223> OTHER INFORMATION: Residues can be absent or present

<400> SEQUENCE: 162

Gly Gly Gly Ser Gly Gly Gly Ser Gly Gly Gly Ser Gly Gly Gly Ser
1               5                   10                  15

Gly Gly Gly Ser Gly Gly Gly Ser Gly Gly Gly Ser Gly Gly Gly Ser
            20                  25                  30

Gly Gly Gly Ser Gly Gly Gly Ser Gly Gly Ser Gly Gly Ser Gly Gly
        35                  40                  45

Ser Gly Gly Ser Gly Gly Ser Gly Gly Ser Gly Gly Ser Gly Gly Ser
    50                  55                  60

Gly Gly Ser Gly Gly Ser
65                  70

<210> SEQ ID NO 163
<211> LENGTH: 45
<212> TYPE: PRT
<213> ORGANISM: Artificial Sequence
<220> FEATURE:
<223> OTHER INFORMATION: GlySer linker
<220> FEATURE:
<221> NAME/KEY: MISC_FEATURE
<222> LOCATION: (5)..(40)
<223> OTHER INFORMATION: Residues can be present or absent

<400> SEQUENCE: 163
```

```
Gly Gly Gly Ser Gly Gly Gly Ser Gly Gly Ser Gly Gly Gly Ser
1               5                   10                  15

Gly Gly Gly Ser Gly Gly Gly Ser Gly Gly Gly Ser Gly Gly Gly Ser
        20                  25                  30

Gly Gly Gly Ser Gly Gly Gly Ser Gly Gly Gly Gly Ser
        35                  40                  45

<210> SEQ ID NO 164
<211> LENGTH: 20
<212> TYPE: PRT
<213> ORGANISM: Artificial Sequence
<220> FEATURE:
<223> OTHER INFORMATION: GlySer linker

<400> SEQUENCE: 164

Gly Gly Gly Gly Ser Gly Gly Gly Gly Ser Gly Gly Gly Gly Ser Gly
1               5                   10                  15

Gly Gly Gly Ser
            20

<210> SEQ ID NO 165
<211> LENGTH: 15
<212> TYPE: PRT
<213> ORGANISM: Artificial Sequence
<220> FEATURE:
<223> OTHER INFORMATION: GlySer linker

<400> SEQUENCE: 165

Gly Gly Gly Gly Ser Gly Gly Gly Gly Ser Gly Gly Gly Gly Ser
1               5                   10                  15

<210> SEQ ID NO 166
<211> LENGTH: 10
<212> TYPE: PRT
<213> ORGANISM: Artificial Sequence
<220> FEATURE:
<223> OTHER INFORMATION: GlySer linker

<400> SEQUENCE: 166

Gly Gly Gly Gly Ser Gly Gly Gly Gly Ser
1               5                   10

<210> SEQ ID NO 167
<211> LENGTH: 5
<212> TYPE: PRT
<213> ORGANISM: Artificial Sequence
<220> FEATURE:
<223> OTHER INFORMATION: GlySer linker

<400> SEQUENCE: 167

Gly Gly Gly Gly Ser
1               5

<210> SEQ ID NO 168
<211> LENGTH: 8
<212> TYPE: PRT
<213> ORGANISM: Artificial Sequence
<220> FEATURE:
<223> OTHER INFORMATION: GlySer linker

<400> SEQUENCE: 168

Gly Gly Gly Ser Gly Gly Gly Ser
1               5
```

```
<210> SEQ ID NO 169
<211> LENGTH: 4
<212> TYPE: PRT
<213> ORGANISM: Artificial Sequence
<220> FEATURE:
<223> OTHER INFORMATION: GlySer linker

<400> SEQUENCE: 169

Gly Gly Gly Ser
1

<210> SEQ ID NO 170
<211> LENGTH: 6
<212> TYPE: PRT
<213> ORGANISM: Artificial Sequence
<220> FEATURE:
<223> OTHER INFORMATION: GlySer linker

<400> SEQUENCE: 170

Gly Gly Ser Gly Gly Ser
1               5

<210> SEQ ID NO 171
<211> LENGTH: 11
<212> TYPE: PRT
<213> ORGANISM: Artificial Sequence
<220> FEATURE:
<223> OTHER INFORMATION: GlySer linker

<400> SEQUENCE: 171

Gly Gly Ser Gly Gly Gly Ser Gly Gly Ser Gly
1               5                   10

<210> SEQ ID NO 172
<211> LENGTH: 10
<212> TYPE: PRT
<213> ORGANISM: Artificial Sequence
<220> FEATURE:
<223> OTHER INFORMATION: GlySer linker

<400> SEQUENCE: 172

Gly Gly Ser Gly Gly Gly Ser Gly Ser Gly
1               5                   10

<210> SEQ ID NO 173
<211> LENGTH: 8
<212> TYPE: PRT
<213> ORGANISM: Artificial Sequence
<220> FEATURE:
<223> OTHER INFORMATION: GlySer linker

<400> SEQUENCE: 173

Gly Gly Ser Gly Gly Gly Ser Gly
1               5

<210> SEQ ID NO 174
<211> LENGTH: 5
<212> TYPE: PRT
<213> ORGANISM: Artificial Sequence
<220> FEATURE:
<223> OTHER INFORMATION: Spacer
<220> FEATURE:
<221> NAME/KEY: MISC_FEATURE
<222> LOCATION: (1)..(5)
<223> OTHER INFORMATION: Entire sequence can be repeated n times wherein
      n is an integer including 1, 2, 3, 4, 5, 6, 7, 8, 9, or more

<400> SEQUENCE: 174
```

```
Glu Ala Ala Ala Lys
1               5

<210> SEQ ID NO 175
<211> LENGTH: 6
<212> TYPE: PRT
<213> ORGANISM: Artificial Sequence
<220> FEATURE:
<223> OTHER INFORMATION: His tag

<400> SEQUENCE: 175

His His His His His His
1               5

<210> SEQ ID NO 176
<211> LENGTH: 8
<212> TYPE: PRT
<213> ORGANISM: Artificial Sequence
<220> FEATURE:
<223> OTHER INFORMATION: Flag tag

<400> SEQUENCE: 176

Asp Tyr Lys Asp Asp Asp Asp Lys
1               5

<210> SEQ ID NO 177
<211> LENGTH: 8
<212> TYPE: PRT
<213> ORGANISM: Artificial Sequence
<220> FEATURE:
<223> OTHER INFORMATION: Xpress tag

<400> SEQUENCE: 177

Asp Leu Tyr Asp Asp Asp Asp Lys
1               5

<210> SEQ ID NO 178
<211> LENGTH: 15
<212> TYPE: PRT
<213> ORGANISM: Artificial Sequence
<220> FEATURE:
<223> OTHER INFORMATION: Avi tag

<400> SEQUENCE: 178

Gly Leu Asn Asp Ile Phe Glu Ala Gln Lys Ile Glu Trp His Glu
1               5                   10                  15

<210> SEQ ID NO 179
<211> LENGTH: 26
<212> TYPE: PRT
<213> ORGANISM: Artificial Sequence
<220> FEATURE:
<223> OTHER INFORMATION: Calmodulin tag

<400> SEQUENCE: 179

Lys Arg Arg Trp Lys Lys Asn Phe Ile Ala Val Ser Ala Ala Asn Arg
1               5                   10                  15

Phe Lys Lys Ile Ser Ser Ser Gly Ala Leu
            20                  25

<210> SEQ ID NO 180
<211> LENGTH: 9
<212> TYPE: PRT
<213> ORGANISM: Artificial Sequence
<220> FEATURE:
<223> OTHER INFORMATION: HA tag
```

```
<400> SEQUENCE: 180

Tyr Pro Tyr Asp Val Pro Asp Tyr Ala
1               5

<210> SEQ ID NO 181
<211> LENGTH: 10
<212> TYPE: PRT
<213> ORGANISM: Artificial Sequence
<220> FEATURE:
<223> OTHER INFORMATION: Myc tag

<400> SEQUENCE: 181

Glu Gln Lys Leu Ile Ser Glu Glu Asp Leu
1               5                   10

<210> SEQ ID NO 182
<211> LENGTH: 8
<212> TYPE: PRT
<213> ORGANISM: Artificial Sequence
<220> FEATURE:
<223> OTHER INFORMATION: STREP tag

<400> SEQUENCE: 182

Trp Arg His Pro Gln Phe Gly Gly
1               5

<210> SEQ ID NO 183
<211> LENGTH: 8
<212> TYPE: PRT
<213> ORGANISM: Artificial Sequence
<220> FEATURE:
<223> OTHER INFORMATION: STREP tag II

<400> SEQUENCE: 183

Trp Ser His Pro Gln Phe Glu Lys
1               5

<210> SEQ ID NO 184
<211> LENGTH: 13
<212> TYPE: PRT
<213> ORGANISM: Artificial Sequence
<220> FEATURE:
<223> OTHER INFORMATION: Softag 1

<400> SEQUENCE: 184

Ser Leu Ala Glu Leu Leu Asn Ala Gly Leu Gly Gly Ser
1               5                   10

<210> SEQ ID NO 185
<211> LENGTH: 8
<212> TYPE: PRT
<213> ORGANISM: Artificial Sequence
<220> FEATURE:
<223> OTHER INFORMATION: Softag 3

<400> SEQUENCE: 185

Thr Gln Asp Pro Ser Arg Val Gly
1               5

<210> SEQ ID NO 186
<211> LENGTH: 14
<212> TYPE: PRT
<213> ORGANISM: Artificial Sequence
<220> FEATURE:
<223> OTHER INFORMATION: V5 tag

<400> SEQUENCE: 186
```

-continued

```
Gly Lys Pro Ile Pro Asn Pro Leu Leu Gly Leu Asp Ser Thr
1               5                   10

<210> SEQ ID NO 187

<400> SEQUENCE: 187

000

<210> SEQ ID NO 188
<211> LENGTH: 63
<212> TYPE: DNA
<213> ORGANISM: Artificial Sequence
<220> FEATURE:
<223> OTHER INFORMATION: Signal peptide coding sequence

<400> SEQUENCE: 188
ctgctgctcg tgaccagcct gctgctgtgc gaactgcccc accctgcctt tctgctgatc        60
ccc                                                                      63

<210> SEQ ID NO 189
<211> LENGTH: 45
<212> TYPE: DNA
<213> ORGANISM: Artificial Sequence
<220> FEATURE:
<223> OTHER INFORMATION: GlySer linker coding sequence

<400> SEQUENCE: 189
ggaggcggag gatctggcgg agggggctct ggaggaggag gatct                        45

<210> SEQ ID NO 190
<211> LENGTH: 260
<212> TYPE: PRT
<213> ORGANISM: Artificial Sequence
<220> FEATURE:
<223> OTHER INFORMATION: 1H10 scFv in VH-VL orientation

<400> SEQUENCE: 190

Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Ala Ser Val Lys Val Ser Cys Lys Gly Ser Gly Tyr Ile
        35                  40                  45

Phe Thr Ser Tyr Asp Met His Trp Val Arg Gln Ala Pro Gly Gln Gly
    50                  55                  60

Leu Glu Trp Met Gly Ile Ile Asp Pro Ser Gly Gly Ser Thr Ser Tyr
65                  70                  75                  80

Ala Gln Lys Phe Gln Gly Arg Val Thr Met Thr Arg Asp Thr Ser Met
                85                  90                  95

Ser Thr Val Tyr Met Glu Leu Ser Ser Leu Arg Ser Glu Asp Thr Ala
            100                 105                 110

Val Tyr Tyr Cys Thr Arg Asp Tyr Ser Trp Ser Tyr Phe Asp Tyr Trp
        115                 120                 125

Gly Gln Gly Thr Leu Val Thr Val Ser Ser Gly Gly Gly Gly Ser Gly
        130                 135                 140

Gly Gly Gly Ser Gly Gly Gly Gly Ser Ala Ile Gln Met Thr Gln Ser
145                 150                 155                 160

Pro Ser Ser Leu Ser Ala Ser Val Gly Asp Arg Val Thr Ile Thr Cys
                165                 170                 175
```

```
Arg Ala Ser Gln Gly Ile Arg Ile Tyr Leu Gly Trp Tyr Gln Gln Lys
            180                 185                 190

Pro Gly Lys Ala Pro Lys Leu Leu Ile Tyr Ala Thr Ser Ser Leu Gln
            195                 200                 205

Ser Gly Val Pro Ser Arg Phe Ser Gly Ser Gly Ser Gly Thr Asp Phe
            210                 215                 220

Thr Leu Thr Ile Ser Ser Leu Gln Pro Glu Asp Phe Ala Thr Tyr Tyr
225                 230                 235                 240

Cys Leu Gln Asp Tyr Asn Tyr Pro Trp Thr Phe Gly Gln Gly Thr Lys
            245                 250                 255

Val Glu Ile Lys
            260

<210> SEQ ID NO 191
<211> LENGTH: 260
<212> TYPE: PRT
<213> ORGANISM: Artificial Sequence
<220> FEATURE:
<223> OTHER INFORMATION: 1H10 scFv in VL-VH orientation

<400> SEQUENCE: 191

Met Glu Thr Asp Thr Leu Leu Leu Trp Val Leu Leu Leu Trp Val Pro
1               5                   10                  15

Gly Ser Thr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Gly
            35                  40                  45

Ile Arg Ile Tyr Leu Gly Trp Tyr Gln Gln Lys Pro Gly Lys Ala Pro
        50                  55                  60

Lys Leu Leu Ile Tyr Ala Thr Ser Ser Leu Gln Ser Gly Val Pro Ser
65                  70                  75                  80

Arg Phe Ser Gly Ser Gly Ser Gly Thr Asp Phe Thr Leu Thr Ile Ser
            85                  90                  95

Ser Leu Gln Pro Glu Asp Phe Ala Thr Tyr Tyr Cys Leu Gln Asp Tyr
            100                 105                 110

Asn Tyr Pro Trp Thr Phe Gly Gln Gly Thr Lys Val Glu Ile Lys Gly
            115                 120                 125

Gly Gly Gly Ser Gly Gly Gly Gly Ser Gly Gly Gly Gly Ser Gln Val
        130                 135                 140

Gln Leu Val Gln Ser Gly Ala Glu Val Lys Lys Pro Gly Ala Ser Val
145                 150                 155                 160

Lys Val Ser Cys Lys Gly Ser Gly Tyr Ile Phe Thr Ser Tyr Asp Met
            165                 170                 175

His Trp Val Arg Gln Ala Pro Gly Gln Gly Leu Glu Trp Met Gly Ile
            180                 185                 190

Ile Asp Pro Ser Gly Gly Ser Thr Ser Tyr Ala Gln Lys Phe Gln Gly
            195                 200                 205

Arg Val Thr Met Thr Arg Asp Thr Ser Met Ser Thr Val Tyr Met Glu
            210                 215                 220

Leu Ser Ser Leu Arg Ser Glu Asp Thr Ala Val Tyr Tyr Cys Thr Arg
225                 230                 235                 240

Asp Tyr Ser Trp Ser Tyr Phe Asp Tyr Trp Gly Gln Gly Thr Leu Val
            245                 250                 255

Thr Val Ser Ser
            260
```

```
<210> SEQ ID NO 192
<211> LENGTH: 259
<212> TYPE: PRT
<213> ORGANISM: Artificial Sequence
<220> FEATURE:
<223> OTHER INFORMATION: 1A9 scFv in VH-VL orientation

<400> SEQUENCE: 192

Met Glu Thr Asp Thr Leu Leu Leu Trp Val Leu Leu Leu Trp Val Pro
1               5                   10                  15

Gly Ser Thr Gly Glu Val Gln Leu Val Glu Ser Gly Gly Gly Leu Val
            20                  25                  30

Gln Pro Gly Gly Ser Leu Arg Leu Ser Cys Ala Ala Ser Gly Phe Thr
        35                  40                  45

Phe Ser Ile Tyr Asp Met His Trp Val Arg Gln Ala Thr Gly Lys Gly
        50                  55                  60

Leu Glu Trp Val Ser Ala Ile Gly Thr Ala Gly Asp Thr Tyr Tyr Ala
65                  70                  75                  80

Gly Ser Val Lys Gly Arg Phe Thr Ile Ser Arg Glu Asn Ala Lys Asn
                85                  90                  95

Ser Leu Tyr Leu Gln Met Asn Ser Leu Arg Ala Gly Asp Thr Ala Val
            100                 105                 110

Tyr Tyr Cys Ala Arg Glu Tyr Ser Gly Tyr Tyr Phe Asp Tyr Trp Gly
            115                 120                 125

Gln Gly Thr Leu Val Thr Val Ser Ser Gly Gly Gly Gly Ser Gly Gly
        130                 135                 140

Gly Gly Ser Gly Gly Gly Gly Ser Ala Ile Gln Met Thr Gln Ser Pro
145                 150                 155                 160

Ser Ser Leu Ser Ala Ser Val Gly Asp Arg Val Thr Ile Thr Cys Arg
                165                 170                 175

Ala Ser Gln Asp Ile Arg Asn Asp Leu Gly Trp Tyr Gln Gln Lys Pro
                180                 185                 190

Gly Lys Ala Pro Lys Ile Leu Ile Tyr Gly Ala Ser Ser Leu Gln Ser
            195                 200                 205

Gly Val Pro Ser Arg Phe Ser Gly Ser Gly Ser Gly Thr Asp Phe Thr
        210                 215                 220

Phe Thr Ile Ser Ser Leu Gln Pro Glu Asp Phe Ala Thr Tyr Tyr Cys
225                 230                 235                 240

Leu Gln Glu Tyr Asn Tyr Pro Cys Thr Phe Gly Gln Gly Thr Lys Leu
                245                 250                 255

Glu Ile Lys

<210> SEQ ID NO 193
<211> LENGTH: 259
<212> TYPE: PRT
<213> ORGANISM: Artificial Sequence
<220> FEATURE:
<223> OTHER INFORMATION: 1A9 scFv in VL-VH orientation

<400> SEQUENCE: 193

Met Glu Thr Asp Thr Leu Leu Leu Trp Val Leu Leu Leu Trp Val Pro
1               5                   10                  15

Gly Ser Thr Gly Ala Ile Gln Met Thr Gln Ser Pro Ser Ser Leu Ser
            20                  25                  30

Ala Ser Val Gly Asp Arg Val Thr Ile Thr Cys Arg Ala Ser Gln Asp
            35                  40                  45
```

-continued

```
Ile Arg Asn Asp Leu Gly Trp Tyr Gln Gln Lys Pro Gly Lys Ala Pro
    50                  55                  60

Lys Ile Leu Ile Tyr Gly Ala Ser Ser Leu Gln Ser Gly Val Pro Ser
65                  70                  75                  80

Arg Phe Ser Gly Ser Gly Ser Gly Thr Asp Phe Thr Phe Thr Ile Ser
                85                  90                  95

Ser Leu Gln Pro Glu Asp Phe Ala Thr Tyr Tyr Cys Leu Gln Glu Tyr
                100                 105                 110

Asn Tyr Pro Cys Thr Phe Gly Gln Gly Thr Lys Leu Glu Ile Lys Gly
                115                 120                 125

Gly Gly Gly Ser Gly Gly Gly Gly Ser Gly Gly Gly Ser Glu Val
        130                 135                 140

Gln Leu Val Glu Ser Gly Gly Gly Leu Val Gln Pro Gly Gly Ser Leu
145                 150                 155                 160

Arg Leu Ser Cys Ala Ala Ser Gly Phe Thr Phe Ser Ile Tyr Asp Met
                165                 170                 175

His Trp Val Arg Gln Ala Thr Gly Lys Gly Leu Glu Trp Val Ser Ala
                180                 185                 190

Ile Gly Thr Ala Gly Asp Thr Tyr Tyr Ala Gly Ser Val Lys Gly Arg
                195                 200                 205

Phe Thr Ile Ser Arg Glu Asn Ala Lys Asn Ser Leu Tyr Leu Gln Met
        210                 215                 220

Asn Ser Leu Arg Ala Gly Asp Thr Ala Val Tyr Tyr Cys Ala Arg Glu
225                 230                 235                 240

Tyr Ser Gly Tyr Tyr Phe Asp Tyr Trp Gly Gln Gly Thr Leu Val Thr
                245                 250                 255

Val Ser Ser
```

```
<210> SEQ ID NO 194
<211> LENGTH: 260
<212> TYPE: PRT
<213> ORGANISM: Artificial Sequence
<220> FEATURE:
<223> OTHER INFORMATION: 1E6 scFv in VH-VL orientation

<400> SEQUENCE: 194
```

```
Met Glu Thr Asp Thr Leu Leu Leu Trp Val Leu Leu Leu Trp Val Pro
1               5                   10                  15

Gly Ser Thr Gly Gln Val Gln Leu Val Glu Ser Gly Gly Gly Val Val
                20                  25                  30

Gln Pro Gly Arg Ser Leu Arg Leu Ser Cys Ala Ala Ser Gly Phe Thr
        35                  40                  45

Phe Ser Ser Tyr Asp Ile His Trp Val Arg Gln Ala Pro Gly Lys Gly
        50                  55                  60

Leu Glu Trp Val Ala Val Ile Trp Tyr Asp Gly Ser His Asn Tyr Tyr
65                  70                  75                  80

Ser Asp Ser Val Lys Gly Arg Phe Thr Ile Ser Arg Asp Asn Ser Lys
                85                  90                  95

Asn Thr Leu Tyr Leu Gln Met Asn Ser Leu Arg Ala Glu Asp Thr Ala
                100                 105                 110

Val Tyr Tyr Cys Ala Arg Asp Tyr Ser Gly Ser Tyr Tyr Asp Tyr Trp
                115                 120                 125

Gly Gln Gly Thr Leu Val Thr Val Ser Ser Gly Gly Gly Gly Ser Gly
        130                 135                 140
```

```
Gly Gly Gly Ser Gly Gly Gly Gly Ser Ala Ile Gln Met Thr Gln Ser
145             150             155             160

Pro Ser Ser Leu Ser Ala Ser Val Gly Asp Arg Val Thr Ile Thr Cys
                165             170             175

Arg Ala Ser Gln Gly Ile Arg Asn Asp Leu Gly Trp Tyr Gln Gln Lys
            180             185             190

Pro Gly Lys Ala Pro Lys Leu Leu Ile Tyr Ala Ala Ser Asn Leu Gln
        195             200             205

Ser Gly Val Pro Ser Arg Phe Ser Gly Ser Gly Ser Gly Thr Asp Phe
    210             215             220

Thr Leu Thr Ile Ser Ser Leu Gln Pro Glu Asp Phe Ala Thr Tyr Tyr
225             230             235             240

Cys Leu Gln Asp Tyr Ser Tyr Pro Arg Thr Phe Gly Gln Gly Thr Lys
            245             250             255

Val Glu Ile Lys
            260
```

```
<210> SEQ ID NO 195
<211> LENGTH: 260
<212> TYPE: PRT
<213> ORGANISM: Artificial Sequence
<220> FEATURE:
<223> OTHER INFORMATION: 1E6 scFv in VL-VH orientation

<400> SEQUENCE: 195
```

```
Met Glu Thr Asp Thr Leu Leu Leu Trp Val Leu Leu Leu Trp Val Pro
1               5               10              15

Gly Ser Thr Gly Ala Ile Gln Met Thr Gln Ser Pro Ser Ser Leu Ser
            20              25              30

Ala Ser Val Gly Asp Arg Val Thr Ile Thr Cys Arg Ala Ser Gln Gly
        35              40              45

Ile Arg Asn Asp Leu Gly Trp Tyr Gln Gln Lys Pro Gly Lys Ala Pro
    50              55              60

Lys Leu Leu Ile Tyr Ala Ala Ser Asn Leu Gln Ser Gly Val Pro Ser
65              70              75              80

Arg Phe Ser Gly Ser Gly Ser Gly Thr Asp Phe Thr Leu Thr Ile Ser
            85              90              95

Ser Leu Gln Pro Glu Asp Phe Ala Thr Tyr Tyr Cys Leu Gln Asp Tyr
        100             105             110

Ser Tyr Pro Arg Thr Phe Gly Gln Gly Thr Lys Val Glu Ile Lys Gly
    115             120             125

Gly Gly Gly Ser Gly Gly Gly Gly Ser Gly Gly Gly Gly Ser Gln Val
    130             135             140

Gln Leu Val Glu Ser Gly Gly Gly Val Val Gln Pro Gly Arg Ser Leu
145             150             155             160

Arg Leu Ser Cys Ala Ala Ser Gly Phe Thr Phe Ser Ser Tyr Asp Ile
            165             170             175

His Trp Val Arg Gln Ala Pro Gly Lys Gly Leu Glu Trp Val Ala Val
            180             185             190

Ile Trp Tyr Asp Gly Ser His Asn Tyr Tyr Ser Asp Ser Val Lys Gly
            195             200             205

Arg Phe Thr Ile Ser Arg Asp Asn Ser Lys Asn Thr Leu Tyr Leu Gln
    210             215             220

Met Asn Ser Leu Arg Ala Glu Asp Thr Ala Val Tyr Tyr Cys Ala Arg
225             230             235             240
```

-continued

```
Asp Tyr Ser Gly Ser Tyr Tyr Asp Tyr Trp Gly Gln Gly Thr Leu Val
            245                 250                 255

Thr Val Ser Ser
            260

<210> SEQ ID NO 196
<211> LENGTH: 262
<212> TYPE: PRT
<213> ORGANISM: Artificial Sequence
<220> FEATURE:
<223> OTHER INFORMATION: 2D3 scFv in VH-VL orientation

<400> SEQUENCE: 196

Met Glu Thr Asp Thr Leu Leu Leu Trp Val Leu Leu Leu Trp Val Pro
1               5                   10                  15

Gly Ser Thr Gly Glu Val Gln Leu Leu Glu Ser Gly Gly Gly Leu Val
            20                  25                  30

Gln Pro Gly Gly Ser Leu Ser Leu Ser Cys Ala Ala Ser Gly Phe Thr
            35                  40                  45

Phe Ser Ile Tyr Ala Met Ser Trp Val Arg Gln Ala Pro Gly Lys Gly
        50                  55                  60

Leu Glu Trp Val Ser Ala Ile Ser Asp Ser Gly Gly Thr Thr Tyr Tyr
65                  70                  75                  80

Ala Asp Ser Val Lys Gly Arg Phe Thr Ile Ser Arg Asp Asn Ser Lys
                85                  90                  95

Asn Met Leu Tyr Leu Glu Met Asn Ser Leu Arg Ala Glu Asp Thr Ala
            100                 105                 110

Ile Tyr Tyr Cys Ala Lys Arg Thr Arg Tyr Phe Asn Gly Met Asp Val
            115                 120                 125

Trp Gly Gln Gly Thr Thr Val Thr Val Ser Ser Gly Gly Gly Gly Ser
            130                 135                 140

Gly Gly Gly Gly Ser Gly Gly Gly Ser Glu Ile Val Met Thr Gln
145                 150                 155                 160

Ser Pro Ala Thr Leu Ser Leu Ser Pro Gly Glu Arg Ala Thr Leu Ser
                165                 170                 175

Cys Arg Ala Ser Gln Ser Gly Ser Ser Ser Phe Leu Ser Trp Tyr Gln
            180                 185                 190

Gln Lys Pro Gly Gln Ala Pro Arg Leu Leu Ile Tyr Gly Ala Ser Thr
            195                 200                 205

Arg Ala Thr Gly Ile Pro Ala Arg Phe Ser Gly Ser Gly Ser Gly Thr
        210                 215                 220

Asp Phe Thr Leu Thr Ile Ser Ser Leu Gln Pro Glu Asp Phe Ala Val
225                 230                 235                 240

Tyr Tyr Cys Gln Gln Asp Tyr Asn Leu Pro Phe Thr Phe Gly Pro Gly
            245                 250                 255

Thr Lys Val Asp Ile Lys
            260

<210> SEQ ID NO 197
<211> LENGTH: 262
<212> TYPE: PRT
<213> ORGANISM: Artificial Sequence
<220> FEATURE:
<223> OTHER INFORMATION: 2D3 scFv in VL-VH orientation

<400> SEQUENCE: 197

Met Glu Thr Asp Thr Leu Leu Leu Trp Val Leu Leu Leu Trp Val Pro
1               5                   10                  15
```

```
Gly Ser Thr Gly Glu Ile Val Met Thr Gln Ser Pro Ala Thr Leu Ser
         20                  25                  30

Leu Ser Pro Gly Glu Arg Ala Thr Leu Ser Cys Arg Ala Ser Gln Ser
         35                  40                  45

Gly Ser Ser Ser Phe Leu Ser Trp Tyr Gln Gln Lys Pro Gly Gln Ala
     50                  55                  60

Pro Arg Leu Leu Ile Tyr Gly Ala Ser Thr Arg Ala Thr Gly Ile Pro
65                  70                  75                  80

Ala Arg Phe Ser Gly Ser Gly Ser Gly Thr Asp Phe Thr Leu Thr Ile
                 85                  90                  95

Ser Ser Leu Gln Pro Glu Asp Phe Ala Val Tyr Tyr Cys Gln Gln Asp
         100                 105                 110

Tyr Asn Leu Pro Phe Thr Phe Gly Pro Gly Thr Lys Val Asp Ile Lys
         115                 120                 125

Gly Gly Gly Gly Ser Gly Gly Gly Gly Ser Gly Gly Gly Gly Ser Glu
     130                 135                 140

Val Gln Leu Leu Glu Ser Gly Gly Gly Leu Val Gln Pro Gly Gly Ser
145                 150                 155                 160

Leu Ser Leu Ser Cys Ala Ala Ser Gly Phe Thr Phe Ser Ile Tyr Ala
                 165                 170                 175

Met Ser Trp Val Arg Gln Ala Pro Gly Lys Gly Leu Glu Trp Val Ser
                 180                 185                 190

Ala Ile Ser Asp Ser Gly Gly Thr Thr Tyr Tyr Ala Asp Ser Val Lys
             195                 200                 205

Gly Arg Phe Thr Ile Ser Arg Asp Asn Ser Lys Asn Met Leu Tyr Leu
         210                 215                 220

Glu Met Asn Ser Leu Arg Ala Glu Asp Thr Ala Ile Tyr Tyr Cys Ala
225                 230                 235                 240

Lys Arg Thr Arg Tyr Phe Asn Gly Met Asp Val Trp Gly Gln Gly Thr
                 245                 250                 255

Thr Val Thr Val Ser Ser
             260
```

```
<210> SEQ ID NO 198
<211> LENGTH: 1092
<212> TYPE: DNA
<213> ORGANISM: Homo sapiens

<400> SEQUENCE: 198
atgccgctgc tgctactgct gcccctgctg tgggcagggg ccctggctat ggatccaaat      60
ttctggctgc aagtgcagga gtcagtgacg gtacaggagg gtttgtgcgt cctcgtgccc     120
tgcactttct tccatcccat accctactac gacaagaact ccccagttca tggttactgg     180
ttccgggaag gagccattat atccagggac tctccagtgg ccacaaacaa gctagatcaa     240
gaagtacagg aggagactca gggcagattc cgcctccttg gggatcccag taggaacaac     300
tgctccctga gcatcgtaga cgccaggagg agggataatg gttcatactt ctttcggatg     360
gagagaggaa gtaccaaata cagttacaaa tctccccagc tctctgtgca tgtgacagac     420
ttgacccaca ggcccaaaat cctcatccct ggcactctag aacccggcca ctccaaaaac     480
ctgacctgct ctgtgtcctg ggcctgtgag cagggaacac ccccgatctt ctcctggttg     540
tcagctgccc ccacctccct gggccccagg actactcact cctcggtgct cataatcacc     600
ccacggcccc aggaccacgg caccaacctg acctgtcagg tgaagttcgc tggagctggt     660
```

-continued

```
gtgactacgg agagaaccat ccagctcaac gtcacctatg ttccacagaa cccaacaact      720
ggtatctttc caggagatgg ctcagggaaa caagagacca gagcaggagt ggttcatggg      780
gccattggag gagctggtgt tacagccctg ctcgctcttt gtctctgcct catcttcttc      840
atagtgaaga cccacaggag gaaagcagcc aggacagcag tgggcaggaa tgacacccac      900
cctaccacag ggtcagcctc cccgaaacac cagaagaagt ccaagttaca tggccccact      960
gaaacctcaa gctgttcagg tgccgcccct actgtggaga tggatgagga gctgcattat     1020
gcttccctca actttcatgg gatgaatcct tccaaggaca cctccaccga atactcagag     1080
gtcaggaccc ag                                                        1092
```

<210> SEQ ID NO 199
<211> LENGTH: 364
<212> TYPE: PRT
<213> ORGANISM: Homo sapiens

<400> SEQUENCE: 199

```
Met Pro Leu Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
        50                  55                  60

Ala Ile Ile Ser Arg Asp Ser Pro Val Ala Thr Asn Lys Leu Asp Gln
65                  70                  75                  80

Glu Val Gln Glu Glu Thr Gln Gly Arg Phe Arg Leu Leu Gly Asp Pro
                85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
            115                 120                 125

Tyr Lys Ser Pro Gln Leu Ser Val His Val Thr Asp Leu Thr His Arg
        130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
            165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
            195                 200                 205

Asn Leu Thr Cys Gln Val Lys Phe Ala Gly Ala Gly Val Thr Thr Glu
        210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
```

-continued

```
            290               295              300
Ser Ala Ser Pro Lys His Gln Lys Lys Ser Lys Leu His Gly Pro Thr
305               310              315              320

Glu Thr Ser Ser Cys Ser Gly Ala Ala Pro Thr Val Glu Met Asp Glu
                325              330              335

Glu Leu His Tyr Ala Ser Leu Asn Phe His Gly Met Asn Pro Ser Lys
            340              345              350

Asp Thr Ser Thr Glu Tyr Ser Glu Val Arg Thr Gln
        355              360

<210> SEQ ID NO 200
<211> LENGTH: 3288
<212> TYPE: DNA
<213> ORGANISM: Artificial Sequence
<220> FEATURE:
<223> OTHER INFORMATION: 1H10-LvHv-intDS-41bb-3z-T-CD19t Top Strand

<400> SEQUENCE: 200
ggatctgcga tcgctccggt gcccgtcagt gggcagagcg cacatcgccc acagtccccg      60
agaagttggg gggagggggtc ggcaattgaa ccggtgccta gagaaggtgg cgcggggtaa     120
actgggaaag tgatgtcgtg tactggctcc gccttttttcc cgagggtggg ggagaaccgt    180
atataagtgc agtagtcgcc gtgaacgttc tttttcgcaa cgggtttgcc gccagaacac    240
agctgaagct tcgaggggct cgcatctctc cttcacgcgc ccgccgccct acctgaggcc    300
gccatccacg ccggttgagt cgcgttctgc cgcctcccgc ctgtggtgcc tcctgaactg    360
cgtccgccgt ctaggtaagt ttaaagctca ggtcgagacc gggcctttgt ccggcgctcc    420
cttggagcct acctagactc agccggctct ccacgctttg cctgaccctg cttgctcaac    480
tctacgtctt tgtttcgttt tctgttctgc gccgttacag atccaagctg tgaccggcgc    540
ctacggctag ccaccatgct gctgctcgtg accagcctgc tgctgtgcga actgccccac    600
cctgcctttc tgctgatccc cgcgatacaa atgacgcaaa gtcccagcag tttgtccgcc    660
tcagtaggcg accgcgttac gattacgtgt agggcgtctc aagggatcag gatctatctg    720
ggctggtatc aacaaaagcc tgggaaagcc ccaaagctcc ttatatatgc aacatcatcc    780
ctgcaaagcg gcgttccatc ccgattcagt ggttctggta gcggtacgga cttcactctc    840
acaatctcat ctcttcaacc agaagacttt gcgacgtatt actgtttgca agactacaat    900
tatccatgga cgttcggcca aggcacgaaa gtcgagataa agggaggcgg aggatctggc    960
ggagggggct ctggaggagg aggatctcaa gtacagcttg ttcaaagtgg tgctgaagtt   1020
aaaaagccag gggccagcgt taaggtatcc tgcaagggaa gtggttacat cttcacatct   1080
tacgacatgc actgggtacg acaggctcct ggacagggtc tggaatggat gggtatcata   1140
gacccctcag gaggatctac gagctatgcc caaaaatttc agggaagagt aacaatgacc   1200
agggacacgt ccatgagcac agtctacatg gaactcagca gtctcagatc agaggatacg   1260
gcggtttact actgtactag ggattattca tggagctatt cgactattg gggacaagga   1320 accttggtaa cagtgtcttc agagtctaag tacggaccgc cctgcccccc ttgccctggc   1380
cagcctagag aaccccaggt gtacaccctg cctcccagcc aggaagagat gaccaagaac   1440
caggtgtccc tgacctgcct ggtcaaaggc ttctacccca gcgatatcgc cgtggaatgg   1500
gagagcaacg gccagcccga gaacaactac aagaccaccc ccctgtgct ggacagcgac   1560 ggcagcttct tcctgtactc ccggctgacc gtggacaaga gccggtggca ggaaggcaac   1620
gtcttcagct gcagcgtgat gcacgaggcc ctgcacaacc actacaccca gaagtccctg   1680
```

-continued

```
agcctgagcc tgggcaagat gttctgggtg ctggtggtgg tcggaggcgt gctggcctgc        1740
tacagcctgc tggtcaccgt ggccttcatc atctttttggg tgaaacgggg cagaaagaaa        1800
ctcctgtata tattcaaaca accatttatg agaccagtac aaactactca agaggaagat        1860
ggctgtagct gccgatttcc agaagaagaa gaaggaggat gtgaactgcg ggtgaagttc        1920
agcagaagcg ccgacgcccc tgcctaccag cagggccaga atcagctgta caacgagctg        1980
aacctgggca aagggaaga gtacgacgtc ctggataagc ggagaggccg ggaccctgag        2040
atgggcggca agcctcggcg gaagaacccc caggaaggcc tgtataacga actgcagaaa        2100
gacaagatgg ccgaggccta cagcgagatc ggcatgaagg gcgagcggag gcggggcaag        2160
ggccacgacg gcctgtatca gggcctgtcc accgccacca aggatacccta cgacgccctg        2220 cacatgcagg ccctgcccccc aaggctcgag ggcggcggag agggcagagg aagtcttcta        2280
acatgcggtg acgtggagga gaatccaggc cctaggatgc cacctccaag actcctcttc        2340
ttcctcctct tcctgacacc aatggaagtc aggcctgagg aacctctagt ggtgaaggtg        2400
gaagagggag ataacgctgt gttacagtgc ctcaagggaa cctcagatgg acccactcag        2460
cagctgacct ggtctcggga gtctccgctt aaacccttcc tgaaactcag ccttggactg        2520
ccaggtctgg aatccacat gaggccactg gctatctggc tgttcatctt caacgtctct        2580
caacagatgg gaggcttcta cctgtgtcag cctggaccac cttctgagaa ggcatggcag        2640
cctggttgga cagtcaatgt ggagggttct ggtgagctgt ccggtggaa tgtttcggac        2700 ctaggtggac tgggatgtgg tctgaagaac aggtcctcag aggggacctag ctctccttcc        2760 gggaagctca tgagccccaa gctgtatgtg tgggccaaag accgccctga gatctgggag        2820
ggagagcctc cgtgtgtccc accgagggac agcctgaacc agagcctcag ccaggacctc        2880
accatggccc ctggctccac actctggctg tcctgtgggg tacccccctga ctctgtgtcc        2940 aggggccccc tctcctggac ccatgtgcac cccaaggggc ctaagtcatt gctgagccta        3000
gagctgaagg acgatcgccc tgccagagat atgtgggtaa tggagacggg tctgttgttg        3060
ccccgggcca cagctcaaga cgctggaaag tattattgtc accgtggcaa cctgaccatg        3120
tcattccacc tggagatcac tgctcggcca gtactatggc actggctgct gaggactggt        3180
ggctggaagg tctcagctgt gactttggct tatctgatct tctgcctgtg ttcccttgtg        3240
ggcattcttc atcttcaaag agccctggtc ctgaggagga aaagatga                     3288
```

```
<210> SEQ ID NO 201
<211> LENGTH: 3285
<212> TYPE: DNA
<213> ORGANISM: Artificial Sequence
<220> FEATURE:
<223> OTHER INFORMATION: 1A9-LvHv-intDS-41bb-3z-T-CD19t Top Strand

<400> SEQUENCE: 201
```

```
ggatctgcga tcgctccggt gcccgtcagt gggcagagcg cacatcgccc acagtccccg          60
agaagttggg gggaggggtc ggcaattgaa ccggtgccta gagaaggtgg cgcggggtaa         120
actgggaaag tgatgtcgtg tactggctcc gcctttttcc cgagggtggg ggagaaccgt         180
atataagtgc agtagtcgcc gtgaacgttc ttttcgcaa cgggtttgcc gccagaacac         240
agctgaagct tcgagggggct cgcatctctc cttcacgcgc ccgccgcccct acctgaggcc         300 gccatccacg ccggttgagt cgcgttctgc cgcctcccgc ctgtggtgcc tcctgaactg         360
cgtccgccgt ctaggtaagt ttaaagctca ggtcgagacc gggcctttgt ccggcgctcc         420
```

```
cttggagcct aacctagactc agccggctct ccacgctttg cctgaccctg cttgctcaac      480
tctacgtctt tgtttcgttt tctgttctgc gccgttacag atccaagctg tgaccggcgc      540
ctacggctag ccaccatgct gctgctcgtg accagcctgc tgctgtgcga actgccccac      600
cctgcctttc tgctgatccc cgcgattcag atgactcaat cccctcctc tctctccgcg       660 tccgtagggg atagggtgac aataacttgt agggcgagcc aggacatccg caatgacctc      720
ggctggtatc aacaaaaacc aggcaaggca cctaagatac tgatttatgg cgcgtcctcc      780
ttgcaatccg gggtgccgtc tcggttcagt ggttcaggta gtggtacgga ctttaccttc      840
acaatctcta gtctgcaacc ggaggatttc gctacttact attgtctcca ggagtataat      900 taccctgta catttgggca aggcaccaag ttggagataa aaggaggcgg aggatctggc       960
ggagggggct ctggaggagg aggatctgaa gtgcagttgg ttgagtctgg aggaggcctg     1020
gtacagccgg gtggtagtct tcggctttcc tgtgctgcta gcgggtttac tttctccata     1080
tacgatatgc actgggtgag gcaagcgacc ggaaaaggtc tggagtgggt ctcagcgatc     1140
ggtacagctg gcgatactta ctatgcgggc agtgtcaagg gacgattcac cataagccgc     1200
gaaaacgcta aaaattccct ctacttgcaa atgaatagcc tgcgagcggg ggacaccgcc     1260
gtatattatt gtgctagaga gtatagcgga tattactttg actattgggg tcaaggcact     1320
ctggtaacgg tgtctagcga gtctaagtac ggaccgccct gcccccttg ccctggccag      1380 cctagagaac cccaggtgta caccctgcct cccagccagg aagagatgac caagaaccag     1440
gtgtccctga cctgcctggt caaaggcttc taccccagcg atatcgccgt ggaatgggag     1500
agcaacggcc agcccgagaa caactacaag accaccccc ctgtgctgga cagcgacggc      1560
agcttcttcc tgtactcccg gctgaccgtg gacaagagcc ggtggcagga aggcaacgtc     1620
ttcagctgca gcgtgatgca cgaggccctg cacaaccact acacccagaa gtccctgagc     1680
ctgagcctgg gcaagatgtt ctgggtgctg gtggtggtcg gaggcgtgct ggcctgctac     1740
agcctgctgt tcaccgtggc cttcatcatc ttttgggtga acggggcag aaagaaactc      1800 ctgtatatat tcaaacaacc atttatgaga ccagtacaaa ctactcaaga ggaagatggc     1860
tgtagctgcc gatttccaga agaagaagaa ggaggatgtg aactgcgggt gaagttcagc     1920
agaagcgccg acgcccctgc ctaccagcag ggccagaatc agctgtacaa cgagctgaac     1980
ctgggcagaa gggaagagta cgacgtcctg gataagcgga gaggccggga ccctgagatg     2040
ggcggcaagc ctcggcggaa gaacccccag gaaggcctgt ataacgaact gcagaaagac     2100
aagatggccg aggcctacag cgagatcggc atgaagggcg agcggaggcg gggcaagggc     2160
cacgacggcc tgtatcaggg cctgtccacc gccaccaagg atacctacga cgccctgcac     2220
atgcaggccc tgcccccaag gctcgagggc ggcggagagg cagaggaag tcttctaaca      2280 tgcggtgacg tggaggagaa tccaggccct aggatgccac ctccaagact cctcttcttc     2340
ctcctcttcc tgacaccaat ggaagtcagg cctgaggaac ctctagtggt gaaggtggaa     2400
gagggagata acgctgtgtt acagtgcctc aagggaacct cagatggacc cactcagcag     2460
ctgacctggt ctcgggagtc tccgcttaaa cccttcctga aactcagcct tggactgcca     2520
ggtctgggaa tccacatgag gccactggct atctggctgt tcatcttcaa cgtctctcaa     2580
cagatgggag gcttctacct gtgtcagcct ggaccacctt ctgagaaggc atggcagcct     2640
ggttggacag tcaatgtgga gggttctggt gagctgttcc ggtggaatgt ttcggaccta     2700
ggtggactgg gatgtggtct gaagaacagg tcctcagagg gacctagctc tccttccggg     2760
aagctcatga gcccccaagct gtatgtgtgg gccaaagacc gccctgagat ctgggaggga     2820
```

```
gagcctccgt gtgtcccacc gagggacagc ctgaaccaga gcctcagcca ggacctcacc      2880
atggcccctg gctccacact ctggctgtcc tgtggggtac cccctgactc tgtgtccagg      2940 ggcccctct cctggaccca tgtgcacccc aagggggcta agtcattgct gagcctagag       3000
ctgaaggacg atcgccctgc cagagatatg tgggtaatgg agacgggtct gttgttgccc      3060
cgggccacag ctcaagacgc tggaaagtat tattgtcacc gtggcaacct gaccatgtca      3120
ttccacctgg agatcactgc tcggccagta ctatggcact ggctgctgag gactggtggc      3180
tggaaggtct cagctgtgac tttggcttat ctgatcttct gcctgtgttc ccttgtgggc      3240
attcttcatc ttcaaagagc cctggtcctg aggaggaaaa gatga                      3285
```

```
<210> SEQ ID NO 202
<211> LENGTH: 3354
<212> TYPE: DNA
<213> ORGANISM: Artificial Sequence
<220> FEATURE:
<223> OTHER INFORMATION: 1E6-LvHv-intDS-41bb-3z-T-CD19t Top Strand

<400> SEQUENCE: 202
```

```
ggatctgcga tcgctccggt gcccgtcagt gggcagagcg cacatcgccc acagtccccg       60
agaagttggg gggaggggtc ggcaattgaa ccggtgccta gagaaggtgg cgcggggtaa      120
actgggaaag tgatgtcgtg tactggctcc gccttttttcc cgagggtggg ggagaaccgt     180
atataagtgc agtagtcgcc gtgaacgttc tttttcgcaa cgggtttgcc gccagaacac      240
agctgaagct tcgagggggct cgcatctctc cttcacgcgc ccgccgccct acctgaggcc      300
gccatccacg ccggttgagt cgcgttctgc cgcctcccgc ctgtggtgcc tcctgaactg      360
cgtccgccgt ctaggtaagt ttaaagctca ggtcgagacc gggcctttgt ccggcgctcc      420
cttggagcct acctagactc agccggctct ccacgctttg cctgaccctg cttgctcaac      480
tctacgtctt tgtttcgttt tctgttctgc gccgttacag atccaagctg tgaccggcgc      540
ctacggctag ccaccatgct gctgctcgtg accagcctgc tgctgtgcga actgcccccac      600 cctgcctttc tgctgatccc cgcaatacaa atgacgcagt ctcctagctc actttctgca      660
agcgtcggag accgagttac aattacgtgt cgggcgagcc agggaattcg gaacgatctc      720
ggctggtatc aacagaaacc cggcaaagcg ccaaaattgc ttatatacgc ggcatcaaac      780
cttcagagtg gtgtgccgtc aagattcagt gggtcaggca gcggaactga ctttaccctg      840
actatctcta gtctccaacc cgaggacttc gcaacgtact attgcctgca agattactcc      900
tacccgcgaa cgttcggcca agggacaaag gttgagatta aggaggcgg aggatctggc       960 ggagggggct ctggaggagg aggatctatg ctgctgctcg tgaccagcct gctgctgtgc     1020
gaactgcccc accctgcctt tctgctgatc ccccaagtgc agttggttga atccggtggc     1080
ggtgtggttc aaccaggcag gagcttgaga ctttcatgtg cagcgtccgg ctttacattc     1140
tccagctacg acatacattg ggtccggcag gcgccaggaa agggcctcga atgggtcgcg    1200
gtaatatggt acgacggcag tcataactac tacagtgatt ctgtaaaagg ccgctttacg     1260
atttcacgcg acaacagcaa gaatacactc tatttgcaaa tgaactctct gcgcgcggaa     1320
gataccgccg tgtattattg tgcgcgggac tacagcgggt cttactacga ctactggggc    1380
caaggaaccc ttgtaacggt ctctagcgag tctaagtacg gaccgccctg ccccccttgc    1440
cctggccagc ctagagaacc ccaggtgtac accctgcctc ccagccagga agagatgacc    1500
aagaaccagg tgtccctgac ctgcctggtc aaaggcttct accccagcga tatcgccgtg    1560
```

-continued

```
gaatgggaga gcaacggcca gcccgagaac aactacaaga ccaccccccc tgtgctggac      1620
agcgacggca gcttcttcct gtactcccgg ctgaccgtgg acaagagccg gtggcaggaa      1680
ggcaacgtct tcagctgcag cgtgatgcac gaggccctgc acaaccacta cacccagaag      1740
tccctgagcc tgagcctggg caagatgttc tgggtgctgg tggtggtcgg aggcgtgctg      1800
gcctgctaca gcctgctggt caccgtggcc ttcatcatct tttgggtgaa acggggcaga      1860
aagaaactcc tgtatatatt caaacaacca tttatgagac cagtacaaac tactcaagag      1920
gaagatggct gtagctgccg atttccagaa gaagaagaag gaggatgtga actgcgggtg      1980
aagttcagca gaagcgccga cgcccctgcc taccagcagg gccagaatca gctgtacaac      2040
gagctgaacc tgggcagaag ggaagagtac gacgtcctgg ataagcggag aggccgggac      2100
cctgagatgg gcggcaagcc tcggcggaag aacccccagg aaggcctgta taacgaactg      2160
cagaaagaca agatggccga ggcctacagc gagatcggca tgaagggcga gcggaggcgg      2220
ggcaagggcc acgacggcct gtatcagggc ctgtccaccg ccaccaagga tacctacgac      2280
gccctgcaca tgcaggccct gccccccaagg ctcgagggcg cggagagggg cagaggaagt      2340
cttctaacat gcggtgacgt ggaggagaat ccaggcccta ggatgccacc tccaagactc      2400
ctcttcttcc tcctcttcct gacaccaatg gaagtcaggc ctgaggaacc tctagtggtg      2460
aaggtggaag agggagataa cgctgtgtta cagtgcctca agggaacctc agatggaccc      2520
actcagcagc tgacctggtc tcgggagtct ccgcttaaac ccttcctgaa actcagcctt      2580
ggactgccag gtctgggaat ccacatgagg ccactggcta tctggctgtt catcttcaac      2640
gtctctcaac agatgggagg cttctacctg tgtcagcctg gaccaccttc tgagaaggca      2700
tggcagcctg gttggacagt caatgtggag ggttctggtg agctgttccg gtggaatgtt      2760
tcggacctag gtggactggg atgtggtctg aagaacaggt cctcagaggg acctagctct      2820
ccttccggga agctcatgag ccccaagctg tatgtgtggg ccaaagaccg ccctgagatc      2880
tgggagggag agcctccgtg tgtcccaccg agggacagcc tgaaccagag cctcagccag      2940
gacctcacca tggcccctgg ctccacactc tggctgtcct gtggggtacc ccctgactct      3000
gtgtccaggg gccccctctc ctggacccat gtgcaccoca aggggcctaa gtcattgctg      3060
agcctagagc tgaaggacga tcgccctgcc agagatatgt gggtaatgga gacgggtctg      3120
ttgttgcccc gggccacagc tcaagacgct ggaaagtatt attgtcaccg tggcaacctg      3180
accatgtcat tccacctgga gatcactgct cggccagtac tatggcactg gctgctgagg      3240
actggtggct ggaaggtctc agctgtgact ttggcttatc tgatcttctg cctgtgttcc      3300
cttgtgggca ttcttcatct tcaaagagcc ctggtcctga ggaggaaaag atga         3354
```

```
<210> SEQ ID NO 203
<211> LENGTH: 3294
<212> TYPE: DNA
<213> ORGANISM: Artificial Sequence
<220> FEATURE:
<223> OTHER INFORMATION: 2D3-LvHv-intDS-41bb-3z-T-CD19t Top Strand

<400> SEQUENCE: 203
```

```
ggatctgcga tcgctccggt gcccgtcagt gggcagagcg cacatcgccc acagtccccg        60
agaagttggg gggaggggtc ggcaattgaa ccggtgccta gagaaggtgg cgcggggtaa       120
actgggaaag tgatgtcgtg tactggctcc gcctttttcc cgagggtggg ggagaaccgt       180
atataagtgc agtagtcgcc gtgaacgttc tttttcgcaa cgggtttgcc gccagaacac       240
agctgaagct tcgaggggct cgcatctctc cttcacgcgc ccgccgccct acctgaggcc       300
```

```
gccatccacg ccggttgagt cgcgttctgc cgcctcccgc ctgtggtgcc tcctgaactg      360
cgtccgccgt ctaggtaagt ttaaagctca ggtcgagacc gggcctttgt ccggcgctcc      420
cttggagcct acctagactc agccggctct ccacgctttg cctgaccctg cttgctcaac      480
tctacgtctt tgtttcgttt tctgttctgc gccgttacag atccaagctg tgaccggcgc      540
ctacggctag ccaccatgct gctgctcgtg accagcctgc tgctgtgcga actgccccac      600
cctgcctttc tgctgatccc cgagattgta atgacgcagt ctccagcgac gctttctctt      660
agtccgggag aaagagccac actgtcctgc cgggcgtccc aatccggttc tagctccttt      720
ctgtcatggt atcaacagaa gccaggtcag gcacctcgcc ttcttattta cggtgcatcc      780
actcgcgcga ccgggattcc tgcaagattt tccgggtctg ggtctggcac agatttcacg      840
ttgactatca gtagtctgca gccagaggat ttcgcagtct attactgtca acaagactac      900
aatcttcctt tcacgtttgg tcccggaact aaggttgata taaaaggagg cggaggatct      960
ggcggagggg gctctggagg aggaggatct gaggtgcaat tgctggaaag tggaggagga     1020
ctcgtgcagc ccggaggttc ccttagcctt tcttcgcgctg caagtgggtt tacgttctct     1080
atatatgcca tgtcttgggt gcggcaagcc cccggaaaag gattggaatg ggtatctgcc     1140
attagtgatt ctgggggtac gacctattat gcagatagtg taaaagggag attcactatc     1200
tcacgcgaca ttcaaagaa tatgctttac cttgagatga acagtcttcg agcagaggat     1260
acagccatat actattgcgc taaacgcacc cgctacttca acggaatgga tgtatgggga     1320
cagggtacaa cagttactgt ttctagcgag tctaagtacg gaccgccctg cccccccttgc     1380 cctggccagc ctagagaacc ccaggtgtac accctgcctc ccagccagga agagatgacc     1440
aagaaccagg tgtccctgac ctgcctggtc aaaggcttct accccagcga tatcgccgtg     1500
gaatgggaga gcaacggcca gcccgagaac aactacaaga ccacccccccc tgtgctggac     1560 agcgacggca gcttcttcct gtactcccgg ctgaccgtgg acaagagccg gtggcaggaa     1620
ggcaacgtct tcagctgcag cgtgatgcac gaggccctgc acaaccacta cacccagaag     1680
tccctgagcc tgagcctggg caagatgttc tgggtgctgg tggtggtcgg aggcgtgctg     1740
gcctgctaca gcctgctggt caccgtggcc ttcatcatct tttgggtgaa acggggcaga     1800
aagaaactcc tgtatatatt caaacaacca tttatgagac cagtacaaac tactcaagag     1860
gaagatggct gtagctgccg atttccagaa gaagaagaag aggatgtgaa actgcgggtg     1920
aagttcagca gaagcgccga cgcccctgcc taccagcagg gccagaatca gctgtacaac     1980
gagctgaacc tgggcagaag ggaagagtac gacgtcctgg ataagcggag aggccgggac     2040
cctgagatgg gcggcaagcc tcggcggaag aacccccagg aaggcctgta taacgaactg     2100
cagaaagaca gatggccga ggcctacagc gagatcggca tgaagggcga gcggaggcgg     2160
ggcaagggcc acgacggcct gtatcagggc ctgtccaccg ccaccaagga tacctacgac     2220
gccctgcaca tgcaggccct gccccccaagg ctcgagggcg cgggagaggg cagaggaagt     2280
cttctaacat gcggtgacgt ggaggagaat ccaggcccta ggatgccacc tccaagactc     2340
ctcttcttcc tcctcttcct gacaccaatg gaagtcaggc ctgaggaacc tctagtggtg     2400
aaggtggaag agggagataa cgctgtgtta cagtgcctca agggaacctc agatggaccc     2460
actcagcagc tgacctggtc tcgggagtct ccgcttaaac ccttcctgaa actcagcctt     2520
ggactgccag tctgggaat ccacatgagg ccactggcta tctggctgtt catcttcaac     2580
gtctctcaac agatgggagg cttctacctg tgtcagcctg gaccaccttc tgagaaggca     2640
```

-continued

```
tggcagcctg gttggacagt caatgtggag ggttctggtg agctgttccg gtggaatgtt    2700
tcggacctag gtggactggg atgtggtctg aagaacaggt cctcagaggg acctagctct    2760
ccttccggga agctcatgag ccccaagctg tatgtgtggg ccaaagaccg ccctgagatc    2820
tgggagggag agcctccgtg tgtcccaccg agggacagcc tgaaccagag cctcagccag    2880
gacctcacca tggcccctgg ctccacactc tggctgtcct gtggggtacc ccctgactct    2940
gtgtccaggg gcccctctc ctggacccat gtgcacccca aggggcctaa gtcattgctg    3000
agcctagagc tgaaggacga tcgccctgcc agagatatgt gggtaatgga gacgggtctg    3060
ttgttgcccc gggccacagc tcaagacgct ggaaagtatt attgtcaccg tggcaacctg    3120
accatgtcat ccacctgga gatcactgct cggccagtac tatggcactg gctgctgagg    3180
actggtggct ggaaggtctc agctgtgact ttggcttatc tgatcttctg cctgtgttcc    3240
cttgtgggca ttcttcatct tcaaagagcc ctggtcctga ggaggaaaag atga          3294
```

```
<210> SEQ ID NO 204
<211> LENGTH: 726
<212> TYPE: PRT
<213> ORGANISM: Artificial Sequence
<220> FEATURE:
<223> OTHER INFORMATION: CD33:CD22 4D protein

<400> SEQUENCE: 204

Met Pro Leu Leu Leu Leu Leu Pro Leu Leu Trp Ala Gly Ala Leu Ala
1               5                   10                  15

Met His His His His His His Gly Gly Gly Asp Pro Asn Phe Trp Leu
            20                  25                  30

Gln Val Gln Glu Ser Val Thr Val Gln Glu Gly Leu Cys Val Leu Val
        35                  40                  45

Pro Cys Thr Phe Phe His Pro Ile Pro Tyr Tyr Asp Lys Asn Ser Pro
    50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
        115                 120                 125

Met Glu Arg Gly Ser Thr Lys Tyr Ser Tyr Lys Ser Pro Gln Leu Ser
    130                 135                 140

Val His Val Thr Asp Leu Thr His Arg Pro Lys Ile Leu Ile Pro Gly
145                 150                 155                 160

Thr Leu Glu Pro Gly His Ser Lys Asn Leu Thr Cys Ser Val Ser Trp
                165                 170                 175

Ala Cys Glu Gln Gly Thr Pro Pro Ile Phe Ser Trp Leu Ser Ala Ala
            180                 185                 190

Pro Thr Ser Leu Gly Pro Arg Thr Thr His Ser Ser Val Leu Ile Ile
        195                 200                 205

Thr Pro Arg Pro Gln Asp His Gly Thr Asn Leu Thr Cys Gln Val Lys
    210                 215                 220

Phe Ala Gly Ala Gly Val Thr Thr Glu Arg Thr Ile Gln Leu Asn Val
225                 230                 235                 240

Thr Tyr Val Pro Gln Asn Pro Thr Thr Gly Ile Phe Pro Gly Asp Gly
                245                 250                 255
```

-continued

```
Ser Gly Lys Gln Glu Thr Arg Ala Gly Val Val His Pro Glu Pro Ser
            260                 265             270

Thr Val Gln Ile Leu His Ser Pro Ala Val Glu Gly Ser Gln Val Glu
            275                 280             285

Phe Leu Cys Met Ser Leu Ala Asn Pro Leu Pro Thr Asn Tyr Thr Trp
            290                 295             300

Tyr His Asn Gly Lys Glu Met Gln Gly Arg Thr Glu Glu Lys Val His
305                 310                 315                 320

Ile Pro Lys Ile Leu Pro Trp His Ala Gly Thr Tyr Ser Cys Val Ala
                325                 330                 335

Glu Asn Ile Leu Gly Thr Gly Gln Arg Gly Pro Gly Ala Glu Leu Asp
            340                 345                 350

Val Gln Tyr Pro Pro Lys Lys Val Thr Thr Val Ile Gln Asn Pro Met
            355                 360                 365

Pro Ile Arg Glu Gly Asp Thr Val Thr Leu Ser Cys Asn Tyr Asn Ser
            370                 375                 380

Ser Asn Pro Ser Val Thr Arg Tyr Glu Trp Lys Pro His Gly Ala Trp
385                 390                 395                 400

Glu Glu Pro Ser Leu Gly Val Leu Lys Ile Gln Asn Val Gly Trp Asp
                405                 410                 415

Asn Thr Thr Ile Ala Cys Ala Ala Cys Asn Ser Trp Cys Ser Trp Ala
                420                 425                 430

Ser Pro Val Ala Leu Asn Val Gln Tyr Ala Pro Arg Asp Val Arg Val
            435                 440                 445

Arg Lys Ile Lys Pro Leu Ser Glu Ile His Ser Gly Asn Ser Val Ser
            450                 455                 460

Leu Gln Cys Asp Phe Ser Ser Ser His Pro Lys Glu Val Gln Phe Phe
465                 470                 475                 480

Trp Glu Lys Asn Gly Arg Leu Leu Gly Lys Glu Ser Gln Leu Asn Phe
                485                 490                 495

Asp Ser Ile Ser Pro Glu Asp Ala Gly Ser Tyr Ser Cys Trp Val Asn
                500                 505                 510

Asn Ser Ile Gly Gln Thr Ala Ser Lys Ala Trp Thr Leu Glu Val Leu
            515                 520                 525

Tyr Ala Pro Arg Arg Leu Arg Val Ser Met Ser Pro Gly Asp Gln Val
            530                 535                 540

Met Glu Gly Lys Ser Ala Thr Leu Thr Cys Glu Ser Asp Ala Asn Pro
545                 550                 555                 560

Pro Val Ser His Tyr Thr Trp Phe Asp Trp Asn Asn Gln Ser Leu Pro
                565                 570                 575

Tyr His Ser Gln Lys Leu Arg Leu Glu Pro Val Lys Val Gln His Ser
            580                 585                 590

Gly Ala Tyr Trp Cys Gln Gly Thr Asn Ser Val Gly Lys Gly Arg Ser
            595                 600                 605

Pro Leu Ser Thr Leu Thr Val Tyr Tyr Ser Pro Glu Thr Gly Ala Ile
            610                 615                 620

Gly Gly Ala Gly Val Thr Ala Leu Leu Ala Leu Cys Leu Cys Leu Ile
625                 630                 635                 640

Phe Phe Ile Val Lys Thr His Arg Arg Lys Ala Ala Arg Thr Ala Val
                645                 650                 655

Gly Arg Asn Asp Thr His Pro Thr Thr Gly Ser Ala Ser Pro Lys His
            660                 665                 670
```

-continued

```
Gln Lys Lys Ser Lys Leu His Gly Pro Thr Glu Thr Ser Ser Cys Ser
        675                 680                 685

Gly Ala Ala Pro Thr Val Glu Met Asp Glu Glu Leu His Tyr Ala Ser
        690                 695                 700

Leu Asn Phe His Gly Met Asn Pro Ser Lys Asp Thr Ser Thr Glu Tyr
705                 710                 715                 720

Ser Glu Val Arg Thr Gln
                725

<210> SEQ ID NO 205
<211> LENGTH: 2178
<212> TYPE: DNA
<213> ORGANISM: Artificial Sequence
<220> FEATURE:
<223> OTHER INFORMATION: CD33:CD22 4D nucleotides

<400> SEQUENCE: 205
atgcctctgc tgctactgct acctctgctg tgggctggag ccctggctat gcatcatcac    60
caccatcacg gcggcggcga tccaaatttc tggctgcaag tgcaggagtc agtgacggta   120
caggagggtt tgtgcgtcct cgtgccctgc actttcttcc atcccatacc ctactacgac   180
aagaactccc cagttcatgg ttactggttc cgggaaggag ccattatatc cagggactct   240
ccagtggcca caaacaagct agatcaagaa gtacaggagg agactcaggg cagattccgc   300
ctccttgggg atcccagtag gaacaactgc tccctgagca tcgtagacgc caggaggagg   360
gataatggtt catacttctt tcggatggag agaggaagta ccaaatacag ttacaaatct   420
ccccagctct ctgtgcatgt gacagacttg acccacaggc ccaaaatcct catccctggc   480
actctagaac ccggccactc caaaaacctg acctgctctg tgtcctgggc ctgtgagcag   540
ggaacacccc cgatcttctc ctggttgtca gctgccccca cctccctggg ccccaggact   600
actcactcct cggtgctcat aatcacccca cggccccagg accacggcac caacctgacc   660
tgtcaggtga agttcgctgg agctggtgtg actacggaga gaaccatcca gctgaacgtc   720
acctatgttc cacagaaccc aacaactggt atctttccag agatggctca agggaaacaa   780
gagaccagag caggagtggt tcatccggaa ccttccacgg ttcagatcct ccactcaccg   840
gctgtggagg gaagtcaagt cgagtttctt tgcatgtcac tggccaatcc tcttccaaca   900
aattacacgt ggtaccacaa tgggaaagaa atgcagggaa ggacagagga gaaagtccac   960
atcccaaaga tcctcccttg gcacgctggg acttattcct gtgtggcaga aaacattctt  1020
ggtactggac agaggggccc tggagctgag ctggatgtcc agtatcctcc caagaaggtg  1080
accacagtga ttcaaaaccc catgccgatt cgagaaggag acacagtgac cctttcctgt  1140
aactacaatt ccagtaaccc cagtgttacc cggtatgaat ggaaacccca tggcgcctgg  1200
gaggagccat cgcttggggt gctgaagatc caaaacgttg ctgggacaa cacaaccatc  1260 gcctgcgcag cttgtaatag ttggtgctcg tgggcctccc ctgtcgccct gaatgtccag  1320 tatgccccccc gagacgtgag ggtccggaaa atcaagcccc tttccgagat tcactctgga  1380
aactcggtca gcctccaatg tgacttctca gcagccacc ccaaagaagt ccagttcttc  1440
tgggagaaaa atgcaggct tctggggaaa gaaagccagc tgaattttga ctccatctcc  1500
ccagaagatg ctgggagtta cagctgctgg gtgaacaact ccataggaca gacagcgtcc  1560
aaggcctgga cacttgaagt gctgtatgca cccaggaggc tgcgtgtgtc catgagccca  1620
ggggaccaag tgatgaaggg gaagagtgca accctgacct gtgagagcga cgccaacccct  1680 cccgtctccc actacacctg gtttgactgg aataaccaaa gcctcccta ccacagccag  1740
```

-continued

```
aagctgagat tggagccggt gaaggtccag cactcgggtg cctactggtg ccagggggacc    1800 aacagtgtgg gcaagggccg ttcgcctctc agcaccctca ccgtctacta tagcccggag    1860 accgggggcca ttggaggagc tggtgttaca gccctgctcg ctctttgtct ctgcctcatc    1920
ttcttcatag tgaagaccca caggaggaaa gcagccagga cagcagtggg caggaatgac    1980
acccacccta ccacagggtc agcctccccg aaacaccaga agaagtccaa gttacatggc    2040
cccactgaaa cctcaagctg ttcaggtgcc gccctactg tggagatgga tgaggagctg    2100
cattatgctt ccctcaactt tcatgggatg aatccttcca aggacacctc caccgaatac    2160
tcagaggtca ggacccag                                                  2178
```

<210> SEQ ID NO 206
<211> LENGTH: 552
<212> TYPE: PRT
<213> ORGANISM: Artificial Sequence
<220> FEATURE:
<223> OTHER INFORMATION: CD33:CD22 2D protein

<400> SEQUENCE: 206

```
Met Pro Leu Leu Leu Leu Pro Leu Leu Trp Ala Gly Ala Leu Ala
1               5                   10                  15

Met His His His His His Gly Gly Gly Asp Pro Asn Phe Trp Leu
            20                  25                  30

Gln Val Gln Glu Ser Val Thr Val Gln Glu Gly Leu Cys Val Leu Val
        35                  40                  45

Pro Cys Thr Phe Phe His Pro Ile Pro Tyr Tyr Asp Lys Asn Ser Pro
    50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
        115                 120                 125

Met Glu Arg Gly Ser Thr Lys Tyr Ser Tyr Lys Ser Pro Gln Leu Ser
    130                 135                 140

Val His Val Thr Asp Leu Thr His Arg Pro Lys Ile Leu Ile Pro Gly
145                 150                 155                 160

Thr Leu Glu Pro Gly His Ser Lys Asn Leu Thr Cys Ser Val Ser Trp
                165                 170                 175

Ala Cys Glu Gln Gly Thr Pro Pro Ile Phe Ser Trp Leu Ser Ala Ala
            180                 185                 190

Pro Thr Ser Leu Gly Pro Arg Thr Thr His Ser Ser Val Leu Ile Ile
        195                 200                 205

Thr Pro Arg Pro Gln Asp His Gly Thr Asn Leu Thr Cys Gln Val Lys
    210                 215                 220

Phe Ala Gly Ala Gly Val Thr Thr Glu Arg Thr Ile Gln Leu Asn Val
225                 230                 235                 240

Thr Tyr Val Pro Gln Asn Pro Thr Thr Gly Ile Phe Pro Gly Asp Gly
                245                 250                 255

Ser Gly Lys Gln Glu Thr Arg Ala Gly Val Val His Pro Arg Asp Val
            260                 265                 270

Arg Val Arg Lys Ile Lys Pro Leu Ser Glu Ile His Ser Gly Asn Ser
```

-continued

```
           275                280                285

Val Ser Leu Gln Cys Asp Phe Ser Ser His Pro Lys Glu Val Gln
    290                295                300

Phe Phe Trp Glu Lys Asn Gly Arg Leu Leu Gly Lys Glu Ser Gln Leu
305                310                315                320

Asn Phe Asp Ser Ile Ser Pro Glu Asp Ala Gly Ser Tyr Ser Cys Trp
                325                330                335

Val Asn Asn Ser Ile Gly Gln Thr Ala Ser Lys Ala Trp Thr Leu Glu
                340                345                350

Val Leu Tyr Ala Pro Arg Arg Leu Arg Val Ser Met Ser Pro Gly Asp
                355                360                365

Gln Val Met Glu Gly Lys Ser Ala Thr Leu Thr Cys Glu Ser Asp Ala
    370                375                380

Asn Pro Pro Val Ser His Tyr Thr Trp Phe Asp Trp Asn Asn Gln Ser
385                390                395                400

Leu Pro Tyr His Ser Gln Lys Leu Arg Leu Glu Pro Val Lys Val Gln
                405                410                415

His Ser Gly Ala Tyr Trp Cys Gln Gly Thr Asn Ser Val Gly Lys Gly
                420                425                430

Arg Ser Pro Leu Ser Thr Leu Thr Val Tyr Tyr Ser Pro Glu Thr Gly
                435                440                445

Ala Ile Gly Gly Ala Gly Val Thr Ala Leu Leu Ala Leu Cys Leu Cys
    450                455                460

Leu Ile Phe Phe Ile Val Lys Thr His Arg Arg Lys Ala Ala Arg Thr
465                470                475                480

Ala Val Gly Arg Asn Asp Thr His Pro Thr Thr Gly Ser Ala Ser Pro
                485                490                495

Lys His Gln Lys Lys Ser Lys Leu His Gly Pro Thr Glu Thr Ser Ser
                500                505                510

Cys Ser Gly Ala Ala Pro Thr Val Glu Met Asp Glu Glu Leu His Tyr
                515                520                525

Ala Ser Leu Asn Phe His Gly Met Asn Pro Ser Lys Asp Thr Ser Thr
    530                535                540

Glu Tyr Ser Glu Val Arg Thr Gln
545                550
```

```
<210> SEQ ID NO 207
<211> LENGTH: 1656
<212> TYPE: DNA
<213> ORGANISM: Artificial Sequence
<220> FEATURE:
<223> OTHER INFORMATION: CD33:CD22 2D nucleotides

<400> SEQUENCE: 207
atgcctctgc tgctactgct acctctgctg tgggctggag ccctggctat gcatcatcac      60
caccatcacg gcggcggcga tccaaatttc tggctgcaag tgcaggagtc agtgacggta     120
caggagggtt tgtgcgtcct cgtgccctgc actttcttcc atcccatacc ctactacgac     180
aagaactccc cagttcatgg ttactggttc cgggaaggag ccattatatc cagggactct     240
ccagtggcca caaacaagct agatcaagaa gtacaggagg agactcaggg cagattccgc     300
ctccttgggg atcccagtag gaacaactgc tccctgagca tcgtagacgc caggaggagg     360
gataatggtt catacttctt tcggatggag agaggaagta ccaaatacag ttacaaatct     420
ccccagctct ctgtgcatgt gacagacttg acccacaggc ccaaaatcct catccctggc     480
```

-continued

```
actctagaac ccggccactc caaaaacctg acctgctctg tgtcctgggc ctgtgagcag      540
ggaacacccc cgatcttctc ctggttgtca gctgccccca cctccctggg ccccaggact      600
actcactcct cggtgctcat aatcacccca cggccccagg accacggcac caacctgacc      660
tgtcaggtga agttcgctgg agctggtgtg actacggaga gaaccatcca gctgaacgtc      720
acctatgttc cacagaaccc aacaactggt atctttccag gagatggctc agggaaacaa      780
gagaccagag caggagtggt tcatccccga gacgtgaggg tccggaaaat caagcccctt      840
tccgagattc actctggaaa ctcggtcagc ctccaatgtg acttctcaag cagccacccc      900
aaagaagtcc agttcttctg ggagaaaaat ggcaggcttc tggggaaaga aagccagctg      960
aattttgact ccatctcccc agaagatgct gggagttaca gctgctgggt gaacaactcc     1020
ataggacaga cagcgtccaa ggcctggaca cttgaagtgc tgtatgcacc caggaggctg     1080
cgtgtgtcca tgagcccagg ggaccaagtg atggagggga gagtgcaac cctgacctgt      1140 gagagcgacg ccaaccctcc cgtctcccac tacacctggt ttgactggaa taaccaaagc     1200
ctcccctacc acagccagaa gctgagattg gagccggtga aggtccagca ctcgggtgcc     1260
tactggtgcc aggggaccaa cagtgtgggc aagggccgtt cgcctctcag caccctcacc     1320
gtctactata gcccggagac cggggccatt ggaggagctg gtgttacagc cctgctcgct     1380
ctttgtctct gcctcatctt cttcatagtg aagacccaca ggaggaaagc agccaggaca     1440
gcagtgggca ggaatgacac ccaccctacc acagggtcag cctccccgaa acaccagaag     1500
aagtccaagt acatggccc cactgaaacc tcaagctgtt caggtgccgc ccctactgtg      1560
gagatggatg aggagctgca ttatgcttcc ctcaactttc atgggatgaa tccttccaag     1620
gacacctcca ccgaatactc agaggtcagg acccag                               1656
```

```
<210> SEQ ID NO 208
<211> LENGTH: 280
<212> TYPE: PRT
<213> ORGANISM: Artificial Sequence
<220> FEATURE:
<223> OTHER INFORMATION: CD33 V-set construct (exon 3 and 4 deleted)
      protein

<400> SEQUENCE: 208

Met Pro Leu Leu Leu Leu Leu Pro Leu Leu Trp Ala Gly Ala Leu Ala
1               5                   10                  15

Met His His His His His His Gly Gly Gly Asp Pro Asn Phe Trp Leu
                20                  25                  30

Gln Val Gln Glu Ser Val Thr Val Gln Glu Gly Leu Cys Val Leu Val
            35                  40                  45

Pro Cys Thr Phe Phe His Pro Ile Pro Tyr Tyr Asp Lys Asn Ser Pro
        50                  55                  60

Val His Gly Tyr Trp Phe Arg Glu Gly Ala Ile Ile Ser Arg Asp Ser
65                  70                  75                  80

Pro Val Ala Thr Asn Lys Leu Asp Gln Glu Val Gln Glu Glu Thr Gln
                85                  90                  95

Gly Arg Phe Arg Leu Leu Gly Asp Pro Ser Arg Asn Asn Cys Ser Leu
            100                 105                 110

Ser Ile Val Asp Ala Arg Arg Arg Asp Asn Gly Ser Tyr Phe Phe Arg
            115                 120                 125

Met Glu Arg Gly Ser Thr Lys Tyr Ser Tyr Lys Ser Pro Gln Leu Ser
        130                 135                 140

Val His Val Thr Tyr Val Pro Gln Asn Pro Thr Thr Gly Ile Phe Pro
```

```
                145                   150                   155                   160

Gly Asp Gly Ser Gly Lys Gln Glu Thr Arg Ala Gly Val Val His Gly
                    165                   170                   175

Ala Ile Gly Gly Ala Gly Val Thr Ala Leu Leu Ala Leu Cys Leu Cys
                180                   185                   190

Leu Ile Phe Phe Ile Val Lys Thr His Arg Arg Lys Ala Ala Arg Thr
            195                   200                   205

Ala Val Gly Arg Asn Asp Thr His Pro Thr Thr Gly Ser Ala Ser Pro
    210                   215                   220

Lys His Gln Lys Lys Ser Lys Leu His Gly Pro Thr Glu Thr Ser Ser
225                   230                   235                   240

Cys Ser Gly Ala Ala Pro Thr Val Glu Met Asp Glu Glu Leu His Tyr
                245                   250                   255

Ala Ser Leu Asn Phe His Gly Met Asn Pro Ser Lys Asp Thr Ser Thr
                260                   265                   270

Glu Tyr Ser Glu Val Arg Thr Gln
            275                   280
```

<210> SEQ ID NO 209
<211> LENGTH: 840
<212> TYPE: DNA
<213> ORGANISM: Artificial Sequence
<220> FEATURE:
<223> OTHER INFORMATION: CD33 V-set construct (exon 3 and 4 deleted)
      nucleotides

<400> SEQUENCE: 209

```
atgcctctgc tgctactgct acctctgctg tgggctggag ccctggctat gcatcatcac      60
caccatcacg gcggcggcga tccaaatttc tggctgcaag tgcaggagtc agtgacggta     120
caggagggtt tgtgcgtcct cgtgccctgc actttcttcc atcccatacc ctactacgac     180
aagaactccc cagttcatgg ttactggttc cgggaaggag ccattatatc cagggactct     240
ccagtggcca caaacaagct agatcaagaa gtacaggagg agactcaggg cagattccgc     300
ctccttgggg atcccagtag gaacaactgc tccctgagca tcgtagacgc caggaggagg     360
gataatggtt catacttctt tcggatggag agaggaagta ccaaatacag ttacaaatct     420
ccccagctct ctgtgcatgt gacatatgtt ccacagaacc caacaactgg tatctttcca     480
ggagatggct cagggaaaca agagaccaga gcaggagtgg ttcatggggc cattggagga     540
gctggtgtta gccctgct cgctctttgt ctctgcctca tcttcttcat agtgaagacc     600
cacaggagga aagcagccag gacagcagtg ggcaggaatg acacccaccc taccacaggg     660
tcagcctccc cgaaacacca gaagaagtcc aagttacatg gccccactga aacctcaagc     720
tgttcaggtg ccgcccctac tgtggagatg gatgaggagc tgcattatgc ttccctcaac     780
tttcatggga tgaatccttc caaggacacc tccaccgaat actcagaggt caggacccag     840
```

<210> SEQ ID NO 210
<211> LENGTH: 17
<212> TYPE: PRT
<213> ORGANISM: Artificial Sequence
<220> FEATURE:
<223> OTHER INFORMATION: CD33 signal peptide

<400> SEQUENCE: 210

```
Met Pro Leu Leu Leu Leu Leu Pro Leu Leu Trp Ala Gly Ala Leu Ala
1               5                   10                  15

Met
```

```
<210> SEQ ID NO 211
<211> LENGTH: 51
<212> TYPE: DNA
<213> ORGANISM: Artificial Sequence
<220> FEATURE:
<223> OTHER INFORMATION: CD33 signal peptide coding sequence

<400> SEQUENCE: 211
atgcctctgc tgctactgct acctctgctg tgggctggag ccctggctat g          51

<210> SEQ ID NO 212
<211> LENGTH: 18
<212> TYPE: DNA
<213> ORGANISM: Artificial Sequence
<220> FEATURE:
<223> OTHER INFORMATION: 6-histidine tag coding sequence

<400> SEQUENCE: 212
catcatcacc accatcac                                                18

<210> SEQ ID NO 213
<211> LENGTH: 242
<212> TYPE: PRT
<213> ORGANISM: Artificial Sequence
<220> FEATURE:
<223> OTHER INFORMATION: CD33 extracellular domain

<400> SEQUENCE: 213

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Asp Leu Thr His Arg Pro
        115                 120                 125

Lys Ile Leu Ile Pro Gly Thr Leu Glu Pro Gly His Ser Lys Asn Leu
    130                 135                 140

Thr Cys Ser Val Ser Trp Ala Cys Glu Gln Gly Thr Pro Pro Ile Phe
145                 150                 155                 160

Ser Trp Leu Ser Ala Ala Pro Thr Ser Leu Gly Pro Arg Thr Thr His
            165                 170                 175

Ser Ser Val Leu Ile Ile Thr Pro Arg Pro Gln Asp His Gly Thr Asn
            180                 185                 190

Leu Thr Cys Gln Val Lys Phe Ala Gly Ala Gly Val Thr Thr Glu Arg
        195                 200                 205

Thr Ile Gln Leu Asn Val Thr Tyr Val Pro Gln Asn Pro Thr Thr Gly
    210                 215                 220

Ile Phe Pro Gly Asp Gly Ser Gly Lys Gln Glu Thr Arg Ala Gly Val
225                 230                 235                 240
```

Val His

<210> SEQ ID NO 214
<211> LENGTH: 726
<212> TYPE: DNA
<213> ORGANISM: Artificial Sequence
<220> FEATURE:
<223> OTHER INFORMATION: CD33 extracellular domain coding sequence

<400> SEQUENCE: 214
gatccaaatt tctggctgca agtgcaggag tcagtgacgg tacaggaggg tttgtgcgtc        60
ctcgtgccct gcactttctt ccatcccata ccctactacg acaagaactc cccagttcat       120
ggttactggt tccgggaagg agccattata tccagggact ctccagtggc cacaaacaag       180
ctagatcaag aagtacagga ggagactcag ggcagattcc gcctccttgg ggatcccagt       240
aggaacaact gctccctgag catcgtagac gccaggagga gggataatgg ttcatacttc       300
tttcggatgg agagaggaag taccaaatac agttacaaat ctccccagct ctctgtgcat       360
gtgacagact tgacccacag gcccaaaatc ctcatccctg gcactctaga acccggccac       420
tccaaaaacc tgacctgctc tgtgtcctgg gcctgtgagc agggaacacc cccgatcttc       480
tcctggttgt cagctgcccc cacctccctg ggccccagga ctactcactc ctcggtgctc       540 ataatcacccc cacggcccca ggaccacggc accaacctga cctgtcaggt gaagttcgct       600
ggagctggtg tgactacgga gagaaccatc cagctgaacg tcacctatgt tccacagaac       660
ccaacaactg gtatctttcc aggagatggc tcagggaaac aagagaccag agcaggagtg       720
gttcat                                                                   726

<210> SEQ ID NO 215
<211> LENGTH: 149
<212> TYPE: PRT
<213> ORGANISM: Artificial Sequence
<220> FEATURE:
<223> OTHER INFORMATION: CD33 extracellular domain lacking CD33 amino
      acids 140-232

<400> SEQUENCE: 215

Asp Pro Asn Phe Trp Leu Gln Val Gln Glu Ser Val Thr Val Gln Glu
1               5                   10                  15

Gly Leu Cys Val Leu Val Pro Cys Thr Phe Phe His Pro Ile Pro Tyr
            20                  25                  30

Tyr Asp Lys Asn Ser Pro Val His Gly Tyr Trp Phe Arg Glu Gly Ala
        35                  40                  45

Ile Ile Ser Arg Asp Ser Pro Val Ala Thr Asn Lys Leu Asp Gln Glu
    50                  55                  60

Val Gln Glu Glu Thr Gln Gly Arg Phe Arg Leu Leu Gly Asp Pro Ser
65                  70                  75                  80

Arg Asn Asn Cys Ser Leu Ser Ile Val Asp Ala Arg Arg Arg Asp Asn
                85                  90                  95

Gly Ser Tyr Phe Phe Arg Met Glu Arg Gly Ser Thr Lys Tyr Ser Tyr
            100                 105                 110

Lys Ser Pro Gln Leu Ser Val His Val Thr Tyr Val Pro Gln Asn Pro
            115                 120                 125

Thr Thr Gly Ile Phe Pro Gly Asp Gly Ser Gly Lys Gln Glu Thr Arg
    130                 135                 140

Ala Gly Val Val His
145

<210> SEQ ID NO 216
<211> LENGTH: 447
<212> TYPE: DNA
<213> ORGANISM: Artificial Sequence
<220> FEATURE:
<223> OTHER INFORMATION: CD33 extracellular domain lacking CD33 amino
      acids 140-232 coding sequence

<400> SEQUENCE: 216
gatccaaatt tctggctgca agtgcaggag tcagtgacgg tacaggaggg tttgtgcgtc        60
ctcgtgccct gcactttctt ccatcccata ccctactacg acaagaactc cccagttcat       120
ggttactggt tccgggaagg agccattata tccagggact ctccagtggc cacaaacaag       180
ctagatcaag aagtacagga ggagactcag ggcagattcc gcctccttgg ggatcccagt       240
aggaacaact gctccctgag catcgtagac gccaggagga gggataatgg ttcatacttc       300
tttcggatgg agagaggaag taccaaatac agttacaaat ctccccagct ctctgtgcat       360
gtgacatatg ttccacagaa cccaacaact ggtatcttc caggagatgg ctcagggaaa        420
caagagacca gagcaggagt ggttcat                                          447

<210> SEQ ID NO 217
<211> LENGTH: 13
<212> TYPE: DNA
<213> ORGANISM: Artificial Sequence
<220> FEATURE:
<223> OTHER INFORMATION: CD33 transmembrane domain

<400> SEQUENCE: 217
gaggagvtaa ccv                                                          13

<210> SEQ ID NO 218
<211> LENGTH: 69
<212> TYPE: DNA
<213> ORGANISM: Artificial Sequence
<220> FEATURE:
<223> OTHER INFORMATION: CD33 transmembrane domain coding sequence

<400> SEQUENCE: 218
ggggccattg gaggagctgg tgttacagcc ctgctcgctc tttgtctctg cctcatcttc        60
ttcatagtg                                                              69

<210> SEQ ID NO 219
<211> LENGTH: 82
<212> TYPE: PRT
<213> ORGANISM: Artificial Sequence
<220> FEATURE:
<223> OTHER INFORMATION: CD33 intracellular domain

<400> SEQUENCE: 219

Lys Thr His Arg Arg Lys Ala Ala Arg Thr Ala Val Gly Arg Asn Asp
1               5                   10                  15

Thr His Pro Thr Thr Gly Ser Ala Ser Pro Lys His Gln Lys Lys Ser
            20                  25                  30

Lys Leu His Gly Pro Thr Glu Thr Ser Ser Cys Ser Gly Ala Ala Pro
        35                  40                  45

Thr Val Glu Met Asp Glu Glu Leu His Tyr Ala Ser Leu Asn Phe His
    50                  55                  60

Gly Met Asn Pro Ser Lys Asp Thr Ser Thr Glu Tyr Ser Glu Val Arg
65                  70                  75                  80

-continued

Thr Gln

<210> SEQ ID NO 220
<211> LENGTH: 246
<212> TYPE: DNA
<213> ORGANISM: Artificial Sequence
<220> FEATURE:
<223> OTHER INFORMATION: CD33 intracellular domain coding sequence

<400> SEQUENCE: 220
aagacccaca ggaggaaagc agccaggaca gcagtgggca ggaatgacac ccaccctacc      60
acagggtcag cctccccgaa acaccagaag aagtccaagt tacatggccc cactgaaacc     120
tcaagctgtt caggtgccgc ccctactgtg gagatggatg aggagctgca ttatgcttcc     180
ctcaactttc atgggatgaa tccttccaag gacacctcca ccgaatactc agaggtcagg     240
acccag                                                               246

<210> SEQ ID NO 221
<211> LENGTH: 353
<212> TYPE: PRT
<213> ORGANISM: Artificial Sequence
<220> FEATURE:
<223> OTHER INFORMATION: Portion of CD22 extracellular domain that
     contains CD22 domains defined as Ig-like C2-type 3, Ig-like
     C2-type 4, Ig-like C2-type 5, Ig-like C2-type 6

<400> SEQUENCE: 221

Pro Glu Pro Ser Thr Val Gln Ile Leu His Ser Pro Ala Val Glu Gly
1               5                   10                  15

Ser Gln Val Glu Phe Leu Cys Met Ser Leu Ala Asn Pro Leu Pro Thr
            20                  25                  30

Asn Tyr Thr Trp Tyr His Asn Gly Lys Glu Met Gln Gly Arg Thr Glu
        35                  40                  45

Glu Lys Val His Ile Pro Lys Ile Leu Pro Trp His Ala Gly Thr Tyr
    50                  55                  60

Ser Cys Val Ala Glu Asn Ile Leu Gly Thr Gly Gln Arg Gly Pro Gly
65                  70                  75                  80

Ala Glu Leu Asp Val Gln Tyr Pro Pro Lys Lys Val Thr Thr Val Ile
                85                  90                  95

Gln Asn Pro Met Pro Ile Arg Glu Gly Asp Thr Val Thr Leu Ser Cys
            100                 105                 110

Asn Tyr Asn Ser Ser Asn Pro Ser Val Thr Arg Tyr Glu Trp Lys Pro
        115                 120                 125

His Gly Ala Trp Glu Glu Pro Ser Leu Gly Val Leu Lys Ile Gln Asn
    130                 135                 140

Val Gly Trp Asp Asn Thr Thr Ile Ala Cys Ala Ala Cys Asn Ser Trp
145                 150                 155                 160

Cys Ser Trp Ala Ser Pro Val Ala Leu Asn Val Gln Tyr Ala Pro Arg
                165                 170                 175

Asp Val Arg Val Arg Lys Ile Lys Pro Leu Ser Glu Ile His Ser Gly
            180                 185                 190

Asn Ser Val Ser Leu Gln Cys Asp Phe Ser Ser Ser His Pro Lys Glu
        195                 200                 205

Val Gln Phe Phe Trp Glu Lys Asn Gly Arg Leu Leu Gly Lys Glu Ser
    210                 215                 220

Gln Leu Asn Phe Asp Ser Ile Ser Pro Glu Asp Ala Gly Ser Tyr Ser
225                 230                 235                 240

-continued

```
Cys Trp Val Asn Asn Ser Ile Gly Gln Thr Ala Ser Lys Ala Trp Thr
                245                 250                 255

Leu Glu Val Leu Tyr Ala Pro Arg Arg Leu Arg Val Ser Met Ser Pro
            260                 265                 270

Gly Asp Gln Val Met Glu Gly Lys Ser Ala Thr Leu Thr Cys Glu Ser
        275                 280                 285

Asp Ala Asn Pro Pro Val Ser His Tyr Thr Trp Phe Asp Trp Asn Asn
    290                 295                 300

Gln Ser Leu Pro Tyr His Ser Gln Lys Leu Arg Leu Glu Pro Val Lys
305                 310                 315                 320

Val Gln His Ser Gly Ala Tyr Trp Cys Gln Gly Thr Asn Ser Val Gly
            325                 330                 335

Lys Gly Arg Ser Pro Leu Ser Thr Leu Thr Val Tyr Tyr Ser Pro Glu
            340                 345                 350

Thr
```

<210> SEQ ID NO 222
<211> LENGTH: 1059
<212> TYPE: DNA
<213> ORGANISM: Artificial Sequence
<220> FEATURE:
<223> OTHER INFORMATION: Portion of CD22 extracellular domain that
      contains CD22 domains defined as Ig-like C2-type 3, Ig-like
      C2-type 4, Ig-like C2-type 5, Ig-like C2-type 6 coding sequence

<400> SEQUENCE: 222

```
ccggaacctt ccacggttca gatcctccac tcaccggctg tggagggaag tcaagtcgag      60
tttctttgca tgtcactggc caatcctctt ccaacaaatt acacgtggta ccacaatggg     120
aaagaaatgc agggaaggac agaggagaaa gtccacatcc caaagatcct cccttggcac     180
gctgggactt attcctgtgt ggcagaaaac attcttggta ctggacagag gggccctgga     240
gctgagctgg atgtccagta tcctcccaag aaggtgacca cagtgattca aaaccccatg     300
ccgattcgag aaggagacac agtgaccctt tcctgtaact acaattccag taaccccagt     360
gttacccggt atgaatggaa accccatggc gcctgggagg agccatcgct tggggtgctg     420
aagatccaaa acgttggctg ggacaacaca accatcgcct cgcagcttg taatagttgg     480 tgctcgtggg cctccctgt cgccctgaat gtccagtatg cccccgaga cgtgagggtc      540 cggaaaatca agcccttttc cgagattcac tctggaaact cggtcagcct ccaatgtgac     600
ttctcaagca gccaccccaa agaagtccag ttcttctggg agaaaaatgg caggcttctg     660
gggaaagaaa gccagctgaa ttttgactcc atctccccag aagatgctgg gagttacagc     720
tgctgggtga caactccat aggacagaca gcgtccaagg cctggacact tgaagtgctg     780
tatgcaccca ggaggctgcg tgtgtccatg agcccagggg accaagtgat ggaggggaag     840
agtgcaaccc tgacctgtga gagcgacgcc aaccctcccg tctcccacta cacctggttt     900
gactggaata accaaagcct ccctaccac agccagaagc tgagattgga ccggtgaag      960 gtccagcact cgggtgccta ctggtgccag gggaccaaca gtgtgggcaa gggccgttcg    1020
cctctcagca ccctcaccgt ctactatagc ccggagacc                          1059
```

<210> SEQ ID NO 223
<211> LENGTH: 179
<212> TYPE: PRT
<213> ORGANISM: Artificial Sequence
<220> FEATURE:
<223> OTHER INFORMATION: Portion of CD22 extracellular domain that
      contains CD22 domains defined as Ig-like C2-type 5, Ig-like -continued C2-type 6

<400> SEQUENCE: 223

```
Pro Arg Asp Val Arg Val Arg Lys Ile Lys Pro Leu Ser Glu Ile His
1               5                   10                  15

Ser Gly Asn Ser Val Ser Leu Gln Cys Asp Phe Ser Ser Ser His Pro
            20                  25                  30

Lys Glu Val Gln Phe Phe Trp Glu Lys Asn Gly Arg Leu Leu Gly Lys
        35                  40                  45

Glu Ser Gln Leu Asn Phe Asp Ser Ile Ser Pro Glu Asp Ala Gly Ser
    50                  55                  60

Tyr Ser Cys Trp Val Asn Asn Ser Ile Gly Gln Thr Ala Ser Lys Ala
65                  70                  75                  80

Trp Thr Leu Glu Val Leu Tyr Ala Pro Arg Arg Leu Arg Val Ser Met
                85                  90                  95

Ser Pro Gly Asp Gln Val Met Glu Gly Lys Ser Ala Thr Leu Thr Cys
            100                 105                 110

Glu Ser Asp Ala Asn Pro Pro Val Ser His Tyr Thr Trp Phe Asp Trp
            115                 120                 125

Asn Asn Gln Ser Leu Pro Tyr His Ser Gln Lys Leu Arg Leu Glu Pro
    130                 135                 140

Val Lys Val Gln His Ser Gly Ala Tyr Trp Cys Gln Gly Thr Asn Ser
145                 150                 155                 160

Val Gly Lys Gly Arg Ser Pro Leu Ser Thr Leu Thr Val Tyr Tyr Ser
                165                 170                 175

Pro Glu Thr
```

<210> SEQ ID NO 224
<211> LENGTH: 537
<212> TYPE: DNA
<213> ORGANISM: Artificial Sequence
<220> FEATURE:
<223> OTHER INFORMATION: Portion of CD22 extracellular domain that
      contains CD22 domains defined as Ig-like C2-type 5, Ig-like
      C2-type 6 coding sequence

<400> SEQUENCE: 224

```
ccccgagacg tgagggtccg gaaaatcaag cccctttccg agattcactc tggaaactcg      60
gtcagcctcc aatgtgactt ctcaagcagc caccccaaag aagtccagtt cttctgggag     120
aaaaatggca ggcttctggg aaagaaagc cagctgaatt ttgactccat ctccccagaa      180
gatgctggga gttacagctg ctgggtgaac aactccatag acagacagc gtccaaggcc      240 tggacacttg aagtgctgta tgcacccagg aggctgcgtg tgtccatgag cccagggggac    300 caagtgatgg aggggaagag tgcaaccctg acctgtgaga gcgacgccaa ccctcccgtc     360
tcccactaca cctggtttga ctggaataac aaaagcctcc cctaccacag ccagaagctg     420
agattggagc cggtgaaggt ccagcactcg ggtgcctact ggtgccaggg gaccaacagt     480
gtgggcaagg gccgttcgcc tctcagcacc ctcaccgtct actatagccc ggagacc        537
```

<210> SEQ ID NO 225
<211> LENGTH: 22
<212> TYPE: PRT
<213> ORGANISM: Artificial Sequence
<220> FEATURE:
<223> OTHER INFORMATION: 1H10, 1A9, 1E6, and/or 1B9 light chain signal
      peptide

<400> SEQUENCE: 225

-continued

```
Met Asp Met Arg Val Pro Ala Gln Leu Leu Gly Leu Leu Leu Trp
1               5                   10                  15

Leu Pro Gly Ala Arg Cys
            20

<210> SEQ ID NO 226
<211> LENGTH: 20
<212> TYPE: PRT
<213> ORGANISM: Artificial Sequence
<220> FEATURE:
<223> OTHER INFORMATION: 1D2 light chain signal peptide

<400> SEQUENCE: 226

Met Arg Val Pro Ala Gln Leu Leu Gly Leu Leu Leu Leu Trp Leu Pro
1               5                   10                  15

Gly Ala Arg Cys
            20

<210> SEQ ID NO 227
<211> LENGTH: 22
<212> TYPE: PRT
<213> ORGANISM: Artificial Sequence
<220> FEATURE:
<223> OTHER INFORMATION: 1H8 light chain signal peptide

<400> SEQUENCE: 227

Met Asp Met Arg Leu Pro Ala Gln Leu Leu Gly Leu Leu Met Leu Trp
1               5                   10                  15

Val Pro Ala Ser Arg Gly
            20

<210> SEQ ID NO 228
<211> LENGTH: 22
<212> TYPE: PRT
<213> ORGANISM: Artificial Sequence
<220> FEATURE:
<223> OTHER INFORMATION: 2D3 light chain signal peptide

<400> SEQUENCE: 228

Met Glu Pro Trp Lys Pro Gln His Ser Phe Phe Phe Leu Leu Leu Trp
1               5                   10                  15

Leu Pro Asp Ser Thr Gly
            20

<210> SEQ ID NO 229
<211> LENGTH: 19
<212> TYPE: PRT
<213> ORGANISM: Artificial Sequence
<220> FEATURE:
<223> OTHER INFORMATION: 1H10 heavy chain signal peptide

<400> SEQUENCE: 229

Met Asp Trp Thr Trp Arg Val Phe Cys Leu Leu Ala Val Ala Pro Gly
1               5                   10                  15

Val His Ser

<210> SEQ ID NO 230
<211> LENGTH: 19
<212> TYPE: PRT
<213> ORGANISM: Artificial Sequence
<220> FEATURE:
<223> OTHER INFORMATION: 1A9 heavy chain signal peptide

<400> SEQUENCE: 230
```

```
Met Glu Leu Gly Leu Ser Trp Val Phe Leu Val Ala Ile Leu Glu Gly
1               5                   10                  15

Val Gln Cys

<210> SEQ ID NO 231
<211> LENGTH: 19
<212> TYPE: PRT
<213> ORGANISM: Artificial Sequence
<220> FEATURE:
<223> OTHER INFORMATION: 1E6 and/or 2E3 heavy chain signal peptide

<400> SEQUENCE: 231

Met Glu Phe Gly Leu Ser Trp Val Phe Leu Val Ala Leu Leu Arg Gly
1               5                   10                  15

Val Gln Cys

<210> SEQ ID NO 232
<211> LENGTH: 19
<212> TYPE: PRT
<213> ORGANISM: Artificial Sequence
<220> FEATURE:
<223> OTHER INFORMATION: 1D2 heavy chain signal peptide

<400> SEQUENCE: 232

Met Glu Ser Gly Leu Ser Trp Val Phe Leu Val Ala Leu Leu Arg Gly
1               5                   10                  15

Val Gln Cys

<210> SEQ ID NO 233
<211> LENGTH: 19
<212> TYPE: PRT
<213> ORGANISM: Artificial Sequence
<220> FEATURE:
<223> OTHER INFORMATION: 1B9 heavy chain signal peptide

<400> SEQUENCE: 233

Met Glu Phe Gly Leu Ser Trp Val Phe Leu Ile Ala Leu Leu Arg Gly
1               5                   10                  15

Val Gln Cys

<210> SEQ ID NO 234
<211> LENGTH: 22
<212> TYPE: PRT
<213> ORGANISM: Artificial Sequence
<220> FEATURE:
<223> OTHER INFORMATION: 1H8 heavy chain signal peptide

<400> SEQUENCE: 234

Met Leu Leu Leu Val Thr Ser Leu Leu Leu Cys Glu Leu Pro His Pro
1               5                   10                  15

Ala Phe Leu Leu Ile Pro
            20

<210> SEQ ID NO 235
<211> LENGTH: 19
<212> TYPE: PRT
<213> ORGANISM: Artificial Sequence
<220> FEATURE:
<223> OTHER INFORMATION: 2D3 heavy chain signal peptide

<400> SEQUENCE: 235

Met Glu Phe Gly Leu Ser Trp Leu Phe Leu Val Ala Ile Leu Lys Gly
1               5                   10                  15
```

Val Gln Cys

<210> SEQ ID NO 236
<211> LENGTH: 738
<212> TYPE: DNA
<213> ORGANISM: Artificial Sequence
<220> FEATURE:
<223> OTHER INFORMATION: My96 Coding Sequence

<400> SEQUENCE: 236
gagatcgtgc tgacacagag ccctggaagc ctggccgtgt ctcctggcga gcgcgtgaca        60
atgagctgca agagcagcca gagcgtgttc ttcagcagct cccagaagaa ctacctggcc       120
tggtatcagc agatccccgg ccagagcccc agactgctga tctactgggc cagcaccaga       180
gaaagcggcg tgcccgatag attcaccggc agcggctctg gcaccgactt caccctgaca       240
atcagcagcg tgcagcccga ggacctggcc atctactact gccaccagta cctgagcagc       300
cggacctttg gccagggcac caagctggaa atcaagagag cggcggagg ctctggcgga        360 ggcggatcta gtggcggagg atctcaggtg cagctgcagc agcctggcgc cgaggtcgtg       420
aaacctggcg cctctgtgaa gatgtcctgc aaggccagcg gctacacctt caccagctac       480
tacatccact ggatcaagca gacccctgga cagggcctgg aatgggtggg agtgatctac       540
cccggcaacg acgacatcag ctacaaccag aagttccagg gcaaggccac cctgaccgcc       600
gacaagtcta gcaccaccgc ctacatgcag ctgtccagcc tgaccagcga ggacagcgcc       660
gtgtactact gcgccagaga agtgcggctg cggtacttcg atgtgtgggg ccagggaacc       720
accgtgaccg tgtcatct                                                     738

<210> SEQ ID NO 237
<211> LENGTH: 9278
<212> TYPE: DNA
<213> ORGANISM: Artificial Sequence
<220> FEATURE:
<223> OTHER INFORMATION: My96_int_41BB_3z_TCD19 Coding Sequence

<400> SEQUENCE: 237
gttagaccag atctgagcct gggagctctc tggctaacta gggaacccac tgcttaagcc        60
tcaataaagc ttgccttgag tgcttcaagt agtgtgtgcc cgtctgttgt gtgactctgg       120
taactagaga tccctcagac cctttttagtc agtgtggaaa atctctagca gtggcgcccg       180
aacagggact tgaaagcgaa agggaaacca gaggagctct ctcgacgcag gactcggctt       240
gctgaagcgc gcacggcaag aggcgagggg cggcgactgg tgagtacgcc aaaaattttg       300
actagcggag gctagaagga gagagatggg tgcgagagcg tcagtattaa gcgggggaga       360
attagatcga tgggaaaaaa ttcggttaag gccagggggga agaaaaaat ataaattaaa       420 acatatagta tgggcaagca gggagctaga acgattcgca gttaatcctg gcctgttaga       480
aacatcagaa ggctgtagac aaatactggg acagctacaa ccatcccttc agacaggatc       540
agaagaactt agatcattat ataatacagt agcaaccctc tattgtgtgc atcaaaggat       600
agagataaaa gacaccaagg aagctttaga caagatagag gaagagcaaa acaaaagtaa       660
gaaaaaagca cagcaagcag cagctgacac aggacacagc aatcaggtca gccaaaatta       720
ccctatagtg cagaacatcc aggggcaaat ggtacatcag gccatatcac ctagaacttt       780
aaatgcatgg gtaaaagtag tagaagagaa ggctttcagc ccagaagtga tacccatgtt       840
ttcagcatta tcagaaggag ccacccccaca agatttaaac accatgctaa acacagtggg       900

-continued

```
gggacatcaa gcagccatgc aaatgttaaa agagaccatc aatgaggaag ctgcaggcaa    960
agagaagagt ggtgcagaga gaaaaaagag cagtgggaat aggagctttg ttccttgggt   1020
tcttgggagc agcaggaagc actatgggcg cagcgtcaat gacgctgacg gtacaggcca   1080
gacaattatt gtctggtata gtgcagcagc agaacaattt gctgagggct attgaggcgc   1140
aacagcatct gttgcaactc acagtctggg gcatcaagca gctccaggca agaatcctgg   1200
ctgtggaaag atacctaaag gatcaacagc tcctggggat ttggggttgc tctggaaaac   1260
tcatttgcac cactgctgtg ccttggatct acaaatggca gtattcatcc acaattttaa   1320
aagaaaaggg gggattgggg ggtacagtgc aggggaaaga atagtagaca taatagcaac   1380
agacatacaa actaaagaat tacaaaaaca aattacaaaa attcaaaatt ttcgggttta   1440
ttacagggac agcagagatc cagtttgggg atcaattgca tgaagaatct gcttagggtt   1500
aggcgttttg cgctgcttcg cgaggatctg cgatcgctcc ggtgcccgtc agtgggcaga   1560
gcgcacatcg cccacagtcc ccgagaagtt ggggggaggg gtcggcaatt gaaccggtgc   1620
ctagagaagg tggcgcgggg taaactggga aagtgatgtc gtgtactggc tccgcctttt   1680
tcccgagggt gggggagaac cgtatataag tgcagtagtc gccgtgaacg ttcttttttcg   1740 caacgggttt gccgccagaa cacagctgaa gcttcgaggg gctcgcatct ctccttcacg   1800
cgcccgccgc cctacctgag gccgccatcc acgccggttg agtcgcgttc tgccgcctcc   1860
cgcctgtggt gcctcctgaa ctgcgtccgc cgtctaggta agtttaaagc tcaggtcgag   1920
accgggcctt tgtccggcgc tcccttggag cctacctaga ctcagccggc tctccacgct   1980
ttgcctgacc ctgcttgctc aactctacgt ctttgtttcg ttttctgttc tgcgccgtta   2040
cagatccaag ctgtgaccgg cgcctacggc tagccaccat gctgctgctc gtgaccagcc   2100
tgctgctgtg cgaactgccc caccctgcct ttctgctgat ccccgagatc gtgctgacac   2160
agagccctgg aagcctggcc gtgtctcctg gcgagcgcgt gacaatgagc tgcaagagca   2220
gccagagcgt gttcttcagc agctcccaga gaactacct ggcctggtat cagcagatcc   2280
ccggccagag ccccagactg ctgatctact gggccagcac cagagaaagc ggcgtgcccg   2340
atagattcac cggcagcggc tctggcaccg acttcaccct gacaatcagc agcgtgcagc   2400
ccgaggacct ggccatctac tactgccacc agtacctgag cagccggacc tttggccagg   2460
gcaccaagct ggaaatcaag agaggcggcg gaggctctgg cggaggcgga tctagtggcg   2520
gaggatctca ggtgcagctg cagcagcctg cgccgaggt cgtgaaacct ggcgcctctg   2580
tgaagatgtc ctgcaaggcc agcggctaca ccttcaccag ctactacatc cactggatca   2640
agcagacccc tggacagggc ctggaatggg tgggagtgat ctaccccggc aacgacgaca   2700
tcagctacaa ccagaagttc cagggcaagg ccaccctgac cgccgacaag tctagcacca   2760
ccgcctacat gcagctgtcc agcctgacca gcgaggacag cgccgtgtac tactgcgcca   2820
gagaagtgcg gctgcggtac ttcgatgtgt ggggccaggg aaccaccgtg accgtgtcat   2880
ctgagtctaa gtacggaccg ccctgcccc cttgccctat gttctgggtg ctggtggtgg   2940
tcggaggcgt gctggcctgc tacagcctgc tggtcaccgt ggccttcatc atcttttggg   3000
tgaaacgggg cagaaagaaa ctcctgtata tattcaaaca accatttatg agaccagtac   3060
aaactactca agaggaagat ggctgtagct gccgatttcc agaagaagaa gaaggaggat   3120
gtgaactgcg ggtgaagttc agcagaagcg ccgacgcccc tgcctaccag cagggccaga   3180
atcagctgta caacgagctg aacctgggca gaagggaaga gtacgacgtc ctggataagc   3240
ggagaggccg ggaccctgag atgggcggca gcctcggcg gaagaacccc caggaaggcc   3300
```

-continued

```
tgtataacga actgcagaaa gacaagatgg ccgaggccta cagcgagatc ggcatgaagg   3360
gcgagcggag gcggggcaag ggccacgacg gcctgtatca gggcctgtcc accgccacca   3420
aggataccta cgacgccctg cacatgcagg ccctgccccc aaggctcgag ggcggcggag   3480
agggcagagg aagtcttcta acatgcggtg acgtggagga gaatccaggc cctaggatgc   3540
cacctccaag actcctcttc ttcctcctct tcctgacacc aatggaagtc aggcctgagg   3600
aacctctagt ggtgaaggtg gaagagggag ataacgctgt gttacagtgc ctcaagggaa   3660
cctcagatgg acccactcag cagctgacct ggtctcggga gtctccgctt aaacccttcc   3720
tgaaactcag ccttggactg ccaggtctgg gaatccacat gaggccactg gctatctggc   3780
tgttcatctt caacgtctct caacagatgg gaggcttcta cctgtgtcag cctggaccac   3840
cttctgagaa ggcatggcag cctggttgga cagtcaatgt ggagggttct ggtgagctgt   3900
tccggtggaa tgtttcggac ctaggtggac tgggatgtgg tctgaagaac aggtcctcag   3960
agggacctag ctctccttcc gggaagctca tgagccccaa gctgtatgtg tgggccaaag   4020
accgccctga gatctgggag ggagagcctc cgtgtgtccc accgagggac agcctgaacc   4080
agagcctcag ccaggacctc accatggccc ctggctccac actctggctg tcctgtgggg   4140 tacccctga ctctgtgtcc aggggccccc tctcctggac ccatgtgcac cccaagggc   4200 ctaagtcatt gctgagccta gagctgaagg acgatcgccc tgccagagat atgtgggtaa   4260
tggagacggg tctgttgttg ccccgggcca cagctcaaga cgctggaaag tattattgtc   4320
accgtggcaa cctgaccatg tcattccacc tggagatcac tgctcggcca gtactatggc   4380
actggctgct gaggactggt ggctggaagg tctcagctgt gactttggct tatctgatct   4440
tctgcctgtg ttcccttgtg ggcattcttc atcttcaaag agccctggtc ctgaggagga   4500
aaagatgagc ggccgctcta gacccgggct gcaggaattc gatatcaagc ttatcgataa   4560
tcaacctctg gattacaaaa tttgtgaaag attgactggt attcttaact atgttgctcc   4620
ttttacgcta tgtggatacg ctgctttaat gcctttgtat catgctattg cttcccgtat   4680
ggctttcatt ttctcctcct tgtataaatc ctggttgctg tctctttatg aggagttgtg   4740
gcccgttgtc aggcaacgtg gcgtggtgtg cactgtgttt gctgacgcaa ccccactgg   4800 ttggggcatt gccaccacct gtcagctcct ttccgggact ttcgctttcc ccctccctat   4860
tgccacggcg gaactcatcg ccgcctgcct tgcccgctgc tggacagggg ctcggctgtt   4920
gggcactgac aattccgtgg tgttgtcggg gaaatcatcg tcctttcctt ggctgctcgc   4980
ctgtgttgcc acctggattc tgcgcgggac gtccttctgc tacgtccctt cggccctcaa   5040
tccagcggac cttccttccc gcggcctgct gccggctctg cggcctcttc cgcgtcttcg   5100
ccttcgccct cagacgagtc ggatctccct ttgggccgcc tccccgcatc gataccgtcg   5160
actagccgta cctttaagac caatgactta caaggcagct gtagatctta gccactttt   5220 aaaagaaaag gggggactgg aagggctaat tcactcccaa agaagacaag atctgctttt   5280
tgcctgtact gggtctctct ggttagacca gatctgagcc tgggagctct ctggctaact   5340
agggaaccca ctgcttaagc ctcaataaag cttgccttga gtgcttcaag tagtgtgtgc   5400
ccgtctgttg tgtgactctg gtaactagag atccctcaga cccttttagt cagtgtggaa   5460
aatctctagc agaattcgat atcaagctta tcgataccgt cgacctcgag ggggggcccg   5520
gtacccaatt cgccctatag tgagtcgtat tacaattcac tggccgtcgt tttacaacgt   5580
cgtgactggg aaaaccctgg cgttacccaa cttaatcgcc ttgcagcaca tccccctttc   5640
```

```
gccagctggc gtaatagcga agaggcccgc accgatcgcc cttcccaaca gttgcgcagc    5700
ctgaatggcg aatggaaatt gtaagcgtta atattttgtt aaaattcgcg ttaaattttt    5760
gttaaatcag ctcatttttt aaccaatagg ccgaaatcgg caaaatccct tataaatcaa    5820
aagaatagac cgagataggg ttgagtgttg ttccagtttg gaacaagagt ccactattaa    5880
agaacgtgga ctccaacgtc aaagggcgaa aaaccgtcta tcagggcgat ggcccactac    5940
gtgaaccatc accctaatca agttttttgg ggtcgaggtg ccgtaaagca ctaaatcgga    6000
accctaaagg gagcccccga tttagagctt gacgggaaa gccggcgaac gtggcgagaa      6060
aggaagggaa gaaagcgaaa ggagcgggcg ctagggcgct ggcaagtgta gcggtcacgc    6120
tgcgcgtaac caccacaccc gccgcgctta atgcgccgct acagggcgcg tcaggtggca    6180
cttttcgggg aaatgtgcgc ggaacccct tttgtttatt tttctaaata cattcaaata     6240
tgtatccgct catgagacaa taaccctgat aaatgcttca ataatattga aaaaggaaga    6300
gtatgagtat tcaacatttc cgtgtcgccc ttattccctt ttttgcggca ttttgccttc    6360 ctgttttgc tcacccagaa acgctggtga aagtaaaaga tgctgaagat cagttgggtg      6420
cacgagtggg ttacatcgaa ctggatctca acagcggtaa gatccttgag agttttcgcc    6480
ccgaagaacg ttttccaatg atgagcactt ttaaagttct gctatgtggc gcggtattat    6540
cccgtattga cgccgggcaa gagcaactcg gtcgccgcat acactattct cagaatgact    6600
tggttgagta ctcaccagtc acagaaaagc atcttacgga tggcatgaca gtaagagaat    6660
tatgcagtgc tgccataacc atgagtgata acactgcggc caacttactt ctgacaacga    6720
tcggaggacc gaaggagcta accgcttttt tgcacaacat gggggatcat gtaactcgcc    6780
ttgatcgttg ggaaccggag ctgaatgaag ccataccaaa cgacgagcgt gacaccacga    6840
tgcctgtagc aatggcaaca acgttgcgca aactattaac tggcgaacta cttactctag    6900
cttcccggca acaattaata gactggatgg aggcggataa agttgcagga ccacttctgc    6960
gctcggccct tccggctggc tggtttattg ctgataaatc tggagccggt gagcgtgggt    7020
ctcgcggtat cattgcagca ctggggccag atggtaagcc ctcccgtatc gtagttatct    7080
acacgacggg gagtcaggca actatggatg aacgaaatag acagatcgct gagataggtg    7140
cctcactgat taagcattgg taactgtcag accaagttta ctcatatata ctttagattg    7200
atttaaaact tcatttttaa tttaaaagga tctaggtgaa gatcctttt gataatctca      7260 tgaccaaaat cccttaacgt gagttttcgt tccactgagc gtcagacccc gtagaaaaga    7320
tcaaaggatc ttcttgagat cctttttttc tgcgcgtaat ctgctgcttg caaacaaaaa    7380
aaccaccgct accagcggtg gtttgtttgc cggatcaaga gctaccaact ctttttccga    7440
aggtaactgg cttcagcaga gcgcagatac caaatactgt tcttctagtg tagccgtagt    7500
taggccacca cttcaagaac tctgtagcac cgcctacata cctcgctctg ctaatcctgt    7560
taccagtggc tgctgccagt ggcgataagt cgtgtcttac cgggttggac tcaagacgat    7620
agttaccgga taaggcgcag cggtcgggct gaacggggg ttcgtgcaca cagcccagct      7680
tggagcgaac gacctacacc gaactgagat acctacagcg tgagctatga aaagcgcca      7740 cgcttcccga agggagaaag gcggacaggt atccggtaag cggcagggtc ggaacaggag    7800
agcgcacgag ggagcttcca gggggaaacg cctggtatct ttatagtcct gtcgggtttc    7860
gccacctctg acttgagcgt cgatttttgt gatgctcgtc aggggggcgg agcctatgga    7920
aaaacgccag caacgcggcc ttttacggt tcctggcctt ttgctggcct tttgctcaca      7980
tgttctttcc tgcgttatcc cctgattctg tggataaccg tattaccgcc tttgagtgag    8040
```

-continued

```
ctgataccgc tcgccgcagc cgaacgaccg agcgcagcga gtcagtgagc gaggaagcgg    8100
aagagcgccc aatacgcaaa ccgcctctcc ccgcgcgttg gccgattcat taatgcagct    8160
ggcacgacag gtttcccgac tggaaagcgg gcagtgagcg caacgcaatt aatgtgagtt    8220
agctcactca ttaggcaccc caggctttac actttatgct tccggctcgt atgttgtgtg    8280
gaattgtgag cggataacaa tttcacacag gaaacagcta tgaccatgat tacgccaagc    8340
tcgaaattaa ccctcactaa agggaacaaa agctggagct ccaccgcggt ggcggcctcg    8400
aggtcgagat ccggtcgacc agcaaccata gtcccgcccc taactccgcc catcccgccc    8460
ctaactccgc ccagttccgc ccattctccg ccccatggct gactaatttt ttttatttat    8520
gcagaggccg aggccgcctc ggcctctgag ctattccaga agtagtgagg aggctttttt    8580
ggaggcctag gcttttgcaa aaagcttcga cggtatcgat tggctcatgt ccaacattac    8640
cgccatgttg acattgatta ttgactagtt attaatagta atcaattacg gggtcattag    8700
ttcatagccc atatatggag ttccgcgtta cataacttac ggtaaatggc ccgcctggct    8760
gaccgcccaa cgacccccgc ccattgacgt caataatgac gtatgttccc atagtaacgc    8820
caatagggac tttccattga cgtcaatggg tggagtattt acggtaaact gcccacttgg    8880
cagtacatca agtgtatcat atgccaagta cgccccctat tgacgtcaat gacggtaaat    8940
ggcccgcctg gcattatgcc cagtacatga ccttatggga ctttcctact ggcagtaca    9000 tctacgtatt agtcatcgct attaccatgg tgatgcggtt ttggcagtac atcaatgggc    9060
gtggatagcg gtttgactca cggggatttc caagtctcca ccccattgac gtcaatggga    9120
gtttgttttg gcaccaaaat caacgggact ttccaaaatg tcgtaacaac tccgccccat    9180
tgacgcaaat gggcggtagg cgtgtacgga attcggagtg cgagccctc agatcctgca     9240 tataagcagc tgctttttgc ctgtactggg tctctctg                           9278
```

<210> SEQ ID NO 238
<211> LENGTH: 107
<212> TYPE: PRT
<213> ORGANISM: Artificial Sequence
<220> FEATURE:
<223> OTHER INFORMATION: 1H10 variable light chain

<400> SEQUENCE: 238

```
Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Ile Tyr
            20                  25                  30

Leu Gly Trp Tyr Gln Gln Lys Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105
```

<210> SEQ ID NO 239
<211> LENGTH: 118
<212> TYPE: PRT
<213> ORGANISM: Artificial Sequence

```
<220> FEATURE:
<223> OTHER INFORMATION: 1H10 variable heavy chain

<400> SEQUENCE: 239

Gln Val Gln Leu Val Gln Ser Gly Ala Glu Val Lys Lys Pro Gly Ala
1               5                   10                  15

Ser Val Lys Val Ser Cys Lys Gly Ser Gly Tyr Ile Phe Thr Ser Tyr
            20                  25                  30

Asp Met His Trp Val Arg Gln Ala Pro Gly Gln Gly Leu Glu Trp Met
        35                  40                  45

Gly Ile Ile Asp Pro Ser Gly Gly Ser Thr Ser Tyr Ala Gln Lys Phe
    50                  55                  60

Gln Gly Arg Val Thr Met Thr Arg Asp Thr Ser Met Ser Thr Val Tyr
65                  70                  75                  80

Met Glu Leu Ser Ser Leu Arg Ser Glu Asp Thr Ala Val Tyr Tyr Cys
                85                  90                  95

Thr Arg Asp Tyr Ser Trp Ser Tyr Phe Asp Tyr Trp Gly Gln Gly Thr
            100                 105                 110

Leu Val Thr Val Ser Ser
        115

<210> SEQ ID NO 240
<211> LENGTH: 107
<212> TYPE: PRT
<213> ORGANISM: Artificial Sequence
<220> FEATURE:
<223> OTHER INFORMATION: 1A9 variable light chain

<400> SEQUENCE: 240

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Asp
            20                  25                  30

Leu Gly Trp Tyr Gln Gln Lys Pro Gly Lys Ala Pro Lys Ile Leu Ile
        35                  40                  45

Tyr Gly Ala Ser Ser Leu Gln Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Phe Ala Thr Tyr Tyr Cys Leu Gln Glu Tyr Asn Tyr Pro Cys
                85                  90                  95

Thr Phe Gly Gln Gly Thr Lys Leu Glu Ile Lys
            100                 105

<210> SEQ ID NO 241
<211> LENGTH: 117
<212> TYPE: PRT
<213> ORGANISM: Artificial Sequence
<220> FEATURE:
<223> OTHER INFORMATION: 1A9 variable heavy chain

<400> SEQUENCE: 241

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ile Tyr
            20                  25                  30

Asp Met His Trp Val Arg Gln Ala Thr Gly Lys Gly Leu Glu Trp Val
        35                  40                  45
```

-continued

```
Ser Ala Ile Gly Thr Ala Gly Asp Thr Tyr Tyr Ala Gly Ser Val Lys
    50              55              60
```

```
Gly Arg Phe Thr Ile Ser Arg Glu Asn Ala Lys Asn Ser Leu Tyr Leu
65              70              75              80
```

```
Gln Met Asn Ser Leu Arg Ala Gly Asp Thr Ala Val Tyr Tyr Cys Ala
            85              90              95
```

```
Arg Glu Tyr Ser Gly Tyr Tyr Phe Asp Tyr Trp Gly Gln Gly Thr Leu
            100             105             110
```

```
Val Thr Val Ser Ser
        115
```

```
<210> SEQ ID NO 242
<211> LENGTH: 107
<212> TYPE: PRT
<213> ORGANISM: Artificial Sequence
<220> FEATURE:
<223> OTHER INFORMATION: 1E6 variable light chain

<400> SEQUENCE: 242
```

```
Ala Ile Gln Met Thr Gln Ser Pro Ser Ser Leu Ser Ala Ser Val Gly
1               5               10              15
```

```
Asp Arg Val Thr Ile Thr Cys Arg Ala Ser Gln Gly Ile Arg Asn Asp
            20              25              30
```

```
Leu Gly Trp Tyr Gln Gln Lys Pro Gly Lys Ala Pro Lys Leu Leu Ile
        35              40              45
```

```
Tyr Ala Ala Ser Asn Leu Gln Ser Gly Val Pro Ser Arg Phe Ser Gly
    50              55              60
```

```
Ser Gly Ser Gly Thr Asp Phe Thr Leu Thr Ile Ser Ser Leu Gln Pro
65              70              75              80
```

```
Glu Asp Phe Ala Thr Tyr Tyr Cys Leu Gln Asp Tyr Ser Tyr Pro Arg
            85              90              95
```

```
Thr Phe Gly Gln Gly Thr Lys Val Glu Ile Lys
            100             105
```

```
<210> SEQ ID NO 243
<211> LENGTH: 118
<212> TYPE: PRT
<213> ORGANISM: Artificial Sequence
<220> FEATURE:
<223> OTHER INFORMATION: 1E6 variable heavy chain

<400> SEQUENCE: 243
```

```
Gln Val Gln Leu Val Glu Ser Gly Gly Gly Val Val Gln Pro Gly Arg
1               5               10              15
```

```
Ser Leu Arg Leu Ser Cys Ala Ala Ser Gly Phe Thr Phe Ser Ser Tyr
            20              25              30
```

```
Asp Ile His Trp Val Arg Gln Ala Pro Gly Lys Gly Leu Glu Trp Val
            35              40              45
```

```
Ala Val Ile Trp Tyr Asp Gly Ser His Asn Tyr Tyr Ser Asp Ser Val
    50              55              60
```

```
Lys Gly Arg Phe Thr Ile Ser Arg Asp Asn Ser Lys Asn Thr Leu Tyr
65              70              75              80
```

```
Leu Gln Met Asn Ser Leu Arg Ala Glu Asp Thr Ala Val Tyr Tyr Cys
            85              90              95
```

```
Ala Arg Asp Tyr Ser Gly Ser Tyr Tyr Asp Tyr Trp Gly Gln Gly Thr
            100             105             110
```

```
Leu Val Thr Val Ser Ser
        115
```

<210> SEQ ID NO 244
<211> LENGTH: 107
<212> TYPE: PRT
<213> ORGANISM: Artificial Sequence
<220> FEATURE:
<223> OTHER INFORMATION: 1D2 variable light chain

<400> SEQUENCE: 244

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Glu Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Ile Ile Ser Ser Leu Gln Pro
65                  70                  75                  80

Glu Asp Phe Ala Thr Tyr Tyr Cys Leu Gln Asp Tyr Ser Tyr Pro Arg
                85                  90                  95

Thr Phe Gly Gln Gly Thr Lys Val Glu Ile Lys
            100                 105

<210> SEQ ID NO 245
<211> LENGTH: 118
<212> TYPE: PRT
<213> ORGANISM: Artificial Sequence
<220> FEATURE:
<223> OTHER INFORMATION: 1D2 variable heavy chain

<400> SEQUENCE: 245

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Asp Ile His Trp Val Arg Gln Ala Pro Gly Lys Gly Leu Glu Trp Val
        35                  40                  45

Ala Val Ile Trp Tyr Asp Gly Ser Gln Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Gly Ser Tyr Tyr Asp Tyr Trp Gly Gln Gly Thr
            100                 105                 110

Leu Val Thr Val Ser Ser
        115

<210> SEQ ID NO 246
<211> LENGTH: 107
<212> TYPE: PRT
<213> ORGANISM: Artificial Sequence
<220> FEATURE:
<223> OTHER INFORMATION: 1B9 variable light chain

<400> SEQUENCE: 246

Ala Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asp Ile Arg Asn Asp
            20                  25                  30

Leu Gly Trp Tyr Leu Gln Arg Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Ser Tyr Pro Arg
                85                  90                  95

Thr Phe Gly Gln Gly Thr Thr Val Glu Ile Lys
            100                 105

<210> SEQ ID NO 247
<211> LENGTH: 118
<212> TYPE: PRT
<213> ORGANISM: Artificial Sequence
<220> FEATURE:
<223> OTHER INFORMATION: 1B9 variable heavy chain

<400> SEQUENCE: 247

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Ile Phe Ser Ser Tyr
            20                  25                  30

Asp Ile His Trp Val Arg Gln Ala Pro Gly Lys Gly Leu Glu Trp Val
            35                  40                  45

Ala Val Ile Trp Tyr Asp Gly Ser His Asn Tyr Tyr Ser Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asp Tyr Ser Gly Ser Tyr Phe Asp Tyr Trp Gly Gln Gly Thr
            100                 105                 110

Leu Val Thr Val Ser Ser
        115

<210> SEQ ID NO 248
<211> LENGTH: 107
<212> TYPE: PRT
<213> ORGANISM: Artificial Sequence
<220> FEATURE:
<223> OTHER INFORMATION: 1H8 variable light chain

<400> SEQUENCE: 248

Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Asn Ile Gly Gly Asn
            20                  25                  30

Leu His Trp Tyr Gln Gln Lys Pro Asp Gln Ser Pro Lys Leu Leu Ile
            35                  40                  45

Arg Tyr Ala Thr Gln Pro Phe Ser Gly Val Pro Ser Arg Phe Gly Gly
        50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys His Gln Ser Ser Ser Leu Pro Leu
                85                  90                  95
```

-continued

Thr Phe Gly Gly Gly Thr Lys Val Glu Ile Lys
            100                 105

<210> SEQ ID NO 249
<211> LENGTH: 120
<212> TYPE: PRT
<213> ORGANISM: Artificial Sequence
<220> FEATURE:
<223> OTHER INFORMATION: 1H8 variable heavy chain

<400> SEQUENCE: 249

Gln Val Gln Leu Val Glu Ser Gly Gly Gly Val Val Gln Pro Gly Gly
1               5                   10                  15

Ser Leu Arg Leu Ser Cys Ala Ala Ser Gly Phe Thr Phe Gly Ser Tyr
            20                  25                  30

Gly Met His Trp Val Arg Gln Ala Pro Gly Lys Gly Leu Glu Trp Val
        35                  40                  45

Ala Val Ile Trp Tyr Asp Gly Ser Asn Glu Tyr Tyr Ala Asp Ser Val
    50                  55                  60

Lys Gly Arg Phe Thr Val Ser Arg Asp Asn Ser Lys His Thr Leu Tyr
65                  70                  75                  80

Leu Gln Met Asn Arg Leu Arg Ala Glu Asp Thr Ala Val Tyr Tyr Cys
                85                  90                  95

Ala Arg Asp Leu Asp Tyr Asp Ser Ser Gly Gly Asp Tyr Trp Gly Gln
            100                 105                 110

Gly Ile Leu Val Leu Val Ser Ser
        115                 120

<210> SEQ ID NO 250
<211> LENGTH: 108
<212> TYPE: PRT
<213> ORGANISM: Artificial Sequence
<220> FEATURE:
<223> OTHER INFORMATION: 2D3 variable light chain

<400> SEQUENCE: 250

Glu Ile Val Met Thr Gln Ser Pro Ala Thr Leu Ser Leu Ser Pro Gly
1               5                   10                  15

Glu Arg Ala Thr Leu Ser Cys Arg Ala Ser Gln Ser Gly Ser Ser Ser
            20                  25                  30

Phe Leu Ser Trp Tyr Gln Gln Lys Pro Gly Gln Ala Pro Arg Leu Leu
        35                  40                  45

Ile Tyr Gly Ala Ser Thr Arg Ala Thr Gly Ile Pro Ala Arg Phe Ser
    50                  55                  60

Gly Ser Gly Ser Gly Thr Asp Phe Thr Leu Thr Ile Ser Ser Leu Gln
65                  70                  75                  80

Pro Glu Asp Phe Ala Val Tyr Tyr Cys Gln Gln Asp Tyr Asn Leu Pro
                85                  90                  95

Phe Thr Phe Gly Pro Gly Thr Lys Val Asp Ile Lys
            100                 105

<210> SEQ ID NO 251
<211> LENGTH: 119
<212> TYPE: PRT
<213> ORGANISM: Artificial Sequence
<220> FEATURE:
<223> OTHER INFORMATION: 2D3 variable heavy chain

<400> SEQUENCE: 251

Glu Val Gln Leu Leu Glu Ser Gly Gly Gly Leu Val Gln Pro Gly Gly
1               5                       10                      15

Ser Leu Ser Leu Ser Cys Ala Ala Ser Gly Phe Thr Phe Ser Ile Tyr
            20                      25                      30

Ala Met Ser Trp Val Arg Gln Ala Pro Gly Lys Gly Leu Glu Trp Val
        35                      40                      45

Ser Ala Ile Ser Asp Ser Gly Gly Thr Thr Tyr Tyr Ala Asp Ser Val
    50                      55                      60

Lys Gly Arg Phe Thr Ile Ser Arg Asp Asn Ser Lys Asn Met Leu Tyr
65                      70                      75                      80

Leu Glu Met Asn Ser Leu Arg Ala Glu Asp Thr Ala Ile Tyr Tyr Cys
                85                      90                      95

Ala Lys Arg Thr Arg Tyr Phe Asn Gly Met Asp Val Trp Gly Gln Gly
            100                     105                     110

Thr Thr Val Thr Val Ser Ser
            115

<210> SEQ ID NO 252
<211> LENGTH: 107
<212> TYPE: PRT
<213> ORGANISM: Artificial Sequence
<220> FEATURE:
<223> OTHER INFORMATION: 2E3 variable light chain

<400> SEQUENCE: 252

Glu Ile Val Leu Thr Gln Ser Pro Gly Thr Leu Ser Leu Ser Pro Gly
1               5                       10                      15

Glu Arg Ala Thr Leu Ser Cys Arg Ala Ser Gln Ser Val Ser Ser Ser
            20                      25                      30

Tyr Leu Ala Trp Tyr Gln Gln Lys Pro Gly Gln Ala Pro Arg Leu Leu
        35                      40                      45

Ile Tyr Gly Thr Ser Ser Arg Ala Thr Gly Ile Pro Asp Arg Phe Ser
    50                      55                      60

Gly Ser Gly Ser Gly Thr Asp Phe Thr Leu Thr Ile Ser Arg Leu Glu
65                      70                      75                      80

Pro Glu Asp Phe Ala Val Tyr Tyr Cys Gln Gln Tyr Gly Ser Ser Pro
                85                      90                      95

Thr Phe Gly Gly Gly Thr Lys Val Glu Ile Lys
            100                     105

<210> SEQ ID NO 253
<211> LENGTH: 122
<212> TYPE: PRT
<213> ORGANISM: Artificial Sequence
<220> FEATURE:
<223> OTHER INFORMATION: 2E3 variable heavy chain

<400> SEQUENCE: 253

Gln Val Cys Leu Val Glu Ser Gly Gly Gly Val Val Gln Pro Gly Lys
1               5                       10                      15

Ser Leu Arg Leu Ser Cys Ala Ala Ser Gly Phe Thr Phe Ser Ser Tyr
            20                      25                      30

Gly Met His Trp Val Arg Gln Ala Pro Gly Lys Gly Leu Glu Trp Val
        35                      40                      45

Ala Val Ile Trp Tyr Gly Gly Ser Asn Lys Tyr Tyr Ala Asp Ser Val
    50                      55                      60

Lys Gly Arg Phe Thr Ile Ser Arg Asp Asn Ser Lys Asn Thr Leu Tyr
65                      70                      75                      80

```
Leu Gln Met Asn Ser Leu Arg Ala Glu Asp Thr Ala Val Tyr Tyr Cys
            85                  90                  95

Ala Arg Asp Gly Thr Gly Glu Asn Tyr Tyr Tyr Val Met Asp Val
            100                 105                 110

Trp Gly Gln Gly Thr Thr Val Thr Val Ser
        115                 120
```

<210> SEQ ID NO 254
<211> LENGTH: 531
<212> TYPE: PRT
<213> ORGANISM: Artificial Sequence
<220> FEATURE:
<223> OTHER INFORMATION: V-set directed CD33/CD3 BsAb

<400> SEQUENCE: 254

```
Met Glu Thr Asp Thr Leu Leu Leu Trp Val Leu Leu Leu Trp Val Pro
1               5                   10                  15

Gly Ser Thr Gly Gln Val Gln Leu Val Gln Ser Gly Ala Glu Val Lys
            20                  25                  30

Lys Pro Gly Glu Ser Val Lys Val Ser Cys Lys Ala Ser Gly Tyr Thr
        35                  40                  45

Phe Thr Asn Tyr Gly Met Asn Trp Val Lys Gln Ala Pro Gly Gln Gly
    50                  55                  60

Leu Glu Trp Met Gly Trp Ile Asn Thr Tyr Thr Gly Glu Pro Thr Tyr
65                  70                  75                  80

Ala Asp Lys Phe Gln Gly Arg Val Thr Met Thr Thr Asp Thr Ser Thr
            85                  90                  95

Ser Thr Ala Tyr Met Glu Ile Arg Asn Leu Gly Gly Asp Asp Thr Ala
            100                 105                 110

Val Tyr Tyr Cys Ala Arg Trp Ser Trp Ser Asp Gly Tyr Tyr Val Tyr
            115                 120                 125

Phe Asp Tyr Trp Gly Gln Gly Thr Ser Val Thr Val Ser Ser Gly Gly
    130                 135                 140

Gly Gly Ser Gly Gly Gly Gly Ser Gly Gly Gly Gly Ser Asp Ile Val
145                 150                 155                 160

Met Thr Gln Ser Pro Asp Ser Leu Thr Val Ser Leu Gly Glu Arg Thr
            165                 170                 175

Thr Ile Asn Cys Lys Ser Ser Gln Ser Val Leu Asp Ser Ser Thr Asn
            180                 185                 190

Lys Asn Ser Leu Ala Trp Tyr Gln Gln Lys Pro Gly Gln Pro Pro Lys
        195                 200                 205

Leu Leu Leu Ser Trp Ala Ser Thr Arg Glu Ser Gly Ile Pro Asp Arg
    210                 215                 220

Phe Ser Gly Ser Gly Ser Gly Thr Asp Phe Thr Leu Thr Ile Asp Ser
225                 230                 235                 240

Pro Gln Pro Glu Asp Ser Ala Thr Tyr Tyr Cys Gln Gln Ser Ala His
            245                 250                 255

Phe Pro Ile Thr Phe Gly Gln Gly Thr Arg Leu Glu Ile Lys Ser Gly
            260                 265                 270

Gly Gly Gly Ser Glu Val Gln Leu Val Glu Ser Gly Gly Gly Leu Val
        275                 280                 285

Gln Pro Gly Gly Ser Leu Lys Leu Ser Cys Ala Ala Ser Gly Phe Thr
    290                 295                 300

Phe Asn Lys Tyr Ala Met Asn Trp Val Arg Gln Ala Pro Gly Lys Gly
305                 310                 315                 320
```

-continued

```
Leu Glu Trp Val Ala Arg Ile Arg Ser Lys Tyr Asn Asn Tyr Ala Thr
            325             330             335

Tyr Tyr Ala Asp Ser Val Lys Asp Arg Phe Thr Ile Ser Arg Asp Asp
            340             345             350

Ser Lys Asn Thr Ala Tyr Leu Gln Met Asn Asn Leu Lys Thr Glu Asp
            355             360             365

Thr Ala Val Tyr Tyr Cys Val Arg His Gly Asn Phe Gly Asn Ser Tyr
    370             375             380

Ile Ser Tyr Trp Ala Tyr Trp Gly Gln Gly Thr Leu Val Thr Val Ser
385             390             395             400

Ser Gly Gly Gly Gly Ser Gly Gly Gly Gly Ser Gly Gly Gly Gly Ser
            405             410             415

Gln Thr Val Val Thr Gln Glu Pro Ser Leu Thr Val Ser Pro Gly Gly
            420             425             430

Thr Val Thr Leu Thr Cys Gly Ser Ser Thr Gly Ala Val Thr Ser Gly
            435             440             445

Asn Tyr Pro Asn Trp Val Gln Gln Lys Pro Gly Gln Ala Pro Arg Gly
    450             455             460

Leu Ile Gly Gly Thr Lys Phe Leu Ala Pro Gly Thr Pro Ala Arg Phe
465             470             475             480

Ser Gly Ser Leu Leu Gly Gly Lys Ala Ala Leu Thr Leu Ser Gly Val
            485             490             495

Gln Pro Glu Asp Glu Ala Glu Tyr Tyr Cys Val Leu Trp Tyr Ser Asn
            500             505             510

Arg Trp Val Phe Gly Gly Gly Thr Lys Leu Thr Val Leu His His His
            515             520             525

His His His
    530
```

<210> SEQ ID NO 255
<211> LENGTH: 505
<212> TYPE: PRT
<213> ORGANISM: Artificial Sequence
<220> FEATURE:
<223> OTHER INFORMATION: V-set directed CD33/CD3 BsAb without leader
      sequence or His tag

<400> SEQUENCE: 255

```
Gln Val Gln Leu Val Gln Ser Gly Ala Glu Val Lys Lys Pro Gly Glu
1               5               10              15

Ser Val Lys Val Ser Cys Lys Ala Ser Gly Tyr Thr Phe Thr Asn Tyr
            20              25              30

Gly Met Asn Trp Val Lys Gln Ala Pro Gly Gln Gly Leu Glu Trp Met
            35              40              45

Gly Trp Ile Asn Thr Tyr Thr Gly Glu Pro Thr Tyr Ala Asp Lys Phe
    50              55              60

Gln Gly Arg Val Thr Met Thr Thr Asp Thr Ser Thr Ser Thr Ala Tyr
65              70              75              80

Met Glu Ile Arg Asn Leu Gly Gly Asp Asp Thr Ala Val Tyr Tyr Cys
            85              90              95

Ala Arg Trp Ser Trp Ser Asp Gly Tyr Tyr Val Tyr Phe Asp Tyr Trp
            100             105             110

Gly Gln Gly Thr Ser Val Thr Val Ser Ser Gly Gly Gly Gly Ser Gly
            115             120             125

Gly Gly Gly Ser Gly Gly Gly Gly Ser Asp Ile Val Met Thr Gln Ser
```

-continued

```
            130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
                165                 170                 175

Ala Trp Tyr Gln Gln Lys Pro Gly Gln Pro Pro Lys Leu Leu Leu Ser
                180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
            210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys Ser Gly Gly Gly Gly Ser
                245                 250                 255

Glu Val Gln Leu Val Glu Ser Gly Gly Gly Leu Val Gln Pro Gly Gly
                260                 265                 270

Ser Leu Lys Leu Ser Cys Ala Ala Ser Gly Phe Thr Phe Asn Lys Tyr
            275                 280                 285

Ala Met Asn Trp Val Arg Gln Ala Pro Gly Lys Gly Leu Glu Trp Val
        290                 295                 300

Ala Arg Ile Arg Ser Lys Tyr Asn Asn Tyr Ala Thr Tyr Tyr Ala Asp
305                 310                 315                 320

Ser Val Lys Asp Arg Phe Thr Ile Ser Arg Asp Asp Ser Lys Asn Thr
                325                 330                 335

Ala Tyr Leu Gln Met Asn Asn Leu Lys Thr Glu Asp Thr Ala Val Tyr
            340                 345                 350

Tyr Cys Val Arg His Gly Asn Phe Gly Asn Ser Tyr Ile Ser Tyr Trp
            355                 360                 365

Ala Tyr Trp Gly Gln Gly Thr Leu Val Thr Val Ser Ser Gly Gly Gly
        370                 375                 380

Gly Ser Gly Gly Gly Gly Ser Gly Gly Gly Ser Gln Thr Val Val
385                 390                 395                 400

Thr Gln Glu Pro Ser Leu Thr Val Ser Pro Gly Gly Thr Val Thr Leu
                405                 410                 415

Thr Cys Gly Ser Ser Thr Gly Ala Val Thr Ser Gly Asn Tyr Pro Asn
                420                 425                 430

Trp Val Gln Gln Lys Pro Gly Gln Ala Pro Arg Gly Leu Ile Gly Gly
            435                 440                 445

Thr Lys Phe Leu Ala Pro Gly Thr Pro Ala Arg Phe Ser Gly Ser Leu
            450                 455                 460

Leu Gly Gly Lys Ala Ala Leu Thr Leu Ser Gly Val Gln Pro Glu Asp
465                 470                 475                 480

Glu Ala Glu Tyr Tyr Cys Val Leu Trp Tyr Ser Asn Arg Trp Val Phe
                485                 490                 495

Gly Gly Gly Thr Lys Leu Thr Val Leu
                500                 505
```

<210> SEQ ID NO 256
<211> LENGTH: 250
<212> TYPE: PRT
<213> ORGANISM: Artificial Sequence
<220> FEATURE:
<223> OTHER INFORMATION: V-set directed CD33 scFv -continued

```
<400> SEQUENCE: 256

Gln Val Gln Leu Val Gln Ser Gly Ala Glu Val Lys Lys Pro Gly Glu
1               5                   10                  15

Ser Val Lys Val Ser Cys Lys Ala Ser Gly Tyr Thr Phe Thr Asn Tyr
                20                  25                  30

Gly Met Asn Trp Val Lys Gln Ala Pro Gly Gln Gly Leu Glu Trp Met
            35                  40                  45

Gly Trp Ile Asn Thr Tyr Thr Gly Glu Pro Thr Tyr Ala Asp Lys Phe
    50                  55                  60

Gln Gly Arg Val Thr Met Thr Thr Asp Thr Ser Thr Ser Thr Ala Tyr
65                  70                  75                  80

Met Glu Ile Arg Asn Leu Gly Gly Asp Asp Thr Ala Val Tyr Tyr Cys
                85                  90                  95

Ala Arg Trp Ser Trp Ser Asp Gly Tyr Tyr Val Tyr Phe Asp Tyr Trp
            100                 105                 110

Gly Gln Gly Thr Ser Val Thr Val Ser Ser Gly Gly Gly Gly Ser Gly
            115                 120                 125

Gly Gly Gly Ser Gly Gly Gly Ser Asp Ile Val Met Thr Gln Ser
    130                 135                 140

Pro Asp Ser Leu Thr Val Ser Leu Gly Glu Arg Thr Thr Ile Asn Cys
145                 150                 155                 160

Lys Ser Ser Gln Ser Val Leu Asp Ser Ser Thr Asn Lys Asn Ser Leu
            165                 170                 175

Ala Trp Tyr Gln Gln Lys Pro Gly Gln Pro Pro Lys Leu Leu Leu Ser
            180                 185                 190

Trp Ala Ser Thr Arg Glu Ser Gly Ile Pro Asp Arg Phe Ser Gly Ser
            195                 200                 205

Gly Ser Gly Thr Asp Phe Thr Leu Thr Ile Asp Ser Pro Gln Pro Glu
    210                 215                 220

Asp Ser Ala Thr Tyr Tyr Cys Gln Gln Ser Ala His Phe Pro Ile Thr
225                 230                 235                 240

Phe Gly Gln Gly Thr Arg Leu Glu Ile Lys
                245                 250

<210> SEQ ID NO 257
<211> LENGTH: 750
<212> TYPE: DNA
<213> ORGANISM: Artificial Sequence
<220> FEATURE:
<223> OTHER INFORMATION: V-set directed CD33 scFv coding sequence

<400> SEQUENCE: 257
caagttcagc tcgtgcagag tggtgcagag gtcaagaagc ctggagagag cgtcaaggtc      60
agctgtaaag catctggcta tacattcact aattacggaa tgaactgggt caagcaggcg     120
ccaggtcagg gacttgaatg gatgggctgg ataaacacat atacaggaga gccaacttat     180
gctgacaaat tccagggtag agtcacgatg acgacggaca catcaacctc caccgcgtat     240
atggaaatca ggaatttggg cggagacgat acagcggttt actactgcgc ccgatggagt     300
tggtctgatg gctattatgt gtatttcgac tactggggtc aggtacaag cgtcacagta      360 agttcaggag gcggaggatc tggcggaggg ggctctggag gaggaggatc tgatattgta     420
atgacccaat cccctgactc attgacagta tccctcggag agcggaccac tataaactgc     480
aaatccagcc agtctgtatt ggactccagc accaacaaaa atagccttgc gtggtatcag     540
caaaagccgg tcaaccacc caagctgctc ttgagttggg cgagtaccag agagagtggg     600
```

-continued

```
atacccgaca ggtttagtgg atctggctct ggcaccgatt ttacgcttac aatcgacagt      660
ccgcaacccg aagactccgc gacgtactac tgtcagcaat ctgcacactt tccaataacc      720
ttcgggcaag ggacacggct ggagatcaaa                                       750
```

```
<210> SEQ ID NO 258
<211> LENGTH: 6
<212> TYPE: PRT
<213> ORGANISM: Artificial Sequence
<220> FEATURE:
<223> OTHER INFORMATION: CDRH2 of 2D3

<400> SEQUENCE: 258

Ser Asp Ser Gly Gly Thr
1               5
```

CHIMERIC ANTIGEN RECEPTORS TARGETING CD33

CROSS REFERENCE TO RELATED APPLICATION

This application is a U.S. National Phase Application based on International Patent Application No. PCT/US2021/025255, filed on Mar. 31, 2021, which claims priority to U.S. Provisional Patent Application No. 63/003,196 filed on Mar. 31, 2020, each of which is incorporated herein by reference in its entirety as if fully set forth herein.

STATEMENT REGARDING FEDERALLY SPONSORED RESEARCH OR DEVELOPMENT

This invention was made with government support under CA234203 and CA245594 awarded by the National Institutes of Health. The government has certain rights in the invention.

REFERENCE TO SEQUENCE LISTING

The Sequence Listing associated with this application is provided in text format in lieu of a paper copy, and is hereby incorporated by reference into the specification. The name of the text file containing the Sequence Listing is 2RS0100_ST25.txt. The text is 203 KB, was created on Sep. 27, 2022, and is being submitted electronically via Patent Center.

FIELD OF THE DISCLOSURE

The current disclosure provides chimeric antigen receptors (CARs) with binding domains derived from a novel suite of human CD33-binding antibodies that can include optimized short and intermediate spacer regions. The current disclosure also provides methods of cell expansion/activation processes utilizing IL-2, IL-7, IL-15, and/or IL-21 that improve cellular proliferation and cell lysis of the CARs as described.

BACKGROUND OF THE DISCLOSURE

According to the World Health Organization, cancer is the second leading cause of death globally, and was responsible for an estimated 9.6 million deaths in 2018. Acute myeloid leukemia (AML) is a type of cancer resulting from a malignancy of clonal, proliferative myeloid blast cells. There are 20,000 new cases of AML per year in the United States and 11,000 deaths from AML each year (Siegel, et al., 2021, CA Cancer J Clin. 71(1): 7-33). Although high complete remission rates can be achieved in younger patients with AML with conventional chemotherapy at rates of 60% to 80% (Döhner, et al., 2017. Blood. 129(4): 424-447), treatment outcomes for older patients, at the age of 65 or older, remains unsatisfactory with as many as 70% of patients dying of their disease within a year of diagnosis (Meyers, et al., Appl Health Econ Health Policy, 11:275-286, 2013). Unfortunately, because of the chemo-refractoriness of leukemic stem cells, relapse after conventional therapy is common (Eppert, et al., 2011. Nat. Med. 17(9): 1086-1093) and current treatment options for relapsed/refractory (R/R) AML are dismal, resulting in less than 30% overall survival at 12 months.

For many years, the chosen treatments for cancer have been surgery, chemotherapy, and/or radiation therapy. In recent years, more targeted therapies have emerged to specifically target cancer cells by identifying and exploiting specific molecular and/or immunophenotypic changes seen primarily in those cells. For example, many cancer cells preferentially express particular markers on their cellular surfaces and these markers have provided targets for antibody-based therapeutics.

CD33 is a member of the sialic acid binding, immunoglobulin-like lectin (SIGLEC) protein family. It is a 67-kDa glycosylated transmembrane protein. CD33 (also known as SIGLEC-3) is a myeloid differentiation antigen that is found at least on some leukemic cells in almost all patients with AML and, perhaps, on AML stem cells in some cases. Based on this broad expression pattern, CD33 has been widely pursued as a therapeutic target in AML. Recent data from several randomized studies have demonstrated that the CD33 antibody-drug conjugate, gemtuzumab ozogamicin (GO), improves survival when added to chemotherapy in defined subsets of patients with newly diagnosed AML. This data has validated CD33 as the first (and so far, only) target for immunotherapy in AML. In parallel to the development of new, more effective CD33-directed therapeutics (e.g. antibody-drug conjugates, radioimmunoconjugates, bispecific antibodies, chimeric antigen receptor [CAR]-modified T cells) to overcome the limitations noted with GO, interest has grown in CD33 as a drug target for other malignant and non-malignant disorders. These efforts include the targeting of CD33 splice variants not recognized by GO as well as the targeting of CD33+ tumor cells in other hematologic malignancies, CD33+ myeloid-derived suppressor cells (MDSCs) in a variety of diseases, and normal CD33+ microglial cells in Alzheimer disease (Walter, Expert Opin Biol Ther. 2020, 20(9):955-958).

The full length CD33 protein ($CD33^{FL}$) is characterized by an amino-terminal, membrane-distant V-set immunoglobulin (Ig)-like domain and a membrane-proximal C2-set Ig-like domain in its extracellular portion (FIG. 2). Shorter isoforms of CD33 exist. A shorter isoform of CD33 includes one variant that lacks exon 2, which encodes the V-set domain ($CD33^{\Delta E2}$). At least at the mRNA level, $CD33^{\Delta E2}$ is broadly expressed in myeloid cells in the bone marrow and peripheral blood of patients with AML. Currently, however, almost all commercially and clinically available CD33 antibodies recognize the immune-dominant V-set Ig-like domain. This means that these antibodies would not recognize shorter forms of CD33 that lack the V-set domain such as $CD33^{\Delta E2}$. This may explain the observation made in one clinical trial in pediatric AML that patients with a single nucleotide polymorphism in the CD33 gene that leads to preferential transcription of $CD33^{\Delta E2}$ and reduced translation of $CD33^{FL}$ did not benefit from the addition of GO (which also binds to the V-set domain of CD33) to intensive chemotherapy.

Beyond antibody-based therapeutics, significant progress has been made in genetically engineering T cells of the immune system to target and kill unwanted cell types, such as cancer cells. Many of these T cells have been genetically engineered to express a chimeric antigen receptor (CAR). CARs are proteins including several distinct subcomponents that allow the genetically modified T cells to recognize and kill cancer cells. The subcomponents include at least an extracellular component and an intracellular component. The extracellular component includes a binding domain that specifically binds a marker that is preferentially present on the surface of unwanted cells (e.g., CD33). When the binding domain binds such markers, the intracellular component signals the T cell to destroy the bound cell. CARs additionally include a transmembrane domain that can link the extracellular component to the intracellular component.

Other subcomponents that can increase a CAR's function can also be used. For example, spacer regions can provide a CAR with additional conformational flexibility, often increasing the binding domain's ability to bind the targeted cell marker. The appropriate length of a spacer region within a particular CAR can depend on numerous factors including how close or far a targeted marker is located from the surface of an unwanted cell's membrane.

When performed ex vivo, genetically modifying T cells can involve numerous cell manipulation steps, and it has been observed that different manipulation conditions can affect the cancer-cell killing properties of the cells. Thus, in designing CARs and genetically modifying cells to express them, numerous considerations must be taken into account, including: targeted cell marker; presence and/or length of spacer; and ex vivo manipulation procedures.

SUMMARY OF THE DISCLOSURE

The current disclosure provides chimeric antigen receptors (CARs) for the treatment of CD33-related disorders. The CARs include binding domains derived from a novel suite of anti-CD33 antibodies. In particular embodiments, the CARs include a binding domain that binds CD33 regardless of which CD33 variant a patient expresses (CD33$^{FL}$ or CD33$^{\Delta E2}$). These CD33 binding domains are referred to as "pan" binders. In particular embodiments, the pan binders bind the membrane-proximal C2-set Ig-like domain of CD33 (see FIG. 2). In particular embodiments, these pan binders are derived from antibodies: 1H10, 1A9, 1E6, 1D2, and 1B9 and can include single chain variable fragments of these antibody binding domains. Additional newly developed CD33 targeting antibodies disclosed herein bind the V-set domain of CD33. These antibodies include 1H8, 2D3, and 2E3 and provide additional CAR-based therapeutic options for patients that express CD33$^{FL}$.

In particular embodiments, the current disclosure provides CARs with a short or intermediate spacer region. In particular embodiments, the short spacer region includes the hinge region of IgG4 (12 amino acids). In particular embodiments, the intermediate spacer region includes the hinge region and the CH3 domain of IgG4 (collectively, 131 amino acids).

In particular embodiments, the current disclosure provides expanding and activating T cells genetically modified to express a CAR disclosed herein utilizing a combination of the cytokines IL-7, IL-15, and IL-21. In particular embodiments, the current disclosure provides expanding and activating T cells genetically modified to express a CAR disclosed herein utilizing a combination of cytokines including IL-2.

The CARs disclosed herein can be used in the treatment of acute myeloid leukemia (AML) and other CD33+ disorders.

BRIEF DESCRIPTION OF THE FIGURES

FIG. 1. Expression of CD33 acute myeloid leukemia (AML) and normal hematopoietic cells indicating that CD33 is over-expressed in AML in comparison to hematopoietic stem cells. Relative expression data collated from bloodspot.eu. HSPC, hematopoietic stem/progenitor cell; MPP, multipotent progenitor. ****$p < 0.0001$, ns not significant by multiple T-test using the two-stage linear step-up procedure of Benjamini, Krieger and Yekutieli, with Q=1%.

FIG. 6. Reducing the binding distance from cell membrane enhances the anti-tumor efficacy of CD33/CD3 BsAbs against human acute lymphoblastic leukemia cells engineered to express CD33 proteins. The human CD33″e9 acute lymphoblastic leukemia (ALL) cell line RS4;11 was engineered to overexpress either $CD33^{FL}$ or $CD33^{\Delta E3\text{-}4}$ via lentiviral gene transfer. Relative expression of the target proteins was flow cytometrically assessed via V-set domain CD33 antibody, P67.6, with representative histograms shown in the bottom panel. Cells were then treated with a V-set domain-targeting CD33/CD3 BsAb at a concentration of 1000 pg/mL and healthy donor T cells enriched from unstimulated peripheral blood mononuclear cells collected from healthy adult volunteers at the effector:target (E:T) cell ratios shown (top panel). Cytotoxicity was quantified flow cytometrically after 2 days as a change in the percentage of dead cells as measured by 4',6-diamidino-2-phenylindole (DAPI) staining. The anti-V-set domain-directed CD33/CD3 BsAb was constructed in the scFv-scFv format using a construct referred to herein as RC1 or A3 that utilizes the sequence as set forth in SEQ ID NO: 254 and described in United States patent application publication US 2016/0317657 A1. *p<0.05; p<0.01; *p<0.001.

FIG. 8. Reducing the binding distance from cell membrane enhances the anti-tumor efficacy of CD33 chimeric antigen receptor (CAR) T cells. The human myeloid leukemia cell line K562 with CRISPR/Cas9-mediated deletion of the endogenous CD33 locus was engineered to overexpress $CD33^{FL}$ or $CD33^{\Delta E3\text{-}4}$ via lentiviral gene transfer. Relative expression of the target proteins was flow cytometrically assessed via V-set domain CD33 antibody, P67.6, with representative histograms. The efficacy of V-set domain-directed CAR T cells was assessed in a chromium[51] release. For CAR T cell generation, healthy donor negative selected human CD8[+] T cells were transduced with an epHIV7 lentivirus encoding the scFv from the $CD33^{V\text{-}set}$/CD3 BsAb described in FIGS. 3, 5A-5C, and 6 linked to an IgG4 CH3 domain spacer, CD28-transmembrane domain, CD3zeta and 4-1BB intracellular signaling domain and truncated CD19 (tCD19) transduction marker. tCD19 CD8[+] CAR-T cells were sorted and expanded in IL-7 and IL-15 (10 ng/mL; Peprotech, Rocky Hill, NJ, USA) each for 14 days with media and cytokine changes every other day. CAR-T cell cytotoxicity was assessed following incubation with chromium[51] labelled targets for 4 hours.

FIG. 9. AML cell lines show different surface expression of CD33. CD33 expression as measured by Quantibrite-PE was measured by staining human AML cell lines with PE-conjugated p67.6 antibody.

FIGS. 10A-10C. Gene maps of chimeric antigen receptor (CAR) inserted into lentiviral vector backbones. VL and VH domain represent variable light (VL) and variable heavy (VH) domain of single chain variable fragments (scFv). Short (10A), intermediate (10B) and long (10C) domains differ by insertion of hinge only (short); hinge and CH3 domain (intermediate); and hinge, CH3 and CH2 domains (long) of human IgG4. All IgG4 domains contain mutated sequences to prevent binding to the human Fc receptor. The mutations include replacing the first six amino acids of the CH2 domain in IgG4 (APEFLG, SEQ ID NO: 52) with the first five amino acids of IgG2 (APPVA, SEQ ID NO: 53). TM is a CD28 transmembrane domain. tCD19 represents truncated CD19 lacking intracellular signaling. CD3ζ and 4-1BB are internal signaling domains of these proteins; T2A represents a cleaving peptide.

FIGS. 12A, 12B. (12A) A kinetic profile was established from purified anti-CD33 antibodies by use of surface plasmon resonance technology (SPR) from the Carterra instrument. SPR is a great way to estimate the kinetic rate constants of binding interactions, of which can fit to a 1:1 Langmuir binding model to determine the on-rate (ka) and off-rate (kd). Both of these rate parameters allow for the calculation of the dissociation rate constant (kD), referred to as binding affinity. The antibody clones were captured as an array on a protein A/G lawn, which was immobilized to a HC30M chip. The first kinetic experiment used a full-length CD33 (CD33$^{FL}$) antigen which started at a concentration of 2 μM preceding a 4-fold titration to 2 nM. Following 10 HBSTE buffer blanks, 6 injections from low to high concentrations were subsequently flowed over the array to assess kinetics of each clone printed to the array, 1-min baseline, 5-min association, 10-min dissociation. The chip was then regenerated with 0.85% phosphoric acid pH 1.7 for a fresh reprint of the same array of clones to the protein A/G lawn, in case any lingering antigen stayed bound to the array preventing an interaction with the 2$^{nd}$ antigen of interest, of which CD33$^{ΔE2}$ flowed over the array of antibodies. Carterra kinetic software was used to process the data to fit the raw data to kinetic curves for each concentration of antigen injected over the array. (12B) SPR assessment of purified ECDs from CD33$^{FL}$ or CD33$^{ΔE2}$ binding to captured 1H10 and 2D3. Experiments were performed at 25° C. on a Biacore T100 instrument with a Series S CM4 chip. Protein A/G at 60 μg/mL in 10 mM sodium acetate, pH 4.0 was immobilized on 2 flow cells (1000 RUs) using standard amine-coupling chemistry. Capture kinetic experiments were run in 10 mM HEPES, pH 7.4, 150 mM NaCl, 3 mM EDTA, 0.05% surfactant P20 and 0.1 mg/mL IgG free bovine serum albumin buffer. Anti-human CD33 antibodies at 0.5 μg/mL were injected at 10 L/min over the second flow cell of immobilized Protein A/G for 30-40 s to capture 40 to 58 RUs of antibody for the CD33$^{FL}$ binding experiments, or 45-80 s to capture 75 to 95 RUs of antibody for the CD33$^{ΔE2}$ binding experiments. Purified ectodomains for CD33$^{FL}$ and CD33$^{ΔE2}$ were run as concentration series at 50 μL/min over both the captured antibody and Protein A/G alone (reference) surfaces. CD33$^{FL}$ series started at a high concentration of 160 nM for 2D3 and 1H10; CD33$^{ΔE2}$ series started at 40 nM for 1H10 and 300 nM for 2D3. CD33 was injected for 7 minutes and allowed to dissociate for 20 or 30 minutes for most pairs. Serial 2-fold dilutions of ectodomain concentrations were run in duplicate, randomized, and included a buffer blank every 4$^{th}$ injection. The CM4 chip was regenerated with 2 30s injections of 0.85% H$_3$PO$_4$ at 50 μL/min and antibody recaptured prior to each CD33 injection. Data was double referenced and analyzed in BiaEval 2.0.4 software with a 1:1 binding model using local Rmax.

Figure 16A:
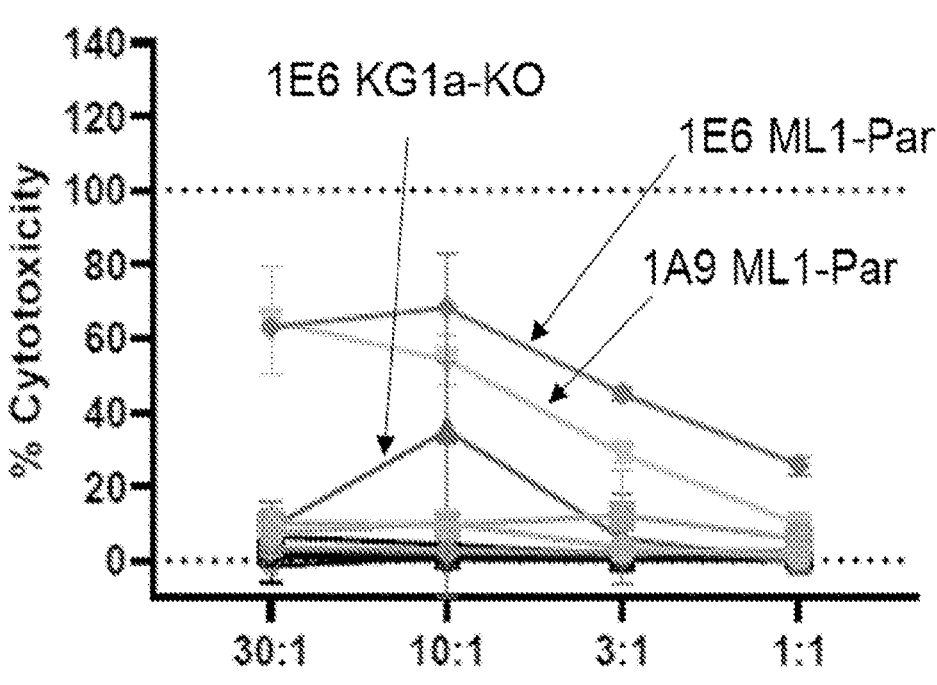
Figure 16B:
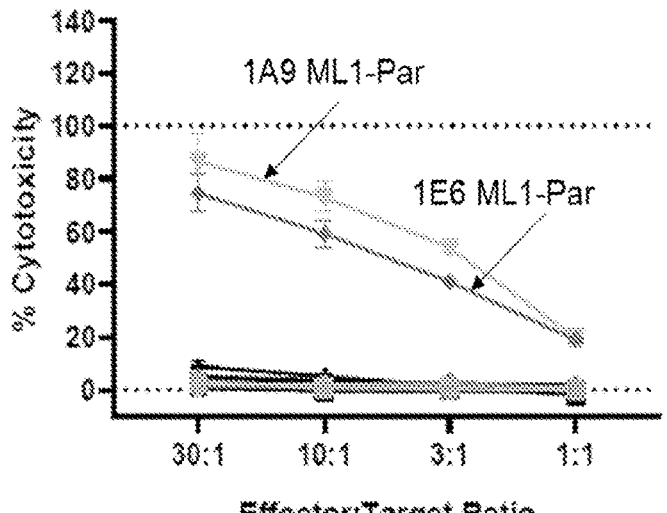
Figure 16C:
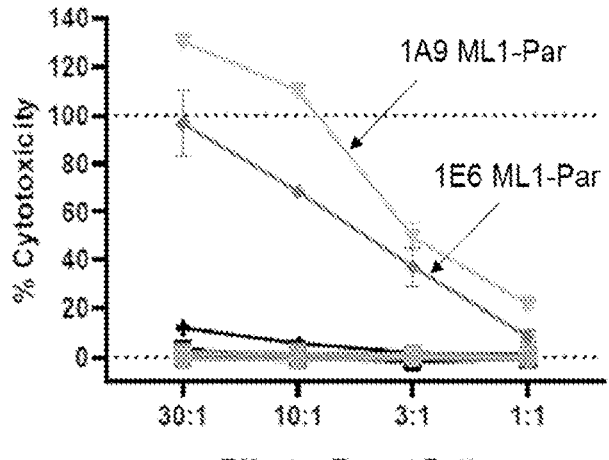
Figure 17A:
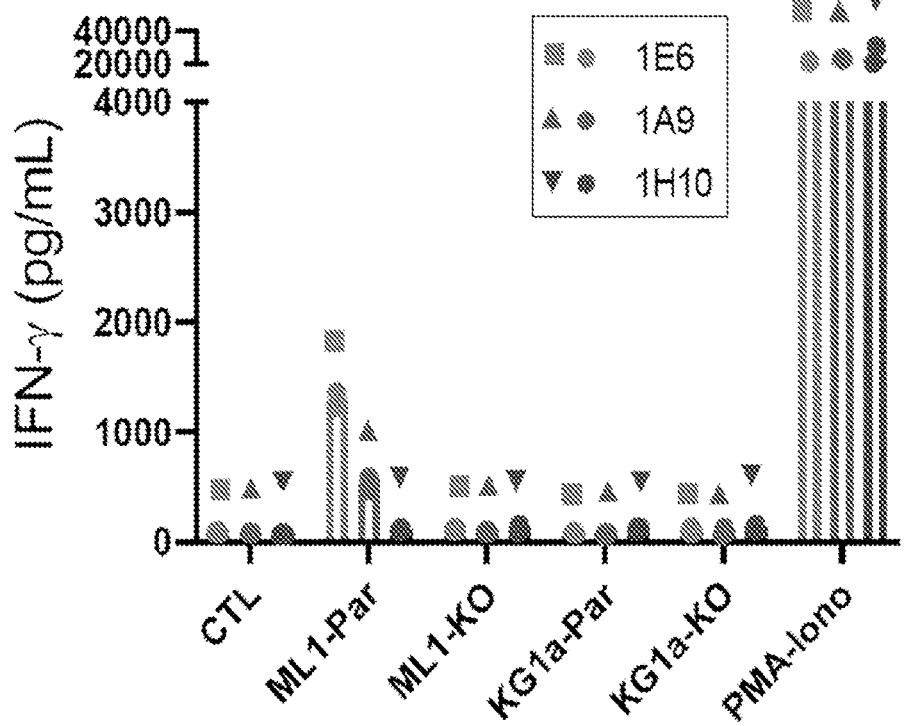
Figure 17B:
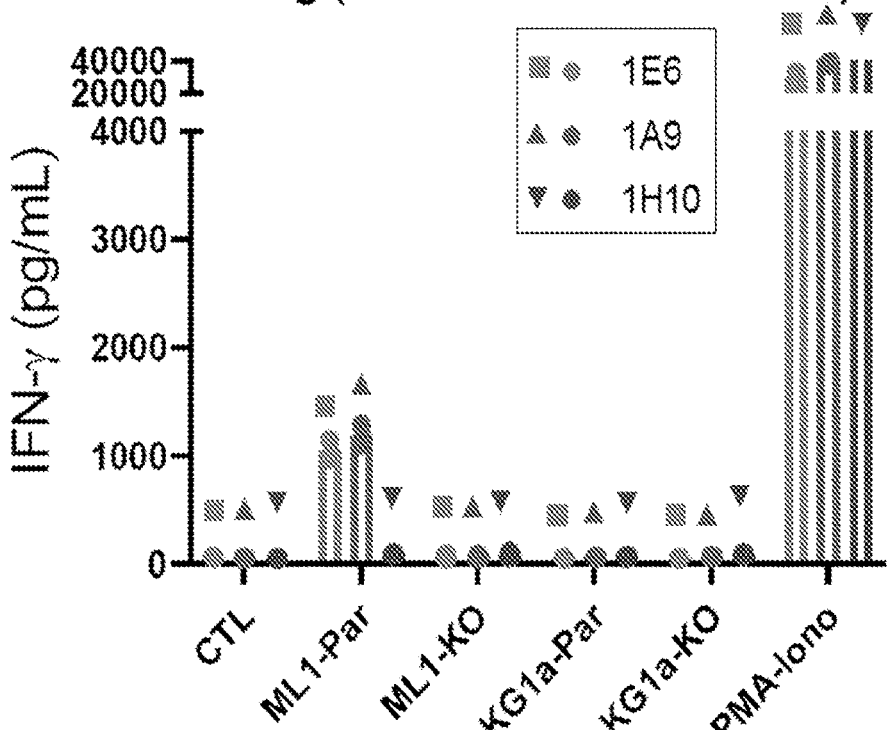
Figure 17C:
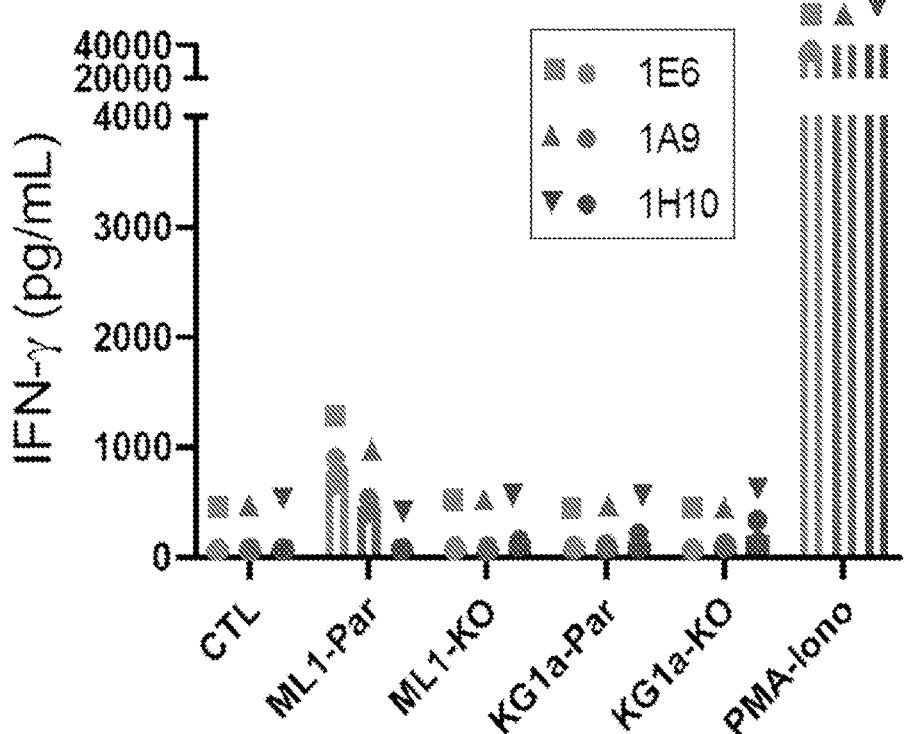
Figure 17D:
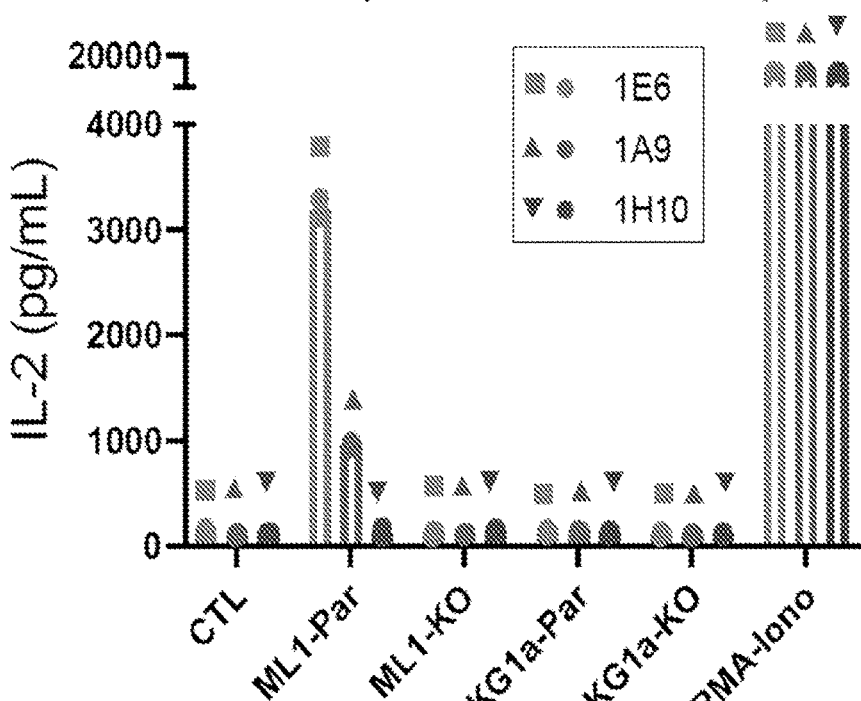
Figure 17E:
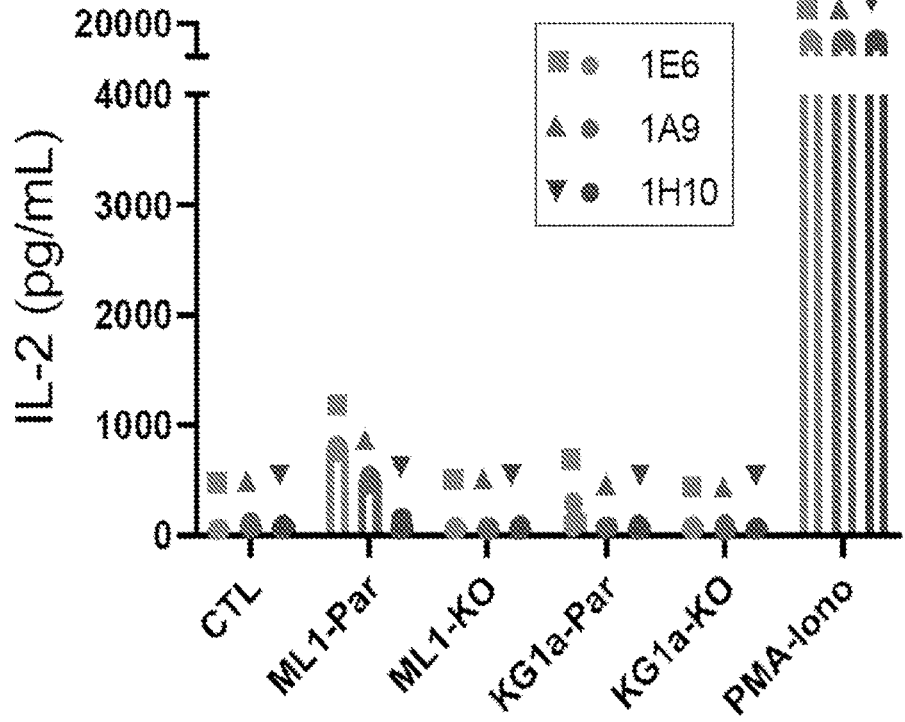
Figure 17F:
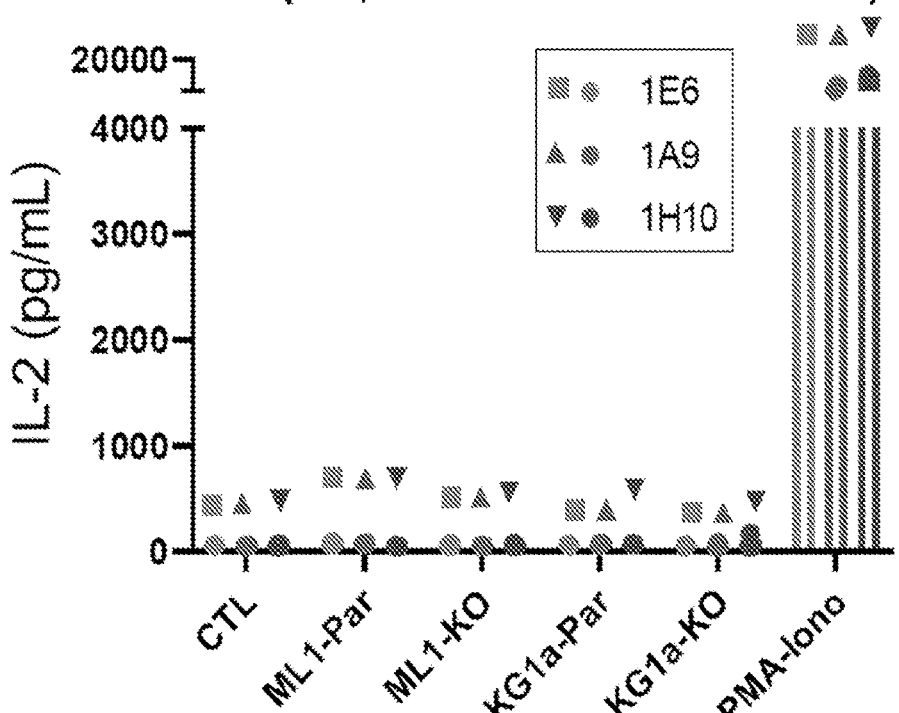
Figure 17G:
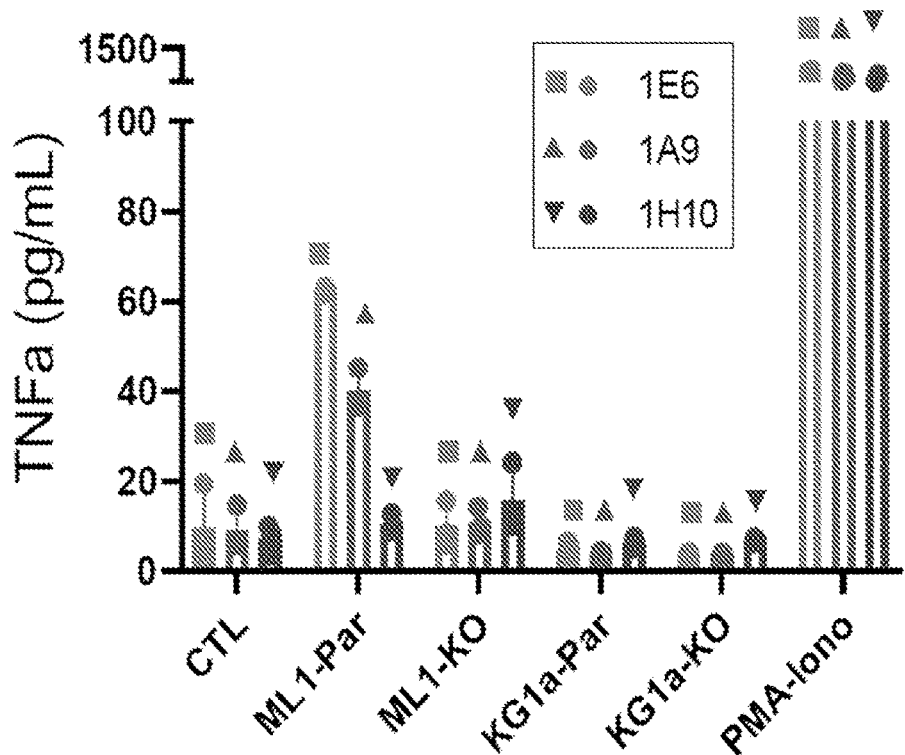
Figure 17H:
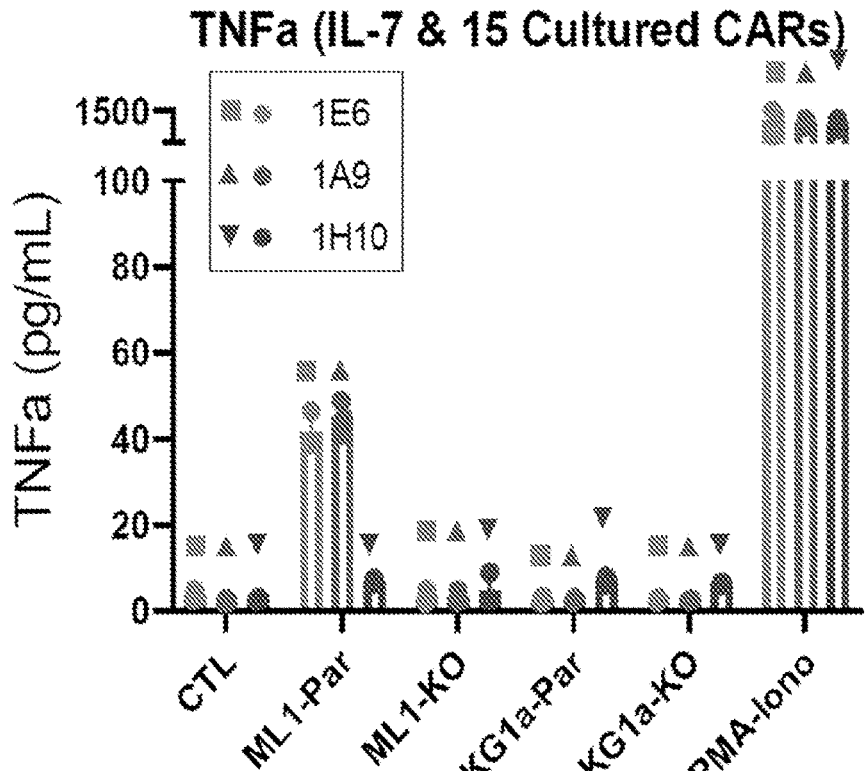
Figure 17I:
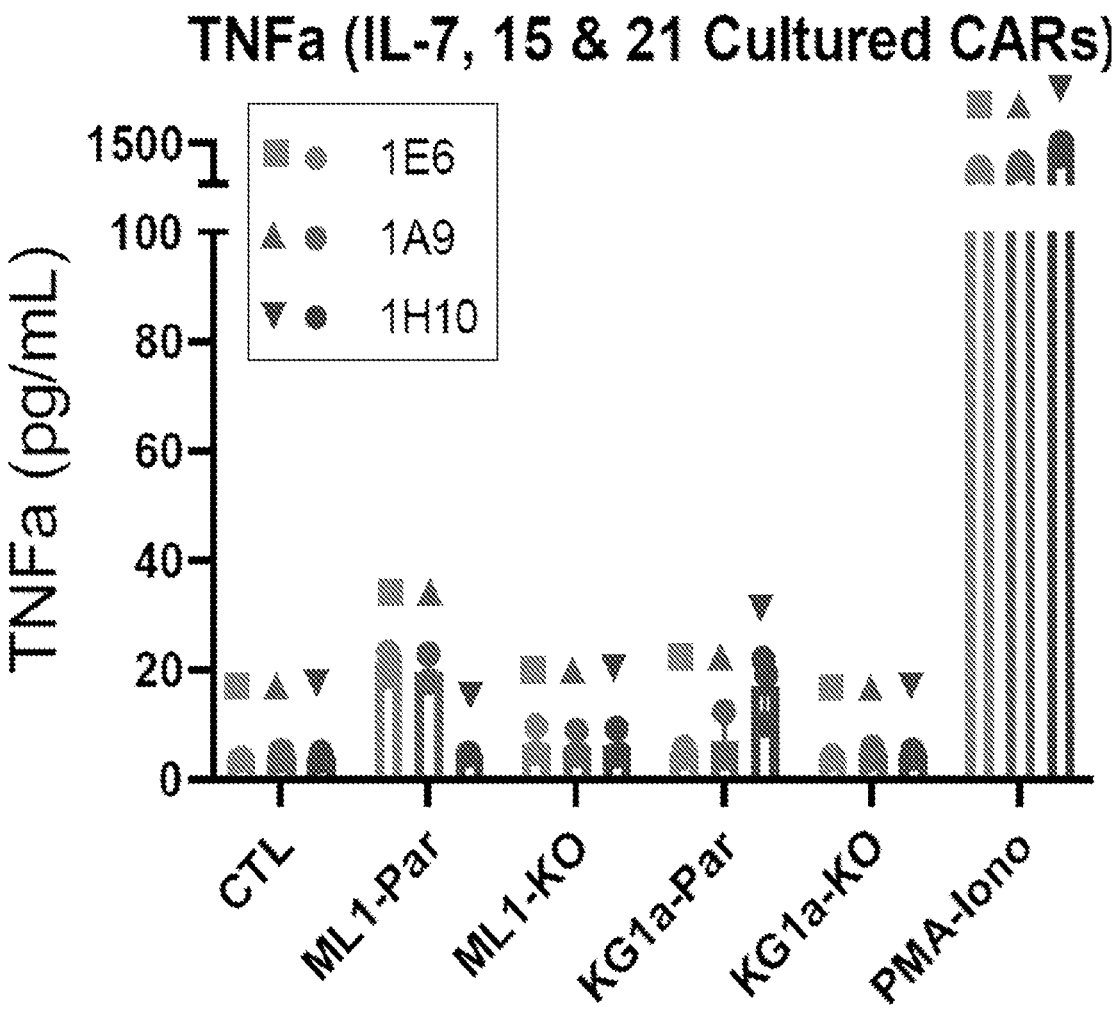
Figure 18A:
Figure 18B:
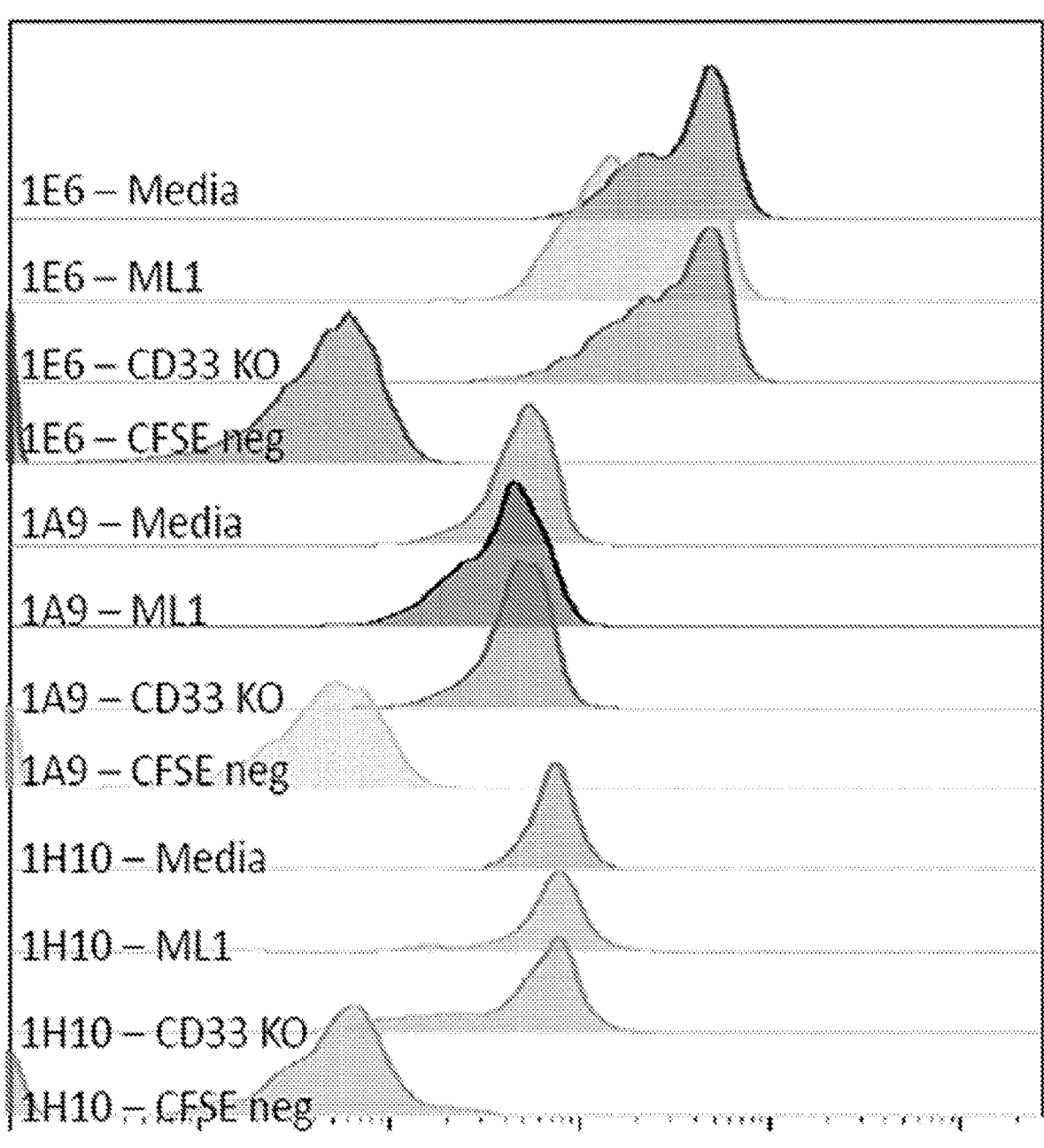
Figure 18C:
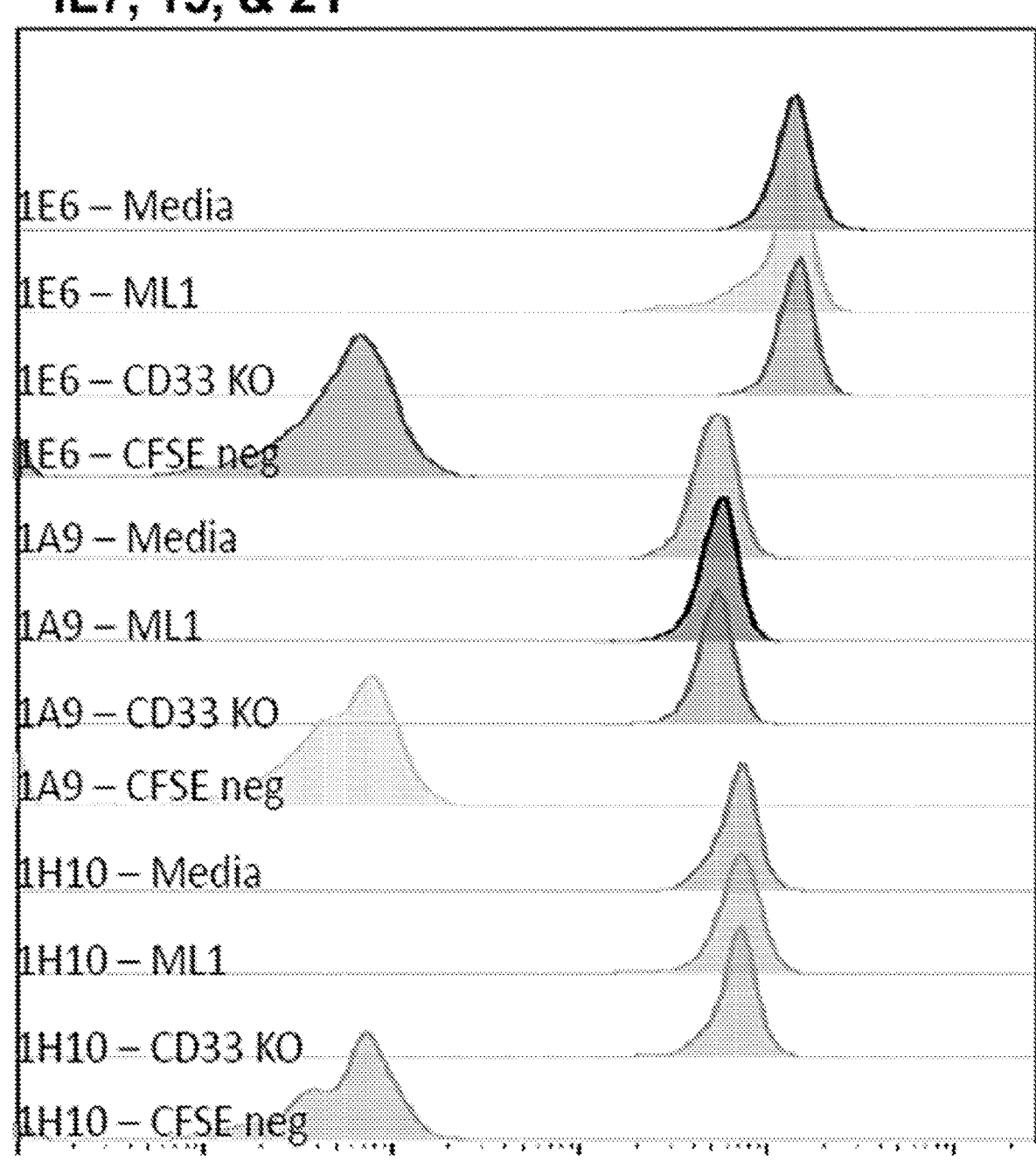
Figures 18D, 18E:
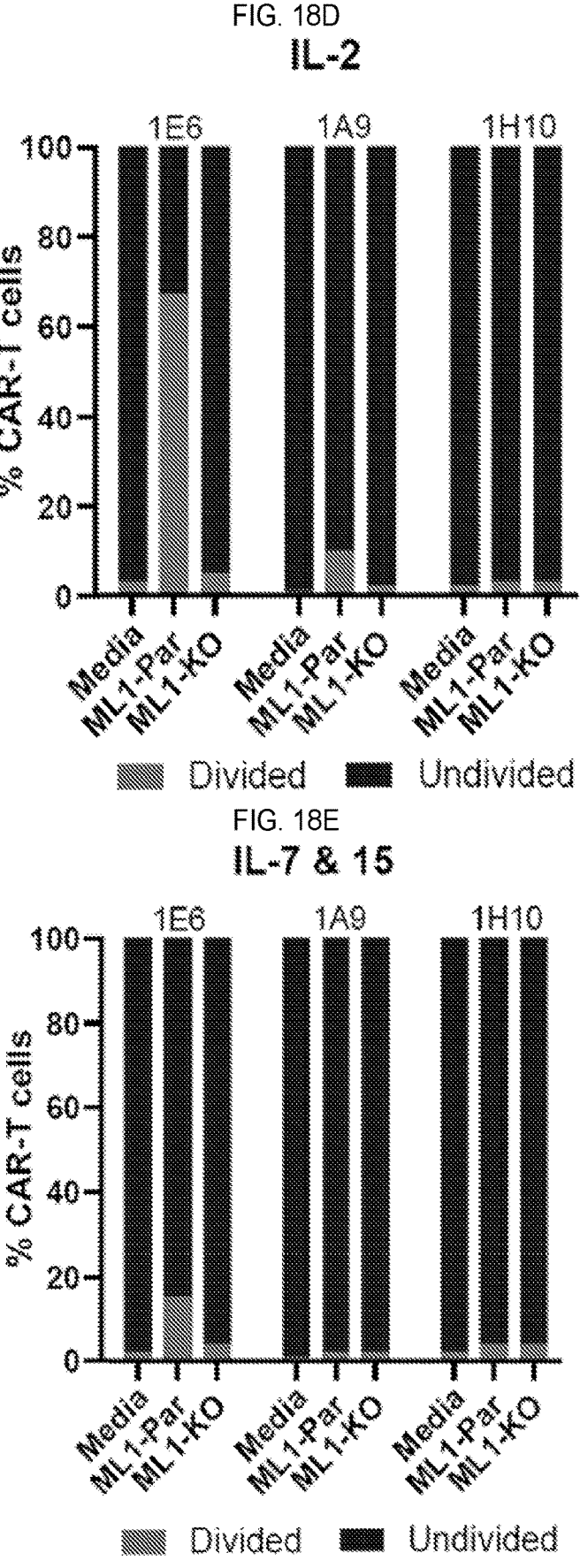

FIGS. 16A-16C. 1E6, 1A9 and 1H10 CD33-directed CAR-T cells with an intermediate spacer show antigen specific lysis in vitro against multiple AML cell lines. Chromium$^{51}$ (Cr$^{51}$)-labeled KG1a and ML-1 cells either expressing endogenous (Par) or deficient for CD33 by CRISPR-Cas9 genetic deletion (KO) were exposed for four hours to (16A) CD33-directed CD8$^+$ CAR-T cells expanded in IL-2 (50 ng/mL), (16B) IL-7 & IL-15 (10 ng/mL each), or (16C) IL-7, IL-15 & IL-21 (10 ng/mL each) at various effector:target ratios. Supernatant was harvested and analyzed for Cr$^{51}$ concentration by scintillation.

FIGS. 17A-17I. CD33-directed CD8$^+$ CAR-T cells expressing 1E6, 1A9 or 1H10 scFvs were expanded in IL-2 (50 ng/mL, 17A, 17D, and 17G), IL-7 & 15 (10 ng/mL each, 17B, 17E, and 17H), or IL-7, IL-15 & IL-21 (10 ng/mL each, 17C, 17F, and 17I) and then exposed: to irradiated AML cell lines (ML-1 or KG1a) replete with endogenous CD33 expression (Par); cell lines deficient in CD33 by CRISPR-Cas9 genetic deletion (KO); media; or phorbol-12 myristate and ionomycin (PMA-Iono). Cell supernatant was then harvested 24 hours later and analyzed for levels of interferon-gamma (IFNγ, 17A-17C), interleukin-2 (IL-2, 17D-17F) or tumor necrosis factor alpha (TNFa, 17G-17I) by enzyme-linked immunosorbent assay (ELISA).

Figure 18F:
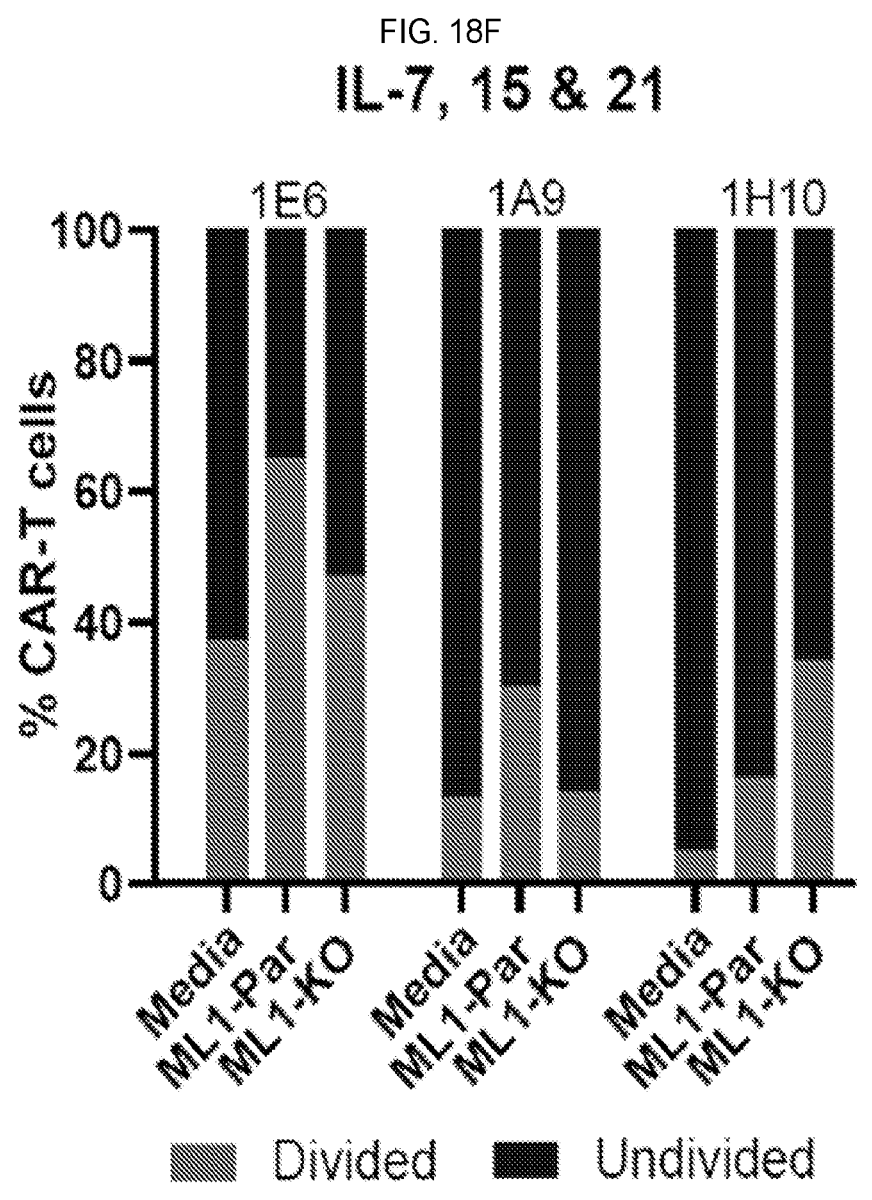

FIGS. 18A-18F. CD33-directed CAR-T cells expanded in IL-7, IL-15 & IL-21 show superior proliferation in vitro. CD8$^+$ CAR-T cells expressing 1E6, 1A9 or 1H10 directed scFvs and expanded in either IL-2 (50 ng/ml, 18A and 18D), IL-7 and 15 (10 ng/ml, 18B and 18E), or IL-7, 15 & 21 (10 ng/ml, 18C and 18F) were labeled with CFSE and exposed to ML-1 cells expressing endogenous CD33 (Par) or deficient for CD33 by CRISPR-Cas9 genetic deletion (KO) or media alone for five days. Cells were then analyzed for CFSE level by flow cytometry. Summary of percent divided cells (18D-18F) with undivided peak isolated by proliferation modeling in FlowJo software.

FIG. 19. Sequences supporting the disclosure: 1H10 VH-VL scFv coding sequence (SEQ ID NO: 2); 1A9 VH-VL scFv coding sequence (SEQ ID NO: 3); 1E6 VH-VL scFv coding sequence (SEQ ID NO: 4); 1D2 VH-VL scFv coding sequence (SEQ ID NO: 5); 1B9 VH-VL scFv coding sequence (SEQ ID NO: 6); 1H8 VH-VL scFv coding sequence (SEQ ID NO: 7); 2D3 VH-VL scFv coding sequence (SEQ ID NO: 8); 2E3 VH-VL scFv coding sequence (SEQ ID NO: 9); Signal peptide coding sequence (SEQ ID NO: 188); G4Sx3 linker coding sequence (SEQ ID NO: 189); IgK signal peptide (SEQ ID NO: 158); 1H10 scFv VH-VL orientation (SEQ ID NO: 190); 1H10 scFv VL-VH orientation (SEQ ID NO: 191); 1A9 scFv VH-VL orientation (SEQ ID NO: 192); 1A9 scFv VL-VH orientation (SEQ ID NO: 193); 1E6 scFv VH-VL orientation (SEQ ID NO: 194); 1E6 scFv VL-VH orientation (SEQ ID NO: 195); 2D3 scFv VH-VL orientation (SEQ ID NO: 196); 2D3 scFv VL-VH orientation (SEQ ID NO: 197); human CD33 full length DNA coding (SEQ ID NO: 198); human CD33 full length protein (SEQ ID NO: 199); IgG4 hinge coding sequence-A (SEQ D NO: 10); IgG4 hinge coding sequence-B (SEQ ID NO: 11); IgG4-int(DS) coding sequence (SEQ ID NO: 12): IgG4-long coding sequence (SEQ ID NO: 13); CD3ζ coding sequence (SEQ ID NO: 14); CD3ζ protein-A (SEQ ID NO: 15); CD3ζ protein-B (SEQ ID NO: 16); 4-1BB signaling coding sequence-A (SEQ ID NO: 17); 4-1BB signaling coding sequence-B (SEQ ID NO: 18); 4-1BB protein-A (SEQ ID NO: 19); 4-1BB protein-B (SEQ ID NO: 20); CD28TM coding sequence-A (SEQ ID NO: 21); CD28TM coding sequence-B (SEQ ID NO: 22); CD28TM coding sequence-C(SEQ ID NO: 23): CD28TM protein-A (SEQ ID NO: 24): CD28TM protein-B (SEQ ID NO: 25): tCD19 coding sequence (SEQ ID NO: 26); T2A coding sequence (SEQ ID NO: 27); Thoseaasigna Virus 2A (T2A) Peptide (SEQ ID NO: 28); Porcine Teschovirus-1 2A (P2A) Peptide (SEQ ID NO: 29); Equine Rhinitis A Virus (ERAV) 2A (E2A) Peptide (SEQ ID NO: 30); Foot-And-Mouth Disease Virus 2A (F2A) Peptide (SEQ ID NO: 31); EF1 promoter-A (SEQ ID NO: 32): EF1 promoter-B (SEQ ID NO: 33); Psi (SEQ ID NO: 34); RRE (SEQ ID NO: 35); Flap (SEQ ID NO: 36); GM-CSFR encoding sequence (SEQ ID NO: 37); WPRE (SEQ ID NO: 38); delU3 (SEQ ID NO: 39); R (SEQ ID NO: 40); U5 (SEQ ID NO: 41); AmpR (SEQ ID NO: 42); CoE1 origin (SEQ ID NO: 43); SV40 (SEQ ID NO: 44). CMV (SEQ ID NO: 45); Glycosylation site: 1H10-intDS-41bb-3z-T-CD19t Top Strand (SEQ ID NO: 46); 1H10-sh-41bb-3z-T-CD19t Top Strand (SEQ ID NO: 47); 1A9-intDS-41bb-3z-T-CD19t Top Strand (SEQ ID NO: 48); 1A9-sh-41bb-3z-T-CD19t Top Strand (SEQ D NO: 49); 1E6-intDS-41bb-3z-T-CD19t Top Strand (SEQ ID NO: 50): 1E6-sh-41bb-3z-T-CD19t Top Strand (SEQ ID NO: 51), 1H10-LvHv-intDS-41bb-3z-T-CD19t Top Strand (SEQ ID NO: 200); 1A9-LvHv-intDS-41bb-3z-T-CD19t Top Strand (SEQ ID NO: 201); 1E6-LvHv-intDS-41bb-3z-T-CD19t Top Strand (SEQ ID NO: 202); 2D3-LvHv-intDS-41bb-3z-T-CD19t Top Strand (SEQ ID NO: 203); CD33:CD22 4D protein (SEQ ID NO: 204); CD33:CD22 4D nucleotides (SEQ ID NO: 205); CD33:CD22 2D protein (SEQ ID NO: 206); CD33:CD22 2D nucleotides (SEQ ID NO: 207); CD33 V-set construct (exon 3 and 4 deleted) protein (SEQ ID NO: 208); CD33 V-set construct (exon 3 and 4 deleted) nucleotides (SEQ ID NO: 209); CD33 signal peptide (SEQ ID NO: 210); CD33 signal peptide coding sequence (SEQ ID NO: 211); 6-histidine tag coding sequence (SEQ ID NO: 212); 3× glycine linker; 3× glycine linker coding sequence; CD33 ECD (SEQ ID NO: 213); CD33 ECD coding sequence (SEQ ID NO: 214); CD33 ECD lacking CD33 amino acids 140-232 (SEQ ID NO: 215); CD33 ECD lacking CD33 amino acids 140-232 coding sequence (SEQ ID NO: 216); CD33 transmembrane domain: (SEQ ID NO: 217); CD33 transmembrane domain coding sequence (SEQ ID NO: 218); CD33 intracellular domain: (SEQ ID NO: 219); CD33 intracellular domain coding sequence (SEQ ID NO: 220); Portion of CD22 ECD that contains CD22 domains defined as Ig-like C2-type 3, Ig-like C2-type 4, Ig-like C2-type 5, Ig-like C2-type 6 (SEQ ID NO: 221); Portion of CD22 ECD that contains CD22 domains defined as Ig-like C2-type 3, Ig-like C2-type 4, Ig-like C2-type 5, Ig-like C2-type 6 coding sequence (SEQ ID NO: 222); Portion of CD22 ECD that contains CD22 domains defined as Ig-like C2-type 5, Ig-like C2-type 6 (SEQ ID NO: 223); Portion of CD22 ECD that contains CD22 domains defined as Ig-like C2-type 5, Ig-like C2-type 6 coding sequence (SEQ ID NO: 224); 1H10, 1A9, 1E6, and/or 11B9 light chain signal peptide (SEQ ID NO: 225); 1D2 light chain signal peptide (SEQ ID NO: 226); 1H8 light chain signal peptide (SEQ ID NO: 227); 2D3 light chain signal peptide (SEQ ID NO: 228); 1H10 heavy chain signal peptide (SEQ ID NO: 229); 1A9 heavy chain signal peptide (SEQ ID NO: 230); 1E6 and/or 2E3 heavy chain signal peptide (SEQ ID NO: 231); 1D2 heavy chain signal peptide (SEQ ID NO: 232); 1B9 heavy chain signal peptide (SEQ ID NO: 233); 1H8 heavy chain signal peptide (SEQ ID NO: 234); 2D3 heavy chain signal peptide (SEQ ID NO: 235); My96_int_41BB_3z_TCD19 coding sequence (SEQ ID NO: 236); My96 coding sequence (SEQ ID NO: 237); V-set directed CD33/CD3 BsAb (RC1, SEQ ID NO: 254); V-set directed CD33/CD3 BsAb without leader sequence or His tag (SEQ ID NO: 255); and V-set directed CD33 scFv protein sequence (SEQ ID NO: 256) and coding sequence (SEQ ID NO: 257).

DETAILED DESCRIPTION

According to the World Health Organization, cancer is the second leading cause of death globally, and was responsible for an estimated 9.6 million deaths in 2018. Acute myeloid leukemia (AML) is a type of cancer resulting from a malignancy of clonal, proliferative myeloid blast cells. AML is also known as acute myelocytic leukemia, acute myelogenous leukemia, acute granulocytic leukemia, and acute nonlymphocytic leukemia.

There are 20,000 new cases of AML per year in the United States (Kouchkovsky and Abdul-Hay, Blood Cancer J. 6(7): e441, 2016) and 11,000 deaths from AML each year (American Cancer Society, August 2018). Although high complete remission rates can be achieved in younger patients with AML with conventional chemotherapy at rates of 60% to 80% (Döhner, et al., 2017. Blood. 129(4): 424-447), treatment outcomes for older patients, at the age of 65 or older, remains unsatisfactory with as many as 70% of patients dying of their disease within a year of diagnosis (Meyers, et al., Appl Health Econ Health Policy, 11:275-286, 2013). Unfortunately, because of the chemo-refractoriness of leukemic stem cells, relapse after conventional therapy is common (Eppert, et al., 2011. Nat. Med. 17(9): 1086-1093) and current treatment options for relapsed/refractory (R/R) AML are dismal, resulting in less than 30% overall survival at 12 months.

For many years, the chosen treatments for cancer have been surgery, chemotherapy, and/or radiation therapy. In recent years, more targeted therapies have emerged to specifically target cancer cells by identifying and exploiting specific molecular changes seen primarily in those cells. For example, many cancer cells preferentially express particular markers on their cellular surfaces and these markers have provided targets for antibody-based therapeutics.

One key to successful targeted therapy is in the choice of the target cancer cell marker. An ideal target marker is immunogenic, plays a critical role in proliferation and differentiation, is expressed only on the surface of all malignant cells and malignant stem cells, and a large portion of patients should test positive for the marker (Cheever, et al., 2009. Clin. Cancer Res. 15(17): 5323-8337).

CD33$^{FL}$ is primarily displayed on maturing and mature cells of the myeloid lineage, with initial expression on multipotent myeloid precursors. It is not found outside the hematopoietic system and is not thought to be expressed on pluripotent hematopoietic stem cells. Consistent with its role as a myeloid differentiation antigen, CD33$^{FL}$ is widely expressed on malignant cells in patients with myeloid neoplasms; e.g., in AML, it is found on at least a subset of the AML blast cells in almost all cases and possibly leukemic stem cells in some. Because of this expression pattern, CD33$^{FL}$ has been widely exploited as an antigen for targeted therapy of AML. (Walter et al., Blood 119(26):6198-6208, 2012; Cowan et al., Front. Biosci. (Landmark Ed) 18:1311-1334, 2013; Laszlo et al., Blood Ref. 28(4):143-153, 2014; and Walter, Expert Opin Investig Drugs 27(4):339-348, 2018) While unconjugated monoclonal CD33 antibodies have proved ineffective in the clinic, several recent randomized trials with the CD33 antibody-drug conjugate (ADC) gemtuzumab ozogamicin (GO) have demonstrated improved survival in subsets of patients with AML, establishing the value of antibodies in this disease and validating CD33$^{FL}$ as the first, and so far only, therapeutic target for immunotherapy of AML (Laszlo et al., Blood Rev. 28(4): 143-153, 2014; Godwin et al., Leukemia 31(9) 31(9):1855-1868, 2017). This data has validated CD33 as the first (and so far, only) target for immunotherapy in AML. In parallel to the development of new, more effective CD33-directed therapeutics (e.g. antibody-drug conjugates, radioimmuno-conjugates, bispecific antibodies, chimeric antigen receptor [CAR]-modified T cells) to overcome the limitations noted with GO, interest has grown in CD33 as a drug target for other malignant and non-malignant disorders. These efforts include the targeting of CD33 splice variants not recognized by GO as well as the targeting of CD33+ tumor cells in other hematologic malignancies, CD33+ myeloid-derived suppressor cells (MDSCs) in a variety of diseases, and normal CD33+ microglial cells in Alzheimer disease (Walter, Expert Opin Biol Ther. 2020, 20(9):955-958).

Figure 2:
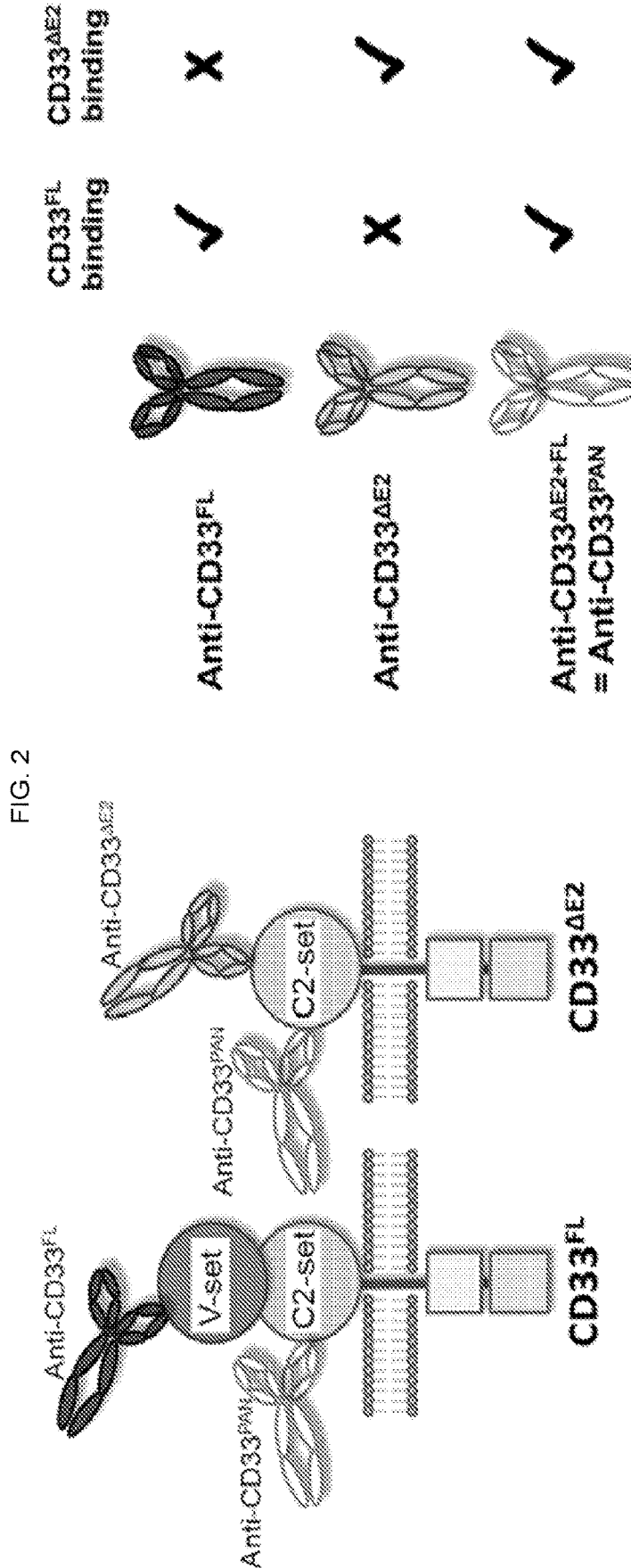
FIG. 2. Diagram of full-length CD33 (CD33$^{FL}$) and CD33 with deletion of exon 2, resulting deletion of V-set domain (CD33$^{\Delta E2}$). Depicted are an antibody that binds CD33$^{FL}$ only (anti-CD33$^{FL}$), CD33$^{\Delta E2}$ only (anti_CD33$^{\Delta E2}$), or CD33$^{FL}$ and CD33$^{\Delta E2}$ (anti_CD33$^{FL+\Delta E2}$ or anti_CD33$^{PAN}$).
Figure 3:
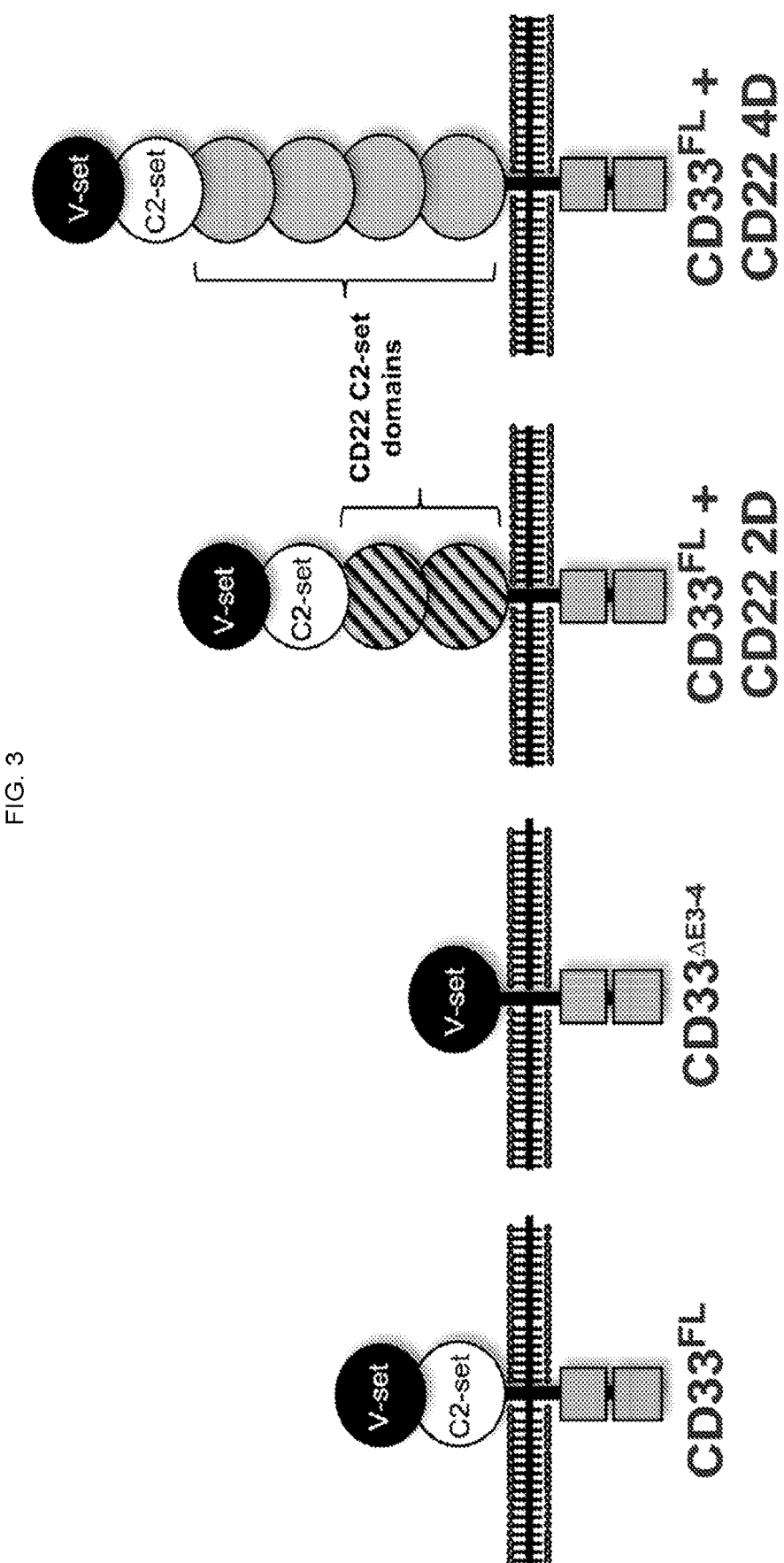
FIG. 3. Schematic of CD33$^{FL}$ and artificial CD33 molecules with deletion of exons 3 and 4, resulting in membrane proximal relocation of the V-set domain (CD33$^{\Delta E3-4}$), or insertion of either 2 C2-set domains of CD22 ("CD33$^{FL}$+CD22 2D") or 4 C2-set domains of CD22 ("CD33$^{FL}$+CD22 4D"). CD33$^{\Delta E3-4}$ was engineered using site-directed mutagenesis to splice out CD33 amino acids (aa) 140-232 of the human CD33$^{FL}$ extracellular domain (ECD). CD33$^{FL}$+CD22 4D was generated using the endogenous CD33 signal peptide (aa 1-17), a 6-histidine tag, 3× glycine linker, the human CD33 ECD (aa 18-259), a portion of the human CD22 ECD including C2-type domains 3-6 (aa 331-683), the CD33 transmembrane domain, and the CD33 intracellular domain (aa 260-364). CD22 aa 331-504 (C2-type domains 3 and 4) were removed from CD33$^{FL}$+CD22 24 to generate CD33$^{FL}$+CD22 2D.
Figure 4:
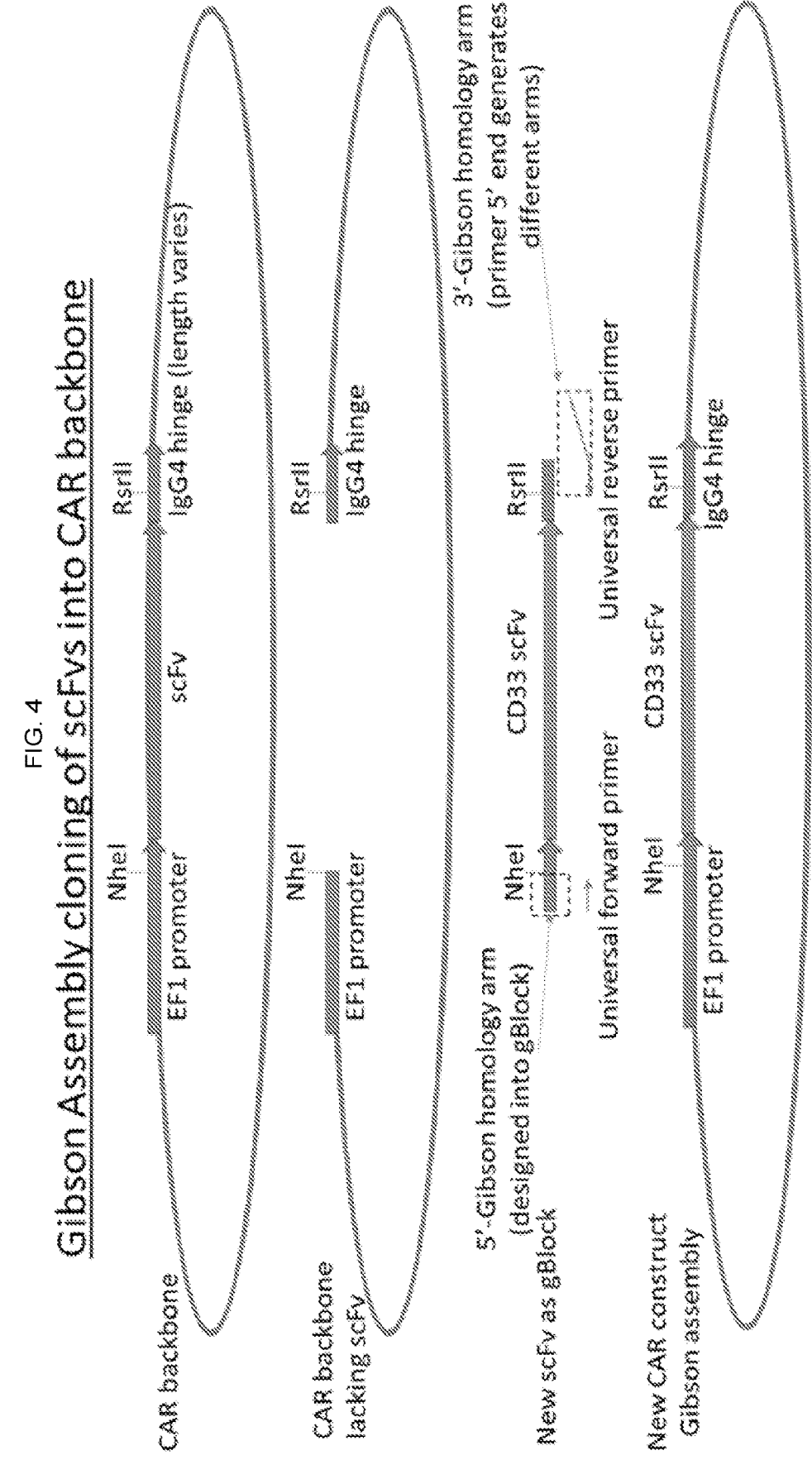
FIG. 4. Cloning strategy for generation of CD33 CAR expression constructs. (i) Supernatants from antibody-secreting mouse hybridoma cells were screened for pan-CD33 binding activity, then screened for lack of binding to CD33 null cell lines, and best individual hybridomas selected, antibody isotyping performed, RNA extracted and used for rapid amplification of cDNA ends (RACE) amplification (Takara) and subsequent isotype-specific polymerase chain reaction (PCR)-based amplification. (ii) Cloning of antibody variable region sequences was performed utilizing either pRACE (Takara) or TOPO (Invitrogen) standard cloning vectors. (iii) Plasmid DNA was purified from individual bacterial colonies, and Sanger DNA sequencing was performed to obtain at least 3 individual identical cDNA sequences corresponding to each antibody variable region for both the antibody heavy and light chains. (iv) Antibody variable region cDNA sequences were translated into amino acid sequences using the ExPASy.org translate tool. (v) Amino acid sequences for each individual antibody variable region were submitted to Integrated DNA Technologies (IDT, Coralville, IA) website for human codon optimization. (vi) Codon optimized single chain variable regions (scFvs) nucleic acid sequences were then combined with nucleic acid sequences contained within the CAR backbone lentiviral backbone-41 BB-3z-T-CD19t, specifically, sequences within the EF1 promoter that flank the 5' end of the granulocyte-macrophage colony-stimulating factor receptor (GM-CSFR) signal peptide, including the GM-CSFR signal peptide were added 5' to the antibody HC variable region, followed by a flexible Gly-Ser linker sequence, and then the antibody LC variable region, and then linker sequence from the CAR backbone lentiviral backbone-41 BB-3z-T-CD19t. (vii) Complete nucleotide sequences were then submitted to IDT for synthesis of gBlocks. (viii) gBlocks were cloned in TOPO, and nucleic acid sequences confirmed by Sanger DNA sequencing. (ix) All gBlocks were generated to include universal priming sequences, CAR_universal_forward primer and CAR_universal_reverse primer. (x) Next, PCR amplification was performed using an appropriate TOPO vector as template, proofreading DNA polymerase, and using CAR_universal_forward primer and a reverse primer selected from 2 options, CAR_universal_rev_sh or CAR_universal_rev_int. In these primers, rev indicates reverse, sh indicates the short linker, and int indicates the intermediate length linker within the CAR construct. (xi) Recipient plasmid (lentiviral backbone-41BB-3z-T-CD19t with sh, or int linker) was digested with RsrII/NheI and cut plasmid and PCR products were gel purified. (xii) Gibson assembly (NEB) was performed using RsrII/NheI digested recipient plasmid (lentiviral backbone-41BB-3z-T-CD19t with sh, or int linker) and appropriate PCR amplicon. (xiii) Sanger DNA sequencing verification was used to confirm the scFv and linker contained in each plasmid. (vii) Maxi prep and lentiviral packaging followed.
Figure 5A:
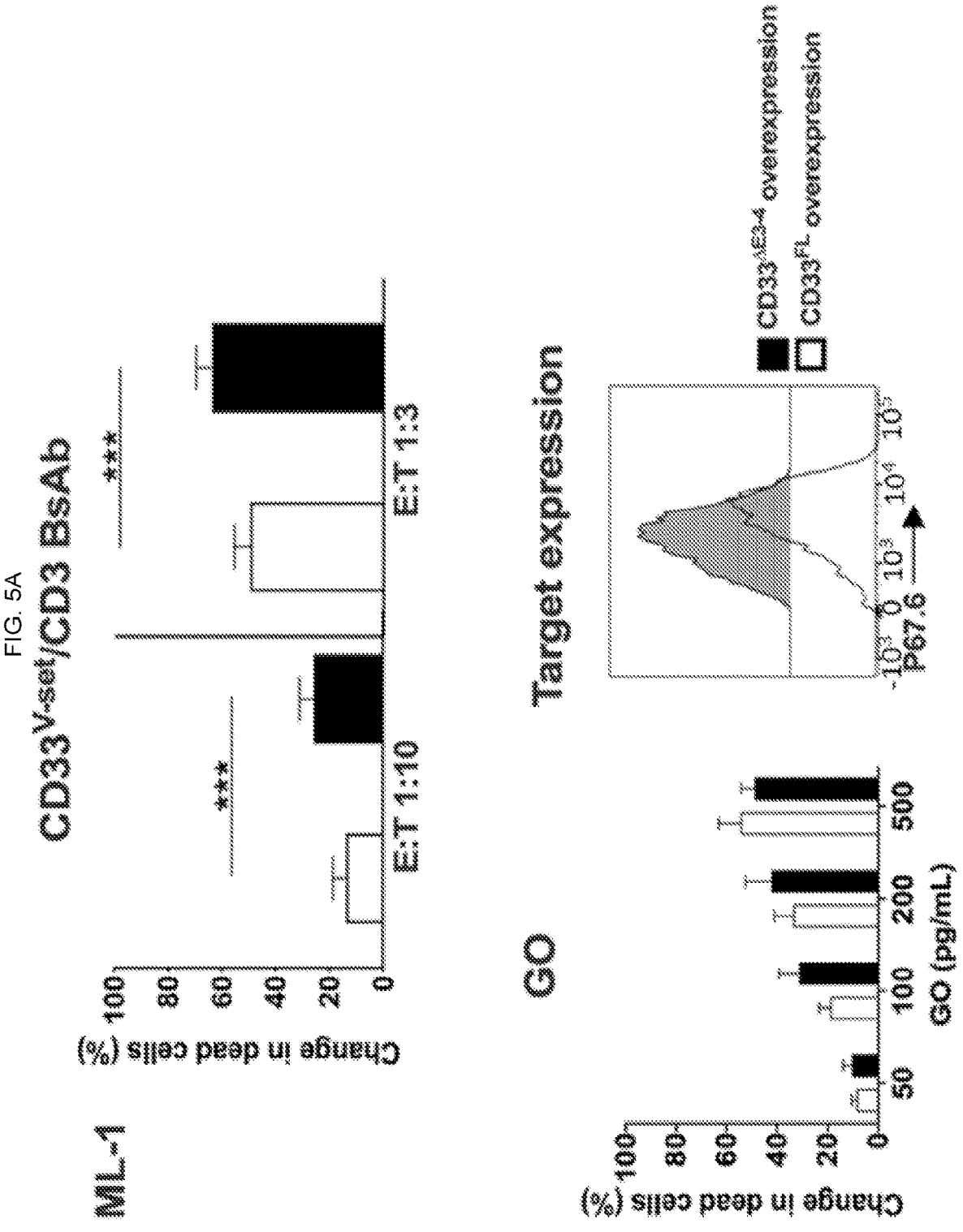
FIGS. 5A-5C. Reducing the binding distance from cell membrane enhances the anti-tumor efficacy of CD33/CD3 BsAbs against human myeloid leukemia cells. Human CD33+ myeloid leukemia cell lines ((5A) ML-1, (5B) HL-60, (5C) K562) with CRISPR/Cas9-mediated deletion of the endogenous CD33 locus were engineered to overexpress either $CD33^{FL}$ or $CD33^{\Delta E3\text{-}4}$ via lentiviral gene transfer. Relative expression of the target proteins was flow cytometrically assessed via V-set domain CD33 antibody, P67.6, with representative histograms shown in the bottom right panel. Cells were then treated with a V-set domain-targeting CD33/CD3 BsAb at a concentration of 1000 pg/mL and healthy donor T cells enriched from unstimulated peripheral blood mononuclear cells collected from healthy adult volunteers at the effector:target (E:T) cell ratios shown (top panel). Myeloid cells were also treated with gemtuzumab ozogamicin (GO) at the concentrations shown (bottom left panel). Cytotoxicity was quantified flow cytometrically after 2 days (for BsAbs) or 3 days (for GO) as a change in the percentage of dead cells as measured by 4',6-diamidino-2-phenylindole (DAPI) staining. The anti-V-set domain-directed CD33/CD3 BsAb was constructed in the scFv-scFv format using a construct referred to herein as RC1 or A3 that utilizes the sequence as set forth in SEQ ID NO: 254 and described in United States patent application publication US 2016/0317657 A1. *p<0.05; p<0.01; *p<0.001.
Figure 5B:
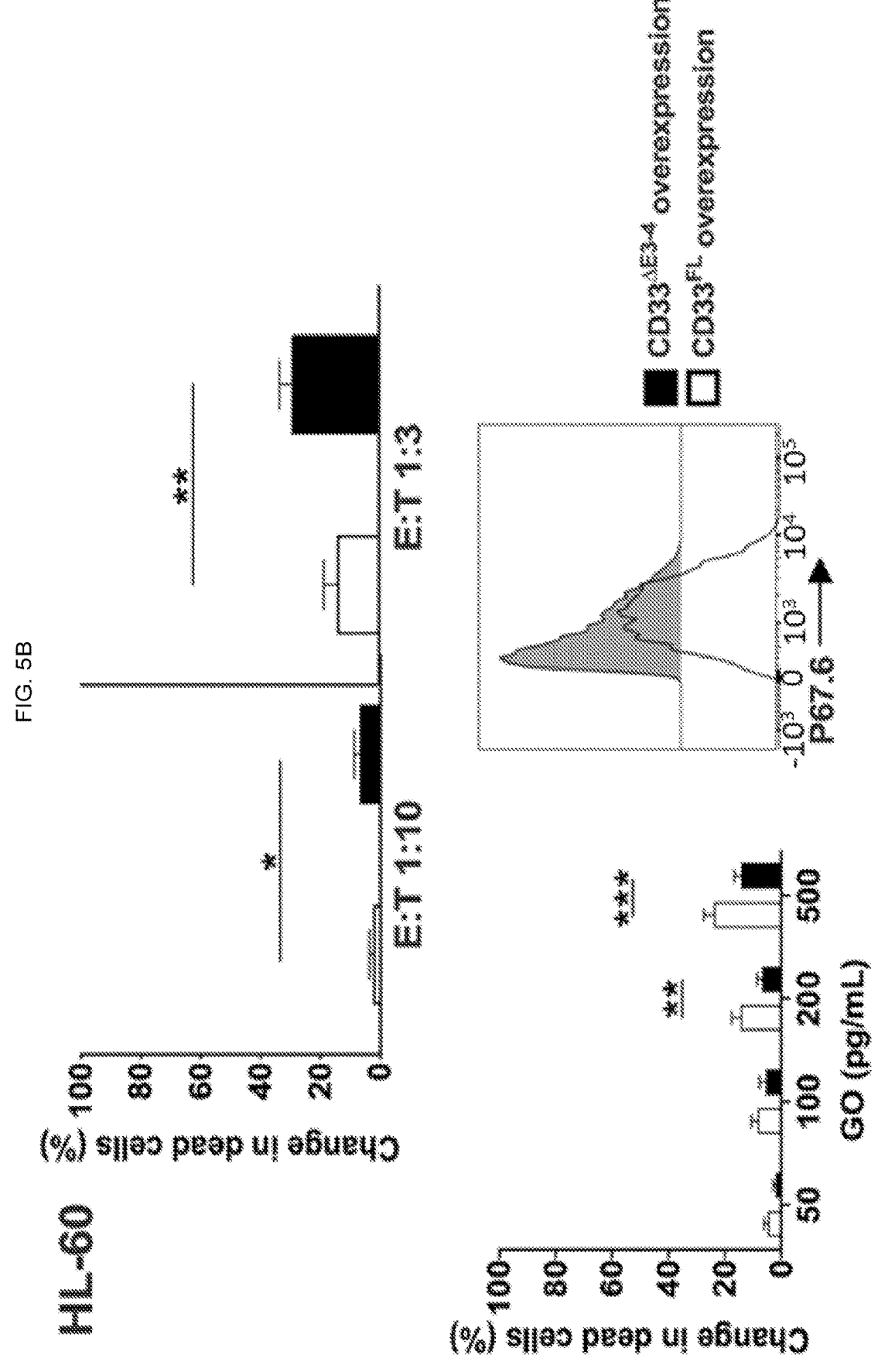
Figure 5C:
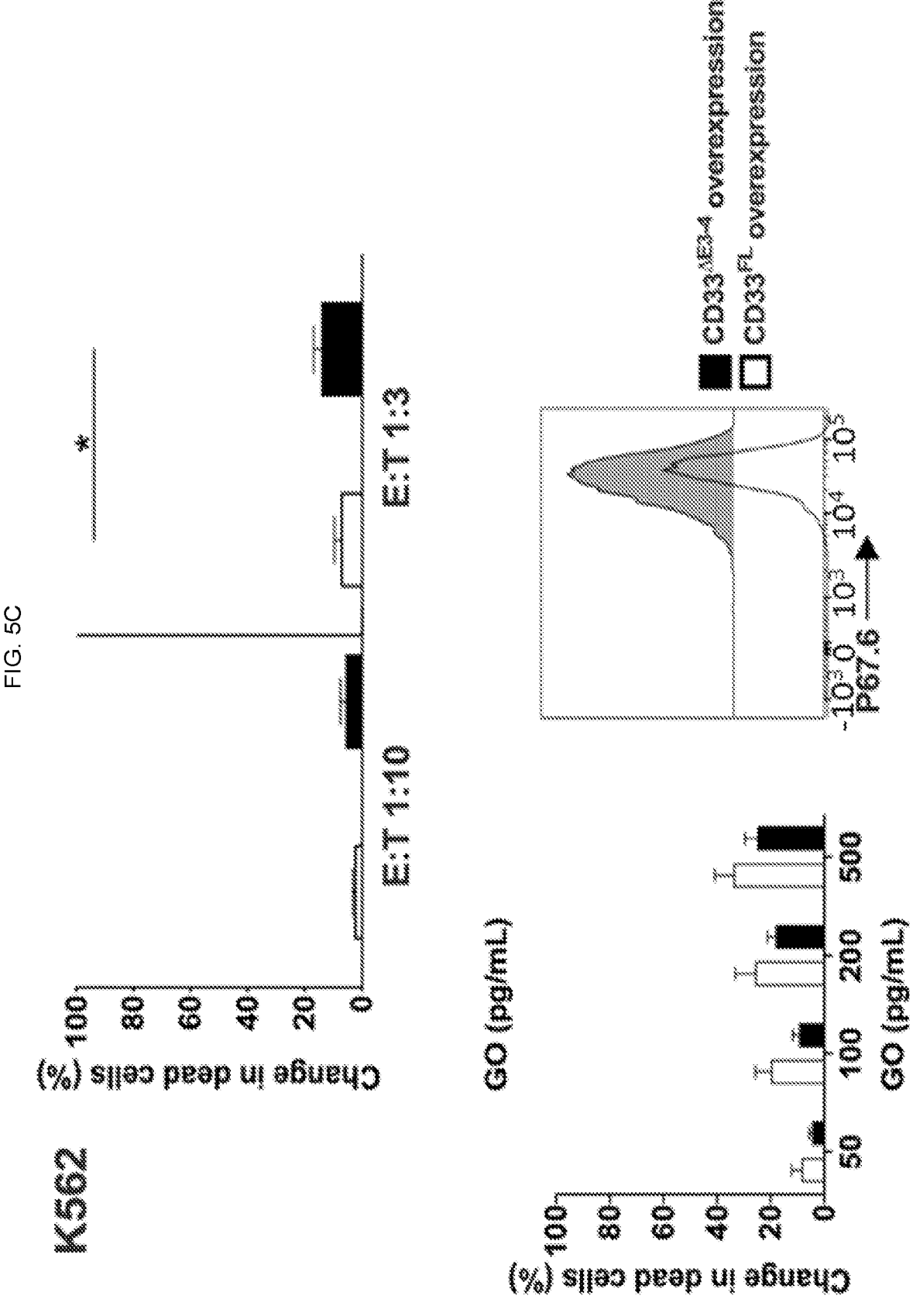
Figure 7:
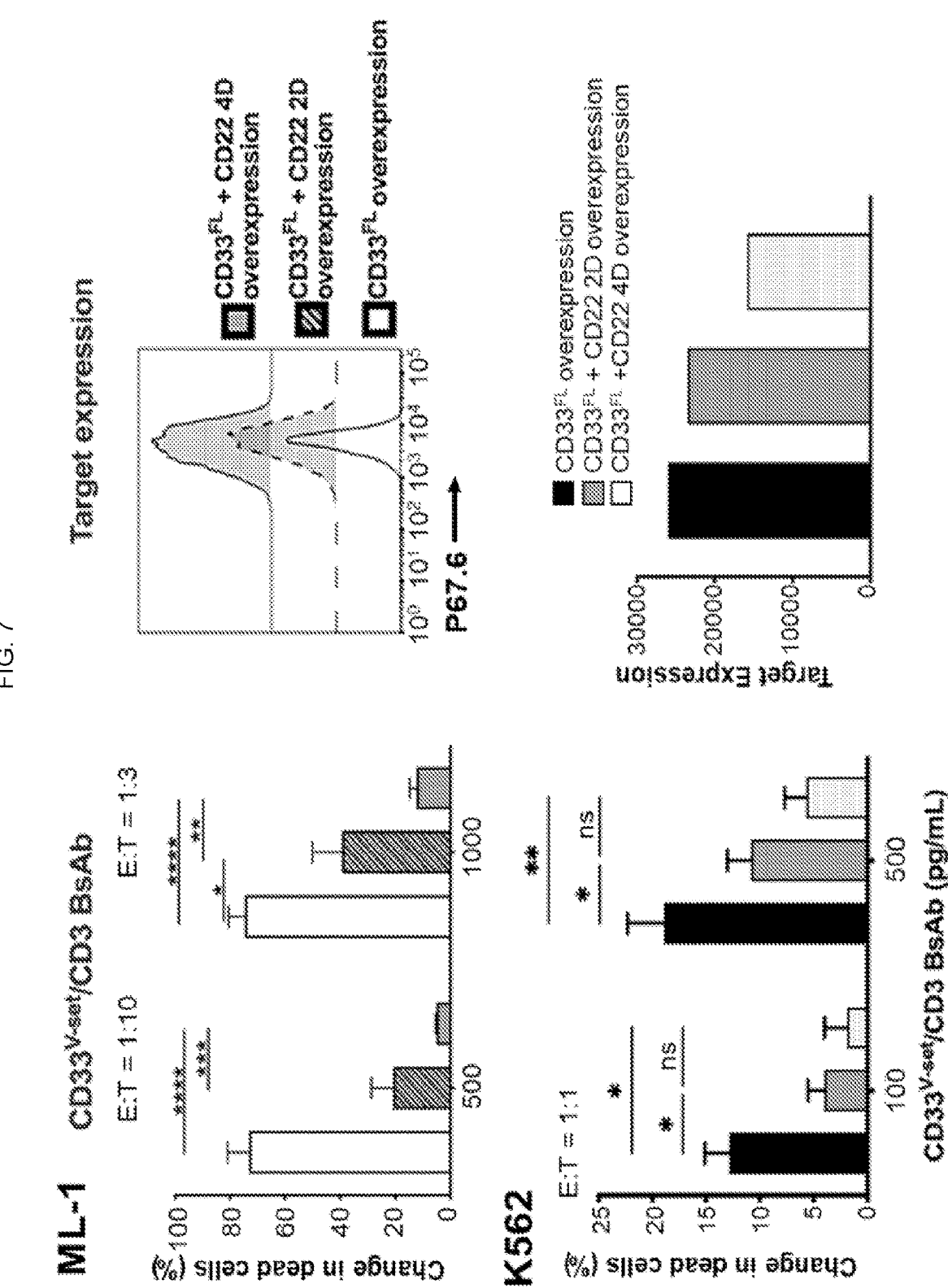
FIG. 7. Increasing the binding distance from cell membrane reduces the anti-tumor efficacy of CD33/CD3 BsAbs. Human myeloid leukemia cell lines (ML-1 [upper panel], K562 [lower panel]) with CRISPR/Cas9-mediated deletion of the endogenous CD33 locus were engineered to overexpress $CD33^{FL}$, $CD33^{FL}$+CD22 2D or $CD33^{FL}$+CD22 4D via lentiviral gene transfer. Relative expression of the CD33 constructs was flow cytometrically assessed using the V-set domain CD33 antibody, P67.6 (right panel). Cells were then treated with a V-set domain-targeting CD33/CD3 BsAb at the concentrations shown (in pg/mL) and healthy donor T cells enriched from unstimulated peripheral healthy donor blood mononuclear cells at an E:T cell ratio of 1:1. Cytotoxicity was quantified flow cytometrically after 2 days as a change in the percentage of dead cells as measured by 4',6-diamidino-2-phenylindole (DAPI) staining. The anti-V-set domain-directed CD33/CD3 BsAb was constructed in the scFv-scFv format using a construct referred to herein as RC1 or A3 that utilizes the sequence as set forth in SEQ ID NO: 254 and described in United States patent application publication US 2016/0317657 A1. *p<0.05; p<0.01; *p<0.001.
Figure 11A:
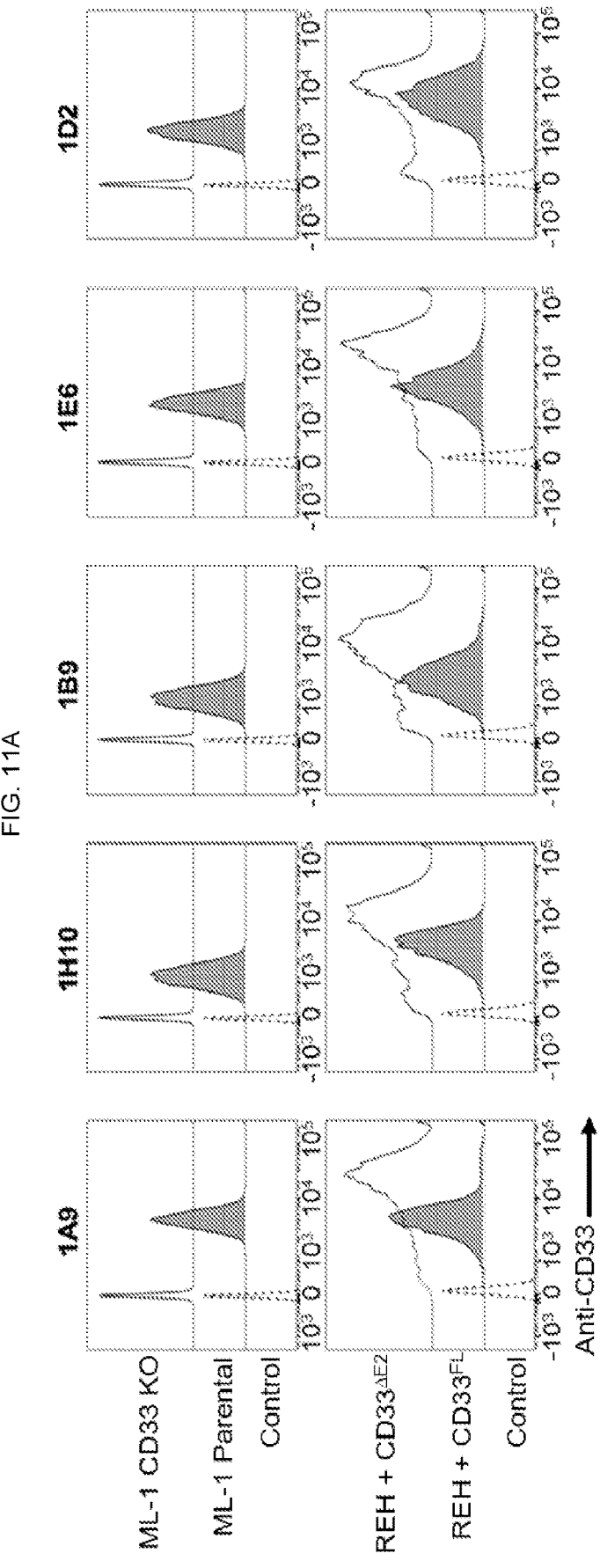
FIGS. 11A, 11B. (11A) Human $CD33^{PAN}$ antibody clones (clones 1A9, 1H10, 1B9, 1E6, and 1D2) and (11B) human $CD33^{V\text{-}set}$ antibody clones (clones 2E3, 2D3, and 1H8) were tested flow cytometrically against CD33+ parental ML-1 cells and ML-1 cells with CRISPR/Cas9-mediated deletion of CD33 ("CD33 KO") as well as against REH sublines engineered to express $CD33^{FL}$ or $CD33^{\Delta E2}$, as indicated. A control without primary antibody was included.
Figure 11B:
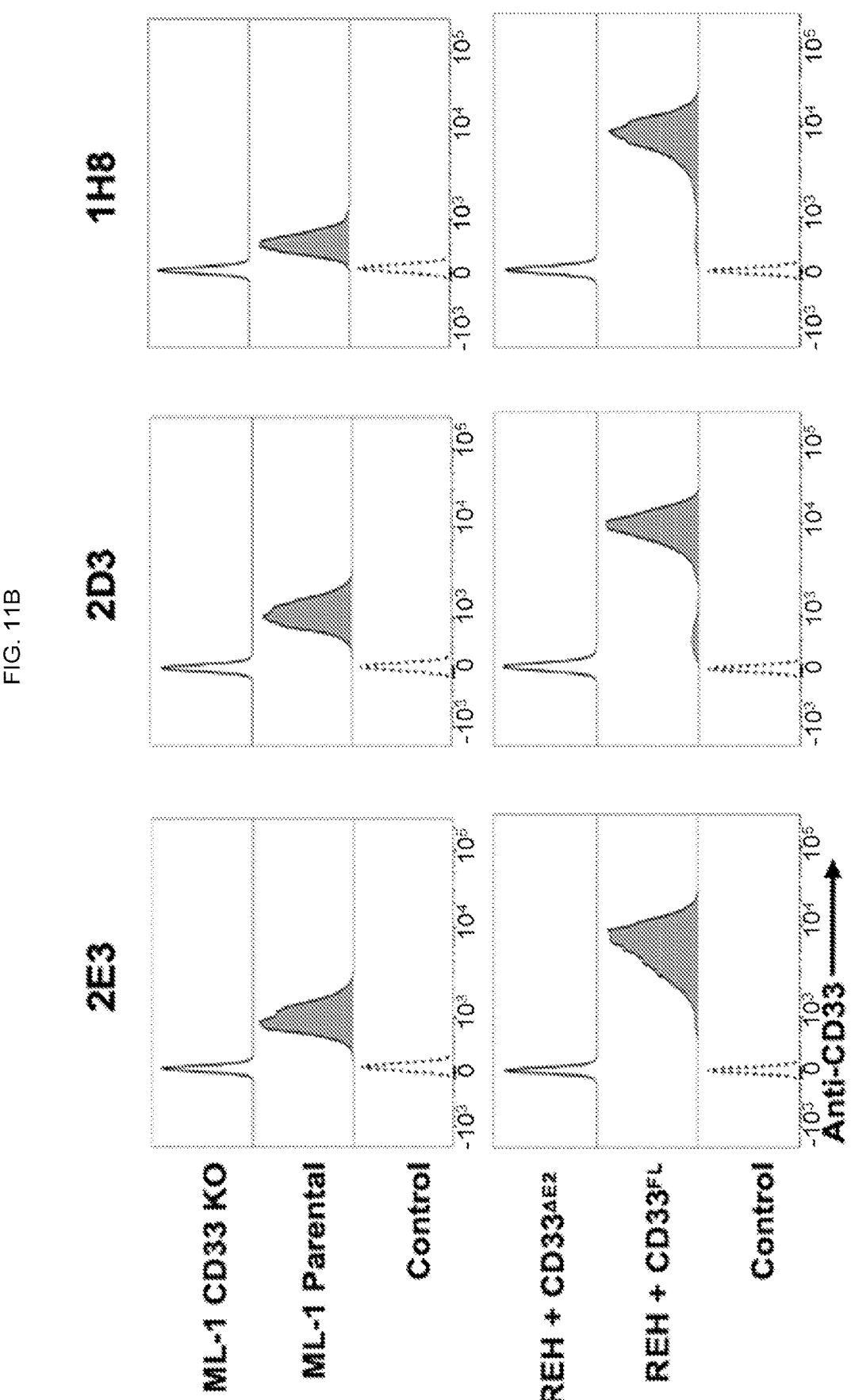
Figure 12B:
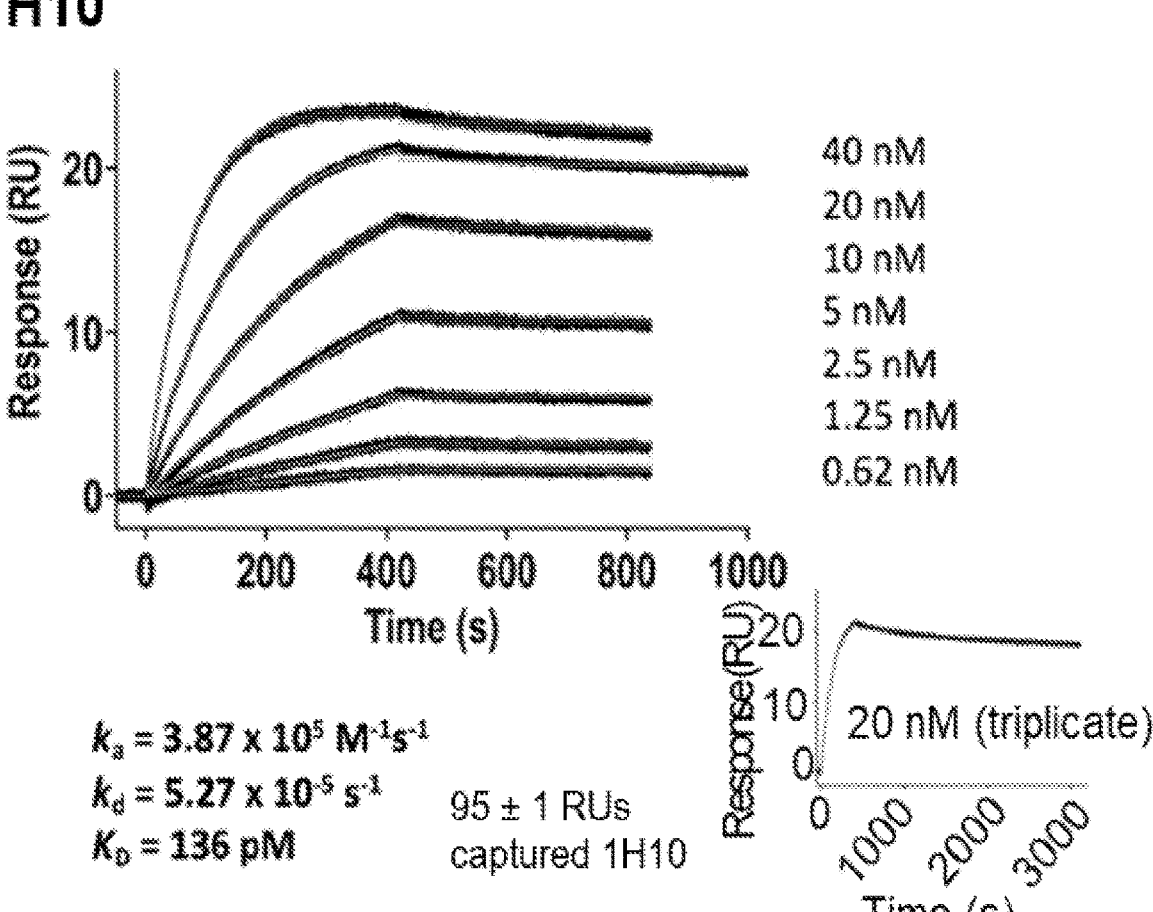
Figures 13, 14:
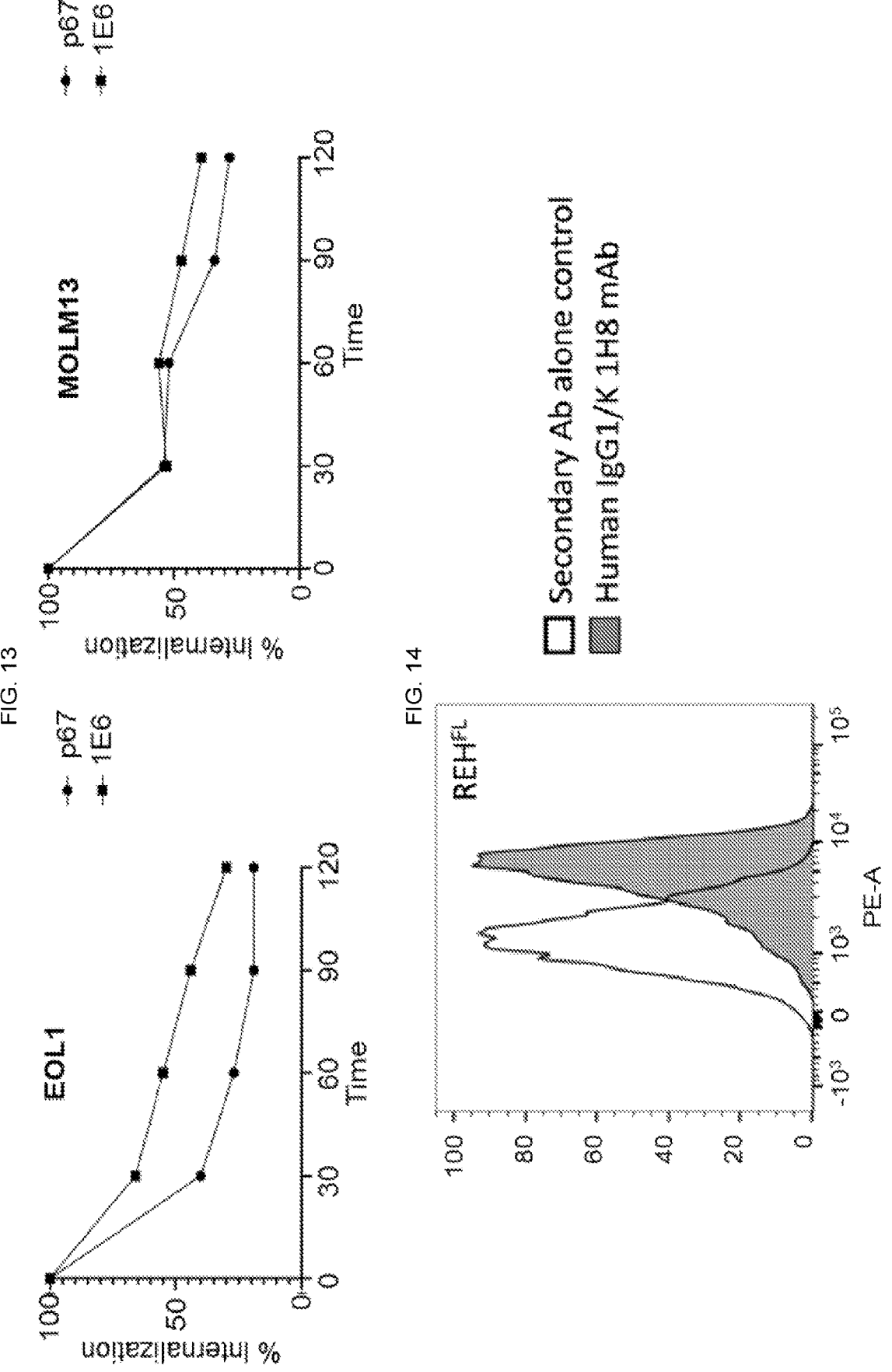
FIG. 13. Internalization of 1E6 and P67.6. AML cell lines were incubated with CD33 antibody at 37° C. for the time indicated. Fluorescently labeled secondary antibody was then added to quantify remaining CD33 antibody on the cell surface. Results are presented as a percentage of the fluorescence signal present at time 0.
FIG. 14. Binding of recombinant fully human CD33$^{V-set}$ antibody 1H8 with human IgG1 framework to REH cells (human acute lymphoblastic leukemia cell line, endogenously CD33$^{neg}$) engineered to express human CD33$^{FL}$.
Figure 15A:
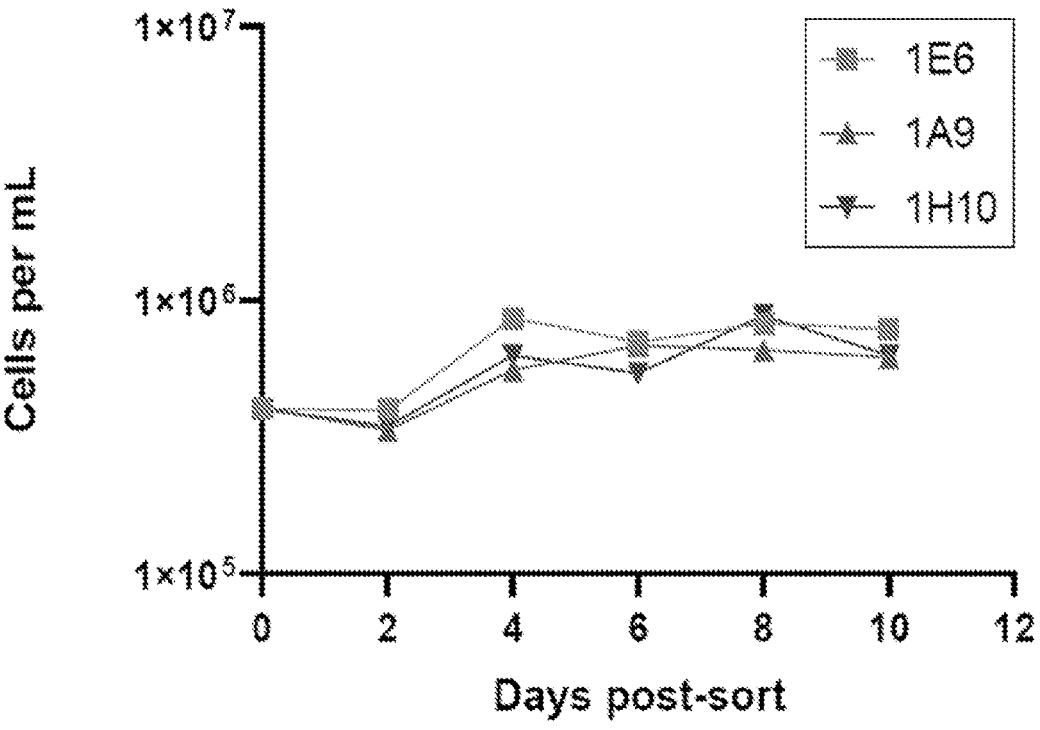
FIGS. 15A-15O. CAR-T cells expressing humanized (1E6, 1A9 and 1H10) scFVs directed against CD33 can be expanded in vitro with cytokines. CD8$^+$ CAR-T cells expressing intermediate spacer CAR and 1E6, 1A9 or 1H10 scFv were sorted by fluorescence-activated cell sorting (FACS) seven days following CD3/CD28 bead stimulation and transduction. Cells were then expanded in IL-2 (50 ng/mL, 15A, 15D, 15G, 15J, and 15M); IL-7 and IL-15 (10 ng/mL each, 15B, 15E, 15H, 15K, and 15N); or IL-7, IL-15 and IL-21 (10 ng/mL each, 15C, 15F, 15I, 15L, and 15O). Media and cytokines were refreshed every other day. Cells were assessed every two days for cell number (15A-15F), cell growth (15G-15I), viability by propidium iodide exclusion (15J-15L) and diameter (15M-15O).
Figure 15B:
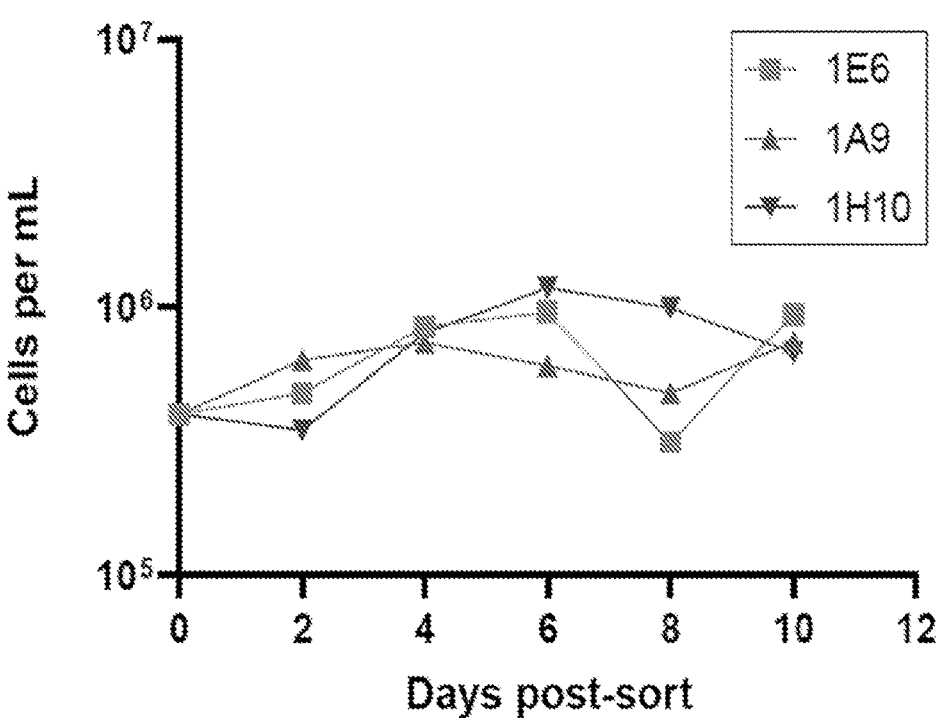
Figure 15C:
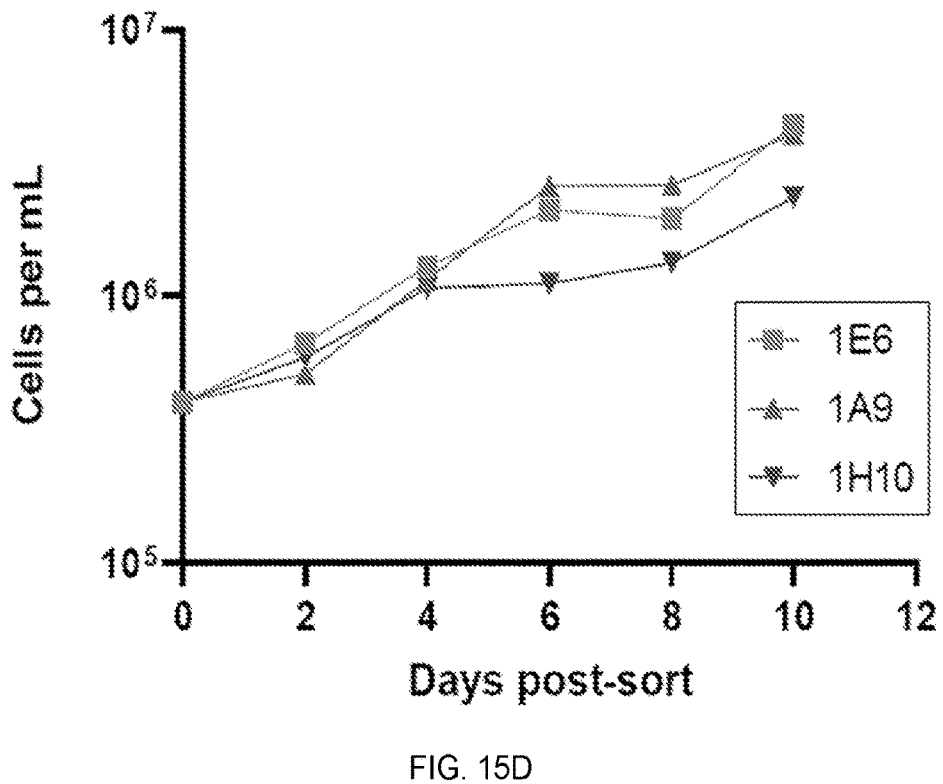
Figure 15D:
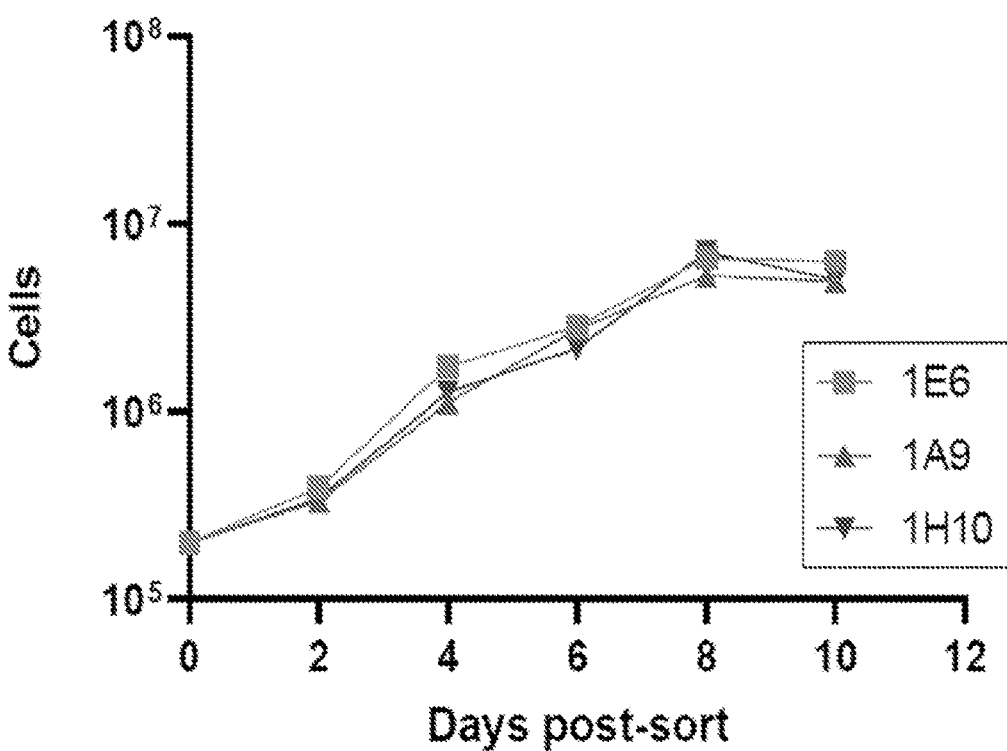
Figure 15E:
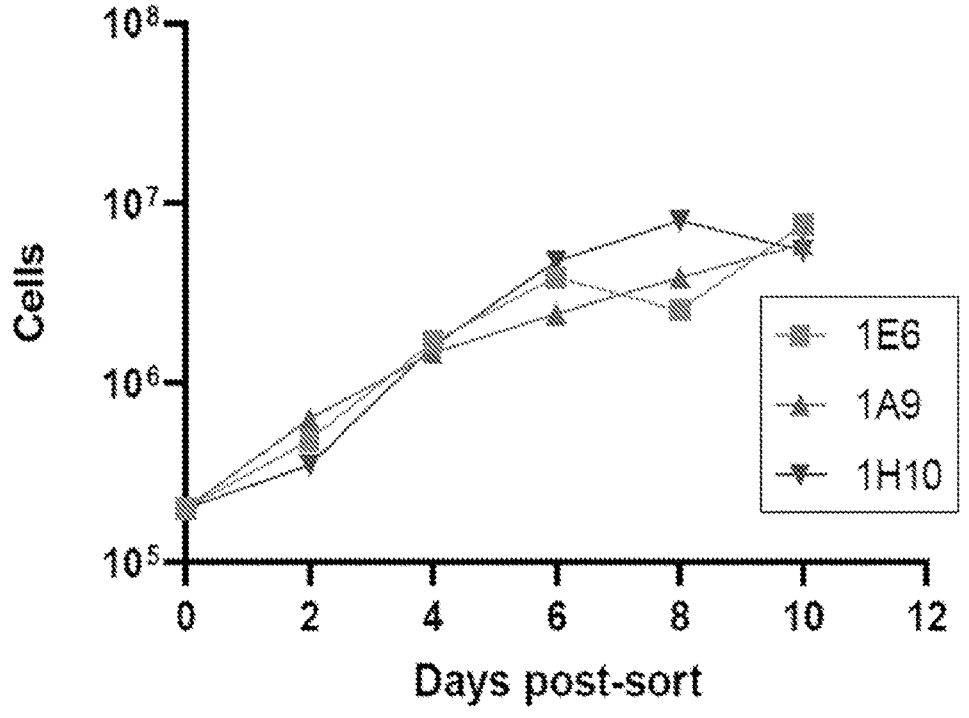
Figure 15F:
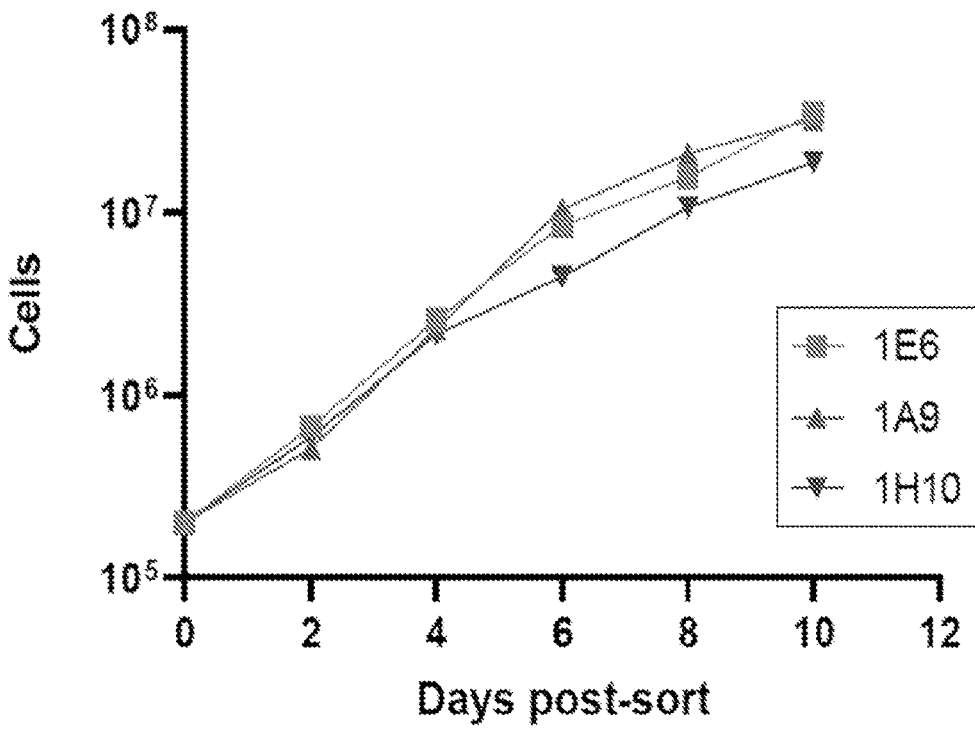
Figure 15G:
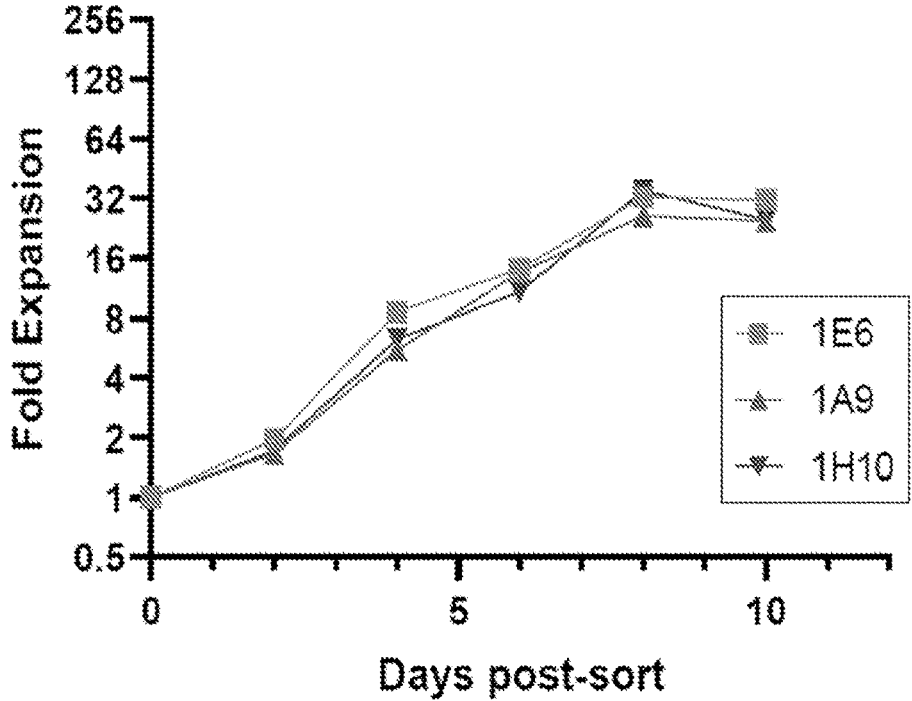
Figure 15H:
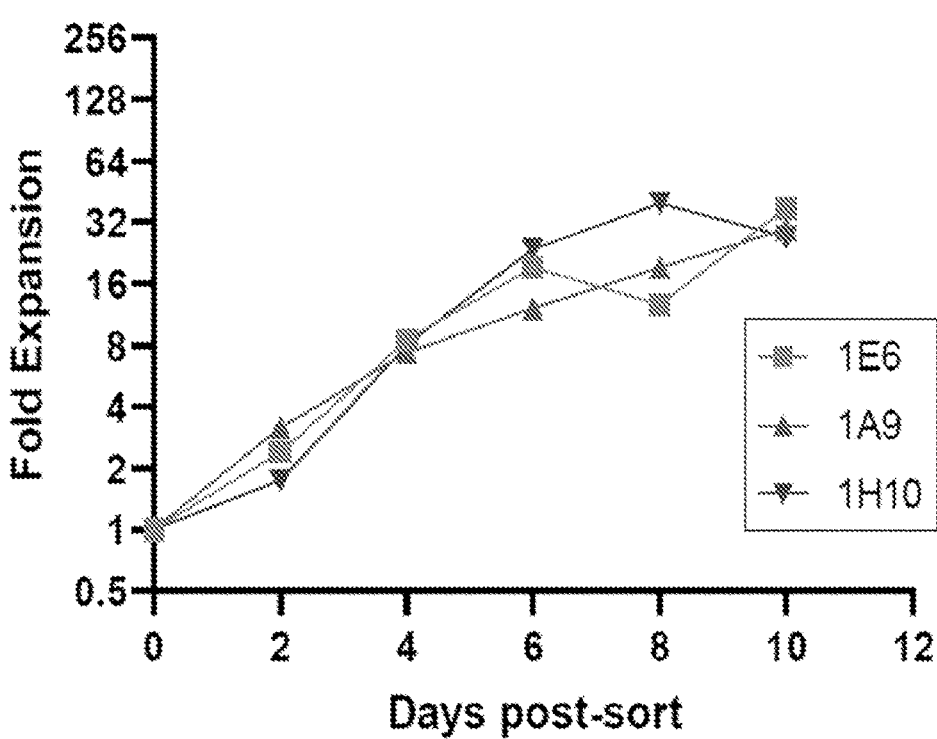
Figure 15I:
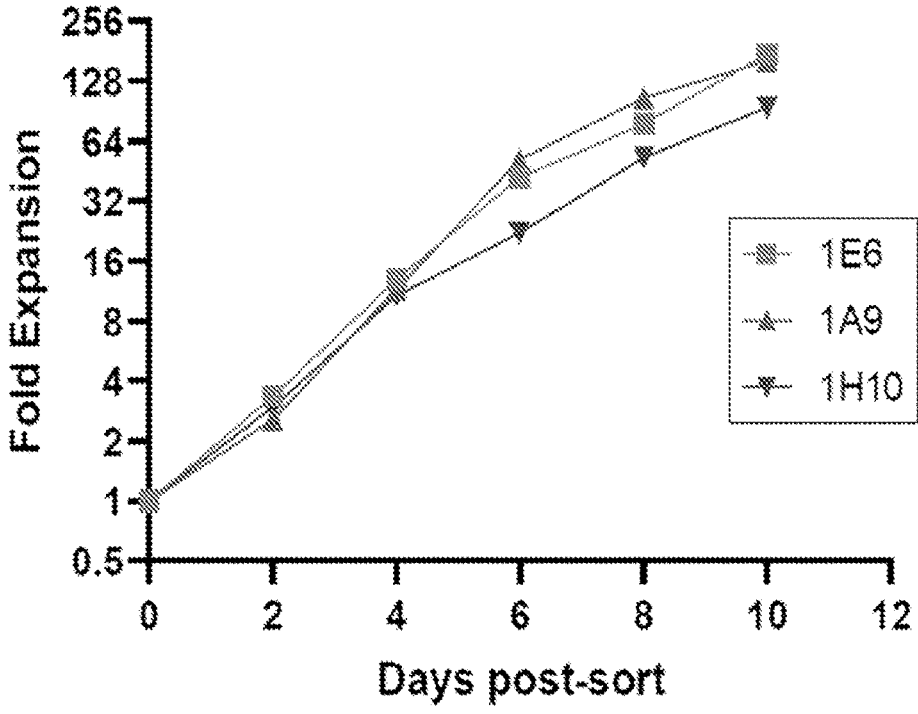
Figure 15J:
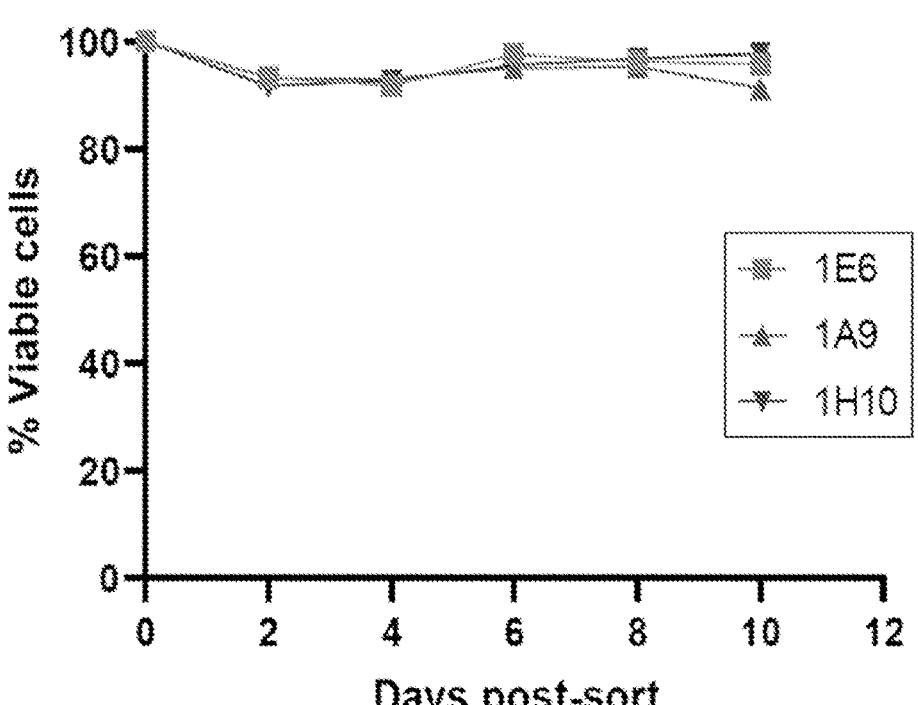
Figure 15K:
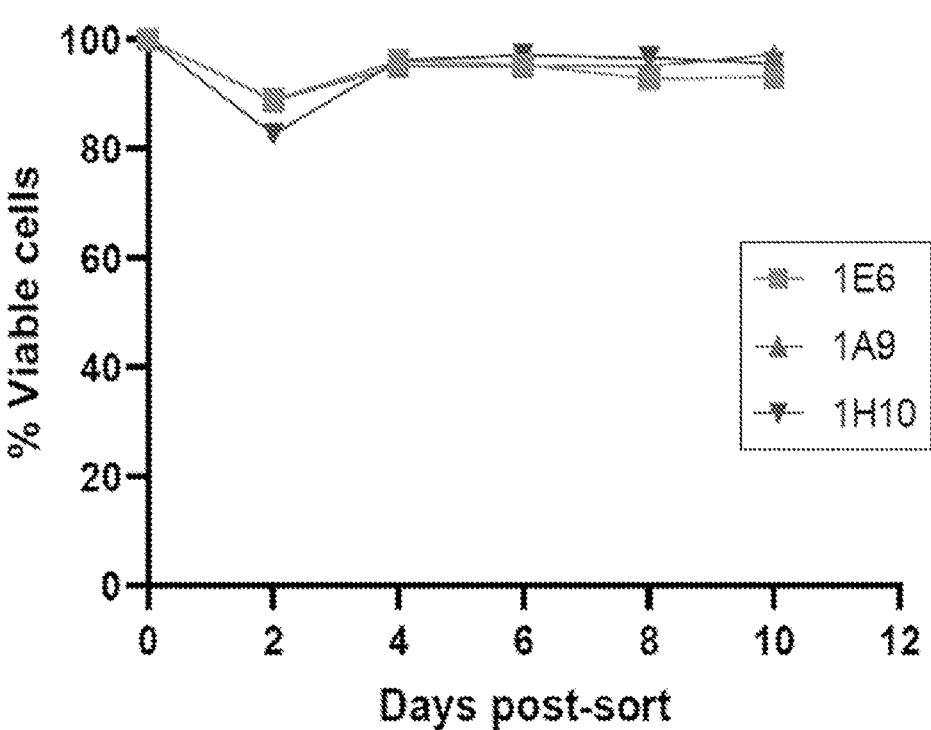
Figure 15L:
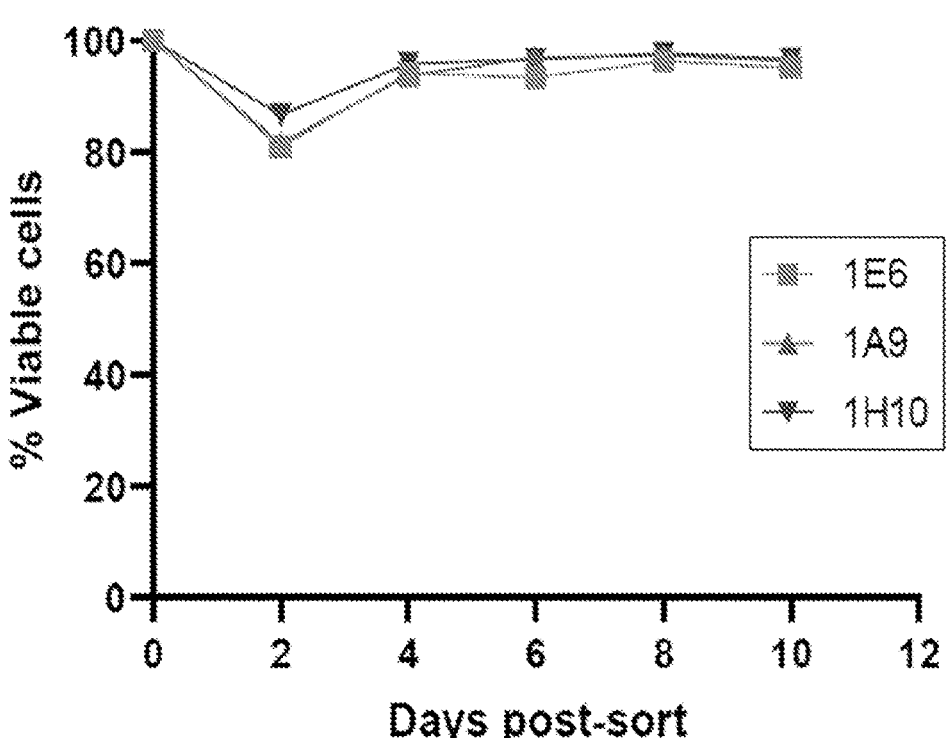
Figure 15M:
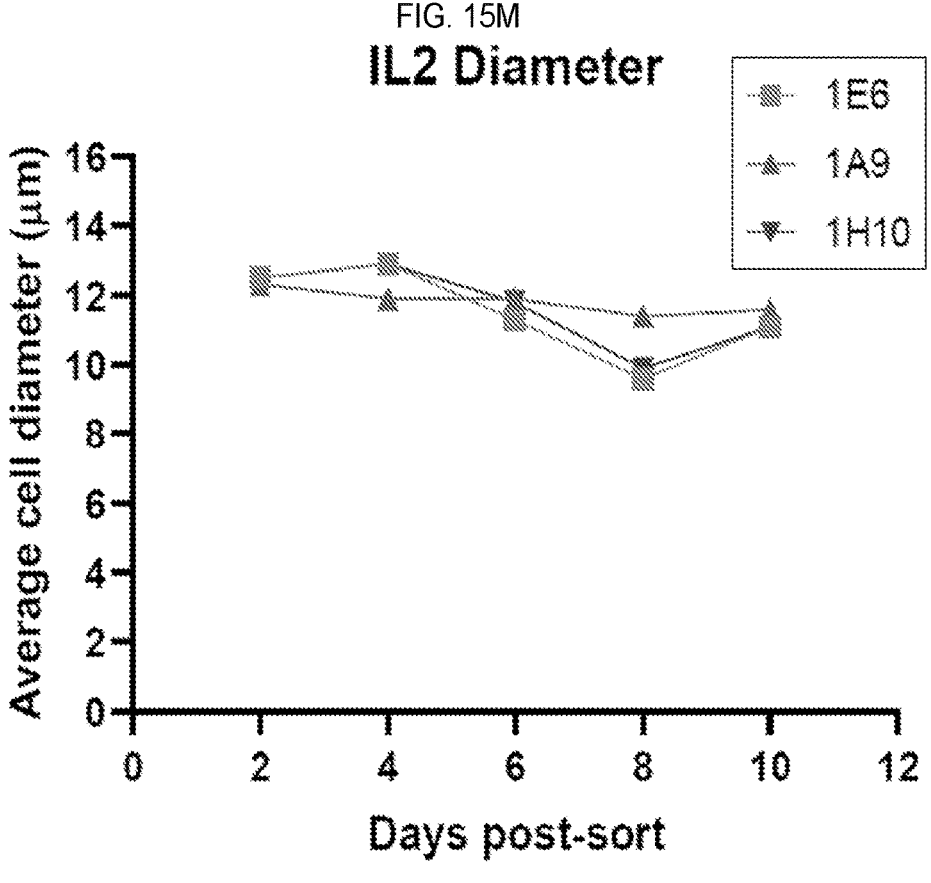
Figure 15N:
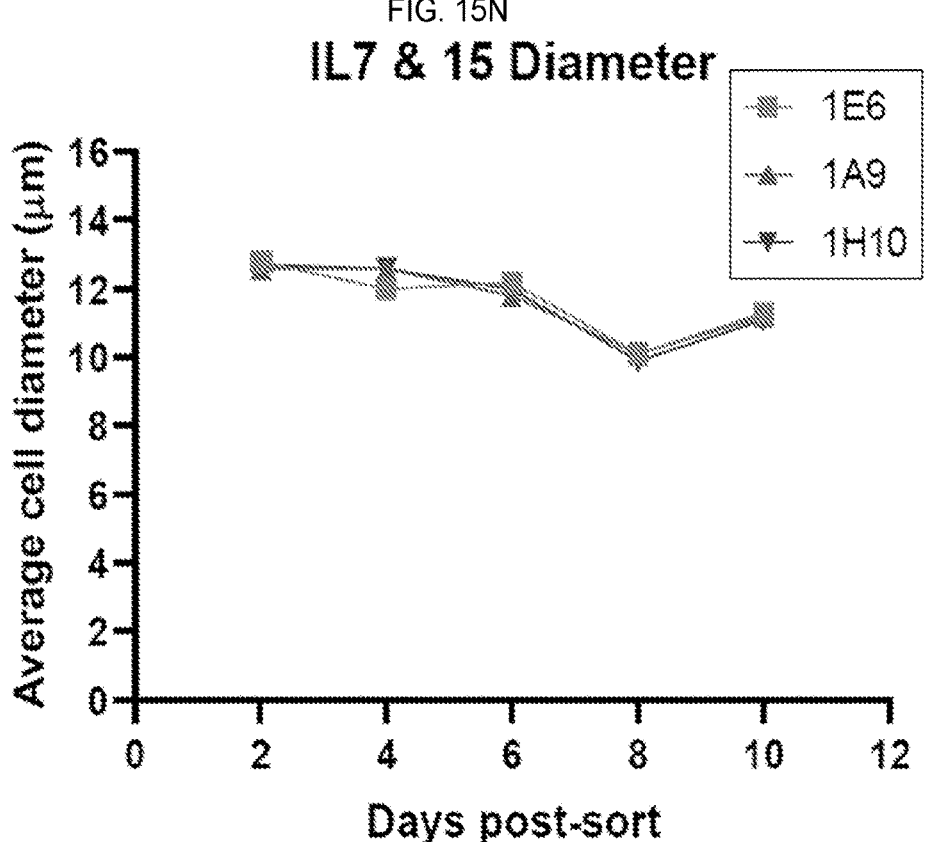
Figure 15O:
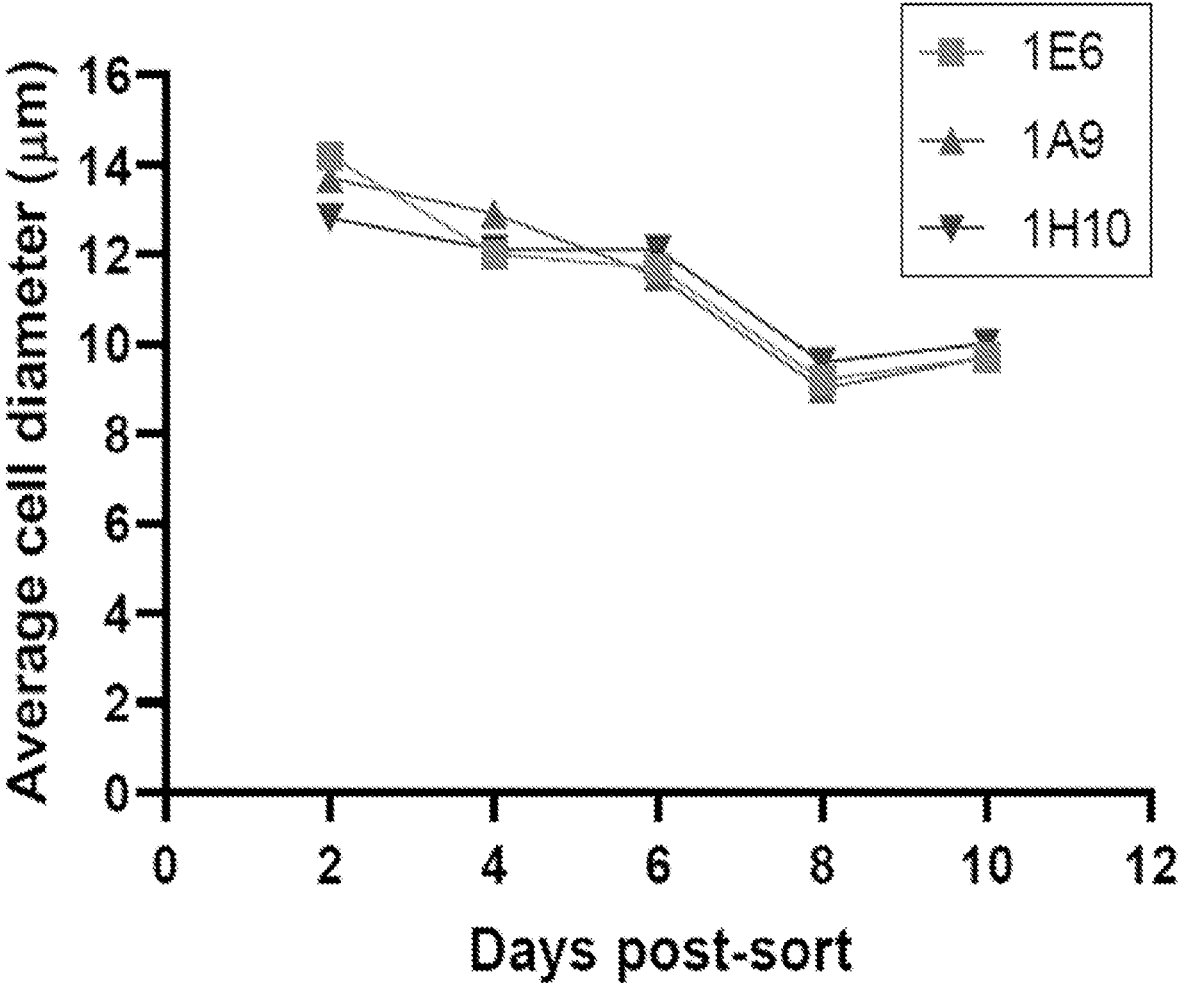

However, some patients express a truncated splice variant form of CD33 that is missing exon 2 and is referred to as CD33$^{\Delta E2}$. CD33$^{\Delta E2}$ has been identified at the mRNA level in normal hematopoietic cells as well as leukemia cells. Regarding the latter, CD33$^{\Delta E2}$ mRNA was identified in 29 of 29 tested AML patient specimens, indicating universal expression in human AML. CD33$^{\Delta E2}$ contains the C2-set Ig-like domain but not the V-set Ig-like domain of CD33 (FIG. 2). Additional splice variants, identified at the mRNA level, include CD33$^{E7a}$ and CD33$^{\Delta E2/E7a}$. CD33$^{E7a}$ uses an alternate exon 7 (E7a) which results in a truncation of the intracellular domain of CD33. CD33$^{\Delta E2/E7a}$ lacks exon 2 and also has the truncation of the intracellular domain of CD33.

Currently, however, almost all commercial diagnostic CD33 antibodies and currently clinically available CD33 antibody-based therapeutics recognize the immune-dominant V-set Ig-like domain that is encoded by exon 2 (FIG. 2). That is, CD33$^{\Delta E2}$ and other CD33 proteins that lack the V-set Ig-like domain are not recognized by almost any commercially and clinically available CD33 antibody This means that these antibodies would not recognize shorter forms of CD33 that lack the V-set domain such as CD33$^{\Delta E2}$. This may explain the observation made in one clinical trial in pediatric AML that patients with a single nucleotide polymorphism in the CD33 gene that leads to preferential transcription of CD33$^{\Delta E2}$ and reduced translation of CD33$^{FL}$ did not benefit from the addition of GO (which also binds to the V-set domain of CD33) to intensive chemotherapy.

Antibodies that recognize and bind the C2-set Ig-like domain of CD33 proteins regardless of the presence/absence of the V-set Ig-like domain (e.g. antibodies that bind the CD33$^{\Delta E2}$ and CD33$^{FL}$ isoforms, referred to as CD33$^{PAN}$ antibodies) would provide a great advance in the targeting of all CD33 isoforms, providing for broader therapeutic efficacy. These pan-binding antibodies would also provide an advance because they bind closer to the cell membrane (FIG. 2). For several therapeutic targets, the specifics of the targeted epitope have been shown to be critically important for antibody-based therapy, with membrane-proximal epitopes resulting in more potent anti-tumor effects than membrane-distal ones, as shown for CD20, CD22, CD25, and EpCAM. See, for instance, Cleary et al., J Immunol. 2017; 198(10):3999-4011; Lin, Pharmgenomics Pers Med.

2010; 3:51-59; Haso et al., Blood. 2013; 121(7):1165-1174; and Bluemel et al., Cancer Immunol Immunother. 2010; 59(8):1197-1209.

Beyond antibody-based therapeutics, significant progress has been made in genetically engineering T cells of the immune system to target and kill unwanted cell types, such as cancer cells. Many of these T cells have been genetically engineered to express a chimeric antigen receptor (CAR). CARs are proteins including several distinct subcomponents that allow the genetically modified T cells to recognize and kill cancer cells. The subcomponents include at least an extracellular component and an intracellular component. The extracellular component includes a binding domain that specifically binds a marker that is preferentially present on the surface of unwanted cells (e.g., CD33). The binding domain is typically a single-chain variable fragment (scFv) derived from a monoclonal antibody (mAb), but it can be based on other formats which include an antibody-like antigen binding site.

When the binding domain binds such markers, the intracellular component signals the T cell to destroy the bound cell. The intracellular components provide such activation signals based on the inclusion of an effector domain. First generation CARs utilized the cytoplasmic domain of CD3ζ as an effector domain. Second generation CARs utilized the cytoplasmic domain of CD3ζ in combination with cluster of differentiation 28 (CD28) or 4-1 BB (CD137) cytoplasmic domains, while third generation CARs have utilized the CD3ζ cytoplasmic domain in combination with the CD28 and 4-1BB cytoplasmic domains as effector domains.

CARs additionally include a transmembrane domain that can link the extracellular component to the intracellular component.

Other subcomponents that can increase a CAR's function can also be used. For example, spacer regions can provide a CAR with additional conformational flexibility, often increasing the binding domain's ability to bind the targeted cell marker. The appropriate length of a spacer region within a particular CAR can depend on numerous factors including how close or far a targeted marker is located from the surface of an unwanted cell's membrane.

When performed ex vivo, genetically modifying T cells can involve numerous cell manipulation steps, and it has been observed that different manipulation conditions can affect the cancer-cell killing properties of the cells. Thus, in designing CARs and genetically modifying cells to express them, numerous considerations must be taken into account, including: targeted cell marker; presence and/or length of spacer; and ex vivo manipulation procedures.

The current disclosure provides chimeric antigen receptors (CARs) for the treatment of CD33-related disorders, such as AML. In particular embodiments, the CARs include a binding domain that binds CD33 regardless of which CD33 variant a patient expresses (e.g. CD33$^{FL}$ or CD33$^{\Delta E2}$). These CD33 binding domains are referred to as "pan" binders. In particular embodiments, the pan binders bind the membrane-proximal C2-set Ig-like domain of CD33. In particular embodiments, these pan binders are derived from newly developed antibodies: 1H10, 1A9, 1E6, 1D2, and 1B9, and can include single chain variable fragments of these antibodies. As described herein, more membrane-proximal binding enhances the immune effector function of the CAR for treatment of AML and other CD33+ disorders. Additional newly developed CD33 targeting antibodies disclosed herein bind the V-set domain of CD33 and include 1H8, 2D3, and 2E3. These antibodies provide additional CAR-based therapeutic options for patients expressing CD33$^{FL}$.

Binding domains of antibodies for use within a treatment can be based on combinations of binding domains based on whether a subject expresses or lacks the V-set domain of CD33. For example, if a subject expresses the V-set domain, a combination therapy including one or more binding domains of 1H10, 1A9, 1E6, 1D2, and 1B9 could be selected in combination with one or more of 1H8, 2D3, and 2E3.

In particular embodiments, the current disclosure provides CARs having a short or intermediate spacer region. In particular embodiments, the short spacer region includes the hinge region of IgG4 (12 amino acids). In particular embodiments, the intermediate spacer region includes the hinge region and the CH3 domain of IgG4 (collectively, 131 amino acids). IgG4 domains utilized as spacer regions can include mutations that prevent binding to the human Fc receptor. In particular embodiments, these mutations include replacing the first six amino acids of the CH2 domain of IgG4 (APEFLG, SEQ ID NO: 52) with the first five amino acids of IgG2 (APPVA, SEQ ID NO: 53).

In particular embodiments, the current disclosure provides expanding and activating T cells genetically modified to express a CAR disclosed herein utilizing a combination of the cytokines IL-7, IL-15, and IL-21. In particular embodiments, the current disclosure provides expanding and activating T cells genetically modified to express a CAR disclosed herein utilizing a combination of cytokines including IL-2. Expansion/activation with this combination of cytokines results in increased proliferation and antigen-specific cell lysis.

Aspects of the current disclosure are now described in more supporting detail as follows: (i) Immune Cells; (ii) Cell Sample Collection and Cell Enrichment; (iii) Genetically Modifying Cell Populations to Express Chimeric Antigen Receptors (CAR); (iii-a) Genetic Engineering Techniques; (iii-b) CAR Subcomponents; (iii-b-i) Binding Domains; (iii-b-ii) Spacer Regions; (iii-b-iii) Transmembrane Domains; (iii-b-iv) Intracellular Effector Domains; (iii-b-v) Linkers; (iii-b-vi) Control Features Including Tag Cassettes, Transduction Markers, and/or Suicide Switches; (iv) Cell Activating Culture Conditions; (v) Ex Vivo Manufactured Cell Formulations; (vi) Methods of Use; (vii) Reference Levels Derived from Control Populations; (viii) Exemplary Embodiments; and (ix) Closing Paragraphs. These headings are provided for organizational purposes only and do not limit the scope or interpretation of the disclosure.

(i) Immune Cells. The present disclosure describes cells genetically modified to express CAR. Genetically modified cells can include T-cells, B cells, natural killer (NK) cells, NK-T cells, monocytes/macrophages, lymphocytes, hematopoietic stem cells (HSCs), hematopoietic progenitor cells (HPC), and/or a mixture of HSC and HPC (i.e., HSPC). In particular embodiments, genetically modified cells include T-cells.

Several different subsets of T-cells have been discovered, each with a distinct function. For example, a majority of T-cells have a T-cell receptor (TCR) existing as a complex of several proteins. The actual T-cell receptor is composed of two separate peptide chains, which are produced from the independent T-cell receptor alpha and beta (TCRα and TCRβ) genes and are called α- and β-TCR chains.

γδ T-cells represent a small subset of T-cells that possess a distinct T-cell receptor (TCR) on their surface. In γδ

T-cells, the TCR is made up of one γ-chain and one δ-chain. This group of T-cells is much less common (2% of total T-cells) than the αβ T-cells.

CD3 is expressed on all mature T cells. Activated T-cells express 4-1BB (CD137), CD69, and CD25. CD5 and transferrin receptor are also expressed on T-cells.

T-cells can further be classified into helper cells (CD4+ T-cells) and cytotoxic T-cells (CTLs, CD8+ T-cells), which include cytolytic T-cells. T helper cells assist other white blood cells in immunologic processes, including maturation of B cells into plasma cells and activation of cytotoxic T-cells and macrophages, among other functions. These cells are also known as CD4+ T-cells because they express the CD4 protein on their surface. Helper T-cells become activated when they are presented with peptide antigens by MHC class II molecules that are expressed on the surface of antigen presenting cells (APCs). Once activated, they divide rapidly and secrete small proteins called cytokines that regulate or assist in the active immune response.

Cytotoxic T-cells destroy virally infected cells and tumor cells and are also implicated in transplant rejection. These cells are also known as CD8+ T-cells because they express the CD8 glycoprotein on their surface. These cells recognize their targets by binding to antigen associated with MHC class I, which is present on the surface of nearly every cell of the body.

"Central memory" T-cells (or "TCM") as used herein refers to an antigen experienced CTL that expresses CD62L or CCR7 and CD45RO on the surface thereof and does not express or has decreased expression of CD45RA as compared to naive cells. In particular embodiments, central memory cells are positive for expression of CD62L, CCR7, CD25, CD127, CD45RO, and CD95, and have decreased expression of CD45RA as compared to naive cells.

"Effector memory" T-cell (or "TEM") as used herein refers to an antigen experienced T-cell that does not express or has decreased expression of CD62L on the surface thereof as compared to central memory cells and does not express or has decreased expression of CD45RA as compared to a naive cell. In particular embodiments, effector memory cells are negative for expression of CD62L and CCR7, compared to naive cells or central memory cells, and have variable expression of CD28 and CD45RA. Effector T-cells are positive for granzyme B and perforin as compared to memory or naive T-cells.

"Naive" T-cells as used herein refers to a non-antigen experienced T cell that expresses CD62L and CD45RA and does not express CD45RO as compared to central or effector memory cells. In particular embodiments, naive CD8+ T lymphocytes are characterized by the expression of phenotypic markers of naive T-cells including CD62L, CCR7, CD28, CD127, and CD45RA.

Natural killer cells (also known as NK cells, K cells, and killer cells) are activated in response to interferons or macrophage-derived cytokines. They serve to contain viral infections while the adaptive immune response is generating antigen-specific cytotoxic T cells that can clear the infection. NK cells express CD8, CD16 and CD56 but do not express CD3.

NK cells include NK-T cells. NK-T cells are a specialized population of T cells that express a semi invariant T cell receptor (TCR ab) and surface antigens typically associated with natural killer cells. NK-T cells contribute to antibacterial and antiviral immune responses and promote tumor-related immunosurveillance or immunosuppression. Like natural killer cells, NK-T cells can also induce perforin-, Fas-, and TNF-related cytotoxicity. Activated NK-T cells are capable of producing IFN-γ and IL-4. In particular embodiments, NK-T cells are CD3+/CD56+.

Macrophages (and their precursors, monocytes) reside in every tissue of the body (in certain instances as microglia, Kupffer cells and osteoclasts) where they engulf apoptotic cells, pathogens and other non-self-components. Monocytes/macrophages express CD11b, F4/80; CD68; CD11c; IL-4Rα; and/or CD163.

Immature dendritic cells (i.e., pre-activation) engulf antigens and other non-self-components in the periphery and subsequently, in activated form, migrate to T-cell areas of lymphoid tissues where they provide antigen presentation to T cells. Dendritic cells express CD1a, CD1b, CD1c, CD1d, CD21, CD35, CD39, CD40, CD86, CD101, CD148, CD209, and DEC-205.

Hematopoietic Stem/Progenitor Cells or HSPC refer to a combination of hematopoietic stem cells and hematopoietic progenitor cells.

Hematopoietic stem cells refer to undifferentiated hematopoietic cells that are capable of self-renewal either in vivo, essentially unlimited propagation in vitro, and capable of differentiation to all other hematopoietic cell types.

A hematopoietic progenitor cell is a cell derived from hematopoietic stem cells or fetal tissue that is capable of further differentiation into mature cell types. In certain embodiments, hematopoietic progenitor cells are $CD24^{lo}$ $Lin^-$ $CD117^+$ hematopoietic progenitor cells. HPCs can differentiate into (i) myeloid progenitor cells which ultimately give rise to monocytes and macrophages, neutrophils, basophils, eosinophils, erythrocytes, megakaryocytes/platelets, or dendritic cells; or (ii) lymphoid progenitor cells which ultimately give rise to T-cells, B-cells, and NK-cells.

HSPC can be positive for a specific marker expressed in increased levels on HSPC relative to other types of hematopoietic cells. For example, such markers include CD34, CD43, CD45RO, CD45RA, CD59, CD90, CD109, CD117, CD133, CD166, HLA DR, or a combination thereof. Also, the HSPC can be negative for an expressed marker relative to other types of hematopoietic cells. For example, such markers include Lin, CD38, or a combination thereof. Preferably, the HSPC are $CD34^+$ cells.

A statement that a cell or population of cells is "positive" for or expressing a particular marker refers to the detectable presence on or in the cell of the particular marker. When referring to a surface marker, the term can refer to the presence of surface expression as detected by flow cytometry, for example, by staining with an antibody that specifically binds to the marker and detecting said antibody, wherein the staining is detectable by flow cytometry at a level substantially above the staining detected carrying out the same procedure with an isotype-matched control under otherwise identical conditions and/or at a level substantially similar to that for cell known to be positive for the marker, and/or at a level substantially higher than that for a cell known to be negative for the marker.

A statement that a cell or population of cells is "negative" for a particular marker or lacks expression of a marker refers to the absence of substantial detectable presence on or in the cell of a particular marker. When referring to a surface marker, the term can refer to the absence of surface expression as detected by flow cytometry, for example, by staining with an antibody that specifically binds to the marker and detecting said antibody, wherein the staining is not detected by flow cytometry at a level substantially above the staining detected carrying out the same procedure with an isotype-matched control under otherwise identical conditions, and/or at a level substantially lower than that for cell known to be positive for the marker, and/or at a level substantially similar as compared to that for a cell known to be negative for the marker.

Cells to be genetically modified according to the teachings of the current disclosure can be patient-derived cells (autologous) or allogeneic when appropriate, and can also be in vivo or ex vivo.

(ii) Cell Sample Collection and Cell Enrichment. Methods of sample collection and enrichment are known by those skilled in the art. In some embodiments, cells are derived from cell lines. The cells in some embodiments are obtained from a xenogeneic source, for example, from mouse, rat, non-human primate, or pig. In particular embodiments, cells are derived from humans.

In some embodiments, T cells are derived or isolated from samples such as whole blood, peripheral blood mononuclear cells (PBMCs), leukocytes, bone marrow, thymus, tissue biopsy, tumor, leukemia, lymphoma, lymph node, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. In particular embodiments, cells from the circulating blood of a subject are obtained, e.g., by apheresis or leukapheresis. The samples, in particular embodiments, contain lymphocytes, including T cells, monocytes, granulocytes, B cells, other nucleated white blood cells, HSC, HPC, HSPC, red blood cells, and/or platelets, and in some aspects contains cells other than red blood cells and platelets and further processing is necessary.

In some embodiments, blood cells collected from a subject are washed, e.g., to remove the plasma fraction and to place the cells in an appropriate buffer or media for subsequent processing steps. In particular embodiments, the cells are washed with phosphate buffered saline (PBS). In some embodiments, the wash solution lacks calcium and/or magnesium and/or many or all divalent cations. Washing can be accomplished using a semi-automated "flow-through" centrifuge (for example, the Cobe 2991 cell processor, Baxter) according to the manufacturer's instructions. Tangential flow filtration (TFF) can also be performed. In particular embodiments, cells can be re-suspended in a variety of biocompatible buffers after washing, such as, Ca++/Mg++ free PBS.

The isolation can include one or more of various cell preparation and separation steps, including separation based on one or more properties, such as size, density, sensitivity or resistance to particular reagents, and/or affinity, e.g., immunoaffinity, to antibodies or other binding partners. In particular embodiments, the isolation is carried out using the same apparatus or equipment sequentially in a single process stream and/or simultaneously. In particular embodiments, the isolation, culture, and/or engineering of the different populations is carried out from the same starting composition or material, such as from the same sample.

In particular embodiments, a sample can be enriched for T cells by using density-based cell separation methods and related methods. For example, white blood cells can be separated from other cell types in the peripheral blood by lysing red blood cells and centrifuging the sample through a Percoll or Ficoll gradient.

In particular embodiments, a bulk T cell population can be used that has not been enriched for a particular T cell type. In particular embodiments, a selected T cell type can be enriched for and/or isolated based on cell-marker based positive and/or negative selection. In positive selection, cells having bound cellular markers are retained for further use.

In negative selection, cells not bound by a capture agent, such as an antibody to a cellular marker are retained for further use. In some examples, both fractions can be retained for a further use.

The separation need not result in 100% enrichment or removal of a particular cell population or cells expressing a particular marker. For example, positive selection of or enrichment for cells of a particular type refers to increasing the number or percentage of such cells but need not result in a complete absence of cells not expressing the marker. Likewise, negative selection, removal, or depletion of cells of a particular type refers to decreasing the number or percentage of such cells but need not result in a complete removal of all such cells.

In some examples, multiple rounds of separation steps are carried out, where the positively or negatively selected fraction from one step is subjected to another separation step, such as a subsequent positive or negative selection.

In some embodiments, an antibody or binding domain for a cellular marker is bound to a solid support or matrix, such as a magnetic bead or paramagnetic bead, to allow for separation of cells for positive and/or negative selection. For example, in some embodiments, the cells and cell populations are separated or isolated using immunomagnetic (or affinity magnetic) separation techniques (reviewed in Methods in Molecular Medicine, vol. 58: Metastasis Research Protocols, Vol. 2: Cell Behavior In Vitro and In Vivo, p 17-25 Edited by: S. A. Brooks and U. Schumacher© Humana Press Inc., Totowa, NJ); see also U.S. Pat. Nos. 4,452,773; 4,795,698; 5,200,084; and EP 452342.

In some embodiments, affinity-based selection is via magnetic-activated cell sorting (MACS) (Miltenyi Biotec, Auburn, CA). MACS systems are capable of high-purity selection of cells having magnetized particles attached thereto. In certain embodiments, MACS operates in a mode wherein the non-target and target species are sequentially eluted after the application of the external magnetic field. That is, the cells attached to magnetized particles are held in place while the unattached species are eluted. Then, after this first elution step is completed, the species that were trapped in the magnetic field and were prevented from being eluted are freed in some manner such that they can be eluted and recovered. In certain embodiments, the non-target cells are labelled and depleted from the heterogeneous population of cells.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. 1(5):355-376). In both cases, cells can be labeled with multiple markers, allowing for the isolation of well-defined cell subsets at high purity.

Cell-markers for different T cell subpopulations are described above. In particular embodiments, specific sub-populations of T cells, such as cells positive or expressing high levels of one or more surface markers, e.g., CCR7, CD45RO, CD8, CD27, CD28, CD62L, CD127, CD4, and/or CD45RA T cells, are isolated by positive or negative selection techniques.

CD3+, CD28+ T cells can be positively selected for and expanded using anti-CD3/anti-CD28 conjugated magnetic beads (e.g., DYNABEADS® M-450 CD3/CD28 T Cell Expander).

In particular embodiments, a CD8+ or CD4+ selection step is used to separate CD4+ helper and CD8+ cytotoxic T cells. Such CD8+ and CD4+ populations can be further sorted into sub-populations by positive or negative selection for markers expressed or expressed to a relatively higher degree on one or more naive, memory, and/or effector T cell subpopulations.

In some embodiments, enrichment for central memory T (TCM) cells is carried out. In particular embodiments, memory T cells are present in both CD62L subsets of CD8+ peripheral blood lymphocytes. PBMC can be enriched for or depleted of CD62L, CD8 and/or CD62L+CD8+ fractions, such as by using anti-CD8 and anti-CD62L antibodies.

In some embodiments, the enrichment for central memory T (TCM) cells is based on positive or high surface expression of CCR7, CD45RO, CD27, CD62L, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CCR7, CD45RO, and/or CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4-based separation are retained, optionally following one or more further positive or negative selection steps.

In a particular example, a sample of PBMCs or other white blood cell sample is subjected to selection of CD4+ cells, where both the negative and positive fractions are retained. The negative fraction then is subjected to negative selection based on expression of CD14 and CD45RA or RORI, and positive selection based on a marker characteristic of central memory T cells, such as CCR7, CD45RO, and/or CD62L, where the positive and negative selections are carried out in either order.

In particular embodiments, cell enrichment results in a bulk CD8+ FACs-sorted cell population.

Other cell types can be enriched based on known marker profiles and techniques. For example, CD34+ HSC, HSP, and HSPC can be enriched using anti-CD34 antibodies directly or indirectly conjugated to magnetic particles in connection with a magnetic cell separator, for example, the CliniMACS® Cell Separation System (Miltenyi Biotec, Bergisch Gladbach, Germany).

(iii) Genetically Modifying Cell Populations to Express Chimeric Antigen Receptors (CAR). Cell populations are genetically modified to express chimeric antigen receptors (CAR) described herein.

(iii-a) Genetic Engineering Techniques. Desired genes encoding CAR disclosed herein can be introduced into cells by any method known in the art, including transfection, electroporation, microinjection, lipofection, calcium phosphate mediated transfection, infection with a viral or bacteriophage vector including the gene sequences, cell fusion, chromosome-mediated gene transfer, microcell-mediated gene transfer, spheroplast fusion, in vivo nanoparticle-mediated delivery, etc. Numerous techniques are known in the art for the introduction of foreign genes into cells (see e.g., Loeffler and Behr, 1993, *Meth. Enzymol.* 217:599-618; Cohen, et al., 1993, *Meth. Enzymol.* 217:618-644; Cline, 1985, *Pharmac. Ther.* 29:69-92) and may be used, provided that the necessary developmental and physiological functions of the recipient cells are not unduly disrupted. The technique can provide for the stable transfer of the gene to the cell, so that the gene is expressible by the cell and, in certain instances, preferably heritable and expressible by its cell progeny.

The term "gene" refers to a nucleic acid sequence (used interchangeably with polynucleotide or nucleotide sequence) that encodes a CAR including a CD33-binding domain as described herein. This definition includes various sequence polymorphisms, mutations, and/or sequence variants wherein such alterations do not substantially affect the function of the encoded CAR. The term "gene" may include not only coding sequences but also regulatory regions such as promoters, enhancers, and termination regions. The term further can include all introns and other DNA sequences spliced from an mRNA transcript, along with variants resulting from alternative splice sites. Gene sequences encoding the molecule can be DNA or RNA that directs the expression of the chimeric molecule. These nucleic acid sequences may be a DNA strand sequence that is transcribed into RNA or an RNA sequence that is translated into protein. The nucleic acid sequences include both the full-length nucleic acid sequences as well as non-full-length sequences derived from the full-length protein. The sequences can also include degenerate codons of the native sequence or sequences that may be introduced to provide codon preference in a specific cell type. Portions of complete gene sequences are referenced throughout the disclosure as is understood by one of ordinary skill in the art.

Gene sequences encoding CAR are provided herein and can also be readily prepared by synthetic or recombinant methods from the relevant amino acid sequences and other description provided herein. In embodiments, the gene sequence encoding any of these sequences can also have one or more restriction enzyme sites at the 5' and/or 3' ends of the coding sequence in order to provide for easy excision and replacement of the gene sequence encoding the sequence with another gene sequence encoding a different sequence. In embodiments, the gene sequence encoding the sequences can be codon optimized for expression in mammalian cells.

"Encoding" refers to the property of specific sequences of nucleotides in a gene, such as a cDNA, or an mRNA, to serve as templates for synthesis of other macromolecules such as a defined sequence of amino acids. Thus, a gene codes for a protein if transcription and translation of mRNA corresponding to that gene produces the protein in a cell or other biological system. A "gene sequence encoding a protein" includes all nucleotide sequences that are degenerate versions of each other and that code for the same amino acid sequence or amino acid sequences of substantially similar form and function.

Polynucleotide gene sequences encoding more than one portion of an expressed CAR can be operably linked to each other and relevant regulatory sequences. For example, there can be a functional linkage between a regulatory sequence and an exogenous nucleic acid sequence resulting in expression of the latter. For another example, a first nucleic acid sequence can be operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary or helpful, join coding regions, into the same reading frame.

In any of the embodiments described herein, a polynucleotide can include a polynucleotide that encodes a self-cleaving polypeptide, wherein the polynucleotide encoding the self-cleaving polypeptide is located between the polynucleotide encoding the CAR construct and a polynucleotide encoding a transduction marker (e.g., tEGFR). Exemplary self-cleaving polypeptides include 2A peptide from porcine teschovirus-1 (P2A), *Thosea asigna* virus (T2A), equine rhinitis A virus (E2A), foot-and-mouth disease virus (F2A), or variants thereof (see FIG. 19). Further exemplary nucleic acid and amino acid sequences of 2A peptides are set forth in, for example, Kim et al. (*PLOS One* 6:e18556 (2011).

A "vector" is a nucleic acid molecule that is capable of transporting another nucleic acid. Vectors may be, e.g., plasmids, cosmids, viruses, or phage. An "expression vector" is a vector that is capable of directing the expression of a protein encoded by one or more genes carried by the vector when it is present in the appropriate environment.

"Lentivirus" refers to a genus of retroviruses that are capable of infecting dividing and non-dividing cells. Several examples of lentiviruses include HIV (human immunodeficiency virus: including HIV type 1, and HIV type 2); equine infectious anemia virus; feline immunodeficiency virus (FIV); bovine immune deficiency virus (BIV); and simian immunodeficiency virus (SIV).

"Retroviruses" are viruses having an RNA genome. "Gammaretrovirus" refers to a genus of the retroviridae family. Exemplary gammaretroviruses include mouse stem cell virus, murine leukemia virus, feline leukemia virus, feline sarcoma virus, and avian reticuloendotheliosis viruses.

Retroviral vectors (see Miller, et al., 1993, *Meth. Enzymol.* 217:581-599) can be used. In such embodiments, the gene to be expressed is cloned into the retroviral vector for its delivery into cells. In particular embodiments, a retroviral vector includes all of the cis-acting sequences necessary for the packaging and integration of the viral genome, i.e., (a) a long terminal repeat (LTR), or portions thereof, at each end of the vector; (b) primer binding sites for negative and positive strand DNA synthesis; and (c) a packaging signal, necessary for the incorporation of genomic RNA into virions. More detail about retroviral vectors can be found in Boesen, et al., 1994, *Biotherapy* 6:291-302; Clowes, et al., 1994, *J. Clin. Invest.* 93:644-651; Kiem, et al., 1994, *Blood* 83:1467-1473; Salmons and Gunzberg, 1993, *Human Gene Therapy* 4:129-141; and Grossman and Wilson, 1993, *Curr. Opin. in Genetics and Devel.* 3:110-114. Adenoviruses, adeno-associated viruses (AAV) and alphaviruses can also be used. See Kozarsky and Wilson, 1993, *Current Opinion in Genetics and Development* 3:499-503, Rosenfeld, et al., 1991, *Science* 252:431-434; Rosenfeld, et al., 1992, *Cell* 68:143-155; Mastrangeli, et al., 1993, *J. Clin. Invest.* 91:225-234; Walsh, et al., 1993, *Proc. Soc. Exp. Biol. Med.* 204:289-300; and Lundstrom, 1999, *J. Recept. Signal Transduct. Res.* 19: 673-686. Other methods of gene delivery include use of mammalian artificial chromosomes (Vos, 1998, *Curr. Op. Genet. Dev.* 8:351-359); liposomes (Tarahovsky and Ivanitsky, 1998, *Biochemistry (Mosc)* 63:607-

618); ribozymes (Branch and Klotman, 1998, *Exp. Nephrol.* 6:78-83); and triplex DNA (Chan and Glazer, 1997, *J. Mol. Med.* 75:267-282).

There are a large number of available viral vectors suitable within the current disclosure, including those identified for human gene therapy applications (see Pfeifer and Verma, 2001, *Ann. Rev. Genomics Hum. Genet.* 2:177). Methods of using retroviral and lentiviral viral vectors and packaging cells for transducing mammalian host cells with viral particles including CAR transgenes are described in, e.g., U.S. Pat. No. 8,119,772; Walchli, et al., 2011, *PLoS One* 6:327930; Zhao, et al., 2005, *J. Immunol.* 174:4415; Engels, et al., 2003, *Hum. Gene Ther.* 14:1155; Frecha, et al., 2010, *Mol. Ther.* 18:1748; and Verhoeyen, et al., 2009, *Methods Mol. Biol.* 506:97. Retroviral and lentiviral vector constructs and expression systems are also commercially available.

Targeted genetic engineering approaches may also be utilized. The CRISPR (Clustered Regularly Interspaced Short Palindromic Repeats)/Cas (CRISPR-associated protein) nuclease system is an engineered nuclease system used for genetic engineering that is based on a bacterial system. Information regarding CRISPR-Cas systems and components thereof are described in, for example, U.S. Pat. Nos. 8,697,359, 8,771,945, 8,795,965, 8,865,406, 8,871,445, 8,889,356, 8,889,418, 8,895,308, 8,906,616, 8,932,814, 8,945,839, 8,993,233 and 8,999,641 and applications related thereto; and WO2014/018423, WO2014/093595, WO2014/093622, WO2014/093635, WO2014/093655, WO2014/093661, WO2014/093694, WO2014/093701, WO2014/093709, WO2014/093712, WO2014/093718, WO2014/145599, WO2014/204723, WO2014/204724, WO2014/204725, WO2014/204726, WO2014/204727, WO2014/204728, WO2014/204729, WO2015/065964, WO2015/089351, WO2015/089354, WO2015/089364, WO2015/089419, WO2015/089427, WO2015/089462, WO2015/089465, WO2015/089473 and WO2015/089486, WO2016205711, WO2017/106657, WO2017/127807 and applications related thereto.

Particular embodiments utilize zinc finger nucleases (ZFNs) as gene editing agents. ZFNs are a class of site-specific nucleases engineered to bind and cleave DNA at specific positions. ZFNs are used to introduce double stranded breaks (DSBs) at a specific site in a DNA sequence which enables the ZFNs to target unique sequences within a genome in a variety of different cells. For additional information regarding ZFNs and ZFNs useful within the teachings of the current disclosure, see, e.g., U.S. Pat. Nos. 6,534,261; 6,607,882; 6,746,838; 6,794,136; 6,824,978; 6,866,997; 6,933,113; 6,979,539; 7,013,219; 7,030,215; 7,220,719; 7,241,573; 7,241,574; 7,585,849; 7,595,376; 6,903,185; 6,479,626; US 2003/0232410 and US 2009/0203140 as well as Gaj et al., Nat Methods, 2012, 9(8):805-7; Ramirez et al., Nucl Acids Res, 2012, 40(12):5560-8; Kim et al., Genome Res, 2012, 22(7): 1327-33; Urnov et al., Nature Reviews Genetics, 2010, 11:636-646; Miller, et al. Nature biotechnology 25, 778-785 (2007); Bibikova, et al. Science 300, 764 (2003); Bibikova, et al. Genetics 161, 1169-1175 (2002); Wolfe, et al. Annual review of biophysics and biomolecular structure 29, 183-212 (2000); Kim, et al. Proceedings of the National Academy of Sciences of the United States of America 93, 1156-1160 (1996); and Miller, et al. The EMBO journal 4, 1609-1614 (1985).

Particular embodiments can use transcription activator like effector nucleases (TALENs) as gene editing agents. TALENs refer to fusion proteins including a transcription activator-like effector (TALE) DNA binding protein and a DNA cleavage domain. TALENs are used to edit genes and genomes by inducing double DSBs in the DNA, which induce repair mechanisms in cells. Generally, two TALENs must bind and flank each side of the target DNA site for the DNA cleavage domain to dimerize and induce a DSB. For additional information regarding TALENs, see U.S. Pat. Nos. 8,440,431; 8,440,432; 8,450,471; 8,586,363; and 8,697,853; as well as Joung and Sander, Nat Rev Mol Cell Biol, 2013, 14(1):49-55; Beurdeley et al., Nat Commun, 2013, 4: 1762; Scharenberg et al., Curr Gene Ther, 2013, 13(4):291-303; Gaj et al., Nat Methods, 2012, 9(8):805-7; Miller, et al. Nature biotechnology 29, 143-148 (2011); Christian, et al. Genetics 186, 757-761 (2010); Boch, et al. Science 326, 1509-1512 (2009); and Moscou, & Bogdanove, Science 326, 1501 (2009).

Particular embodiments can utilize MegaTALs as gene editing agents. MegaTALs have a sc rare-cleaving nuclease structure in which a TALE is fused with the DNA cleavage domain of a meganuclease. Meganucleases, also known as homing endonucleases, are single peptide chains that have both DNA recognition and nuclease function in the same domain. In contrast to the TALEN, the megaTAL only requires the delivery of a single peptide chain for functional activity.

Nanoparticles that result in selective in vivo genetic modification of targeted cell types have been described and can be used within the teachings of the current disclosure. In particular embodiments, the nanoparticles can be those described in WO2014153114, WO2017181110, and WO201822672.

(iii-b) CAR Subcomponents. As described previously, CAR molecules include several distinct subcomponents that allow genetically modified cells to recognize and kill unwanted cells, such as cancer cells. The subcomponents include at least an extracellular component and an intracellular component. The extracellular component includes a binding domain that specifically binds a marker that is preferentially present on the surface of unwanted cells. When the binding domain binds such markers, the intracellular component activates the cell to destroy the bound cell. CAR additionally include a transmembrane domain that links the extracellular component to the intracellular component, and other subcomponents that can increase the CAR's function. For example, the inclusion of a spacer region and/or one or more linker sequences can allow the CAR to have additional conformational flexibility, often increasing the binding domain's ability to bind the targeted cell marker.

(iii-b-i) Binding Domains. The current disclosure provides newly developed binding domains for use in CAR based on antibodies that bind CD33. Antibodies are produced from two genes, a heavy chain gene and a light chain gene. Generally, an antibody includes two identical copies of a heavy chain, and two identical copies of a light chain. Within a variable heavy chain and variable light chain, segments referred to as complementary determining regions (CDRs) dictate epitope binding. Each heavy chain has three CDRs (i.e., CDRH1, CDRH2, and CDRH3) and each light chain has three CDRs (i.e., CDRL1, CDRL2, and CDRL3). CDR regions are flanked by framework residues (FR). The precise amino acid sequence boundaries of a given CDR or FR can be readily determined using any of a number of well-known schemes, including those described by: Kabat et al. (1991) "Sequences of Proteins of Immunological Interest," 5th Ed. Public Health Service, National Institutes of Health, Bethesda, Md. (Kabat numbering scheme); Al-Lazikani et al. (1997) J Mol Biol 273: 927-948 (Chothia numbering scheme); North et al. (2011) J Mol Biol 406(2):

228-256 (North numbering scheme); Maccallum et al. (1996) J Mol Biol 262: 732-745 (Contact numbering scheme); Martin et al. (1989) Proc. Natl. Acad. Sci., 86: 9268-9272 (AbM numbering scheme); Lefranc M P et al. (2003) Dev Comp Immunol 27(1): 55-77 (IMGT numbering scheme); and Honegger and Pluckthun (2001) J Mol Biol 309(3): 657-670 ("Aho" numbering scheme). The boundaries of a given CDR or FR may vary depending on the scheme used for identification. For example, the Kabat scheme is based on structural alignments, while the Chothia scheme is based on structural information. Numbering for both the Kabat and Chothia schemes is based upon the most common antibody region sequence lengths, with insertions accommodated by insertion letters, for example, "30a," and deletions appearing in some antibodies. The two schemes place certain insertions and deletions ("indels") at different positions, resulting in differential numbering. The Contact scheme is based on analysis of complex crystal structures and is similar in many respects to the Chothia numbering scheme. In particular embodiments, the antibody CDR sequences disclosed herein are according to Kabat numbering. CDR residues can be identified using software programs such as ABodyBuilder.

CD33 binding domains for use in CARs are derived from antibodies the 1H10, 1A9, 1E6, 1D2, 11B9, 1H8, 2D3, or 2E3. In particular embodiments, the antibodies include the following CDR sets. A CDR set refers to 3 light chain CDRs and 3 heavy chain CDRs that together result in binding to CD33.

TABLE 1

Antibody CDR Sequences using North.

| Antibody | CDR | SEQUENCE | SEQ ID NO: |
|---|---|---|---|
| 1H10 | CDRL1 | RASQGIRIYLG | 54 |
|  | CDRL2 | YATSSLQS | 55 |
|  | CDRL3 | LQDYNYPWT | 56 |
|  | CDRH1 | KGSGYIFTSYDMH | 57 |
|  | CDRH2 | IIDPSGGSTS | 58 |
|  | CDRH3 | TRDYSWSYFDY | 59 |
| 1A9 | CDRL1 | RASQDIRNDLG | 60 |
|  | CDRL2 | YGASSLQS | 61 |
|  | CDRL3 | LQEYNYPCT | 62 |
|  | CDRH1 | AASGFTFSIYDMH | 63 |
|  | CDRH2 | AIGTAGDTY | 64 |
|  | CDRH3 | AREYSGYYFDY | 65 |
| 1E6 | CDRL1 | RASQGIRNDLG | 66 |
|  | CDRL2 | YAASNLQS | 67 |
|  | CDRL3 | LQDYSYPRT | 68 |
|  | CDRH1 | AASGFTFSSYDIH | 69 |
|  | CDRH2 | VIWYDGSHNY | 70 |
|  | CDRH3 | ARDYSGSYYDY | 71 |
| 1D2 | CDRL1 | RASQGIRNDLG | 66 |
|  | CDRL2 | YATSSLQS | 55 |
|  | CDRL3 | LQDYSYPRT | 68 |
|  | CDRH1 | AASGFTFSSYDIH | 69 |
|  | CDRH2 | VIWYDGSQKY | 72 |
|  | CDRH3 | ARDYSGSYYDY | 71 |
| 1B9 | CDRL1 | RASQDIRNDLG | 60 |
|  | CDRL2 | YAASSLQS | 73 |
|  | CDRL3 | LQDYSYPRT | 68 |
|  | CDRH1 | AASGFIFSSYDIH | 74 |
|  | CDRH2 | VIWYDGSHNY | 70 |
|  | CDRH3 | ARDYSGSYFDY | 75 |
| 1H8 | CDRL1 | RASQNIGGNLH | 76 |
|  | CDRL2 | RYATQPFS | 93 |

TABLE 1-continued

Antibody CDR Sequences using North.

| Antibody | CDR | SEQUENCE | SEQ ID NO: |
|---|---|---|---|
|  | CDRL3 | HQSSSLPLT | 78 |
|  | CDRH1 | AASGFTFGSYGMH | 94 |
|  | CDRH2 | VIWYDGSNEY | 95 |
|  | CDRH3 | ARDLDYDSSGGDY | 96 |
| 2D3 | CDRL1 | RASQSGSSSFLS | 97 |
|  | CDRL2 | YGASTRAT | 98 |
|  | CDRL3 | QQDYNLPFT | 84 |
|  | CDRH1 | AASGFTFSIYAMS | 99 |
|  | CDRH2 | AISDSGGTTY | 100 |
|  | CDRH3 | AKRTRYFNGMDV | 101 |
| 2E3 | CDRL1 | RASQSVSSSYLA | 102 |
|  | CDRL2 | YGTSSRAT | 103 |
|  | CDRL3 | QQYGSSPT | 90 |
|  | CDRH1 | AASGFTFSSYGMH | 104 |
|  | CDRH2 | VIWYGGSNKY | 105 |
|  | CDRH3 | ARDGTGENYYYYVMDV | 106 |

TABLE 2

Antibody CDR Sequences using IMGT

| Antibody | CDR | SEQUENCE | SEQ ID NO: |
|---|---|---|---|
| 1H10 | CDRL1 | QGIRIY | 107 |
|  | CDRL2 | ATS | N/A |
|  | CDRL3 | LQDYNYPWT | 56 |
|  | CDRH1 | GYIFTSYD | 108 |
|  | CDRH2 | IDPSGGST | 109 |
|  | CDRH3 | TRDYSWSYFDY | 59 |
| 1A9 | CDRL1 | QDIRND | 110 |
|  | CDRL2 | GAS | N/A |
|  | CDRL3 | LQEYNYPCT | 62 |
|  | CDRH1 | GFTFSIYD | 111 |
|  | CDRH2 | IGTAGDT | 112 |
|  | CDRH3 | AREYSGYYFDY | 65 |
| 1E6 | CDRL1 | QGIRND | 113 |
|  | CDRL2 | AAS | N/A |
|  | CDRL3 | LQDYSYPRT | 68 |
|  | CDRH1 | GFTFSSYD | 114 |
|  | CDRH2 | IWYDGSHN | 115 |
|  | CDRH3 | ARDYSGSYYDY | 71 |
| 1D2 | CDRL1 | QGIRND | 113 |
|  | CDRL2 | ATS | N/A |
|  | CDRL3 | LQDYSYPRT | 68 |
|  | CDRH1 | GFTFSSYD | 114 |
|  | CDRH2 | IWYDGSQK | 116 |
|  | CDRH3 | ARDYSGSYYDY | 71 |
| 1B9 | CDRL1 | QDIRND | 110 |
|  | CDRL2 | AAS | N/A |
|  | CDRL3 | LQDYSYPRT | 68 |
|  | CDRH1 | GFIFSSYD | 117 |
|  | CDRH2 | IWYDGSHN | 115 |
|  | CDRH3 | ARDYSGSYFDY | 75 |
| 1H8 | CDRL1 | QNIGGN | 118 |
|  | CDRL2 | YAT | N/A |
|  | CDRL3 | HQSSSLPLT | 78 |
|  | CDRH1 | GFTFGSYG | 119 |
|  | CDRH2 | IWYDGSNE | 120 |
|  | CDRH3 | ARDLDYDSSGGDY | 96 |
| 2D3 | CDRL1 | QSGSSSF | 121 |
|  | CDRL2 | GAS | N/A |
|  | CDRL3 | QQDYNLPFT | 84 |
|  | CDRH1 | GFTFSIYA | 122 |

TABLE 2-continued

| Antibody CDR Sequences using IMGT | | | |
|---|---|---|---|
| Antibody | CDR | SEQUENCE | SEQ ID NO: |
| | CDRH2 | ISDSGGTT | 123 |
| | CDRH3 | AKRTRYFNGMDV | 101 |
| 2E3 | CDRL1 | QSVSSSY | 124 |
| | CDRL2 | GTS | N/A |
| | CDRL3 | QQYGSSPT | 90 |
| | CDRH1 | GFTFSSYG | 125 |
| | CDRH2 | IWYGGSNK | 126 |
| | CDRH3 | ARDGTGENYYYVMDV | 106 |

TABLE 3

| Antibody CDR Sequences using Kabat. | | | |
|---|---|---|---|
| Antibody | CDR | SEQUENCE | SEQ ID NO: |
| 1H10 | CDRL1 | RASQGIRIYLG | 54 |
| | CDRL2 | ATSSLQS | 127 |
| | CDRL3 | LQDYNYPWT | 56 |
| | CDRH1 | SYDMH | 128 |
| | CDRH2 | IIDPSGGSTSYAQKFQG | 129 |
| | CDRH3 | DYSWSYFDY | 130 |
| 1A9 | CDRL1 | RASQDIRNDLG | 60 |
| | CDRL2 | GASSLQS | 131 |
| | CDRL3 | LQEYNYPCT | 62 |
| | CDRH1 | IYDMH | 132 |
| | CDRH2 | AIGTAGDTYYAGSVKG | 133 |
| | CDRH3 | EYSGYYFDY | 134 |
| 1E6 | CDRL1 | RASQGIRNDLG | 66 |
| | CDRL2 | AASNLQS | 135 |
| | CDRL3 | LQDYSYPRT | 68 |
| | CDRH1 | SYDIH | 136 |
| | CDRH2 | VIWYDGSHNYYSDSVKG | 137 |
| | CDRH3 | DYSGSYYDY | 138 |
| 1D2 | CDRL1 | RASQGIRNDLG | 66 |
| | CDRL2 | ATSSLQS | 127 |
| | CDRL3 | LQDYSYPRT | 68 |
| | CDRH1 | SYDIH | 136 |
| | CDRH2 | VIWYDGSQKYYADSVKG | 139 |
| | CDRH3 | DYSGSYYDY | 138 |
| 1B9 | CDRL1 | RASQDIRNDLG | 60 |
| | CDRL2 | AASSLQS | 140 |
| | CDRL3 | LQDYSYPRT | 68 |
| | CDRH1 | SYDIH | 136 |
| | CDRH2 | VIWYDGSHNYYSDSVKG | 137 |
| | CDRH3 | DYSGSYFDY | 141 |
| 1H8 | CDRL1 | RASQNIGGNLH | 76 |
| | CDRL2 | YATQPFS | 77 |
| | CDRL3 | HQSSSLPLT | 78 |
| | CDRH1 | SYGMH | 79 |
| | CDRH2 | VIWYDGSNEYYADSVKG | 142 |
| | CDRH3 | DLDYDSSGGDY | 143 |
| 2D3 | CDRL1 | RASQSGSSSFLS | 97 |
| | CDRL2 | GASTRAT | 83 |
| | CDRL3 | QQDYNLPFT | 84 |
| | CDRH1 | IYAMS | 85 |
| | CDRH2 | AISDSGGTTYYADSVKG | 144 |
| | CDRH3 | RTRYFNGMDV | 145 |
| 2E3 | CDRL1 | RASQSVSSSYLA | 102 |
| | CDRL2 | GTSSRAT | 89 |
| | CDRL3 | QQYGSSPT | 90 |
| | CDRH1 | SYGMH | 79 |

TABLE 3-continued

| Antibody CDR Sequences using Kabat. | | | |
|---|---|---|---|
| Antibody | CDR | SEQUENCE | SEQ ID NO: |
| | CDRH2 | VIWYGGSNKYYADSVKG | 146 |
| | CDRH3 | DGTGENYYYVMDV | 147 |

TABLE 4

| Antibody CDR Sequences using Chothia | | | |
|---|---|---|---|
| Antibody | CDR | SEQUENCE | SEQ ID NO: |
| 1H10 | CDRL1 | RASQGIRIYLG | 54 |
| | CDRL2 | ATSSLQS | 127 |
| | CDRL3 | LQDYNYPWT | 56 |
| | CDRH1 | GYIFTSY | 148 |
| | CDRH2 | DPSGGS | 149 |
| | CDRH3 | DYSWSYFDY | 130 |
| 1A9 | CDRL1 | RASQDIRNDLG | 60 |
| | CDRL2 | GASSLQS | 131 |
| | CDRL3 | LQEYNYPCT | 62 |
| | CDRH1 | GFTFSIY | 150 |
| | CDRH2 | GTAGD | 151 |
| | CDRH3 | EYSGYYFDY | 134 |
| 1E6 | CDRL1 | RASQGIRNDLG | 66 |
| | CDRL2 | AASNLQS | 135 |
| | CDRL3 | LQDYSYPRT | 68 |
| | CDRH1 | GFTFSSY | 152 |
| | CDRH2 | WYDGSH | 153 |
| | CDRH3 | DYSGSYYDY | 138 |
| 1D2 | CDRL1 | RASQGIRNDLG | 66 |
| | CDRL2 | ATSSLQS | 127 |
| | CDRL3 | LQDYSYPRT | 68 |
| | CDRH1 | GFTFSSY | 152 |
| | CDRH2 | WYDGSQ | 154 |
| | CDRH3 | DYSGSYYDY | 138 |
| 1B9 | CDRL1 | RASQDIRNDLG | 60 |
| | CDRL2 | AASSLQS | 140 |
| | CDRL3 | LQDYSYPRT | 68 |
| | CDRH1 | GFIFSSY | 155 |
| | CDRH2 | WYDGSH | 153 |
| | CDRH3 | DYSGSYFDY | 141 |
| 1H8 | CDRL1 | RASQNIGGNLH | 76 |
| | CDRL2 | YATQPFS | 77 |
| | CDRL3 | HQSSSLPLT | 78 |
| | CDRH1 | GFTFGSY | 156 |
| | CDRH2 | WYDGSN | 157 |
| | CDRH3 | DLDYDSSGGDY | 143 |
| 2D3 | CDRL1 | RASQSGSSSFLS | 97 |
| | CDRL2 | GASTRAT | 83 |
| | CDRL3 | QQDYNLPFT | 84 |
| | CDRH1 | GFTFSIY | 150 |
| | CDRH2 | SDSGGT | 158 |
| | CDRH3 | RTRYFNGMDV | 145 |
| 2E3 | CDRL1 | RASQSVSSSYLA | 102 |
| | CDRL2 | GTSSRAT | 89 |
| | CDRL3 | QQYGSSPT | 90 |
| | CDRH1 | GFTFSSY | 152 |
| | CDRH2 | WYGGSN | 159 |
| | CDRH3 | DGTGENYYYVMDV | 147 |

TABLE 5

Antibody CDR Sequences-Set 5.

| Antibody | CDR | SEQUENCE | SEQ ID NO: |
|----------|-----|----------|------------|
| 1H10 | CDRL1 | RASQGIRIYLG | 54 |
| | CDRL2 | YATSSLQS | 55 |
| | CDRL3 | LQDYNYPWT | 56 |
| | CDRH1 | KGSGYIFTSYDMH | 57 |
| | CDRH2 | IIDPSGGSTS | 58 |
| | CDRH3 | TRDYSWSYFDY | 59 |
| | | | |
| 1A9 | CDRL1 | RASQDIRNDLG | 60 |
| | CDRL2 | YGASSLQS | 61 |
| | CDRL3 | LQEYNYPCT | 62 |
| | CDRH1 | AASGFTFSIYDMH | 63 |
| | CDRH2 | AIGTAGDTY | 64 |
| | CDRH3 | AREYSGYYFDY | 65 |
| | | | |
| 1E6 | CDRL1 | RASQGIRNDLG | 66 |
| | CDRL2 | YAASNLQS | 67 |
| | CDRL3 | LQDYSYPRT | 68 |
| | CDRH1 | AASGFTFSSYDIH | 69 |
| | CDRH2 | VIWYDGSHNY | 70 |
| | CDRH3 | ARDYSGSYYDY | 71 |
| | | | |
| 1D2 | CDRL1 | RASQGIRNDLG | 66 |
| | CDRL2 | YATSSLQS | 55 |
| | CDRL3 | LQDYSYPRT | 68 |
| | CDRH1 | AASGFTFSSYDIH | 69 |
| | CDRH2 | VIWYDGSQKY | 72 |
| | CDRH3 | ARDYSGSYYDY | 71 |
| | | | |
| 1B9 | CDRL1 | RASQDIRNDLG | 60 |
| | CDRL2 | YAASSLQS | 73 |
| | CDRL3 | LQDYSYPRT | 68 |
| | CDRH1 | AASGFIFSSYDIH | 74 |
| | CDRH2 | VIWYDGSHNY | 70 |
| | CDRH3 | ARDYSGSYFDY | 75 |
| | | | |
| 1H8 | CDRL1 | RASQNIGGNLH | 76 |
| | CDRL2 | YATQPFS | 77 |
| | CDRL3 | HQSSSLPLT | 78 |
| | CDRH1 | SYGMH | 79 |
| | CDRH2 | IWYDGSNEYYADSVKG | 80 |
| | CDRH3 | DLDYDSSG | 81 |
| | | | |
| 2D3 | CDRL1 | QSGSSSFLS | 82 |
| | CDRL2 | GASTRAT | 83 |
| | CDRL3 | QQDYNLPFT | 84 |
| | CDRH1 | IYAMS | 85 |
| | CDRH2 | ISDSGGTTYYADSVKG | 86 |
| | CDRH3 | RTRYFNG | 87 |
| | | | |
| 2E3 | CDRL1 | QSVSSSYLA | 88 |
| | CDRL2 | GTSSRAT | 89 |
| | CDRL3 | QQYGSSPT | 90 |
| | CDRH1 | SYGMH | 79 |
| | CDRH2 | IWYGGSNKYYADSVKG | 91 |
| | CDRH3 | DGTGENYYYYV | 92 |

Particular embodiments include an scFV derived from the CDRs, VL or VH of 1H10, 1A9; 1E6; 1D2; 11B9; 11H8; 2D3; or 2E3 for use in a CAR. Examples of such scFvs are provided in FIG. 19. scFvs can be formed in a VH-VL orientation or a VL-VH orientation. scFvs for use in CAR can also be formulated from the variable chains of these antibodies.

In particular embodiments, the 1H10 antibody includes a variable light chain including the sequence:
AIQMTQSPSSLSASVGDRVTITCRASQ-
GIRIYLGWYQQKPGKAPKLLI-
YATSSLQSGVPSRFSG SGSGTDFTLTISSLQPED-
FATYYCLQDYNYPWTFGQGTKVEIK (SEQ ID NO: 238) and a variable heavy chain including the sequence:

(SEQ ID NO: 239)
QVQLVQSGAEVKKPGASVKVSCKGSGYIFTSYDMHWVRQAPGQGLEW

MGIIDPSGGSTSYAQKFQGRVTMTRDTSMSTVYMELSSLRSEDTAVY

YCTRDYSWSYFDYWGQGTLVTVSS.

In particular embodiments, the 1A9 antibody includes a variable light chain including the sequence:
AIQMTQSPSSLSASVGDRVTIT-
CRASQDIRNDLGWYQQKPGKAPKILIY-
GASSLQSGVPSRFSG SGSGTDFTFTISSLQPED-
FATYYCLQEYNYPCTFGQGTKLEIK (SEQ ID NO: 240) and a variable heavy chain including the sequence:

(SEQ ID NO: 241)
EVQLVESGGGLVQPGGSLRLSCAASGFTFSIYDMHWVRQATGKGLEW

VSAIGTAGDTYYAGSVKGRFTISRENAKNSLYLQMNSLRAGDTAVYY

CAREYSGYYFDYWGQGTLVTVSS.

In particular embodiments, the 1E6 antibody includes a variable light chain including the sequence:
AIQMTQSPSSLSASVGDRVTITCRASQ-
GIRNDLGWYQQKPGKAPKLLI-
YAASNLQSGVPSRFS GSGSGTDFTLTISSLQPED-
FATYYCLQDYSYPRTFGQGTKVEIK (SEQ ID NO: 242) and a variable heavy chain including the sequence:

(SEQ ID NO: 243)
QVQLVESGGGVVQPGRSLRLSCAASGFTFSSYDIHWVRQAPGKGLEW

VAVIWYDGSHNYYSDSVKGRFTISRDNSKNTLYLQMNSLRAEDTAVY

YCARDYSGSYYDYWGQGTLVTVSS.

In particular embodiments, the 1D2 antibody includes a variable light chain including the sequence:
AIQMTQSPSSLSASVGDRVTITCRASQ-
GIRNDLGWYQQKPGKAPELLI-
YATSSLQSGVPSRFSG SGSGTDFTLIISSLQPED-
FATYYCLQDYSYPRTFGQGTKVEIK (SEQ ID NO: 244) and a variable heavy chain including the sequence:

(SEQ ID NO: 245)
QVQLVESGGGVVQPGRSLRLSCAASGFTFSSYDIHWVRQAPGKGLEW

VAVIWYDGSQKYYADSVKGRFTISRDNSKNTLYLQMNSLRAEDTAVY

YCARDYSGSYYDYWGQGTLVTVSS.

In particular embodiments, the 1B9 antibody includes a variable light chain including the sequence:
AIQMTQSPSSLSASVGDRVTIT-
CRASQDIRNDLGWYLQRPGKAPKLLI-
YAASSLQSGVPSRFSG SGSGTDFTLTISSLQPED-
FATYYCLQDYSYPRTFGQGTTVEIK (SEQ ID NO: 246) and a variable heavy chain including the sequence:

(SEQ ID NO: 247)
QVQLVESGGGVVQPGRSLRLSCAASGFIFSSYDIHWVRQAPGKGLEW

VAVIWYDGSHNYYSDSVKGRFTISRDNSKNTLYLQMNSLRAEDTAVY

YCARDYSGSYFDYWGQGTLVTVSS.

In particular embodiments, the CD33$^{V\text{-}set}$ antibody includes 1H8. In particular embodiments, the 1H8 antibody includes a variable light chain including the sequence:

EIVLTQSPDFQSVTPKEKVTITCRASQNIGG-
NLHWYQQKPDQSPKLLIRYATQPFSGVPSRFGG
SGSGTDFTLTINSLEAEDAATYY-
CHQSSSLPLTFGGGTKVEIK (SEQ ID NO: 248) and
a variable heavy chain including the sequence:

(SEQ ID NO: 249)
QVQLVESGGGVVQPGGSLRLSCAASGFTFGSYGMHWVRQAPGKGLEW

VAVIWYDGSNEYYADSVKGRFTVSRDNSKHTLYLQMNRLRAEDTAVY

YCARDLDYDSSGGDYWGQGILVLVSS.

In particular embodiments, the CD33$^{V\text{-}set}$ antibody includes 2D3. In particular embodiments, the 2D3 antibody includes a variable light chain including the sequence:

EIVMTQSPATLSLSPGER-
ATLSCRASQSGSSSFLSWYQQKPGQAPRLLIY-
GASTRATGIPARFS  GSGSGTDFTLTISSLQPED-
FAVYYCQQDYNLPFTFGPGTKVDIK (SEQ ID NO:
250) and a variable heavy chain including the
sequence:

(SEQ ID NO: 251)
EVQLLESGGGLVQPGGSLSLSCAASGFTFSIYAMSWVRQAPGKGLEW

VSAISDSGGTTYYADSVKGRFTISRDNSKNMLYLEMNSLRAEDTAIY

YCAKRTRYFNGMDVWGQGTTVTVSS.

In particular embodiments, the CD33$^{V\text{-}set}$ antibody includes 2E3. In particular embodiments, the 2E3 antibody includes a variable light chain including the sequence:

EIVLTQSPGTLSLSPGERATLSCRASQSVSSSY-
LAWYQQKPGQAPRLLIYGTSSRATGIPDRFS
GSGSGTDFTLTISRLEPED-
FAVYYCQQYGSSPTFGGGTKVEIK (SEQ ID NO:
252) and a variable heavy chain including the
sequence:

(SEQ ID NO: 253)
QVCLVESGGGVVQPGKSLRLSCAASGFTFSSYGMHWVRQAPGKGLEW

VAVIWYGGSNKYYADSVKGRFTISRDNSKNTLYLQMNSLRAEDTAVY

YCARDGTGENYYYYVMDVWGQGTTVTVS.

In some instances, additional scFv based on the binding domains described herein and for use in a CAR can be prepared according to methods known in the art (see, for example, Bird et al., (1988) Science 242:423-426 and Huston et al., (1988) Proc. Natl. Acad. Sci. USA 85:5879-5883). ScFv molecules can be produced by linking VH and VL regions of an antibody together using flexible polypeptide linkers. If a short polypeptide linker is employed (e.g., between 5-10 amino acids) intrachain folding is prevented. Interchain folding is also required to bring the two variable regions together to form a functional epitope binding site. For examples of linker orientations and sizes see, e.g., Hollinger et al. 1993 Proc Natl Acad. Sci. U.S.A. 90:6444-6448, US 2005/0100543, US 2005/0175606, US 2007/0014794, and WO2006/020258 and WO2007/024715. More particularly, linker sequences that are used to connect the VL and VH of an scFv are generally five to 35 amino acids in length. In particular embodiments, a VL-VH linker includes from five to 35, ten to 30 amino acids or from 15 to 25 amino acids. Variation in the linker length may retain or enhance activity, giving rise to superior efficacy in activity studies. scFv are commonly used as the binding domains of CAR.

Other binding fragments, such as Fv, Fab, Fab', F(ab')2, can also be used within the CAR disclosed herein. Additional examples of antibody-based binding domain formats for use in a CAR include scFv-based grababodies and soluble VH domain antibodies. These antibodies form binding regions using only heavy chain variable regions. See, for example, Jespers et al., Nat. Biotechnol. 22:1161, 2004; Cortez-Retamozo et al., Cancer Res. 64:2853, 2004; Baral et al., Nature Med. 12:580, 2006; and Barthelemy et al., J. Biol. Chem. 283:3639, 2008.

Functional variants include one or more residue additions or substitutions that do not substantially impact the physiological effects of the protein. Functional fragments include one or more deletions or truncations that do not substantially impact the physiological effects of the protein. A lack of substantial impact can be confirmed by observing experimentally comparable results in an activation study or a binding study. Functional variants and functional fragments of intracellular domains (e.g., intracellular signaling domains) transmit activation or inhibition signals comparable to a wild-type reference when in the activated state of the current disclosure. Functional variants and functional fragments of binding domains bind their cognate antigen or ligand at a level comparable to a wild-type reference.

In particular embodiments, a VL region in a binding domain of the present disclosure is derived from or based on a VL of an antibody disclosed herein and contains one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions), or a combination of the above-noted changes, when compared with the VL of the antibody disclosed herein. An insertion, deletion or substitution may be anywhere in the VL region, including at the amino- or carboxy-terminus or both ends of this region, provided that each CDR includes zero changes or at most one, two, or three changes and provided a binding domain containing the modified VL region can still specifically bind its target with an affinity similar to the wild type binding domain.

In particular embodiments, a binding domain VH region of the present disclosure can be derived from or based on a VH of an antibody disclosed herein and can contain one or more (e.g., 2, 3, 4, 5, 6, 7, 8, 9, 10) insertions, one or more (e.g., 2, 3, 4, 5, 6, 7, 8, 9, 10) deletions, one or more (e.g., 2, 3, 4, 5, 6, 7, 8, 9, 10) amino acid substitutions (e.g., conservative amino acid substitutions or non-conservative amino acid substitutions), or a combination of the above-noted changes, when compared with the VH of the antibody disclosed herein. An insertion, deletion or substitution may be anywhere in the VH region, including at the amino- or carboxy-terminus or both ends of this region, provided that each CDR includes zero changes or at most one, two, or three changes and provided a binding domain containing the modified VH region can still specifically bind its target with an affinity similar to the wild type binding domain.

In particular embodiments, a binding domain includes or is a sequence that is at least 90%, at least 91%, at least 92%, at least 93%, at least 94%, at least 95%, at least 96%, at least 97%, at least 98%, at least 99%, at least 99.5%, or 100% identical to an amino acid sequence of a light chain variable region (VL) or to a heavy chain variable region (VH), or both, wherein each CDR includes zero changes or at most one, two, or three changes, from an antibody disclosed herein or fragment or derivative thereof that specifically binds to CD33.

(iii-b-ii) Spacer regions are used to create appropriate distances and/or flexibility from other CAR sub-components. As indicated, in particular embodiments, the length of a spacer region is customized for binding CD33-expressing cells and mediating destruction. In particular embodiments, a spacer region length can be selected based upon the location of a cellular marker epitope, affinity of a binding domain for the epitope, and/or the ability of the CD33-targeting agent to mediate cell destruction following CD33 binding.

Spacer regions typically include those having 10 to 250 amino acids, 10 to 200 amino acids, 10 to 150 amino acids, 10 to 100 amino acids, 10 to 50 amino acids, or 10 to 25 amino acids.

In particular embodiments, a spacer region is 5 amino acids, 8 amino acids, 10 amino acids, 12 amino acids, 14 amino acids, 20 amino acids, 21 amino acids, 26 amino acids, 27 amino acids, 45 amino acids, or 50 amino acids. These lengths qualify as short spacer regions.

In particular embodiments, a spacer region is 100 amino acids, 110 amino acids, 120 amino acids, 125 amino acids, 128 amino acids, 131 amino acids, 135 amino acids, 140 amino acids, 150 amino acids, 160 amino acids, or 170 amino acids. These lengths qualify as intermediate spacer regions.

Exemplary spacer regions include all or a portion of an immunoglobulin hinge region. An immunoglobulin hinge region may be a wild-type immunoglobulin hinge region or an altered wild-type immunoglobulin hinge region. In certain embodiments, an immunoglobulin hinge region is a human immunoglobulin hinge region. As used herein, a "wild type immunoglobulin hinge region" refers to a naturally occurring upper and middle hinge amino acid sequences interposed between and connecting the CH1 and CH2 domains (for IgG, IgA, and IgD) or interposed between and connecting the CH1 and CH3 domains (for IgE and IgM) found in the heavy chain of an antibody.

An immunoglobulin hinge region may be an IgG, IgA, IgD, IgE, or IgM hinge region. An IgG hinge region may be an IgG1, IgG2, IgG3, or IgG4 hinge region. Sequences from IgG1, IgG2, IgG3, IgG4 or IgD can be used alone or in combination with all or a portion of a CH2 region; all or a portion of a CH3 region; or all or a portion of a CH2 region and all or a portion of a CH3 region.

In particular embodiments, the spacer is a short spacer including an IgG4 hinge region. In particular embodiments the short spacer is encoded by either of SEQ ID NOs: 10 or 11. In particular embodiments, the spacer is an intermediate spacer including an IgG4 hinge region and an IgG4 hinge CH3 region. In particular embodiments the intermediate spacer is encoded by SEQ ID NO: 12. In particular embodiments, the spacer is a long spacer including an IgG4 hinge region, an IgG4 CH3 region, and an IgG4 CH2 region. In particular embodiments the long spacer is encoded by SEQ ID NO: 13.

Other examples of hinge regions that can be used CAR described herein include the hinge region present in the extracellular regions of type 1 membrane proteins, such as CD8a, CD4, CD28 and CD7, which may be wild-type or variants thereof.

In particular embodiments, a spacer region includes a hinge region that includes a type II C-lectin interdomain (stalk) region or a cluster of differentiation (CD) molecule stalk region. A "stalk region" of a type II C-lectin or CD molecule refers to the portion of the extracellular domain (ECD) of the type II C-lectin or CD molecule that is located between the C-type lectin-like domain (CTLD; e.g., similar to CTLD of natural killer cell receptors) and the hydrophobic portion (transmembrane domain). For example, the ECD of human CD94 (GenBank Accession No. AAC50291.1) corresponds to amino acid residues 34-179, but the CTLD corresponds to amino acid residues 61-176, so the stalk region of the human CD94 molecule includes amino acid residues 34-60, which are located between the hydrophobic portion (transmembrane domain) and CTLD (see Boyington et al., Immunity 10:15, 1999; for descriptions of other stalk regions, see also Beavil et al., Proc. Nat'l. Acad. Sci. USA 89:153, 1992; and Figdor et al., Nat. Rev. Immunol. 2:11, 2002). These type II C-lectin or CD molecules may also have junction amino acids (described below) between the stalk region and the transmembrane region or the CTLD. In another example, the 233 amino acid human NKG2A protein (GenBank Accession No. P26715.1) has a hydrophobic portion (transmembrane domain) ranging from amino acids 71-93 and an ECD ranging from amino acids 94-233. The CTLD includes amino acids 119-231 and the stalk region includes amino acids 99-116, which may be flanked by additional junction amino acids. Other type II C-lectin or CD molecules, as well as their extracellular ligand-binding domains, stalk regions, and CTLDs are known in the art (see, e.g., GenBank Accession Nos. NP 001993.2; AAH07037.1; NP 001773.1; AAL65234.1; CAA04925.1; for the sequences of human CD23, CD69, CD72, NKG2A, and NKG2D and their descriptions, respectively).

(iii-b-iii) Transmembrane Domains. As indicated, transmembrane domains within a CAR serve to connect the extracellular component and intracellular component through the cell membrane. The transmembrane domain can anchor the expressed molecule in the modified cell's membrane.

The transmembrane domain can be derived either from a natural and/or a synthetic source. When the source is natural, the transmembrane domain can be derived from any membrane-bound or transmembrane protein. Transmembrane domains can include at least the transmembrane region(s) of the α, β or ζ chain of a T-cell receptor, CD28, CD27, CD3 epsilon, CD45, CD4, CD5, CD8, CD9, CD16, CD22; CD33, CD37, CD64, CD80, CD86, CD134, CD137 and CD154. In particular embodiments, a transmembrane domain may include at least the transmembrane region(s) of, e.g., KIRDS2, OX40, CD2, CD27, LFA-1 (CD 11a, CD18), ICOS (CD278), 4-1BB (CD137), GITR, CD40, BAFFR, HVEM (LIGHTR), SLAMF7, NKp80 (KLRF1), NKp44, NKp30, NKp46, CD160, CD19, IL2Rβ, IL2Rγ, IL7R a, ITGA1, VLA1, CD49a, ITGA4, IA4, CD49D, ITGA6, VLA-6, CD49f, ITGAD, CDI ld, ITGAE, CD103, ITGAL, CDI la, ITGAM, CDI lb, ITGAX, CDI lc, ITGB1, CD29, ITGB2, CD18, ITGB7, TNFR2, DNAM1(CD226), SLAMF4 (CD244, 2B4), CD84, CD96 (Tactile), CEACAM1, CRT AM, Ly9(CD229), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKG2D, or NKG2C. In particular embodiments, a variety of human hinges can be employed as well including the human Ig (immunoglobulin) hinge (e.g., an IgG4 hinge, an IgD hinge), a GS linker (e.g., a GS linker described herein), a KIR2DS2 hinge or a CD8a hinge.

In particular embodiments, a transmembrane domain has a three-dimensional structure that is thermodynamically stable in a cell membrane, and generally ranges in length from 15 to 30 amino acids. The structure of a transmembrane domain can include an α helix, a β barrel, a β sheet, a β helix, or any combination thereof.

A transmembrane domain can include one or more additional amino acids adjacent to the transmembrane region, e.g., one or more amino acid within the extracellular region of the CAR (e.g., up to 15 amino acids of the extracellular region) and/or one or more additional amino acids within the intracellular region of the CAR (e.g., up to 15 amino acids of the intracellular components). In one aspect, the transmembrane domain is from the same protein that the signaling domain, co-stimulatory domain or the hinge domain is derived from. In another aspect, the transmembrane domain is not derived from the same protein that any other domain of the CAR is derived from. In some instances, the transmembrane domain can be selected or modified by amino acid substitution to avoid binding of such domains to the transmembrane domains of the same or different surface membrane proteins to minimize interactions with other unintended members of the receptor complex. In particular embodiments, the transmembrane domain is encoded by the nucleic acid sequence encoding the CD28 transmembrane domain (SEQ ID NOs: 21-23). In particular embodiments, the transmembrane domain includes the amino acid sequence of the CD28 transmembrane domain (SEQ ID NOs: 24 and 25).

(iii-b-iv) Intracellular Effector Domains. The intracellular effector domains of a CAR are responsible for activation of the cell in which the CAR is expressed. The term "effector domain" is thus meant to include any portion of the intracellular domain sufficient to transduce an activation signal. An effector domain can directly or indirectly promote a biological or physiological response in a cell when receiving the appropriate signal. In certain embodiments, an effector domain is part of a protein or protein complex that receives a signal when bound, or it binds directly to a target molecule, which triggers a signal from the effector domain. An effector domain may directly promote a cellular response when it contains one or more signaling domains or motifs, such as an immunoreceptor tyrosine-based activation motif (ITAM). In other embodiments, an effector domain will indirectly promote a cellular response by associating with one or more other proteins that directly promote a cellular response, such as co-stimulatory domains.

Effector domains can provide for activation of at least one function of a modified cell upon binding to the cellular marker expressed by a cancer cell. Activation of the modified cell can include one or more of differentiation, proliferation and/or activation or other effector functions. In particular embodiments, an effector domain can include an intracellular signaling component including a T cell receptor and a co-stimulatory domain which can include the cytoplasmic sequence from co-receptor or co-stimulatory molecule.

An effector domain can include one, two, three or more intracellular signaling components (e.g., receptor signaling domains, cytoplasmic signaling sequences), co-stimulatory domains, or combinations thereof. Exemplary effector domains include signaling and stimulatory domains selected from: 4-1BB (CD137), CARD11, CD3γ, CD3δ, CD3ε, CD3ζ, CD27, CD28, CD79A, CD79B, DAP10, FcRα, FcRβ (FcεR1b), FcRγ, Fyn, HVEM (LIGHTR), ICOS, LAG3, LAT, Lck, LRP, NKG2D, NOTCH1, pTα, PTCH2, OX40, ROR2, Ryk, SLAMF1, Slp76, TCRα, TCRβ, TRIM, Wnt, Zap70, or any combination thereof. In particular embodiments, exemplary effector domains include signaling and co-stimulatory domains selected from: CD86, FcγRIIa, DAP12, CD30, CD40, PD-1, lymphocyte function-associated antigen-1 (LFA-1), CD2, CD7, LIGHT, NKG2C, B7-H3, a ligand that specifically binds with CD83, CDS, ICAM-1, GITR, BAFFR, SLAMF7, NKp80 (KLRF1), CD127, CD160, CD19, CD4, CD8a, CD8P, IL2Rβ, IL2Rγ, IL7Ra, ITGA4, VLA1, CD49a, IA4, CD49D, ITGA6, VLA-6, CD49f, ITGAD, CD11d, ITGAE, CD103, ITGAL, CD11a, ITGAM, CD11b, ITGAX, CD11c, ITGB1, CD29, ITGB2, CD18, ITGB7, TNFR2, TRANCE/RANKL, DNAM1 (CD226), SLAMF4 (CD244, 2B4), CD84, CD96 (Tactile), CEACAM1, CRTAM, Ly9 (CD229), PSGL1, CD100 (SEMA4D), CD69, SLAMF6 (NTB-A, Ly108), SLAM (CD150, IPO-3), BLAME (SLAMF8), SELPLG (CD162), LTBR, GADS, PAG/Cbp, NKp44, NKp30, or NKp46.

Intracellular signaling component sequences that act in a stimulatory manner may include ITAMs. Examples of ITAMs including primary cytoplasmic signaling sequences include those derived from CD3γ, CD3δ, CD3ε, CD3ζ, CD5, CD22, CD66d, CD79a, CD79b, and common FcRγ (FCER1G), FcγRIIa, FcRβ (Fcε Rib), DAP10, and DAP12. In particular embodiments, variants of CD3ζ retain at least one, two, three, or all ITAM regions.

In particular embodiments, an effector domain includes a cytoplasmic portion that associates with a cytoplasmic signaling protein, wherein the cytoplasmic signaling protein is a lymphocyte receptor or signaling domain thereof, a protein including a plurality of ITAMs, a co-stimulatory domain, or any combination thereof.

Additional examples of intracellular signaling components include the cytoplasmic sequences of the CD3ζ chain, and/or co-receptors that act in concert to initiate signal transduction following binding domain engagement.

A co-stimulatory domain is a domain whose activation can be required for an efficient lymphocyte response to cellular marker binding. Some molecules are interchangeable as intracellular signaling components or co-stimulatory domains. Examples of costimulatory domains include CD27, CD28, 4-1BB (CD 137), OX40, CD30, CD40, PD-1, ICOS, lymphocyte function-associated antigen-1 (LFA-1), CD2, CD7, LIGHT, NKG2C, B7-H3, and a ligand that specifically binds with CD83. For example, CD27 co-stimulation has been demonstrated to enhance expansion, effector function, and survival of human CART cells in vitro and augments human T cell persistence and anti-cancer activity in vivo (Song et al. Blood. 2012; 119(3):696-706). Further examples of such co-stimulatory domain molecules include CDS, ICAM-1, GITR, BAFFR, HVEM (LIGHTR), SLAMF7, NKp80 (KLRF1), NKp44, NKp30, NKp46, CD160, CD19, CD4, CD8α, CD8β, IL2Rβ, IL2Rγ, IL7Rα, ITGA4, VLA1, CD49a, ITGA4, IA4, CD49D, ITGA6, VLA-6, CD49f, ITGAD, CD11d, ITGAE, CD103, ITGAL, CD11a, ITGAM, CDI lb, ITGAX, CDIIc, ITGBI, CD29, ITGB2, CD18, ITGB7, TNFR2, TRANCE/RANKL, DNAM1 (CD226), SLAMF4 (CD244, 2B4), CD84, CD96 (Tactile), NKG2D, CEACAM1, CRTAM, Ly9 (CD229), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, and CD19a.

In particular embodiments, the nucleic acid sequences encoding the intracellular signaling components includes CD3z encoding sequence (SEQ ID NO: 14) and a variant of the 4-1BB signaling encoding sequence (SEQ ID NOs: 17 and 18). In particular embodiments, the amino acid sequence of the intracellular signaling component includes a variant of CD3ζ (SEQ ID NOs: 15 and 16) and a portion of the 4-1BB (SEQ ID NO: 19 and 20) intracellular signaling component.

In particular embodiments, the intracellular signaling component includes (i) all or a portion of the signaling domain of CD3ζ, (ii) all or a portion of the signaling domain of 4-1BE, or (iii) all or a portion of the signaling domain of CD3ζ and 4-1BE. In particular embodiments, the intracellular signaling component includes (i) all or a portion of the signaling domain of CD3ζ, (ii) all or a portion of the signaling domain of 4-1BE, (iii) all or a portion of the signaling domain of CD28, (iv) or all or a portion of the signaling domain of CD3ζ, 4-1BE, and CD28.

Intracellular components may also include one or more of a protein of a Wnt signaling pathway (e.g., LRP, Ryk, or ROR2), NOTCH signaling pathway (e.g., NOTCH1, NOTCH2, NOTCH3, or NOTCH4), Hedgehog signaling pathway (e.g., PTCH or SMO), receptor tyrosine kinases (RTKs) (e.g., epidermal growth factor (EGF) receptor family, fibroblast growth factor (FGF) receptor family, hepatocyte growth factor (HGF) receptor family, insulin receptor (IR) family, platelet-derived growth factor (PDGF) receptor family, vascular endothelial growth factor (VEGF) receptor family, tropomycin receptor kinase (Trk) receptor family, ephrin (Eph) receptor family, AXL receptor family, leukocyte tyrosine kinase (LTK) receptor family, tyrosine kinase with immunoglobulin-like and EGF-like domains 1 (TIE) receptor family, receptor tyrosine kinase-like orphan (ROR) receptor family, discoidin domain (DDR) receptor family, rearranged during transfection (RET) receptor family, tyrosine-protein kinase-like (PTK7) receptor family, related to receptor tyrosine kinase (RYK) receptor family, or muscle specific kinase (MuSK) receptor family); G-protein-coupled receptors, GPCRs (Frizzled or Smoothened); serine/threonine kinase receptors (BMPR or TGFR); or cytokine receptors (IL1R, IL2R, IL7R, or IL15R).

(iii-b-v) Linkers. As used herein, a linker can include any portion of a CAR molecule that serves to connect two other subcomponents of the molecule. Some linkers serve no purpose other than to link components while many linkers serve an additional purpose. Linkers can, for example, link VL and VH of antibody derived binding domains of scFvs and serve as junction amino acids between subcomponent portions of a CAR.

Linkers can be flexible, rigid, or semi-rigid, depending on the desired function of the linker. Linkers can include junction amino acids. For example, in particular embodiments, linkers provide flexibility and room for conformational movement between different components of CAR. Commonly used flexible linkers include Gly-Ser linkers. In particular embodiments, the linker sequence includes sets of glycine and serine repeats such as from one to ten repeats of $(Gly_xSer_y)_n$, wherein x and y are independently an integer from 0 to 10 provided that x and y are not both 0 and wherein n is an integer of 1, 2, 3, 4, 5, 6, 7, 8, 9 or 10). Particular examples include (Gly4Ser)n (SEQ ID NO: 160), (Gly3Ser)n(Gly4Ser)n (SEQ ID NO: 161), (Gly3Ser)n(Gly2Ser)n (SEQ ID NO: 162), or (Gly3Ser)n(Gly4Ser)1 (SEQ ID NO: 163). In particular embodiments, the linker is (Gly4Ser)4 (SEQ ID NO: 164), (Gly4Ser)3 (SEQ ID NO: 165), (Gly4Ser)2 (SEQ ID NO: 166), (Gly4Ser)1 (SEQ ID NO: 167), (Gly3Ser)2 (SEQ ID NO: 168), (Gly3Ser)1 (SEQ ID NO: 169), (Gly2Ser)2 (SEQ ID NO: 170) or (Gly2Ser)1, GGSGGGSGGSG (SEQ ID NO: 171), GGSGGGSGSG (SEQ ID NO: 172), or GGSGGGSG (SEQ ID NO: 173).

In particular embodiments, a linker region is (GGGGS)n (SEQ ID NO: 160) wherein n is an integer including, 1, 2, 3, 4, 5, 6, 7, 8, 9, or more. In particular embodiments, the spacer region is (EAAAK)n (SEQ ID NO: 174) wherein n is an integer including 1, 2, 3, 4, 5, 6, 7, 8, 9, or more.

In some situations, flexible linkers may be incapable of maintaining a distance or positioning of CAR needed for a particular use. In these instances, rigid or semi-rigid linkers may be useful. Examples of rigid or semi-rigid linkers include proline-rich linkers. In particular embodiments, a proline-rich linker is a peptide sequence having more proline residues than would be expected based on chance alone. In particular embodiments, a proline-rich linker is one having at least 30%, at least 35%, at least 36%, at least 39%, at least 40%, at least 48%, at least 50%, or at least 51% proline residues. Particular examples of proline-rich linkers include fragments of proline-rich salivary proteins (PRPs).

Linkers can be susceptible to cleavage (cleavable linker), such as, acid-induced cleavage, photo-induced cleavage, peptidase-induced cleavage, esterase-induced cleavage, and disulfide bond cleavage. Alternatively, linkers can be substantially resistant to cleavage (e.g., stable linker or noncleavable linker). In some aspects, the linker is a procharged linker, a hydrophilic linker, or a dicarboxylic acid-based linker.

Junction amino acids can be a linker which can be used to connect sequences when the distance provided by a spacer region is not needed and/or wanted. For example, junction amino acids can be short amino acid sequences that can be used to connect co-stimulatory intracellular signaling components. In particular embodiments, junction amino acids are 9 amino acids or less (e.g., 2, 3, 4, 5, 6, 7, 8, or 9 amino acids). In particular embodiments, a glycine-serine doublet can be used as a suitable junction amino acid linker. In particular embodiments, a single amino acid, e.g., an alanine, a glycine, can be used as a suitable junction amino acid.

(iii-b-vi) Control Features Including Tag Cassettes, Transduction Markers, and/or Suicide Switches. In particular embodiments, CAR constructs can include one or more tag cassettes and/or transduction markers. Tag cassettes and transduction markers can be used to activate, promote proliferation of, detect, enrich for, isolate, track, deplete and/or eliminate genetically modified cells in vitro, in vivo and/or ex vivo. "Tag cassette" refers to a unique synthetic peptide sequence affixed to, fused to, or that is part of a CAR, to which a cognate binding molecule (e.g., ligand, antibody, or other binding partner) is capable of specifically binding where the binding property can be used to activate, promote proliferation of, detect, enrich for, isolate, track, deplete and/or eliminate the tagged protein and/or cells expressing the tagged protein. Transduction markers can serve the same purposes but are derived from naturally occurring molecules and are often expressed using a skipping element that separates the transduction marker from the rest of the CAR molecule.

Tag cassettes that bind cognate binding molecules include, for example, His tag (HHHHHH; SEQ ID NO: 175), Flag tag (DYKDDDDK; SEQ ID NO: 176), Xpress tag (DLYDDDDK; SEQ ID NO: 177), Avi tag (GLNDIFEAQKIEWHE; SEQ ID NO: 178), Calmodulin tag (KRRWKKNFIAVSAANRFKKISSSGAL; SEQ ID NO: 179), Polyglutamate tag, HA tag (YPYDVPDYA; SEQ ID NO: 180), Myc tag (EQKLISEEDL; SEQ ID NO: 181), Strep tag (which refers the original STREP® tag (WRHPQFGG; SEQ ID NO: 182), STREP® tag II (WSHPQFEK SEQ ID NO: 183 (IBA Institut fur Bioanalytik, Germany); see, e.g., U.S. Pat. No. 7,981,632), Softag 1 (SLAELLNAGLGGS; SEQ ID NO: 184), Softag 3 (TQDPSRVG; SEQ ID NO: 185), and V5 tag (GKPIPNPLLGLDST; SEQ ID NO: 186).

Conjugate binding molecules that specifically bind tag cassette sequences disclosed herein are commercially available. For example, His tag antibodies are commercially available from suppliers including Life Technologies, Pierce Antibodies, and GenScript.Flag tag antibodies are commercially available from suppliers including Pierce Antibodies, GenScript, and Sigma-Aldrich. Xpress tag antibodies are commercially available from suppliers including Pierce Antibodies, Life Technologies and GenScript. Avi tag antibodies are commercially available from suppliers including Pierce Antibodies, IsBio, and Genecopoeia. Calmodulin tag antibodies are commercially available from suppliers including Santa Cruz Biotechnology, Abcam, and Pierce Antibodies. HA tag antibodies are commercially available from suppliers including Pierce Antibodies, Cell Signal and Abcam. Myc tag antibodies are commercially available from suppliers including Santa Cruz Biotechnology, Abcam, and Cell Signal. Strep tag antibodies are commercially available from suppliers including Abcam, Iba, and Qiagen.

Transduction markers may be selected from at least one of a truncated CD19 (tCD19; see Budde et al., Blood 122: 1660, 2013); a truncated human EGFR (tEGFR; see Wang et al., Blood 118: 1255, 2011); an extracellular domain of human CD34; and/or RQR8 which combines target epitopes from CD34 (see Fehse et al, Mol. Therapy 1(5 Pt 1); 448-456, 2000) and CD20 antigens (see Philip et al, Blood 124: 1277-1278).

In particular embodiments, a polynucleotide encoding an iCaspase9 construct (iCasp9) may be inserted into a CAR construct as a suicide switch.

Control features may be present in multiple copies in a CAR or can be expressed as distinct molecules with the use of a skipping element (SEQ ID NOs: 187). For example, a CAR can have one, two, three, four or five tag cassettes and/or one, two, three, four, or five transduction markers could also be expressed. For example, embodiments can include a CAR construct having two Myc tag cassettes, or a His tag and an HA tag cassette, or a HA tag and a Softag 1 tag cassette, or a Myc tag and a SBP tag cassette. Exemplary transduction markers and cognate pairs are described in U.S. Ser. No. 13/463,247.

One advantage of including at least one control feature in a CAR is that cells expressing CAR administered to a subject can be increased or depleted using the cognate binding molecule to a tag cassette. In certain embodiments, the present disclosure provides a method for depleting a modified cell expressing a CAR by using an antibody specific for the tag cassette, using a cognate binding molecule specific for the control feature, or by using a second modified cell expressing a CAR and having specificity for the control feature. Elimination of modified cells may be accomplished using depletion agents specific for a control feature. For example, if tEGFR is used, then an anti-tEGFR binding domain (e.g., antibody, scFv) fused to or conjugated to a cell-toxic reagent (such as a toxin, radiometal) may be used, or an anti-tEGFR/anti-CD3 bispecific scFv, or an anti-tEGFR CAR T cell may be used.

In certain embodiments, modified cells expressing a chimeric molecule may be detected or tracked in vivo by using antibodies that bind with specificity to a control feature (e.g., anti-Tag antibodies), or by other cognate binding molecules that specifically bind the control feature, which binding partners for the control feature are conjugated to a fluorescent dye, radio-tracer, iron-oxide nanoparticle or other imaging agent known in the art for detection by X-ray, CT-scan, MRI-scan, PET-scan, ultrasound, flow-cytometry, near infrared imaging systems, or other imaging modalities (see, e.g., Yu, et al., *Theranostics* 2:3, 2012).

Thus, modified cells expressing at least one control feature with a CAR can be, e.g., more readily identified, isolated, sorted, induced to proliferate, tracked, and/or eliminated as compared to a modified cell without a tag cassette.

(iv) Cell Activating Culture Conditions. Cell populations can be incubated in a culture-initiating composition to expand genetically modified cell populations. The incubation can be carried out in a culture vessel, such as a bag, cell culture plate, flask, chamber, chromatography column, cross-linked gel, cross-linked polymer, column, culture dish, hollow fiber, microtiter plate, silica-coated glass plate, tube, tubing set, well, vial, or other container for culture or cultivating cells.

Culture conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors, and any other agents designed to activate the cells.

In some aspects, incubation is carried out in accordance with techniques such as those described in U.S. Pat. No. 6,040,177, Klebanoff et al. (2012) J Immunother. 35(9): 651-660, Terakura et al. (2012) Blood. 1:72-82, and/or Wang et al. (2012) J Immunother. 35(9):689-701.

Exemplary culture media for culturing T cells include (i) RPMI supplemented with non-essential amino acids, sodium pyruvate, and penicillin/streptomycin; (ii) RPMI with HEPES, 5-15% human serum, 1-3% L-Glutamine, 0.5-1.5% penicillin/streptomycin, and $0.25 \times 10^{-4}$-$0.75 \times 10^{-4}$ M β-MercaptoEthanol; (iii) RPMI-1640 supplemented with 10% fetal bovine serum (FBS), 2 mM L-glutamine, 10 mM HEPES, 100 U/ml penicillin and 100 m/mL streptomycin; (iv) DMEM medium supplemented with 10% FBS, 2 mM L-glutamine, 10 mM HEPES, 100 U/ml penicillin and 100 m/mL streptomycin; and (v) X-Vivo 15 medium (Lonza, Walkersville, MD) supplemented with 5% human AB serum (Gemcell, West Sacramento, CA), 1% HEPES (Gibco, Grand Island, NY), 1% Pen-Strep (Gibco), 1% GlutaMax (Gibco), and 2% N-acetyl cysteine (Sigma-Aldrich, St. Louis, MO). T cell culture media are also commercially available from Hyclone (Logan, UT). Additional T cell activating components that can be added to such culture media are described in more detail below.

In some embodiments, the T cells are expanded by adding to the culture-initiating composition feeder cells, such as non-dividing peripheral blood mononuclear cells (PBMC), (e.g., such that the resulting population of cells contains at least 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can include gamma-irradiated PBMC feeder cells. In some embodiments, the PBMC are irradiated with gamma rays in the range of 3000 to 3600 rads to prevent cell division. In some aspects, the feeder cells are added to culture medium prior to the addition of the populations of T cells.

Optionally, the incubation may further include adding non-dividing EBV-transformed lymphoblastoid cells (LCL) as feeder cells. LCL can be irradiated with gamma rays in the range of 6000 to 10,000 rads. The LCL feeder cells in some aspects is provided in any suitable amount, such as a ratio of LCL feeder cells to initial T lymphocytes of at least 10:1.

In some embodiments, the stimulating conditions include temperature suitable for the growth of human T lymphocytes, for example, at least 25° C., at least 30° C., or 37° C.

The activating culture conditions for T cells include conditions whereby T cells of the culture-initiating composition proliferate or expand. T cell activating conditions can include one or more cytokines, for example, interleukin (IL)-2, IL-7, IL-15 and/or IL-21. IL-2 can be included at a range of 10-100 ng/mL (e.g., 40, 50, or 60 ng/mL). IL-7, IL-15, and/or IL-21 can be individually included at a range of 0.1-50 ng/mL (e.g., 5, 10, or 15 ng/mL). Particular embodiments utilize IL-2 at 50 ng/mL. Particular embodiments utilize IL-7, IL-15 and IL-21 individually included at 10 ng/mL.

In particular embodiments, T cell activating culture condition conditions can include T cell stimulating epitopes. T cell stimulating epitopes include CD3, CD27, CD2, CD4, CD5, CD7, CD8, CD28, CD30, CD40, CD56, CD83, CD90, CD95, 4-1BB (CD 137), B7-H3, CTLA-4, Frizzled-1 (FZD1), FZD2, FZD3, FZD4, FZD5, FZD6, FZD7, FZD8, FZD9, FZD10, HVEM, ICOS, IL-1R, LAT, LFA-1, LIGHT, MHCI, MHCII, NKG2D, OX40, ROR2 and RTK.

CD3 is a primary signal transduction element of T cell receptors. As indicated previously, CD3 is expressed on all mature T cells. In particular embodiments, the CD3 stimulating molecule (i.e., CD3 binding domain) can be derived from the OKT3 antibody (see U.S. Pat. Nos. 5,929,212; 4,361,549; ATCC® CRL-8001™; and Arakawa et al., J. Biochem. 120, 657-662 (1996)), the 20G6-F3 antibody, the 4B4-D7 antibody, the 4E7-C9, or the 18F5-H10 antibody.

In particular embodiments, CD3 stimulating molecules can be included within culture media at a concentration of at least 0.25 or 0.5 ng/ml or at a concentration of 2.5-10 µg/mL. Particular embodiments utilize a CD3 stimulating molecule (e.g., OKT3) at 5 µg/mL.

In particular embodiments, activating molecules associated with avi-tags can be biotinylated and bound to streptavidin beads. This approach can be used to create, for example, a removable T cell epitope stimulating activation system.

An exemplary binding domain for CD28 can include or be derived from TGN1412, CD80, CD86 or the 9D7 antibody. Additional antibodies that bind CD28 include 9.3, KOLT-2, 15E8, 248.23.2, EX5.3D10, and CD28.3 (deposited as a synthetic single chain Fv construct under GenBank Accession No. AF451974.1; see also Vanhove et al., BLOOD, 15 Jul. 2003, Vol. 102, No. 2, pages 564-570). Further, 1YJD provides a crystal structure of human CD28 in complex with the Fab fragment of a mitogenic antibody (5.11A1). In particular embodiments, antibodies that do not compete with 9D7 are selected.

4-1BB binding domains can be derived from LOB12, IgG2a, LOB12.3, or IgG1 as described in Taraban et al. Eur J Immunol. 2002 December; 32(12):3617-27. In particular embodiments a 4-1EE binding domain is derived from a monoclonal antibody described in U.S. Pat. No. 9,382,328. Additional 4-1BB binding domains are described in U.S. Pat. Nos. 6,569,997, 6,303,121, and Mittler et al. Immunol Res. 2004; 29(1-3):197-208.

OX40 (CD134) and/or ICOS activation may also be used. OX40 binding domains are described in US20100196359, US 20150307617, WO 2015/153513, WO2013/038191 and Melero et al. Clin Cancer Res. 2013 Mar. 1; 19(5):1044-53. Exemplary binding domains that can bind and activate ICOS are described in e.g., US20080279851 and Deng et al. Hybrid Hybridomics. 2004 June; 23(3):176-82.

When in soluble form, T-cell activating agents can be coupled with another molecule, such as polyethylene glycol (PEG) molecule. Any suitable PEG molecule can be used. Typically, PEG molecules up to a molecular weight of 1000 Da are soluble in water or culture media. In some cases, such PEG based reagent can be prepared using commercially available activated PEG molecules (for example, PEG-NHS derivatives available from NOF North America Corporation, Irvine, Calif., USA, or activated PEG derivatives available from Creative PEGWorks, Chapel Hills, N.C., USA).

In particular embodiments, cell stimulating agents are immobilized on a solid phase within the culture media. In particular embodiments, the solid phase is a surface of the culture vessel (e.g., bag, cell culture plate, chamber, chromatography column, cross-linked gel, cross-linked polymer, column, culture dish, hollow fiber, microtiter plate, silica-coated glass plate, tube, tubing set, well, vial, other structure or container for culture or cultivation of cells).

In particular embodiments, a solid phase can be added to a culture media. Such solid phases can include, for example, beads, hollow fibers, resins, membranes, and polymers.

Exemplary beads include magnetic beads, polymeric beads, and resin beads (e.g., Strep-Tactin® Sepharose, Strep-Tactin® Superflow, and Strep-Tactin® MacroPrep IBA GmbH, Gottingen)). Anti-CD3/anti-CD28 beads are commercially available reagents for T cell expansion (Invitrogen). These beads are uniform, 4.5 µm superparamagnetic, sterile, non-pyrogenic polystyrene beads coated with a mixture of affinity purified monoclonal antibodies against the CD3 and CD28 cell surface molecules on human T cells. Hollow fibers are available from TerumoBCT Inc. (Lakewood, Colo., USA). Resins include metal affinity chromatography (IMAC) resins (e.g., TALON® resins (Westburg, Leusden)). Membranes include paper as well as the membrane substrate of a chromatography matrix (e.g., a nitrocellulose membrane or a polyvinylidene difluoride (PVDF) membrane).

Exemplary polymers include polysaccharides, such as polysaccharide matrices. Such matrices include agarose gels (e.g., Superflow™ agarose or a Sepharose® material such as Superflow™ Sepharose® that are commercially available in different bead and pore sizes) or a gel of crosslinked dextran(s). A further illustrative example is a particulate cross-linked agarose matrix, to which dextran is covalently bonded, that is commercially available (in various bead sizes and with various pore sizes) as Sephadex® or Superdex®, both available from GE Healthcare.

Synthetic polymers that may be used include polyacrylamide, polymethacrylate, a copolymer of polysaccharide and agarose (e.g. a polyacrylamide/agarose composite) or a polysaccharide and N,N'-methylenebisacrylamide. An example of a copolymer of a dextran and N,N'-methylenebisacrylamide is the Sephacryl® (Pharmacia Fine Chemicals, Inc., Piscataway, NJ) series of materials.

Particular embodiments may utilize silica particles coupled to a synthetic or to a natural polymer, such as polysaccharide grafted silica, polyvinylpyrrolidone grafted silica, polyethylene oxide grafted silica, poly(2-hydroxyethylaspartamide) silica and poly(N-isopropylacrylamide) grafted silica.

Cell activating agents can be immobilized to solid phases through covalent bonds or can be reversibly immobilized through non-covalent attachments.

In particular embodiments, a T-cell activating culture media includes a FACS-sorted T cell population cultured within RPMI with HEPES, 5-15% human serum, 1-3% L-Glutamine, 0.5-1.5% Pen/strep, $0.25 \times 10^{-4}$-$0.75 \times 10^{-4}$ M β-MercaptoEthanol, with IL-7, IL-15 and IL-21 individually included at 5-15 (e.g., 10) ng/µl. The culture is carried out on a flat-bottom well plate with 0.1-0.5×10e6 plated cells/well. On Day 3 post activation cells are transferred to a TC-treated plate.

In particular embodiments, a T-cell activating culture media includes a FACS-sorted CD8+ T population cultured within RPMI with HEPES, 10% human serum, 2% L-Glutamine, 1% Pen/strep, $0.5\times10^{-4}$ M β-MercaptoEthanol, with IL-7, IL-15 and IL-21 individually included at 5-15 (e.g., 10) ng/µl. The culture is carried out on a flat-bottom non-tissue culture (TC)-treated 96/48-well plate with 0.1-0.5× 10e6 plated cells/well. On Day 3 post activation cells are transferred to TC-treated plate.

Culture conditions for HSC/HSP can include expansion with a Notch agonist (see, e.g., U.S. Pat. Nos. 7,399,633; 5,780,300; 5,648,464; 5,849,869; and 5,856,441 and growth factors present in the culture condition as follows: 25-300 ng/ml SCF, 25-300 ng/ml Flt-3L, 25-100 ng/ml TPO, 25-100 ng/ml IL-6 and 10 ng/ml IL-3. In more specific embodiments, 50, 100, or 200 ng/ml SCF; 50, 100, or 200 ng/ml of Flt-3L; 50 or 100 ng/ml TPO; 50 or 100 ng/ml IL-6; and 10 ng/ml IL-3 can be used.

(v) Ex Vivo Manufactured Cell Formulations. In particular embodiments, genetically modified cells can be harvested from a culture medium and washed and concentrated into a carrier in a therapeutically-effective amount. Exemplary carriers include saline, buffered saline, physiological saline, water, Hanks' solution, Ringer's solution, Nonnosol-R (Abbott Labs), PLASMA-LYTE A® (Baxter Laboratories, Inc., Morton Grove, IL), glycerol, ethanol, and combinations thereof.

In particular embodiments, carriers can be supplemented with human serum albumin (HSA) or other human serum components or fetal bovine serum. In particular embodiments, a carrier for infusion includes buffered saline with 5% HAS or dextrose. Additional isotonic agents include polyhydric sugar alcohols including trihydric or higher sugar alcohols, such as glycerin, erythritol, arabitol, xylitol, sorbitol, or mannitol.

Carriers can include buffering agents, such as citrate buffers, succinate buffers, tartrate buffers, fumarate buffers, gluconate buffers, oxalate buffers, lactate buffers, acetate buffers, phosphate buffers, histidine buffers, and/or trimethylamine salts.

Stabilizers refer to a broad category of excipients which can range in function from a bulking agent to an additive which helps to prevent cell adherence to container walls. Typical stabilizers can include polyhydric sugar alcohols; amino acids, such as arginine, lysine, glycine, glutamine, asparagine, histidine, alanine, ornithine, L-leucine, 2-phenylalanine, glutamic acid, and threonine; organic sugars or sugar alcohols, such as lactose, trehalose, stachyose, mannitol, sorbitol, xylitol, ribitol, myoinisitol, galactitol, glycerol, and cyclitols, such as inositol; PEG; amino acid polymers; sulfur-containing reducing agents, such as urea, glutathione, thioctic acid, sodium thioglycolate, thioglycerol, alpha-monothioglycerol, and sodium thiosulfate; low molecular weight polypeptides (i.e., <10 residues); proteins such as HSA, bovine serum albumin, gelatin or immunoglobulins; hydrophilic polymers such as polyvinylpyrrolidone; monosaccharides such as xylose, mannose, fructose and glucose; disaccharides such as lactose, maltose and sucrose; trisaccharides such as raffinose, and polysaccharides such as dextran.

Where necessary or beneficial, compositions or formulations can include a local anesthetic such as lidocaine to ease pain at a site of injection.

Exemplary preservatives include phenol, benzyl alcohol, meta-cresol, methyl paraben, propyl paraben, octadecyldimethylbenzyl ammonium chloride, benzalkonium halides, hexamethonium chloride, alkyl parabens such as methyl or propyl paraben, catechol, resorcinol, cyclohexanol, and 3-pentanol.

Therapeutically effective amounts of cells within compositions or formulations can be greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

In compositions and formulations disclosed herein, cells are generally in a volume of a liter or less, 500 mls or less, 250 mls or less or 100 mls or less. Hence the density of administered cells is typically greater than $10^4$ cells/ml, $10^7$ cells/ml or $10^8$ cells/ml.

As indicated, compositions include at least one genetically modified cell type (e.g., modified T cells, NK cells, or stem cells). Formulations can include different types of genetically modified cells (e.g., T cells, NK cells, and/or stem cells in combination).

Different types of genetically-modified cells or cell subsets (e.g., modified T cells, NK cells, and/or stem cells) can be provided in different ratios e.g., a 1:1:1 ratio, 2:1:1 ratio, 1:2:1 ratio, 1:1:2 ratio, 5:1:1 ratio, 1:5:1 ratio, 1:1:5 ratio, 10:1:1 ratio, 1:10:1 ratio, 1:1:10 ratio, 2:2:1 ratio, 1:2:2 ratio, 2:1:2 ratio, 5:5:1 ratio, 1:5:5 ratio, 5:1:5 ratio, 10:10:1 ratio, 1:10:10 ratio, 10:1:10 ratio, etc. These ratios can also apply to numbers of cells expressing the same or different CAR components. If only two of the cell types are combined or only 2 combinations of expressed CAR components are included within a formulation, the ratio can include any 2-number combination that can be created from the 3 number combinations provided above. In embodiments, the combined cell populations are tested for efficacy and/or cell proliferation in vitro, in vivo and/or ex vivo, and the ratio of cells that provides for efficacy and/or proliferation of cells is selected. Particular embodiments include a 1:1 ratio of CD4 T cells and CD8 T cells.

The cell-based compositions disclosed herein can be prepared for administration by, e.g., injection, infusion, perfusion, or lavage. The compositions and formulations can further be formulated for bone marrow, intravenous, intradermal, intraarterial, intranodal, intralymphatic, intraperitoneal, intralesional, intratumoral, intravesicular, and/or subcutaneous injection.

(vi) Methods of Use. Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with compositions and formulations disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. For example, an effective amount can provide an immunogenic anti-cancer effect. Effective amounts are often administered for research purposes. Effective amounts disclosed herein can cause a statistically significant effect in an animal model or in vitro assay relevant to the assessment of a cancer's development or progression. An immunogenic composition can be provided in an effective amount, wherein the effective amount stimulates an immune response.

A "prophylactic treatment" includes a treatment administered to a subject who does not display signs or symptoms of a cancer or displays only early signs or symptoms of a cancer such that treatment is administered for the purpose of diminishing or decreasing the risk of developing the cancer further. Thus, a prophylactic treatment functions as a preventative treatment against a CD33-expressing cancer. In particular embodiments, prophylactic treatments reduce, delay, or prevent metastasis from a primary a cancer tumor site from occurring.

A "therapeutic treatment" includes a treatment administered to a subject who displays symptoms or signs of a cancer and is administered to the subject for the purpose of diminishing or eliminating those signs or symptoms of the cancer. The therapeutic treatment can reduce, control, or eliminate the presence or activity of the cancer and/or reduce control or eliminate side effects of the cancer.

Function as an effective amount, prophylactic treatment or therapeutic treatment are not mutually exclusive, and in particular embodiments, administered dosages may accomplish more than one treatment type.

In particular embodiments, therapeutically effective amounts provide anti-cancer effects. Anti-cancer effects include a decrease in the number of cancer cells, decrease in the number of metastases, a decrease in tumor volume, an increase in life expectancy, induced chemo- or radiosensitivity in cancer cells, inhibited angiogenesis near cancer cells, inhibited cancer cell proliferation, inhibited tumor growth, prevented or reduced metastases, prolonged subject life, reduced cancer-associated pain, and/or reduced relapse or re-occurrence of cancer following treatment.

A "tumor" is a swelling or lesion formed by an abnormal growth of cells (called neoplastic cells or tumor cells). A "tumor cell" is an abnormal cell that grows by a rapid, uncontrolled cellular proliferation and continues to grow after the stimuli that initiated the new growth cease. Tumors show partial or complete lack of structural organization and functional coordination with the normal tissue, and usually form a distinct mass of tissue, which may be benign, pre-malignant or malignant.

In particular embodiments, therapeutically effective amounts induce an immune response. The immune response can be against a cancer cell.

Examples of CD33-related disorders include hematological cancers such as leukemias and lymphomas and other myelo- or lymphoproliferative disorders.

Exemplary leukemias include acute lymphoblastic leukemia (ALL), AML, chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), and megakaryocytic leukemia.

Exemplary sub-types of AML include: acute basophilic leukemia, acute erythroid leukemia (AML-M6), acute megakaryoblastic leukemia (AML-M7), acute monoblastic leukemia (AML-M5a), acute monocytic leukemia (AML-M5b), acute myeloblasts leukemia with granulocytic maturation, acute myeloblasts leukemia without maturation, acute myelomonocytic leukemia (AML-M4), acute panmyelosis with myelofibrosis, acute promyelocytic leukemia (APL), erythroleukemia (AML-M6a), minimally differentiated acute myeloblasts leukemia, myelomonocytic leukemia with bone marrow eosinophilia, and pure erythroid leukemia (AML-M6b).

An exemplary lymphoma includes multiple myeloma.

Compositions disclosed herein can also be used to treat a complication or disease related to the above-noted lymphoproliferative disorders and hematological cancers. For example, complications relating to AML may include a preceding myelodysplastic syndrome (MDS, formerly known as "preleukemia"), secondary leukemia, in particular secondary AML, high white blood cell count, and absence of Auer rods. Among others, leukostasis and involvement of the central nervous system (CNS), hyperleukocytosis, residual disease, are also considered complications or diseases related to AML.

Compositions disclosed herein can be used to target myeloid-derived suppressor cells (MDSCs). MDSCs are a major player in the immunosuppressive tumor microenvironment and have been found to inhibit the antitumor reactivity of T cells and NK cells. Particular MDSCs have high CD33 expression and can be targeted with anti-CD33 treatments, including monocytic MDSCs and immature MDSCs.

Compositions disclosed herein may also find use in the treatment of other pathological conditions or genetic syndromes associated with the risk of AML such as Down syndrome, trisomy, Fanconi anemia, Bloom syndrome, Ataxia-telangiectasia, Diamond-Blackfan anemia, Schwachman-Diamond syndrome, Li-Fraumeni syndrome, Neurofibromatosis type 1, Severe congenital neutropenia (also called Kostmann syndrome).

For administration, therapeutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of cancer, stage of cancer, previous or concurrent therapeutic interventions, idiopathy of the subject and route of administration.

Therapeutically effective amounts of cell-based compositions can include $10^4$ to $10^9$ cells/kg body weight, or $10^3$ to $10^1$ cells/kg body weight. Therapeutically effective amounts to administer can include greater than $10^2$ cells, greater than $10^3$ cells, greater than $10^4$ cells, greater than $10^5$ cells, greater than $10^6$ cells, greater than $10^7$ cells, greater than $10^8$ cells, greater than $10^9$ cells, greater than $10^{10}$ cells, or greater than $10^{11}$.

Therapeutically effective amounts can be achieved by administering single or multiple doses during the course of a treatment regimen (e.g., daily, every other day, every 3 days, every 4 days, every 5 days, every 6 days, weekly, every 2 weeks, every 3 weeks, monthly, every 2 months, every 3 months, every 4 months, every 5 months, every 6 months, every 7 months, every 8 months, every 9 months, every 10 months, every 11 months or yearly). In particular embodiments, the treatment protocol may be dictated by a clinical trial protocol or an FDA-approved treatment protocol.

Therapeutically effective amounts can be administered by, e.g., injection, infusion, perfusion, or lavage. Routes of administration can include bolus intravenous, intradermal, intraarterial, intraparenteral, intranodal, intralymphatic, intraperitoneal, intralesional, intraprostatic, intrathecal, intratumoral, intravesicular, and/or subcutaneous.

In certain embodiments, cells are administered to a patient in conjunction with (e.g., before, simultaneously or following) any number of relevant treatment modalities. In particular embodiments, cells may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludaribine, cyclosporin, FK506, rapamycin, mycoplienolic acid, steroids, FR901228, cytokines, and irradiation.

(vii) Reference Levels Derived from Control Populations. Obtained values for parameters associated with a therapy described herein can be compared to a reference level derived from a control population, and this comparison can indicate whether a therapy described herein is effective for a subject in need thereof. Reference levels can be obtained from one or more relevant datasets from a control population. A "dataset" as used herein is a set of numerical values resulting from evaluation of a sample (or population of samples) under a desired condition. The values of the dataset can be obtained, for example, by experimentally obtaining measures from a sample and constructing a dataset from these measurements. As is understood by one of ordinary skill in the art, the reference level can be based on e.g., any mathematical or statistical formula useful and known in the art for arriving at a meaningful aggregate reference level from a collection of individual data points; e.g., mean, median, median of the mean, etc. Alternatively, a reference level or dataset to create a reference level can be obtained from a service provider such as a laboratory, or from a database or a server on which the dataset has been stored.

A reference level from a dataset can be derived from previous measures derived from a control population. A "control population" is any grouping of subjects or samples of like specified characteristics. The grouping could be according to, for example, clinical parameters, clinical assessments, therapeutic regimens, disease status, severity of condition, etc. In particular embodiments, the grouping is based on age range (e.g., 60-65 years) and non-immuno-compromised status. In particular embodiments, a normal control population includes individuals that are age-matched to a test subject and non-immune compromised. In particular embodiments, age-matched includes, e.g., 0-10 years old; 30-40 years old, 60-65 years old, 70-85 years old, etc., as is clinically relevant under the circumstances. In particular embodiments, a control population can include those that have a CD33-related disorder and have not been administered a therapeutically effective amount In particular embodiments, the relevant reference level for values of a particular parameter associated with a therapy described herein is obtained based on the value of a particular corresponding parameter associated with a therapy in a control population to determine whether a therapy disclosed herein has been therapeutically effective for a subject in need thereof.

In particular embodiments, conclusions are drawn based on whether a sample value is statistically significantly different or not statistically significantly different from a reference level. A measure is not statistically significantly different if the difference is within a level that would be expected to occur based on chance alone. In contrast, a statistically significant difference or increase is one that is greater than what would be expected to occur by chance alone. Statistical significance or lack thereof can be determined by any of various methods well-known in the art. An example of a commonly used measure of statistical significance is the β-value. The β-value represents the probability of obtaining a given result equivalent to a particular data point, where the data point is the result of random chance alone. A result is often considered significant (not random chance) at a β-value less than or equal to 0.05. In particular embodiments, a sample value is "comparable to" a reference level derived from a normal control population if the sample value and the reference level are not statistically significantly different.

(viii) Exemplary Embodiments

1. A chimeric antigen receptor (CAR) including
an extracellular component including a binding domain having a complementarity determining region (CDR) set of antibody 1H10, 1A9, 1E6, 1D2, 1B9, 1H8, 2D3, or 2E3, according to North, IMGT, Kabat, Chothia or Set 5;
an intracellular component including an effector domain; and
a transmembrane domain linking the extracellular component to the intracellular component.

2. A CAR of embodiment 1, wherein the binding domain includes a single chain variable fragment (scFv).

3. A CAR of embodiment 2, wherein the scFv is encoded by
the 1H10 scFv coding sequence as set forth in SEQ ID NO: 2;
the 1A9 scFv coding sequence as set forth in SEQ ID NO: 3;
the 1E6 scFv coding sequence as set forth in SEQ ID NO: 4;
the 1D2 scFv coding sequence as set forth in SEQ ID NO: 5;
the 1B9 scFv coding sequence as set forth in SEQ ID NO: 6;
the 1H8 scFv coding sequence as set forth in SEQ ID NO: 7;
the 2D3 scFv coding sequence as set forth in SEQ ID NO: 8; or
the 2E3 scFv coding sequence as set forth in SEQ ID NO: 9.

4. A CAR of embodiment 2, wherein the scFv is
the 1H10 scFv in the VH-VL orientation as set forth in SEQ ID NO: 190;
the 1H10 scFv in the VL-VH orientation as set forth in SEQ ID NO: 191;
the 1A9 scFv in the VH-VL orientation as set forth in SEQ ID NO: 192;
the 1A9 scFv in the VL-VH orientation as set forth in SEQ ID NO: 193;
the 1E6 scFv in the VH-VL orientation as set forth in SEQ ID NO: 194;
the 1E6 scFv in the VL-VH orientation as set forth in SEQ ID NO: 195;
the 2D3 scFv in the VH-VL orientation as set forth in SEQ ID NO: 196; or
the 2D3 scFv in the VL-VH orientation as set forth in SEQ ID NO: 197.

5. A CAR of any of embodiments 1-4, wherein the extracellular component further includes a spacer region.

6. A CAR of embodiment 5, wherein the spacer region is 135 amino acids or less or 16 amino acids of less.

7. A CAR of embodiments 5 or 6, wherein the spacer region is 131 amino acids or less and includes the hinge region and CH3 domain of IgG4.

8. A CAR of embodiments 5 or 6, wherein the spacer region is 12 amino acids or less and includes the hinge region of IgG4.

9. A CAR of embodiments 7 or 8 wherein the IgG4 is human IgG4.

10. A CAR of any of embodiments 5-8, wherein the spacer region is encoded by the IgG4 hinge coding sequence-A as set forth in SEQ ID NO: 10; the IgG4 hinge coding sequence-B as set forth in SEQ ID NO: 11; or the IgG4-int(DS) coding sequence as set forth in SEQ ID NO: 12.

11. A CAR of any of embodiments 1-10, wherein the effector domain includes all or a portion of the signaling domain of CD3ζ; all or a portion of the signaling domain of 4-11BE, all or a portion of the signaling domain of CD28, all or a portion of the signaling domain of CD3ζ and 4-1BB; all or a portion of the signaling domain of CD3ζ and CD28; or all or a portion of the signaling domain of CD3ζ, 4-1EE, and CD28

12. A CAR of any of embodiments 1-11, wherein the effector domain includes all or a portion of the signaling domain of CD3ζ and 4-1BE.

13. A CAR of embodiments 11 or 12, wherein the CD3ζ signaling domain is encoded by the CD3ζ coding sequence as set forth in SEQ ID NO: 14.

14. A CAR of any of embodiments 11-13, wherein the CD3ζ has the sequence as set forth in SEQ ID NO: 15 or SEQ ID NO: 16.

15. A CAR of any of embodiments 11-14, wherein the 4-1EE signaling domain is encoded by 4-11BE signaling coding sequence-A as set forth in SEQ ID NO: 17 or 4-11BE signaling coding sequence-B as set forth in SEQ ID NO: 18.

16. A CAR of any of embodiments 11-15, wherein the 4-1BE has the sequence as set forth in SEQ ID NO: 19 or SEQ ID NO: 20.

17. A CAR of any of embodiments 1-16, wherein the transmembrane domain includes a CD28 transmembrane domain.

18. A CAR of embodiment 17, wherein the CD28 transmembrane domain is encoded by

CD28TM coding sequence-A (SEQ ID NO: 21);

CD28TM coding sequence-B (SEQ ID NO: 22); or or CD28TM coding sequence-C(SEQ ID NO: 23).

19. A CAR of embodiment 17, wherein the CD28 transmembrane domain has the sequence as set forth in SEQ ID NO: 24 or SEQ ID NO: 25.

20. A CAR of any of embodiments 1-19, further including a control feature selected from a tag cassette, a transduction marker, and/or a suicide switch.

21. A genetic construct encoding a CAR of any of embodiments 1-20.

22. A genetic construct of embodiment 21, wherein the genetic construct includes the 1H10-intDS-41bb-3z-T-CD19t Top Strand as set forth in SEQ ID NO: 46;

1H10-sh-41bb-3z-T-CD19t Top Strand as set forth in SEQ ID NO: 47;

1A9-intDS-41bb-3z-T-CD19t Top Strand as set forth in SEQ ID NO: 48;

1A9-sh-41bb-3z-T-CD19t Top Strand as set forth in SEQ ID NO: 49;

1E6-intDS-41bb-3z-T-CD19t Top Strand as set forth in SEQ ID NO: 50;

1E6-sh-41bb-3z-T-CD19t Top Strand as set forth in SEQ ID NO: 51;

1H10-LvHv-intDS-41bb-3z-T-CD19t Top Strand as set forth in SEQ ID NO: 200;

1A9-LvHv-intDS-41bb-3z-T-CD19t Top Strand as set forth in SEQ ID NO: 201;

1E6-LvHv-intDS-41bb-3z-T-CD19t Top Strand as set forth in SEQ ID NO: 202; or

2D3-LvHv-intDS-41bb-3z-T-CD19t Top Strand as set forth in SEQ ID NO: 203.

23. A nanoparticle encapsulating the genetic construct of embodiments 21 or 22.

24. A cell genetically modified to express the CAR of any of embodiments 1-20 and/or including a genetic construct of embodiments 21 or 22.

25. A cell of embodiment 24, wherein the cell is an autologous cell or an allogeneic cell in reference to a subject.

26. A cell of embodiments 24 or 25, wherein the cell is in vivo or ex vivo.

27. A cell of any of embodiments 24-26, wherein the cell is a T cell, B cell, natural killer (NK) cell, NK-T cell, monocyte/macrophage, hematopoietic stem cells (HSC), or a hematopoietic progenitor cell (HPC).

28. A cell of any of embodiments 24-27, wherein the cell is a T cell selected from a CD3+ T cell, a CD4+ T cell, a CD8+ T cell, a central memory T cell, an effector memory T cell, and/or a naïve T cell.

29. A cell of any of embodiments 24-28, wherein the cell is a CD8+ T cell.

30. A cell of any of embodiments 24-29, wherein the cell has been incubated in a cell media including IL-2, IL-7, IL-15, and/or IL-21.

31. A cell embodiment 30, wherein the cell has been incubated in a cell media including IL-2.

32. A cell of embodiment 31, wherein the cell media includes 10-100 ng/mL IL-2.

33. A cell of embodiments 31 or 32, wherein the cell media includes 50 ng/mL IL-2.

34. A cell of embodiment 30, wherein the cell has been incubated in a cell media including IL-7 and IL-15.

35. A cell of embodiment 34, wherein the cell media includes 5-15 ng/mL IL-7 and 5-15 ng/mL IL-15.

36. A cell of embodiments 34 or 35, wherein the cell media includes 10 ng/mL IL-7 and 10 ng/mL IL-15.

37. A cell of embodiment 30, wherein the cell media includes IL-7, IL-15, and IL-21.

38. A cell of embodiment 37, wherein the cell media includes 5-15 ng/mL IL-7, 5-15 ng/mL IL-15, and 5-15 ng/mL IL-21.

39. A cell of embodiments 37 or 38, wherein the cell media includes 10 ng/mL IL-7, 10 ng/mL IL-15, and 10 ng/mL IL-21.

40. A population of cells of any of embodiments 24-39 formulated for administration to a subject.

41. A method of treating a subject with a CD33-related disorder including administering a therapeutically effective amount of the nanoparticle of embodiment 23 or the population of cells of embodiment 40 to the subject thereby treating the subject with the CD33-related disorder.

42. A method of embodiment 41, wherein the cell population includes autologous cells or allogeneic cells.

43. A method of embodiments 41 or 42, wherein the CD33-related disorder includes acute myeloid leukemia (AML).

44. A method of embodiments 41 or 42, wherein the CD33-related disorder includes acute lymphoblastic leukemia (ALL), chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), or megakaryocytic leukemia.

45. A method of any of embodiments 41-44, further including determining whether the subject expresses or lacks the V-set domain of CD33, and if the subject expresses the V-set domain of CD33, selecting a combination therapy including a composition encoding a binding domain of one or more of 1H10, 1A9, 1E6, 1D2, and 1B9 and a binding domain of one or more of one or more of 1H8, 2D3, and 2E3.

46. A method of any of embodiments 41-44, further including determining whether the subject expresses or lacks the V-set domain of CD33, and if the subject does not express the V-set domain of CD33, selecting a therapy including a composition encoding a binding domain of one or more of 6H9, 9G2, 3A5, 7D5, 1 H7, and 2D5.

47. A method of activating an immune response against CD33-expressing cells in a subject in need thereof including administering a therapeutically effective amount of the nanoparticle of embodiment 23 or the population of cells of embodiment 40 to the subject activating an immune response against CD33-expressing cells in the subject in need.

48. A method of embodiment 47, wherein the cell population includes autologous cells or allogeneic cells.

49. A method of embodiments 47 or 48, wherein the CD33-expressing cells include acute myeloid leukemia (AML) cells.

50. A method of embodiments 47 or 48, wherein the CD33-expressing cells include acute lymphoblastic leukemia (ALL), chronic myelogenous leukemia (CML), chronic myelomonocytic leukemia (CML), mast cell leukemia, myelodysplastic syndrome (MDS), B-cell acute lymphoblastic leukemia (B-ALL), T-cell acute lymphoblastic leukemia (T-ALL), or megakaryocytic leukemia.

51. A method of any of embodiments 47-50, wherein the cell population includes autologous cells or allogeneic cells.

52. A method of any of embodiments 47-51, further including determining whether the subject expresses or lacks the V-set domain of CD33, and if the subject expresses the V-set domain of CD33, selecting a combination therapy including a composition encoding a binding domain of one or more of 1H10, 1A9, 1E6, 1D2, and 1B9 and a binding domain of one or more of one or more of 1H8, 2D3, and 2E3.

53. A method of any of embodiments 47-51, further including determining whether the subject expresses or lacks the V-set domain of CD33, and if the subject does not express the V-set domain of CD33, selecting a therapy including a composition encoding a binding domain of one or more of 6H9, 9G2, 3A5, 7D5, 1 H7, and 2D5.

54. A kit including a nucleotide sequence encoding a CAR including a binding domain of one or more of 1H10, 1A9, 1E6, 1D2, and 1B9 and a nucleotide sequence encoding a CAR including a binding domain of one or more of one or more of 1H8, 2D3, and 2E3.

55. A kit including a nucleotide sequence encoding a CAR including a binding domain of one or more of 1H10, 1A9, 1E6, 1D2, and 1B9.

(ix) Closing Paragraphs. The nucleic acid and amino acid sequences provided herein are shown using letter abbreviations for nucleotide bases and amino acid residues, as defined in 37 C.F.R. § 1.822 and set forth in the tables in WIPO Standard ST.25 (1998), Appendix 2, Tables 1 and 3. Only one strand of each nucleic acid sequence is shown, but the complementary strand is understood as included in embodiments where it would be appropriate.

To the extent not explicitly provided herein, coding sequences for proteins disclosed herein and protein sequences for coding sequences disclosed herein can be readily derived from one of ordinary skill in the art.

Variants of the sequences disclosed and referenced herein are also included. Guidance in determining which amino acid residues can be substituted, inserted, or deleted without abolishing biological activity can be found using computer programs well known in the art, such as DNASTAR™ (Madison, Wisconsin.) software. Preferably, amino acid changes in the protein variants disclosed herein are conservative amino acid changes, i.e., substitutions of similarly charged or uncharged amino acids. A conservative amino acid change involves substitution of one of a family of amino acids which are related in their side chains.

In a peptide or protein, suitable conservative substitutions of amino acids are known to those of skill in this art and generally can be made without altering a biological activity of a resulting molecule. Those of skill in this art recognize that, in general, single amino acid substitutions in non-essential regions of a polypeptide do not substantially alter biological activity (see, e.g., Watson et al. Molecular Biology of the Gene, 4th Edition, 1987, The Benjamin/Cummings Pub. Co., p. 224). Naturally occurring amino acids are generally divided into conservative substitution families as follows: Group 1: Alanine (Ala), Glycine (Gly), Serine (Ser), and Threonine (Thr); Group 2: (acidic): Aspartic acid (Asp), and Glutamic acid (Glu); Group 3: (acidic; also classified as polar, negatively charged residues and their amides): Asparagine (Asn), Glutamine (Gln), Asp, and Glu; Group 4: Gln and Asn; Group 5: (basic; also classified as polar, positively charged residues): Arginine (Arg), Lysine (Lys), and Histidine (His); Group 6 (large aliphatic, nonpolar residues): Isoleucine (Ile), Leucine (Leu), Methionine (Met), Valine (Val) and Cysteine (Cys); Group 7 (uncharged polar): Tyrosine (Tyr), Gly, Asn, Gln, Cys, Ser, and Thr; Group 8 (large aromatic residues): Phenylalanine (Phe), Tryptophan (Trp), and Tyr; Group 9 (nonpolar): Proline (Pro), Ala, Val, Leu, Ile, Phe, Met, and Trp; Group 11 (aliphatic): Gly, Ala, Val, Leu, and Ile; Group 10 (small aliphatic, nonpolar or slightly polar residues): Ala, Ser, Thr, Pro, and Gly; and Group 12 (sulfur-containing): Met and Cys. Additional information can be found in Creighton (1984) Proteins, W.H. Freeman and Company.

In making such changes, the hydropathic index of amino acids may be considered. The importance of the hydropathic amino acid index in conferring interactive biologic function on a protein is generally understood in the art (Kyte and Doolittle, 1982, *J. Mol. Biol.* 157(1), 105-32). Each amino acid has been assigned a hydropathic index on the basis of its hydrophobicity and charge characteristics (Kyte and Doolittle, 1982). These values are: Ile (+4.5); Val (+4.2); Leu (+3.8); Phe (+2.8); Cys (+2.5); Met (+1.9); Ala (+1.8); Gly (−0.4); Thr (−0.7); Ser (−0.8); Trp (−0.9); Tyr (−1.3); Pro (−1.6); His (−3.2); Glutamate (−3.5); Gln (−3.5); aspartate (−3.5); Asn (−3.5); Lys (−3.9); and Arg (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those within ±1 are particularly preferred, and those within ±0.5 are even more particularly preferred. It is also understood in the art that the substitution of like amino acids can be made effectively on the basis of hydrophilicity.

As detailed in U.S. Pat. No. 4,554,101, the following hydrophilicity values have been assigned to amino acid residues: Arg (+3.0); Lys (+3.0); aspartate (+3.0±1); glutamate (+3.0±1); Ser (+0.3); Asn (+0.2); Gln (+0.2); Gly (0); Thr (−0.4); Pro (−0.5±1); Ala (−0.5); His (−0.5); Cys (−1.0); Met (−1.3); Val (−1.5); Leu (−1.8); Ile (−1.8); Tyr (−2.3); Phe (−2.5); Trp (−3.4). It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those within ±1 are particularly preferred, and those within ±0.5 are even more particularly preferred.

As outlined above, amino acid substitutions may be based on the relative similarity of the amino acid side-chain substituents, for example, their hydrophobicity, hydrophilicity, charge, size, and the like.

As indicated elsewhere, variants of gene sequences can include codon optimized variants, sequence polymorphisms, splice variants, and/or mutations that do not affect the function of an encoded product to a statistically significant degree.

Variants of the protein, nucleic acid, and gene sequences disclosed herein also include sequences with at least 70% sequence identity, 80% sequence identity, 85% sequence, 90% sequence identity, 95% sequence identity, 96% sequence identity, 97% sequence identity, 98% sequence identity, or 99% sequence identity to the protein, nucleic acid, or gene sequences disclosed herein.

"% sequence identity" refers to a relationship between two or more sequences, as determined by comparing the sequences. In the art, "identity" also means the degree of sequence relatedness between protein, nucleic acid, or gene sequences as determined by the match between strings of such sequences. "Identity" (often referred to as "similarity") can be readily calculated by known methods, including (but not limited to) those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wisconsin.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wisconsin.); BLASTP, BLASTN, BLASTX (Altschul, et al., J. Mol. Biol. 215:403-410 (1990); DNASTAR (DNASTAR, Inc., Madison, Wisconsin.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. As used herein "default values" will mean any set of values or parameters, which originally load with the software when first initialized.

Variants also include nucleic acid molecules that hybridizes under stringent hybridization conditions to a sequence disclosed herein and provide the same function as the reference sequence. Exemplary stringent hybridization conditions include an overnight incubation at 42° C. in a solution including 50% formamide, 5×SSC (750 mM NaCl, 75 mM trisodium citrate), 50 mM sodium phosphate (pH 7.6), 5×Denhardt's solution, 10% dextran sulfate, and 20 µg/ml denatured, sheared salmon sperm DNA, followed by washing the filters in 0.1×SSC at 50° C. Changes in the stringency of hybridization and signal detection are primarily accomplished through the manipulation of formamide concentration (lower percentages of formamide result in lowered stringency); salt conditions, or temperature. For example, moderately high stringency conditions include an overnight incubation at 37° C. in a solution including 6×SSPE (20×SSPE=3M NaCl; 0.2M NaH2PO4; 0.02M EDTA, pH 7.4), 0.5% SDS, 30% formamide, 100 µg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

"Specifically binds" refers to an association of a binding domain (of, for example, a CAR binding domain or a nanoparticle selected cell targeting ligand) to its cognate binding molecule with an affinity or $K_a$ (i.e., an equilibrium association constant of a particular binding interaction with units of 1/M) equal to or greater than $10^5$ $M^{-1}$, while not significantly associating with any other molecules or components in a relevant environment sample. Binding domains may be classified as "high affinity" or "low affinity". In particular embodiments, "high affinity" binding domains refer to those binding domains with a $K_a$ of at least $10^7$ $M^{-1}$, at least $10^8$ $M^{-1}$, at least $10^9$ $M^{-1}$, at least $10^{10}$ $M^{-1}$, at least $10^{11}$ $M^{-1}$, at least $10^{12}$ $M^{-1}$, or at least $10^{13}$ $M^{-1}$. In particular embodiments, "low affinity" binding domains refer to those binding domains with a $K_a$ of up to $10^7$ $M^{-1}$, up to $10^6$ $M^{-1}$, up to $10^5$ $M^{-1}$. Alternatively, affinity may be defined as an equilibrium dissociation constant ($K_d$) of a particular binding interaction with units of M (e.g., $10^{-5}$ M to $10^{-13}$ M). In certain embodiments, a binding domain may have "enhanced affinity," which refers to a selected or engineered binding domains with stronger binding to a cognate binding molecule than a wild type (or parent) binding domain. For example, enhanced affinity may be due to a $K_a$ (equilibrium association constant) for the cognate binding molecule that is higher than the reference binding domain or due to a $K_d$(dissociation constant) for the cognate binding molecule that is less than that of the reference binding domain, or due to an off-rate ($K_{off}$) for the cognate binding molecule that is less than that of the reference binding domain. A variety of assays are known for detecting binding domains that specifically bind a particular cognate binding molecule as well as determining binding affinities, such as Western blot, ELISA, and BIACORE® analysis (see also, e.g., Scatchard, et al., 1949, *Ann. N.Y. Acad. Sci.* 51:660; and U.S. Pat. Nos. 5,283,173, 5,468,614, or the equivalent).

Unless otherwise indicated, the practice of the present disclosure can employ conventional techniques of immunology, molecular biology, microbiology, cell biology and recombinant DNA. These methods are described in the following publications. See, e.g., Sambrook, et al. Molecular Cloning: A Laboratory Manual, 2nd Edition (1989); F. M. Ausubel, et al. eds., Current Protocols in Molecular Biology, (1987); the series Methods IN Enzymology (Academic Press, Inc.); M. MacPherson, et al., PCR: A Practical Approach, IRL Press at Oxford University Press (1991); MacPherson et al., eds. PCR 2: Practical Approach, (1995); Harlow and Lane, eds. Antibodies, A Laboratory Manual, (1988); and R. I. Freshney, ed. Animal Cell Culture (1987).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically significant reduction in CD33-expressing cell lysis in an vitro assay cell killing assay, as described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; 19% of the stated value; ±18% of the stated value; 17% of the stated value; 16% of the stated value; ±15% of the stated value; 14% of the stated value; ±13% of the stated value; 12% of the stated value; 11% of the stated value; 10% of the stated value; 9% of the stated value; 8% of the stated value; 7% of the stated value; ±6% of the stated value; 5% of the stated value; 4% of the stated value; ±3% of the stated value; 2% of the stated value; or +1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context.

Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Eds. Attwood T et al., Oxford University Press, Oxford, 2006).

What is claimed is:

1. A genetic construct comprising:
the sequence of SEQ ID NO: 50; SEQ ID NO: 51; SEQ ID NO: 202; SEQ ID NO: 46; SEQ ID NO: 47; SEQ ID NO: 200; SEQ ID NO: 48; SEQ ID NO: 49; SEQ ID NO: 201; or SEQ ID NO: 203.

2. The genetic construct of claim 1, wherein the genetic construct is within a viral vector.

3. The genetic construct of claim 1, wherein the genetic construct is within a nanoparticle.

4. The genetic construct of claim 1, wherein the genetic construct is within a cell.

*   *   *   *   *